US010761085B2

(12) United States Patent
Watanabe et al.

(10) Patent No.: US 10,761,085 B2
(45) Date of Patent: Sep. 1, 2020

(54) METHOD FOR DETERMINING A PROTEIN-PROTEIN INTERACTION

(71) Applicant: MEDICAL & BIOLOGICAL LABORATORIES CO., LTD., Nagoya-shi, Aichi (JP)

(72) Inventors: Taku Watanabe, Ina (JP); Toru Shoji, Ina (JP); Shun Matsuzawa, Ina (JP)

(73) Assignee: MEDICAL & BIOLOGICAL LABORATORIES CO., LTD., Nagoya-shi, Aichi (JP)

( * ) Notice: Subject to any disclaimer, the term of this patent is extended or adjusted under 35 U.S.C. 154(b) by 68 days.

(21) Appl. No.: 15/317,587

(22) PCT Filed: Jun. 10, 2015

(86) PCT No.: PCT/JP2015/066760
§ 371 (c)(1),
(2) Date: Dec. 9, 2016

(87) PCT Pub. No.: WO2015/190529
PCT Pub. Date: Dec. 17, 2015

(65) Prior Publication Data
US 2017/0122932 A1    May 4, 2017

(30) Foreign Application Priority Data

Jun. 10, 2014  (JP) .................. 2014-119441

(51) Int. Cl.
| C12Q 1/02 | (2006.01) |
| C12N 15/09 | (2006.01) |
| G01N 33/50 | (2006.01) |
| C07K 14/435 | (2006.01) |
| G01N 33/58 | (2006.01) |
| G01N 33/68 | (2006.01) |

(52) U.S. Cl.
CPC ....... *G01N 33/5005* (2013.01); *C07K 14/435* (2013.01); *C07K 14/43504* (2013.01); *C12N 15/09* (2013.01); *C12Q 1/02* (2013.01); *G01N 33/582* (2013.01); *G01N 33/6845* (2013.01); *C07K 2319/00* (2013.01); *C07K 2319/60* (2013.01); *C07K 2319/70* (2013.01)

(58) Field of Classification Search
None
See application file for complete search history.

(56) References Cited

U.S. PATENT DOCUMENTS

| 7,202,349 | B2 | 4/2007 | Davis et al. |
| 7,282,347 | B2 | 10/2007 | Bjorn et al. |
| 9,494,595 | B2* | 11/2016 | Watanabe ......... G01N 33/6845 |
| 9,766,250 | B2* | 9/2017 | Watanabe ......... G01N 33/6845 |
| 2006/0257887 | A1 | 11/2006 | Waldo et al. |
| 2007/0031912 | A1 | 2/2007 | Miyawaki et al. |
| 2010/0273673 | A1 | 10/2010 | Kim et al. |
| 2013/0052660 | A1 | 2/2013 | Lee et al. |
| 2014/0335539 | A1 | 11/2014 | Watanabe et al. |
| 2017/0010277 | A1* | 1/2017 | Watanabe ......... G01N 33/6845 |

FOREIGN PATENT DOCUMENTS

| EP | 1 184 463 A1 | 3/2002 |
| JP | 2004-524019 A | 8/2004 |
| JP | 2006-308568 A | 11/2006 |
| JP | 2008-521447 A | 6/2008 |
| JP | 2010-94110 A | 4/2010 |
| JP | 2010-537189 A | 12/2010 |
| JP | 2011-211983 A | 10/2011 |
| WO | 98/44350 A1 | 10/1998 |
| WO | 00/17221 A1 | 3/2000 |
| WO | 2006/017279 A2 | 2/2006 |
| WO | 2006/099486 A2 | 9/2006 |
| WO | 2009/049892 A1 | 4/2009 |
| WO | 2009/087097 A1 | 7/2009 |
| WO | 2010/066113 A1 | 6/2010 |
| WO | 2013/084950 A1 | 6/2013 |

OTHER PUBLICATIONS

Carette et al. Connexin 33 Impairs Gap Junction Functionality by Accelerating Connexin 43 Gap Junction Plaque Endocytosis. 2009. Traffic. vol. 10, pp. 1272-1285. (Year: 2009).*
English Translation of International Preliminary Report on Patentability dated Dec. 22, 2016 from the International Bureau in International Application No. PCT/JP2015/066760.
Communication, dated Nov. 23, 2017, issued by the European Patent Office in counterpart European Patent Application No. 15806561.5.
Junko Hashimoto, et al., "Novel in Vitro Protein Fragment Complementation Assay Applicable to High-Throughput Screening in a 1536-Well Format", J Biomol Screen, 2009, pp. 970-979, vol. 14, No. 8.

(Continued)

*Primary Examiner* — Channing S Mahatan
(74) *Attorney, Agent, or Firm* — Sughrue Mion, PLLC

(57) ABSTRACT

A method for determining an interaction between a first protein and a second protein comprises the steps of:
 expressing in a cell or introducing into a cell
  a first fusion protein comprising the first protein, a multimerizable protein, and a fluorescent protein, and
  a second fusion protein comprising the second protein and a multimerizable protein;
 detecting a fluorescent focus formed by an association between the first fusion protein and the second fusion protein in the cell; and
 determining an interaction between the first protein and the second protein according to the detection of the fluorescent focus.

4 Claims, 37 Drawing Sheets
Specification includes a Sequence Listing.

(56) References Cited

OTHER PUBLICATIONS

International Search Report for PCT/JP2015/066760 dated Aug. 25, 2015 [PCT/ISA/210].
Written Opinion for PCT/JP2015/066760 dated Aug. 25, 2015 [PCT/ISA/237].
Communication, dated May 7, 2019, issued by the Japanese Patent Office in counterpart application No. 2016-527845.

* cited by examiner

METHOD FOR DETERMINING A PROTEIN-PROTEIN INTERACTION

CROSS REFERENCE TO RELATED APPLICATIONS

This application is a National Stage of International Application No. PCT/JP2015/066760, filed on Jun. 10, 2015, which claims priority from Japanese Patent Application No. 2014-119441, filed on Jun. 10, 2014, the contents of all of which are incorporated herein by reference in their entirety.

TECHNICAL FIELD

The present invention relates to a method for determining a protein-protein interaction, as well as a vector and a kit for use in the method.

BACKGROUND ART

Methods for determining a protein-protein interaction can be roughly categorized into two groups. One is a method characterized by using a protein having been separated from living cells. Examples of such a method include surface plasmon resonance, protein mass spectroscopy, and anisotropy measurements. However, these methods have difficulty determining an interaction in an environment similar to an actual intracellular environment.

Then, as the second method, a method has been developed, in which a protein-protein interaction is determined using living cells. Typical methods thereof are a yeast two hybrid system which detects a transcriptional activity of a reporter, and modified methods thereof. Besides, another method has been also developed which utilizes reconstitution of enzymes such as β-galactosidase and dihydrofolate reductase (DHFR).

Nevertheless, these methods have problems that they are incapable of determining a position where a protein-protein interaction has taken place (positional information on the protein-protein interaction), as well as a period until a protein-protein interaction takes place, a period until the interaction ends, a duration of the interaction, and the like (temporal information on the protein-protein interaction).

Meanwhile, the method for determining a protein-protein interaction using living cells also includes a method utilizing reconstitution of a fluorescent protein. Nevertheless, once reconstituted, the fluorescent protein does not dissociate. Accordingly, this method has a problem that it is incapable of determining a period until a protein-protein interaction ends, a duration of the interaction, and the like. Further, there is another problem that a period until a protein-protein interaction takes place and the like cannot be determined because emission of fluorescence requires a certain time after a protein-protein interaction takes place.

On the other hand, as a method for determining a protein-protein interaction in living cells, fluorescence resonance energy transfer (FRET) has been developed which detects energy transfer dependent on a distance between molecules. This method has an advantage of obtaining positional information and temporal information on where and when a protein-protein interaction takes place. Nevertheless, since a positional relation between a donor fluorescent protein and an acceptor fluorescent protein used in the method is important to determine the protein-protein interaction, the method involves a complicated step of investigating the optimization of a linker (spacer) connecting these fluorescent proteins to a detection-target protein, so that such a system has been difficult to construct. Further, it has also been difficult to analyze the result due to cross excitation by which an acceptor fluorescent protein is excited, and due to bleed-through in which fluorescence of a donor fluorescent protein bleeds through a filter (absorption filter) set for detecting fluorescence of an acceptor fluorescent protein. Moreover, use of fluorescent proteins of two colors (donor fluorescent protein and acceptor fluorescent protein) also brings about a problem that only a limited number of fluorescent proteins are usable in order to obtain information other than a detection-target protein.

Recently, Tobias Meyer et al. have reported a method for determining a protein-protein interaction by utilizing intracellular localization (PTL 1). In this method, one of proteins subjected to interaction determination is fused to a protein that specifically binds to a particular site in a cell, while the other of the proteins subjected to interaction determination is fused to a fluorescent protein or the like. Then, these fusion proteins are expressed in a cell, and the protein-protein interaction is determined on the basis of a signal of the fluorescent protein or the like at the particular site in the cell.

In addition, Nibert et al. have reported a method for determining a protein-protein interaction by using a fusion protein in which one of proteins subjected to interaction determination is fused to a protein for forming a viral inclusion body, and using, as an indicator, accumulation of the other of the proteins subjected to interaction determination in the viral inclusion body (PTL 2).

However, in these methods for determining a protein-protein interaction by utilizing intracellular localization, one of proteins subjected to interaction determination is forcibly (artificially) translocated and confined at a particular site in a cell. Accordingly, the determination is impossible at a site where a protein-protein interaction naturally takes place, that is, in an intracellular environment unique to the protein-protein interaction, which brings about a problem that positional information on the protein-protein interaction cannot be obtained, and other similar problems. Moreover, it is also impossible to determine the interaction between proteins localized in a natural state at the same site as the site of the intracellular localization.

Against this problem, Sara Peterson Bjorn et al. have reported a method for determining a protein-protein interaction (redistribution-trap method) in which proteins are allowed to interact with each other in an intracellular environment where the proteins naturally function, and then the cells are stimulated with a drug or the like to thereby induce aggregate formation from the interacting proteins, the aggregate formation being indicative of the interaction (PTL 3).

However, this method needs to stimulate cells at certain time so that the aggregate formation can be induced, and also needs to remove the drug or the like used for the stimulation to determine the presence or absence of an interaction subsequently after the stimulation. Hence, the method has problems such as being incapable of obtaining temporal information on when the protein-protein interaction takes place, and incapable of determining a protein-protein interaction that changes (takes place, ends, takes place again, and so forth) for a certain period and at a certain position.

CITATION LIST

Patent Literature

[PTL 1] International Publication No. WO2000/017221
[PTL 2] International Publication No. WO2006/099486

[PTL 3] U.S. Pat. No. 7,282,347
[PTL 4] International Publication No. WO2013/084950

SUMMARY OF INVENTION

Technical Problem

The present invention has been made in consideration of the above-described problems in the conventional techniques. An object of the present invention is to provide a method capable of determining a protein-protein interaction in a cell in an intracellular environment unique to the protein-protein interaction, and also capable of obtaining positional information and temporal information on the protein-protein interaction.

Solution to Problem

The present inventors have conducted earnest studies in order to achieve the above object. As a result, the inventors have come up with an idea of utilizing, in determining an interaction between two proteins (a first protein and a second protein): a first fusion protein comprising the first protein, a multimerizable protein, and a fluorescent protein; and a second fusion protein comprising the second protein and a multimerizable protein (see FIGS. 1 and 2). To be more specific, the inventors have come up with a system as follows. When these two fusion proteins are expressed in a cell, an interaction if any between the first protein and the second protein induces multimer formation between the multimerizable protein and another multimerizable protein. Thereby, the fusion proteins autonomously form an assembly, and the fluorescent protein contained in the fusion protein is detected as a fluorescent focus.

Then, the inventors actually constructed this system, and expressed these fusion proteins in cells. The result revealed that determination of certain protein-protein interactions is possible on the basis of fluorescent foci detected in the cells. Moreover, it was also revealed that the system enables determination of a position where a protein-protein interaction takes place (positional information on the protein-protein interaction), as well as a period until a protein-protein interaction takes place, a period until the interaction ends, and the like (temporal information on the protein-protein interaction). Further, the result of comparing this method with another method for determining a protein-protein interaction on the basis of a fluorescent focus (PTL 4) previously invented by the present inventors revealed that the method of the present invention is superior to the method of PTL 4 in the efficiency of determining homomultimer formation; here, at least the first protein and the second protein are the same molecules, and these molecules form a dimer or a higher multimer as the homomultimer.

In addition, after verifying the effectiveness of the systems for detecting a fluorescent focus formed by assembly formation between the first fusion protein and the second fusion protein shown in FIGS. 1 and 2, the inventors have come up with other detection systems for determining a protein-protein interaction (see FIGS. 3 to 6). Specifically, the inventors have come up with detection systems for determining a protein-protein interaction by expressing in a cell or introducing into a cell the first fusion protein and the second fusion protein separately for reconstitution of the fusion proteins in the cell.

To be more specific, as shown in FIG. 3, in determining an interaction between a first protein and a second protein, when a third fusion protein comprising the first protein and a multimerizable protein, a fourth fusion protein comprising the second protein and a multimerizable protein, and fifth fusion proteins each comprising a multimerizable protein and a fluorescent protein are expressed in a cell or introduced into a cell, the multimerizable proteins associate with each other. Thereby, the third fusion protein binds to the fifth fusion protein while the fourth fusion protein binds to the fifth fusion protein, so that proteins respectively corresponding to the first fusion protein and the second fusion protein shown in FIGS. 1 and 2 are presumably expressed in the cell. Moreover, if such a presumption is correct, as in the case of the systems for detecting a fluorescent focus formed by assembly formation between the first fusion protein and the second fusion protein shown in FIGS. 1 and 2, the following can be expected also from a system for detecting a fluorescent focus formed by assembly formation among the third fusion protein, the fourth fusion protein, and the fifth fusion protein shown in FIG. 3: an interaction if any between the first protein and the second protein induces multimer formation between the multimerizable protein and another multimerizable protein; thereby, the fusion proteins autonomously form an assembly, and the fluorescent proteins contained in the fusion proteins are detected as fluorescent foci.

Moreover, as shown in FIG. 4, when a first labeled protein comprising an affinity tag and the first protein, a second labeled protein comprising an affinity tag and the second protein, and sixth fusion proteins each comprising a multimerizable protein, a fluorescent protein, and a binding partner having an affinity for any of the affinity tags and bound to the sixth fusion protein are expressed in a cell or introduced into a cell, the affinity tags bind to the binding partners. Thereby, the first labeled protein binds to the sixth fusion protein comprising the binding partner bound thereto while the second labeled protein binds to the sixth fusion protein comprising the binding partner bound thereto, so that protein complexes respectively corresponding to the first fusion protein and the second fusion protein shown in FIG. 2 are presumably expressed in the cell. Specifically, it is presumed that the complex composed of the fluorescent protein, the multimerizable protein, the binding partner, the affinity tag, and the first protein functions as the first fusion protein shown in FIG. 2, while the complex composed of the fluorescent protein, the multimerizable protein, the binding partner, the affinity tag, and the second protein functions as the second fusion protein shown in FIG. 2. Moreover, as in the case of the system shown in FIG. 2, when these protein complexes are expressed, an interaction if any between the first protein and the second protein induces multimer formation between the multimerizable protein and another multimerizable protein; thereby, the fusion proteins autonomously form an assembly, and the fluorescent proteins contained in the fusion proteins are detected as fluorescent foci.

Further, as shown in FIG. 5, when a seventh fusion protein comprising the first protein and a first partial peptide constituting a fluorescent protein, an eighth fusion protein comprising the second protein and a first partial peptide constituting a fluorescent protein, and ninth fusion proteins each comprising a multimerizable protein and a second partial peptide capable of reconstituting any of the fluorescent proteins by binding to the first partial peptide are expressed in a cell or introduced into a cell, the fluorescent proteins are expressed in the cell by the reconstitution. Moreover, as in the case of the system shown in FIG. 2, an interaction if any between the first protein and the second protein induces multimer formation between the multimerizable protein and another multimerizable protein; thereby, the fusion proteins autonomously form an assembly, and the fluorescent proteins contained in the fusion proteins are detected as fluorescent foci.

Furthermore, as shown in FIG. 6, when a tenth fusion protein comprising the first protein and a third partial peptide constituting a multimerizable protein, an eleventh fusion protein comprising the second protein and a third partial peptide constituting a multimerizable protein, and twelfth fusion proteins each comprising a fluorescent protein and a fourth partial peptide capable of reconstituting any of the multimerizable proteins by binding to the third partial peptide are expressed in a cell or introduced into a cell, the multimerizable proteins are expressed in the cell by the reconstitution. Moreover, as in the case of the system shown in FIG. 2, an interaction if any between the first protein and the second protein induces multimer formation between the multimerizable protein and another multimerizable protein; thereby, the fusion proteins autonomously form an assembly, and the fluorescent proteins contained in the fusion proteins are detected as fluorescent foci.

Thus, the inventors actually constructed the detection system shown in FIG. 3, too, and expressed the above-described fusion proteins in cells. The result revealed that the system for detecting a fluorescent focus formed by assembly formation among the third fusion protein, the fourth fusion protein, and the fifth fusion protein also enables determination of certain protein-protein interactions on the basis of fluorescent foci detected in the cells. Moreover, the inventors constructed the detection system shown in FIG. 4, too, and expressed the above-described fusion proteins in cells. The result revealed that the system for detecting a fluorescent focus formed by an association among the first labeled protein, the second labeled protein, and the sixth fusion protein comprising the binding partner bound thereto also enables determination of certain protein-protein interactions on the basis of fluorescent foci detected in the cells.

Further, based on the systems shown in FIG. 1 and so forth, the present inventors have come up with a system shown in FIG. 7 as an embodiment for detecting an interaction among three or more proteins. Specifically, when a thirteenth fusion protein comprising the first protein and a multimerizable protein, a fourteenth fusion protein comprising the second protein and a multimerizable protein, and a fifteenth fusion protein comprising a third protein and a fluorescent protein are expressed in a cell or introduced into a cell, an interaction if any among the first protein, the second protein, and the third protein, as in the cases of the systems shown in FIG. 1 and so forth, induces multimer formation between the multimerizable protein and another multimerizable protein; thereby, the fusion proteins autonomously form an assembly, and the fluorescent protein contained in the fusion protein is detected as a fluorescent focus.

Hence, the inventors actually constructed the detection system shown in FIG. 7, too, and expressed the above fusion proteins in cells. The result revealed that the system for detecting a fluorescent focus formed by an association among the thirteenth fusion protein, the fourteenth fusion protein, and the fifteenth fusion protein, that is, a fluorescent focus formed by the assembly formation, also enables determination of certain protein-protein interactions on the basis of fluorescent foci detected in the cells.

Further, based on the above results, the present inventors have come up with a system shown in FIG. 8 as a system for determining a protein-protein interaction. Specifically, the inventors have come up with a construction of a system in which a sixteenth fusion protein comprising the first protein, a first multimerizable protein, and a fluorescent protein, and a seventeenth fusion protein comprising the second protein and a second multimerizable protein are expressed in a cell or introduced into a cell. In a case where the first multimerizable protein is a different protein from the second multimerizable protein, the first protein and the second protein interact with each other, further inducing multimer formation between the multimerizable protein and another multimerizable protein; thereby, the fusion proteins autonomously form an assembly, and the fluorescent protein contained in the fusion protein is detected as a fluorescent focus.

Then, the inventors actually constructed the detection system shown in FIG. 8, too, and expressed the above fusion proteins in cells. The result revealed that the system for detecting a fluorescent focus formed by an association between the sixteenth fusion protein and the seventeenth fusion protein, that is, a fluorescent focus formed by the assembly formation, also enables determination of certain protein-protein interactions on the basis of fluorescent foci detected in the cells.

Thus, the present invention relates to a method for determining a protein-protein interaction, as well as a vector and a kit for use in the method. More specifically, the present invention provides the following inventions.

<1> A method for determining an interaction between a first protein and a second protein, the method comprising the following steps (1) to (3):
(1) expressing in a cell or introducing into a cell
a first fusion protein comprising the first protein, a multimerizable protein, and a fluorescent protein, and
a second fusion protein comprising the second protein and a multimerizable protein;
(2) detecting a fluorescent focus formed by an association between the first fusion protein and the second fusion protein in the cell; and
(3) determining an interaction between the first protein and the second protein according to the detection of the fluorescent focus.

<2> The method according to <1>, wherein the second fusion protein further comprises a fluorescent protein.

<3> The method according to <1> or <2>, wherein the fluorescent protein is a monomeric fluorescent protein.

<4> A method for detecting an interaction between a first protein and a second protein, the method comprising the following steps (1) to (3):
(1) expressing in a cell or introducing into a cell
a third fusion protein comprising the first protein and a multimerizable protein,
a fourth fusion protein comprising the second protein and a multimerizable protein, and
a fifth fusion protein comprising a multimerizable protein and a fluorescent protein;
(2) detecting a fluorescent focus formed by an association among the third fusion protein, the fourth fusion protein, and the fifth fusion protein in the cell; and
(3) determining an interaction between the first protein and the second protein according to the detection of the fluorescent focus.

<5> The method according to <4>, wherein the fluorescent protein is a monomeric fluorescent protein.

<6> A vector comprising a DNA encoding a multimerizable protein, a DNA encoding a fluorescent protein, and a cloning site, wherein
the vector is capable of expressing a fusion protein comprising the multimerizable protein, the fluorescent protein, and a certain protein when a DNA encoding the certain protein is inserted in the cloning site.

<7> A kit for use in the method according to any one of <1> to <3>, the kit comprising an instruction and at least one substance selected from the group consisting of the following (a) to (h):
 (a) the vector according to <6>;
 (b) a vector encoding the first fusion protein;
 (c) a vector encoding the second fusion protein;
 (d) a transformed cell comprising a vector encoding the first fusion protein;
 (e) a transformed cell comprising a vector encoding the second fusion protein;
 (f) a transformed cell comprising a vector encoding the first fusion protein and a vector encoding the second fusion protein;
 (g) the first fusion protein; and
 (h) the second fusion protein.

<8> A kit for use in the method according to <4> or <5>, the kit comprising an instruction and at least one substance selected from the group consisting of the following (a) to (h):
 (a) a vector comprising a DNA encoding the multimerizable protein and a cloning site, wherein the vector is capable of expressing a fusion protein comprising the multimerizable protein and a certain protein when a DNA encoding the certain protein is inserted in the cloning site;
 (b) a vector encoding the third fusion protein;
 (c) a vector encoding the fourth fusion protein;
 (d) a vector encoding the fifth fusion protein;
 (e) a transformed cell comprising a vector encoding the fifth fusion protein;
 (f) the third fusion protein;
 (g) the fourth fusion protein; and
 (h) the fifth fusion protein.

<9> A method for detecting an interaction between a first protein and a second protein, the method comprising the following steps (1) to (3):
 (1) expressing in a cell or introducing into a cell
  a first labeled protein comprising an affinity tag and the first protein,
  a second labeled protein comprising an affinity tag and the second protein, and
  a sixth fusion protein comprising a multimerizable protein, a fluorescent protein, and a binding partner having an affinity for any of the affinity tags and bound to the sixth fusion protein;
 (2) detecting a fluorescent focus formed by an association among the first labeled protein, the second labeled protein, and the sixth fusion protein comprising the binding partner bound thereto in the cell; and
 (3) determining an interaction between the first protein and the second protein according to the detection of the fluorescent focus.

<10> A kit for use in the method according to <9>, the kit comprising an instruction and at least one substance selected from the group consisting of the following (a) to (h):
 (a) a vector comprising a DNA encoding the affinity tag and a cloning site, wherein the vector is capable of expressing a fusion protein comprising the affinity tag when a DNA encoding a certain protein is inserted in the cloning site;
 (b) a vector encoding the first labeled protein;
 (c) a vector encoding the second labeled protein;
 (d) a vector encoding the sixth fusion protein comprising the binding partner bound thereto;
 (e) a transformed cell comprising a vector encoding the sixth fusion protein comprising the binding partner bound thereto;
 (f) the first labeled protein;
 (g) the second labeled protein; and
 (h) the sixth fusion protein comprising the binding partner bound thereto.

<11> A method for detecting an interaction between a first protein and a second protein, the method comprising the following steps (1) to (3):
 (1) expressing in a cell or introducing into a cell
  a seventh fusion protein comprising the first protein and a first partial peptide constituting a fluorescent protein,
  an eighth fusion protein comprising the second protein and a first partial peptide constituting a fluorescent protein, and
  a ninth fusion protein comprising a multimerizable protein and a second partial peptide capable of reconstituting any of the fluorescent proteins by binding to the first partial peptide;
 (2) detecting a fluorescent focus formed by an association among the seventh fusion protein, the eighth fusion protein, and the ninth fusion protein in the cell; and
 (3) determining an interaction between the first protein and the second protein according to the detection of the fluorescent focus.

<12> A kit for use in the method according to <11>, the kit comprising an instruction and at least one substance selected from the group consisting of the following (a) to (h):
 (a) a vector comprising a DNA encoding the first partial peptide and a cloning site, wherein the vector is capable of expressing a fusion protein comprising the first partial peptide when a DNA encoding a certain protein is inserted in the cloning site;
 (b) a vector encoding the seventh fusion protein;
 (c) a vector encoding the eighth fusion protein;
 (d) a vector encoding the ninth fusion protein;
 (e) a transformed cell comprising a vector encoding the ninth fusion protein;
 (f) the seventh fusion protein;
 (g) the eighth fusion protein; and
 (h) the ninth fusion protein.

<13> A method for detecting an interaction between a first protein and a second protein, the method comprising the following steps (1) to (3):
 (1) expressing in a cell or introducing into a cell
  a tenth fusion protein comprising the first protein and a third partial peptide constituting a multimerizable protein,
  an eleventh fusion protein comprising the second protein and a third partial peptide constituting a multimerizable protein, and
  a twelfth fusion protein comprising a fluorescent protein and a fourth partial peptide capable of reconstituting any of the multimerizable proteins by binding to the third partial peptide;
 (2) detecting a fluorescent focus formed by an association among the tenth fusion protein, the eleventh fusion protein, and the twelfth fusion protein in the cell; and
 (3) determining an interaction between the first protein and the second protein according to the detection of the fluorescent focus.

<14> A kit for use in the method according to <13>, the kit comprising an instruction and at least one substance selected from the group consisting of the following (a) to (h):

(a) a vector comprising a DNA encoding the third partial peptide and a cloning site, wherein the vector is capable of expressing a fusion protein comprising the third partial peptide when a DNA encoding a certain protein is inserted in the cloning site;
  (b) a vector encoding the tenth fusion protein;
  (c) a vector encoding the eleventh fusion protein;
  (d) a vector encoding the twelfth fusion protein;
  (e) a transformed cell comprising a vector encoding the twelfth fusion protein;
  (f) the tenth fusion protein;
  (g) the eleventh fusion protein; and
  (h) the twelfth fusion protein.
<15> A method for detecting an interaction among a first protein, a second protein, and a third protein, the method comprising the following steps (1) to (3):
  (1) expressing in a cell or introducing into a cell
    a thirteenth fusion protein comprising the first protein and a multimerizable protein,
    a fourteenth fusion protein comprising the second protein and a multimerizable protein, and
    a fifteenth fusion protein comprising the third protein and a fluorescent protein;
  (2) detecting a fluorescent focus formed by an association among the thirteenth fusion protein, the fourteenth fusion protein, and the fifteenth fusion protein in the cell; and
  (3) determining an interaction among the first protein, the second protein, and the third protein according to the detection of the fluorescent focus.
<16> A kit for use in the method according to <15>, the kit comprising an instruction and at least one substance selected from the group consisting of the following (a) to (h):
  (a) a vector comprising a DNA encoding the multimerizable protein and a cloning site, wherein the vector is capable of expressing a fusion protein comprising the multimerizable protein when a DNA encoding a certain protein is inserted in the cloning site;
  (b) a vector comprising a DNA encoding the fluorescent protein and a cloning site, wherein the vector is capable of expressing a fusion protein comprising the fluorescent protein when a DNA encoding a certain protein is inserted in the cloning site;
  (c) a vector encoding the thirteenth fusion protein;
  (d) a vector encoding the fourteenth fusion protein;
  (e) a vector encoding the fifteenth fusion protein;
  (f) the thirteenth fusion protein;
  (g) the fourteenth fusion protein; and
  (h) the fifteenth fusion protein.
<17> A method for determining an interaction between a first protein and a second protein, wherein
  a first multimerizable protein is a different protein from a second multimerizable protein, and
  the method comprises the following steps (1) to (3):
  (1) expressing in a cell or introducing into a cell
    a sixteenth fusion protein comprising the first protein, the first multimerizable protein, and a fluorescent protein, and
    a seventeenth fusion protein comprising the second protein and the second multimerizable protein;
  (2) detecting a fluorescent focus formed by an association between the sixteenth fusion protein and the seventeenth fusion protein in the cell; and
  (3) determining an interaction between the first protein and the second protein according to the detection of the fluorescent focus.

<18> A kit for use in the method according to <17>, the kit comprising an instruction and at least one substance selected from the group consisting of the following (a) to (f):
  (a) a vector comprising a DNA encoding the first multimerizable protein, a DNA encoding the fluorescent protein, and a cloning site, wherein the vector is capable of expressing a fusion protein comprising the first multimerizable protein, the fluorescent protein, and a certain protein when a DNA encoding the certain protein is inserted in the cloning site;
  (b) a vector comprising a DNA encoding the second multimerizable protein, a DNA encoding the fluorescent protein, and a cloning site, wherein the vector is capable of expressing a fusion protein comprising the second multimerizable protein, the fluorescent protein, and a certain protein when a DNA encoding the certain protein is inserted in the cloning site;
  (c) a vector encoding the sixteenth fusion protein;
  (d) a vector encoding the seventeenth fusion protein;
  (e) the sixteenth fusion protein; and
  (f) the seventeenth fusion protein.

Advantageous Effects of Invention

The present invention makes it possible to determine a protein-protein interaction in an intracellular environment unique thereto, and to obtain positional information and temporal information on the protein-protein interaction based on the determination result. Particularly, the present invention makes it possible to efficiently determine homomultimer formation in an intracellular environment unique to the homomultimer formation, and also to efficiently obtain positional information and temporal information on the homomultimer formation based on the determination result.

Figure 20:
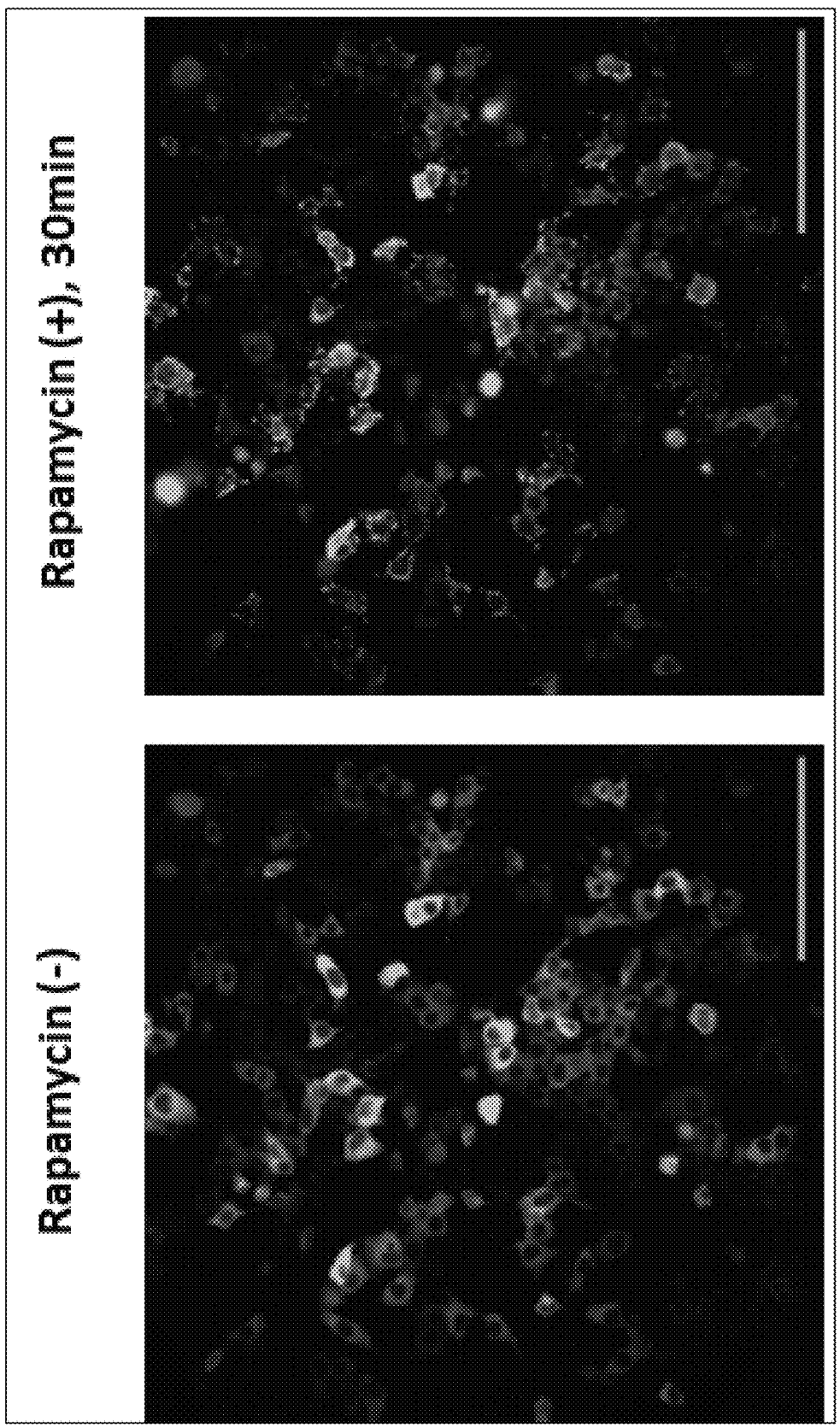
FIG. 20 shows micrographs for illustrating the result of expressing in cells a protein (mTOR(FRB domain)-mAG1-PB1) composed of mAG1 and a PB1 domain of a p62 protein fused to the C-terminus of an analysis target FRB domain of a mTOR protein, and a protein (PB1-mAG1-FKBP12) composed of a PB1 domain of a p62 protein and mAG1 fused to the N-terminus of an analysis target FKBP12 to analyze whether or not it is possible to determine a protein-protein interaction between FKBP12 and mTOR (FRB domain) on the basis of a fluorescent focus. Note that, in the figure, "Rapamycin (−)" shows the result of observing the cells before the addition of rapamycin, which is an inducer for the protein-protein interaction. "Rapamycin (+), 30 min" shows the result of observing the cells when 30 minutes elapsed after the rapamycin addition. In the figure, the scale bars represent 100 μm.
Figure 21:
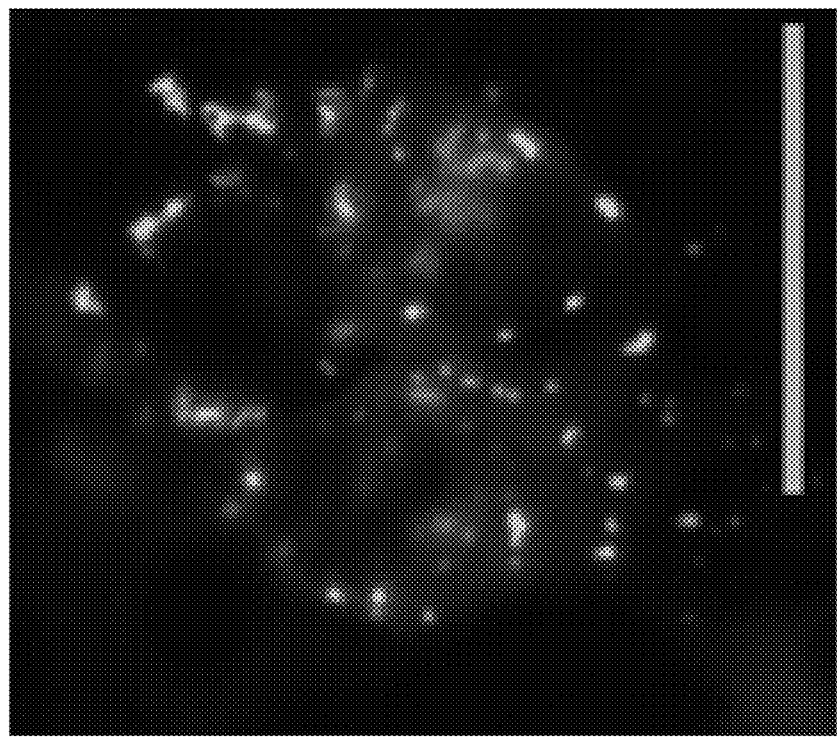
Figure 21:
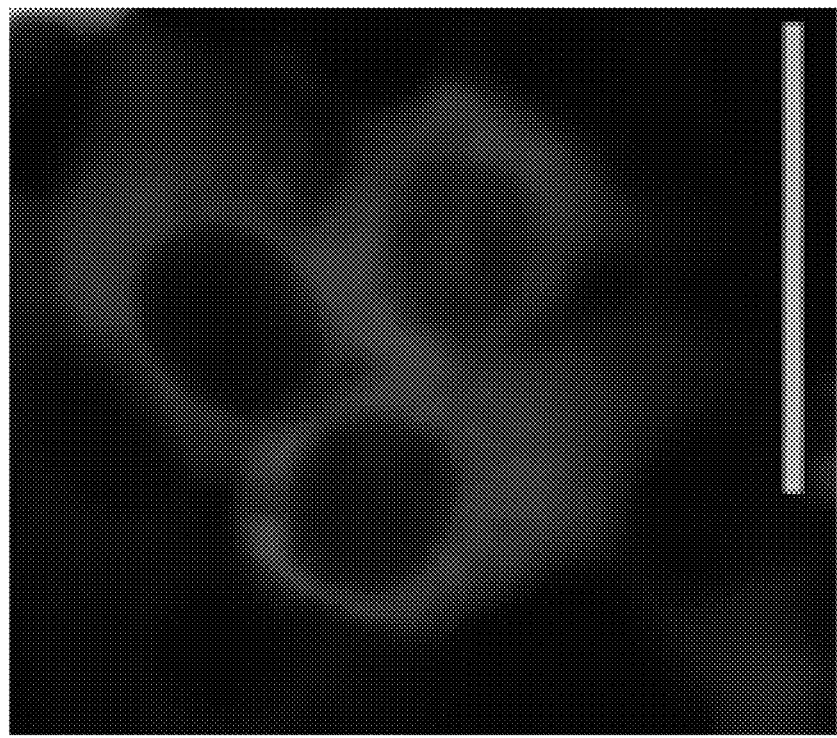

FIG. 21 shows photographs obtained by partially enlarging the micrographs shown in FIG. 20. In the figure, the scale bars represent 20 μm.

Figure 22:
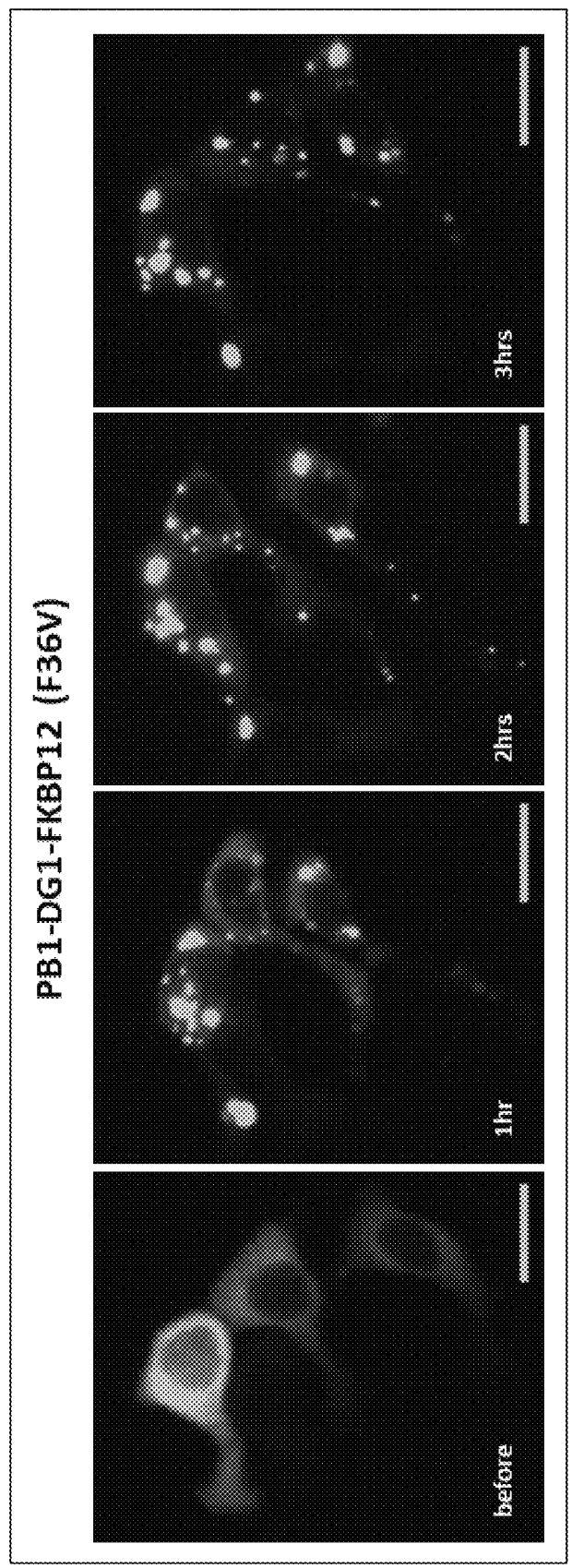

FIG. 22 shows micrographs for illustrating the result of expressing in cells a protein (PB1-DG1-FKBP12 mutant, i.e., PB1-DG1-FKBP12 (F36V)) composed of a PB1 domain of a p62 protein and a fluorescent protein DG1 fused to the N-terminus of an analysis target FKBP12 mutant, and then adding a drug B/B Homodimerizer to the cells to analyze whether or not it is possible to determine, on the basis of a fluorescent focus, homodimer formation of the FKBP12 mutant attributable to the drug addition. The figure shows the result of analyzing the cells before the drug addition, the cells 1 hour after the drug addition, the cells 2 hours after the drug addition, and the cells 3 hours after the drug addition, in this order from the left. Moreover, in the figure, the scale bars represent 20 μm.

Figure 23:
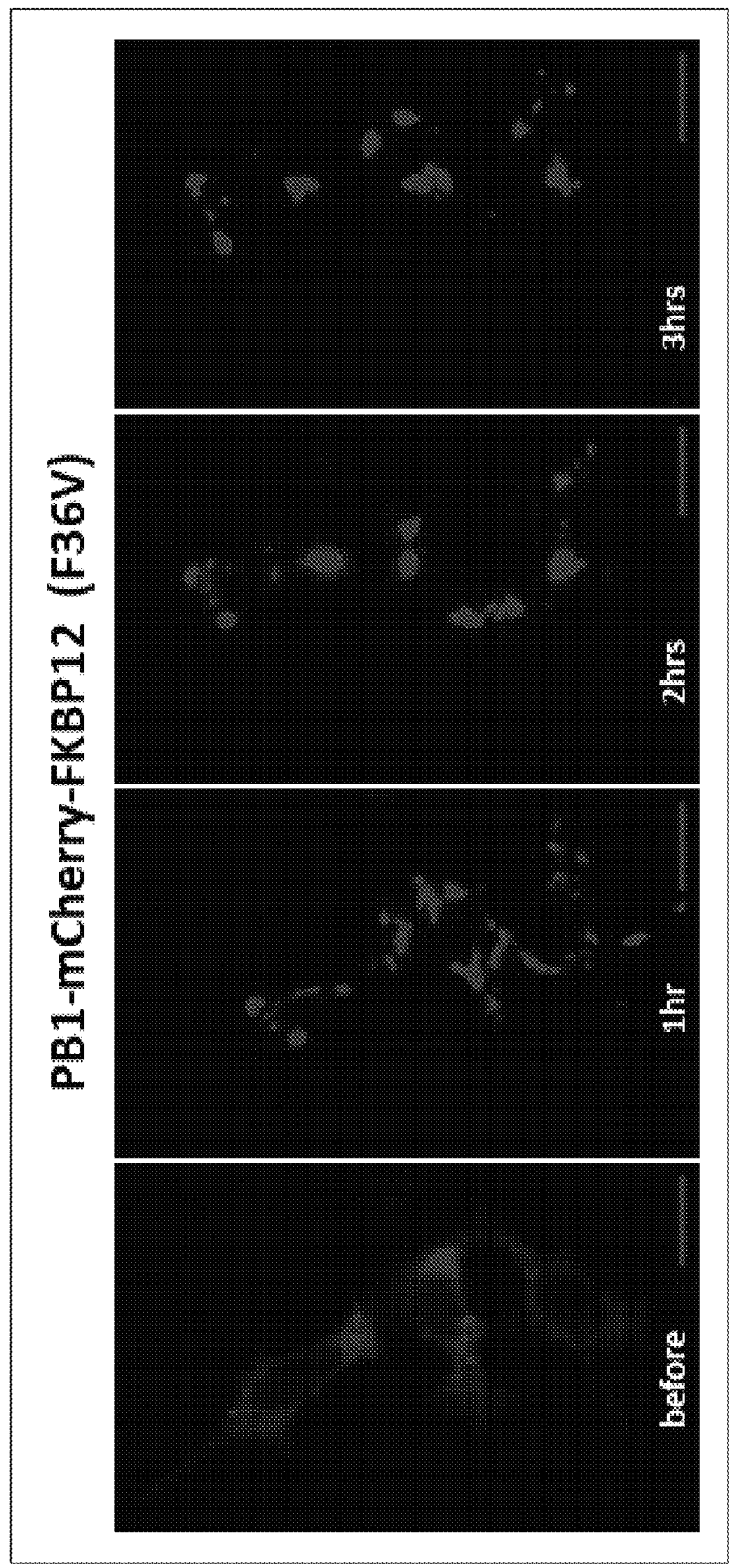

FIG. 23 shows micrographs for illustrating the result of expressing in cells a protein (PB1-mCherry-FKBP12 mutant, i.e., PB1-mCherry-FKBP12 (F36V)) composed of a PB1 domain of a p62 protein and a fluorescent protein mCherry fused to the N-terminus of an analysis target FKBP12 mutant, and then adding a drug B/B Homodimerizer to the cells to analyze whether or not it is possible to determine, on the basis of a fluorescent focus, homodimer formation of the FKBP12 mutant attributable to the drug addition. The figure shows the result of analyzing the cells before the drug addition, the cells 1 hour after the drug addition, the cells 2 hours after the drug addition, and the cells 3 hours after the drug addition, in this order from the left. Moreover, in the figure, the scale bars represent 20 μm.

Figure 24:
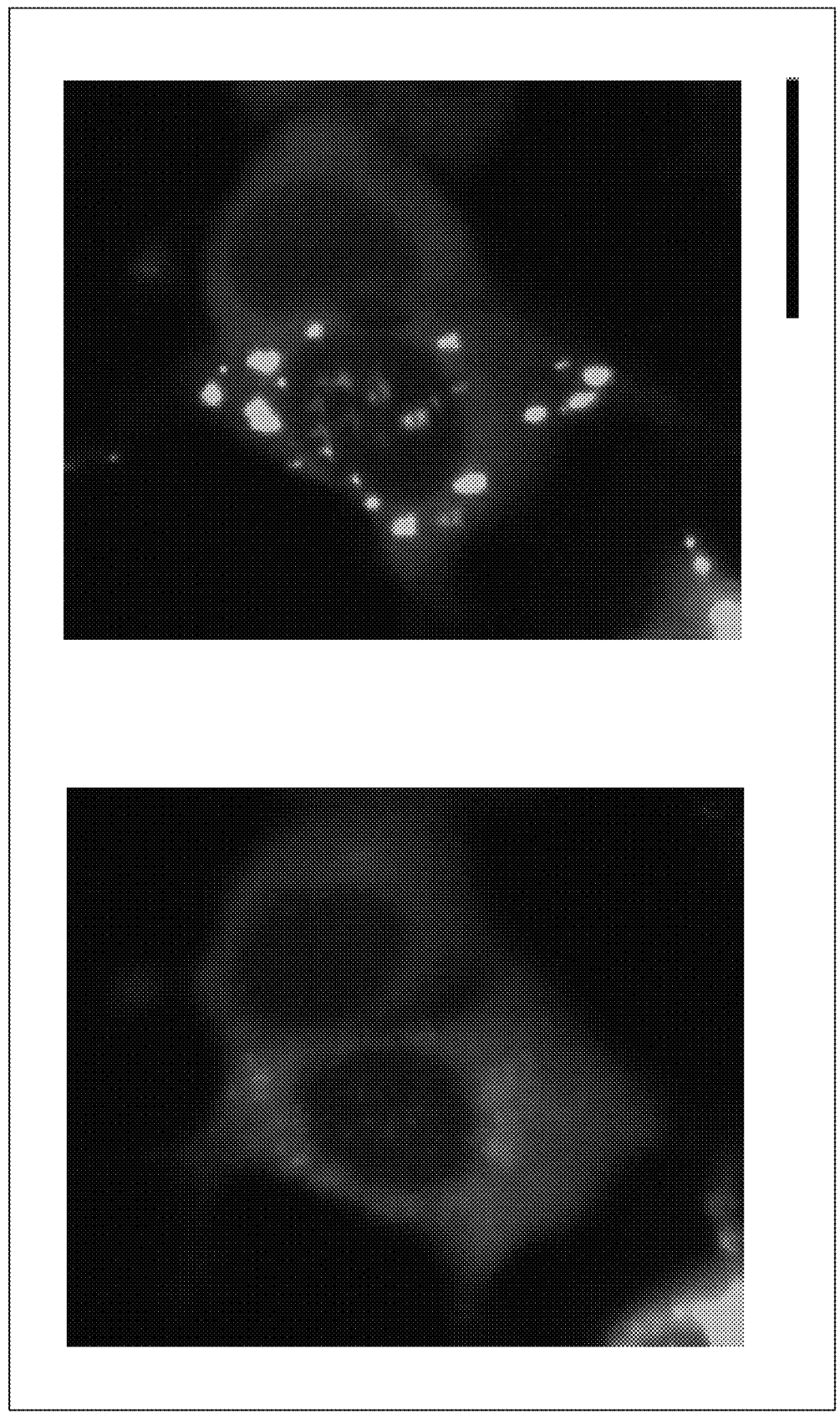

FIG. 24 shows micrographs for illustrating the result of expressing in cells a protein (Tankyrase-mAG1-FKBP12 mutant, Tankyrase-mAG1-FKBP12 (F36V)) composed of a SAM domain of a Tankyrase 1 protein as a multimerizable protein and mAG1 fused to the N-terminus of an analysis target FKBP12 mutant, and then adding a drug B/B Homodimerizer to the cells to analyze whether or not it is possible to determine, on the basis of a fluorescent focus, homodimer formation of the FKBP12 mutant attributable to the drug addition. The figure shows the result of analyzing the cells before the drug addition and the cells 3 hours after the drug addition, in this order from the left. Moreover, in the figure, the scale bar represents 20 μm.

Figure 25:
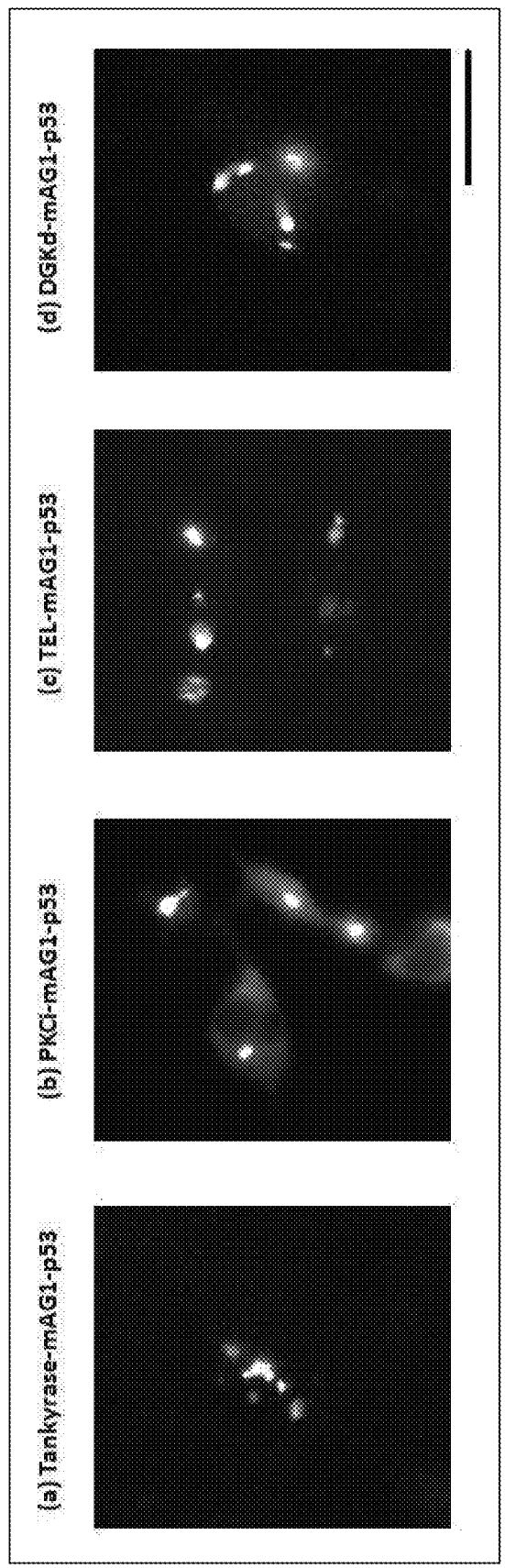

FIG. 25 shows micrographs for illustrating the result of expressing in cells a protein (Tankyrase-mAG1-p53, PKCi-mAG1-p53, TEL-mAG1-p53, or DGKd-mAG1-p53) composed of a SAM domain of a Tankyrase 1 protein, a PB1 domain of a PKCiota protein, a SAM domain of a TEL protein, or a SAM domain of a DGK delta protein, as a multimerizable protein, fused to the N-terminus of p53 to analyze whether or not it is possible to determine homomultimer formation of p53 on the basis of a fluorescent focus. In the figure, the scale bar represents 20 μm.

Figure 26:
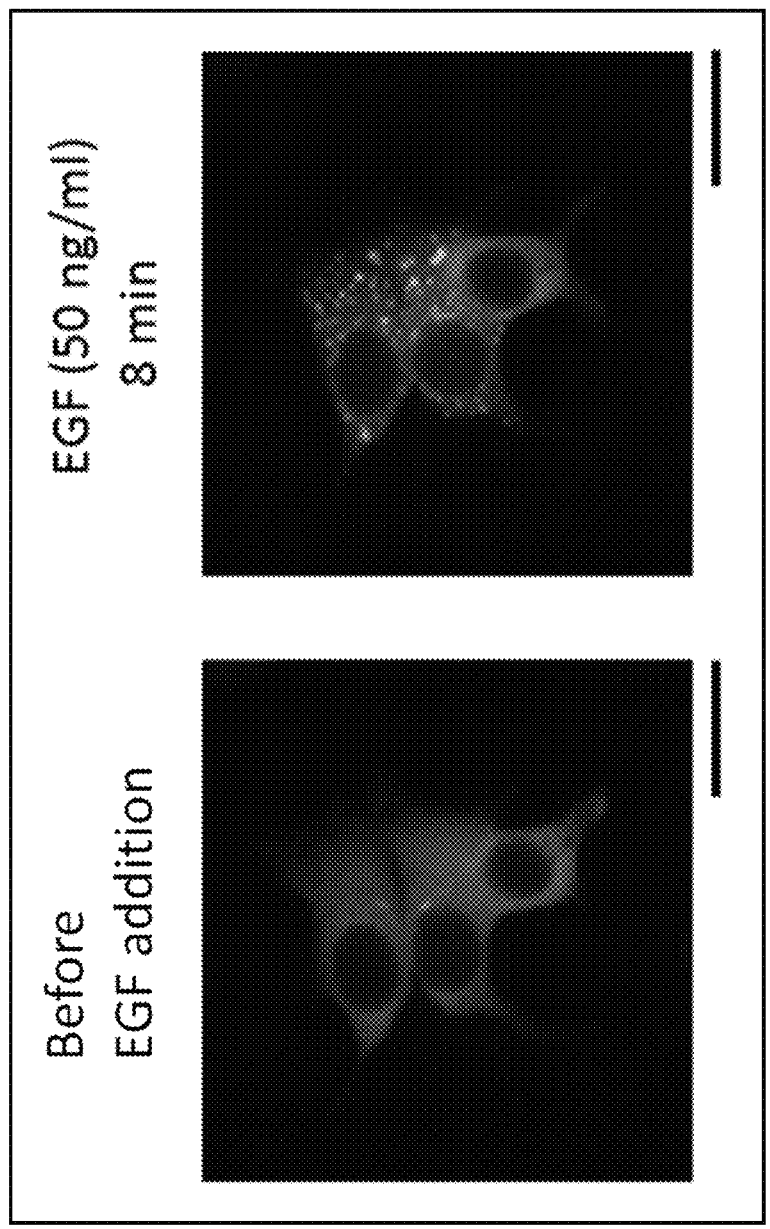

FIG. 26 shows micrographs for illustrating the result of expressing in cells a protein (ERK2-mAG1-PB1) composed of mAG1 and a PB1 domain of a p62 protein fused to the C-terminus of ERK2, and then adding EGF to the cells to analyze whether or not it is possible to determine, on the basis of a fluorescent focus, homodimer formation of ERK2 attributable to the addition. Note that, in the figure, "before EGF addition" shows the result of observing the cells before the EGF addition. "EGF (50 ng/ml), 8 min" shows the result of observing the cells when 8 minutes elapsed after the EGF addition. In the figure, the scale bars represent 20 μm.

Figure 27:
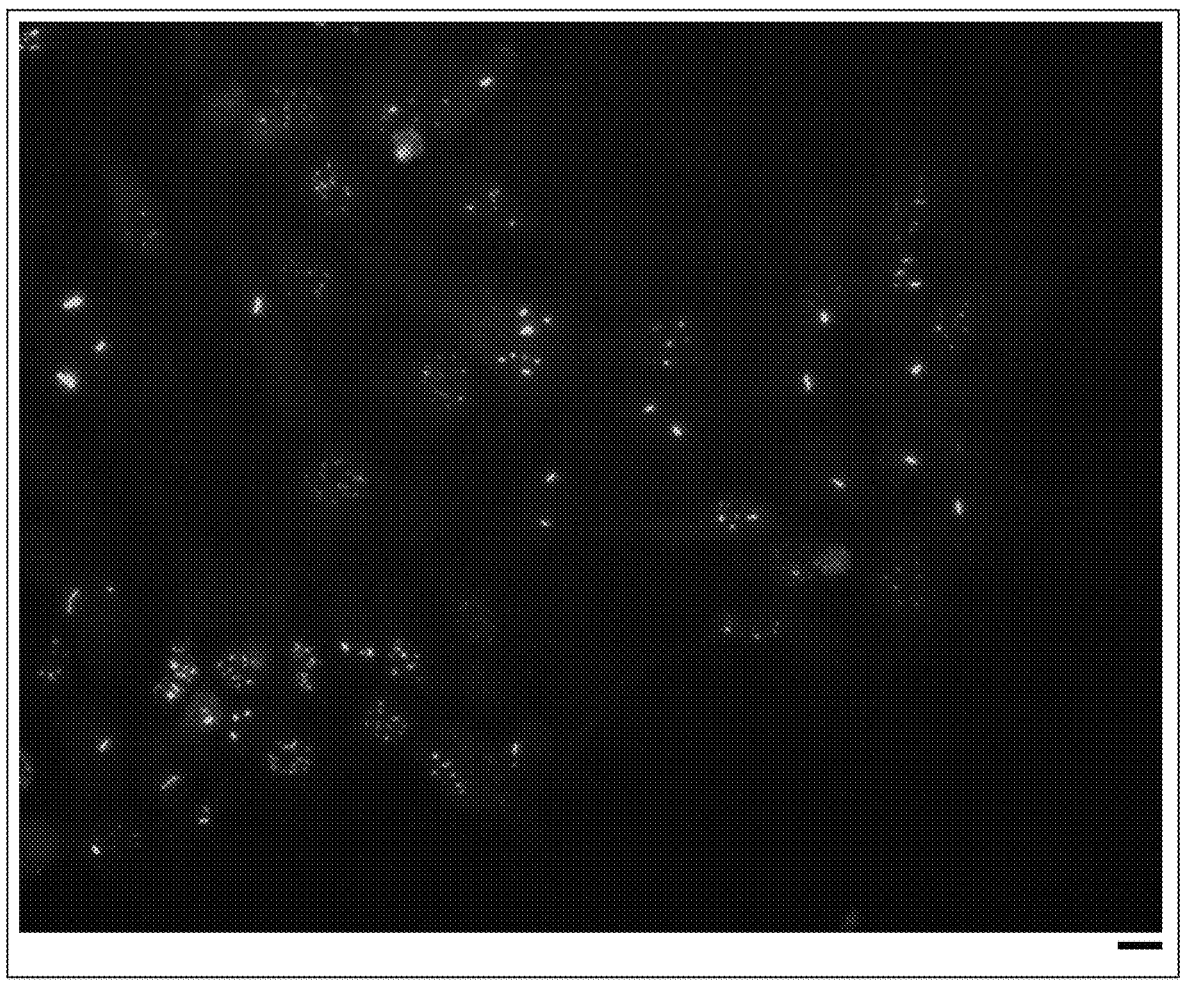

FIG. 27 is a micrograph for illustrating the result of observing, 8 minutes after EGF addition, cells constitutively expressing a protein (ERK2-PB1-mAG1) composed of a PB1 domain of a p62 protein and mAG1 fused to the C-terminus of ERK2 to analyze whether or not it is possible to determine, on the basis of a fluorescent focus, homodimer formation of ERK2 attributable to the addition. In the figure, the scale bar represents 20 μm.

Figure 28:
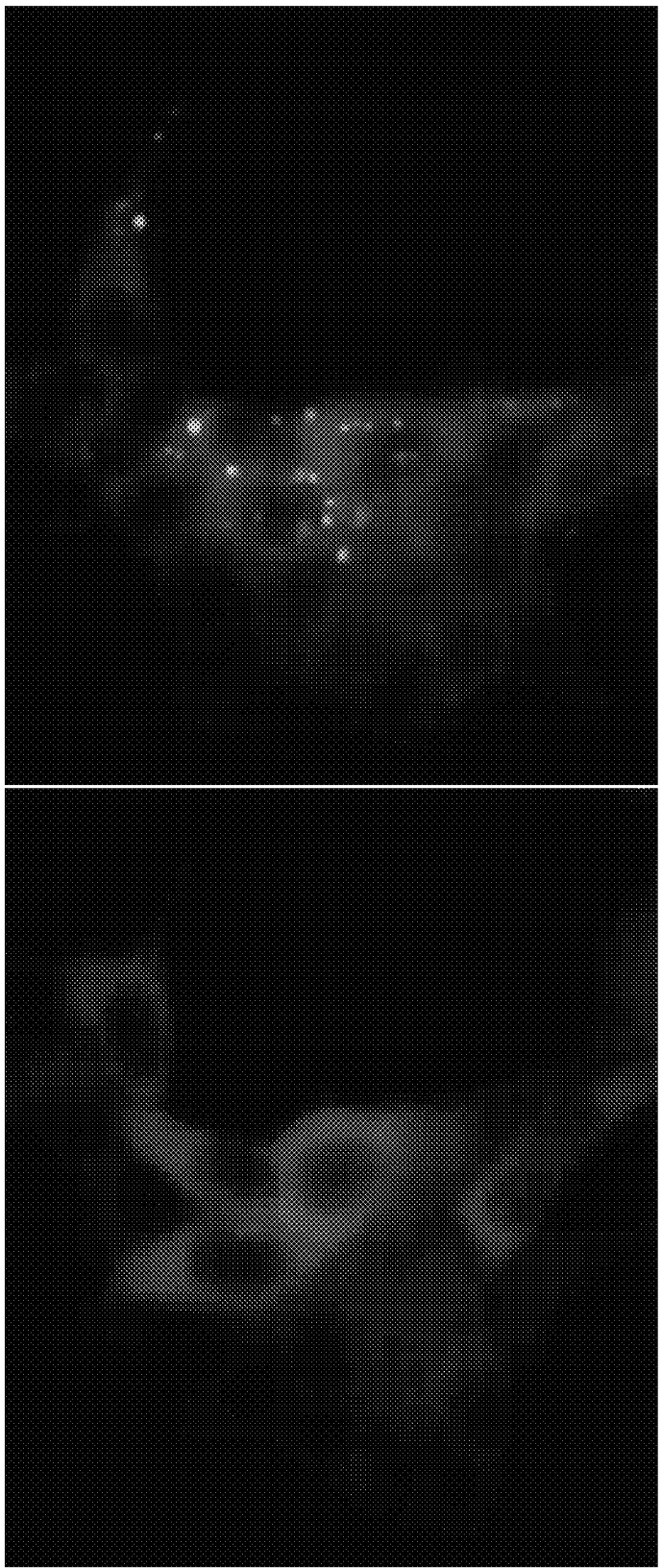

FIG. 28 shows micrographs for illustrating the result of expressing in cells a protein (PB1-mAG1-STAT3) composed of a PB1 domain of a p62 protein and mAG1 fused to the N-terminus of STAT3, and then adding IL-6 to the cells to analyze whether or not it is possible to determine, on the basis of a fluorescent focus, homodimer formation of STAT3 attributable to the addition. Note that, in the figure, "before" shows the result of observing the cells before the IL-6 addition. "IL6 (100 ng/ml), 50 min" shows the result of observing the cells when 50 minutes elapsed after the IL-6 addition. In the figure, the scale bar represents 20 μm.

Figure 29:
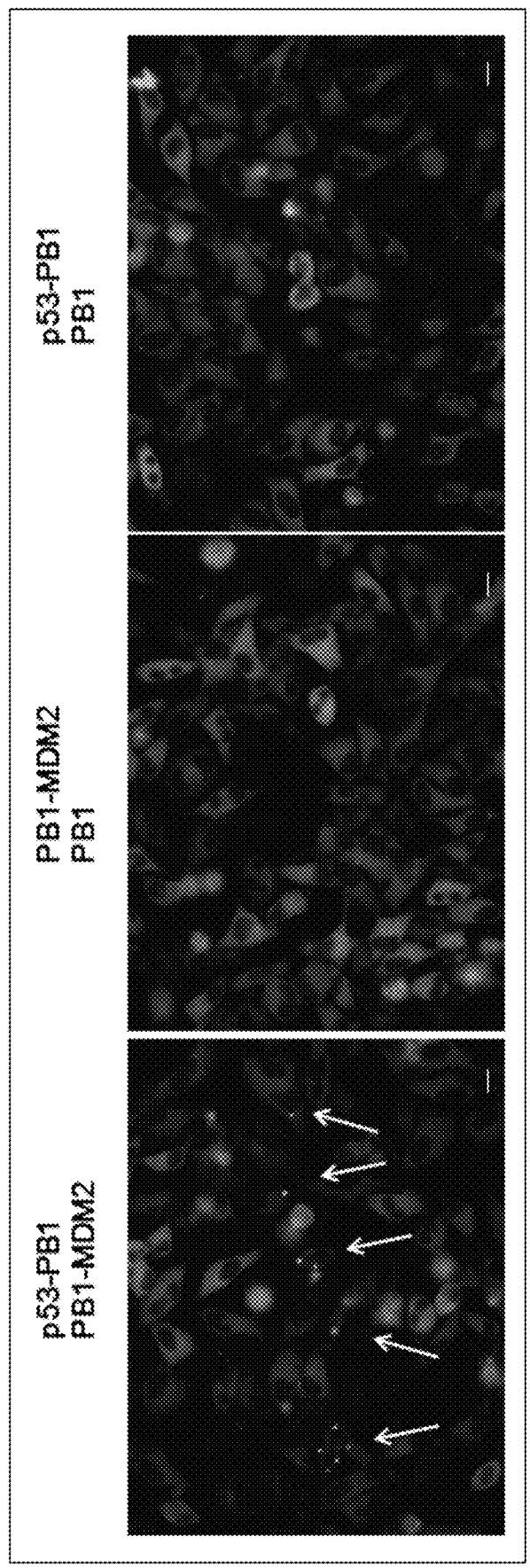

FIG. 29 shows micrographs for illustrating the result of analyzing whether or not it is possible to determine a protein-protein interaction between p53 and MDM2 on the basis of a fluorescent focus by transiently expressing p53-PB1 and PB1-MDM2, PB1-MDM2 and PB1, or p53-PB1 and PB1 in cells constitutively expressing a fusion protein (PB1-mAG1) comprising a PB1 domain of a p62 protein and mAG1. Note that "p53-PB1" means a protein composed of a PB1 domain of a p62 protein fused to the C-terminus of a portion of a p53 protein. "PB1-MDM2" means a protein composed of a PB1 domain of a p62 protein fused to the N-terminus of MDM2. "PB1" means a PB1 domain of a p62 protein. Moreover, in the figure, the scale bars represent 20 μm, and arrows indicate detected fluorescent foci.

Figure 30:
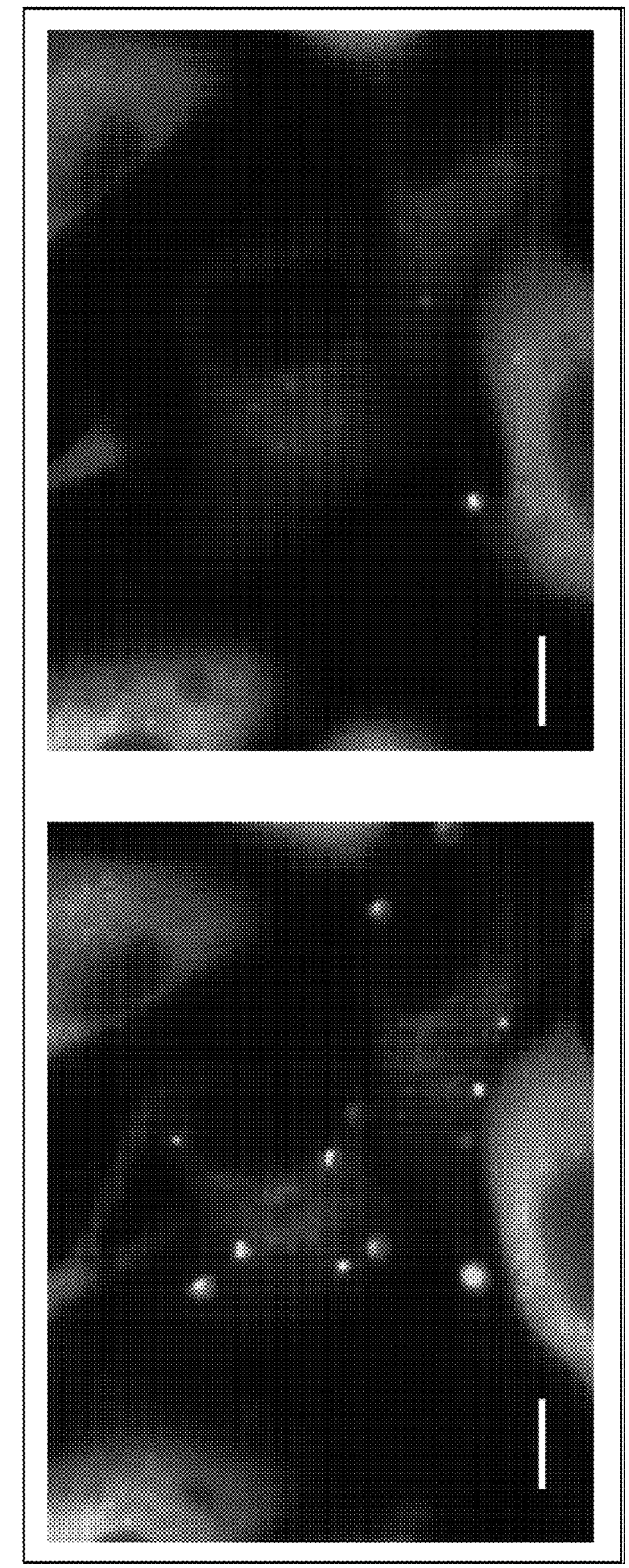

FIG. 30 shows micrographs for illustrating the result of analyzing whether or not it is possible to determine, on the basis of a fluorescent focus, a termination of the protein-protein interaction between p53 and MDM2 by adding Nutlin-3 to the cells constitutively expressing PB1-mAG1 and further transiently expressing p53(70)-PB1 and PB1-MDM2. In the figure, the photograph on the left shows the result of analyzing the cells before the Nutlin-3 addition, and the photograph on the right shows the result of analyzing the cells after the Nutlin-3 addition. Moreover, in the figure, the scale bars represent 10 μm.

Figure 31:
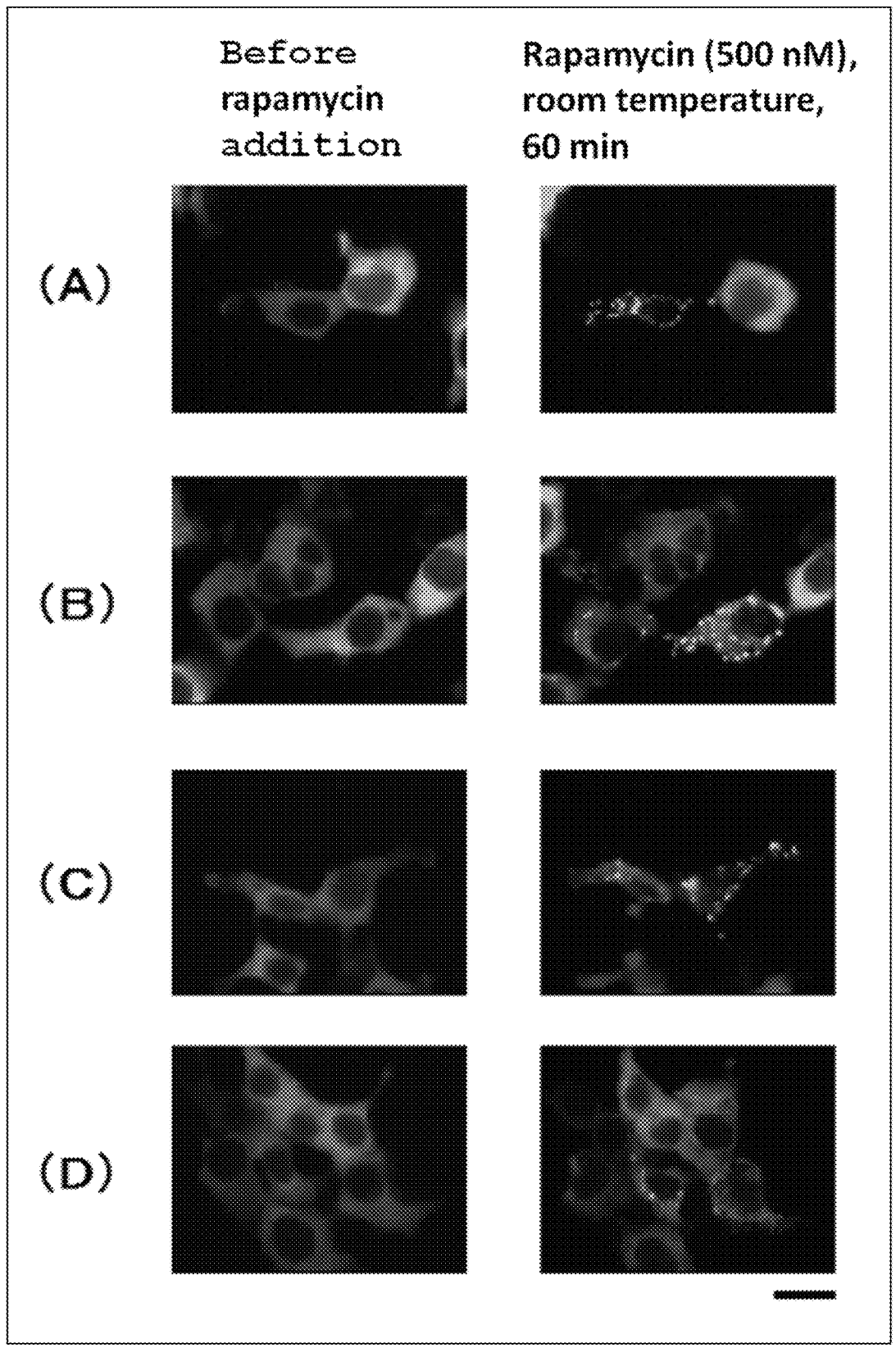

FIG. 31 shows micrographs for illustrating the result of analyzing whether or not it is possible to determine a protein-protein interaction between FKBP12 and mTOR (FRB domain) on the basis of a fluorescent focus by expressing in cells: a protein (PB1-mTOR(FRB domain) or mTOR (FRB domain)-PB1) composed of a PB1 domain of a p62 protein fused to the N-terminus or the C-terminus of mTOR (FRB domain); a protein (PB1-FKBP12 or FKBP12-PB1) composed of a PB1 domain of a p62 protein fused to the N-terminus or the C-terminus of FKBP12; and mAG1 fused to the N-terminus of a PB1 domain of a p62 protein (mAG1-PB1), in combinations of the following (A) to (D).

Note that, in the figure, "before rapamycin addition" shows the result of observing the cells before the addition of rapamycin, which is an inducer for the protein-protein interaction. "Rapamycin (500 nM), room temperature, 60 min" shows the result of observing the cells when 60 minutes elapsed after the rapamycin addition. In the figure, the scale bar represents 20 μm. (A) PB1-mTOR(FRB domain), PB1-FKBP12, and mAG1-PB1; (B) PB1-mTOR (FRB domain), FKBP12-PB1, and mAG1-PB1; (C) mTOR (FRB domain)-PB1, PB1-FKBP12, and mAG1-PB1; and (D) mTOR(FRB domain)-PB1, FKBP12-PB1, and mAG1-PB1.

Figure 32:
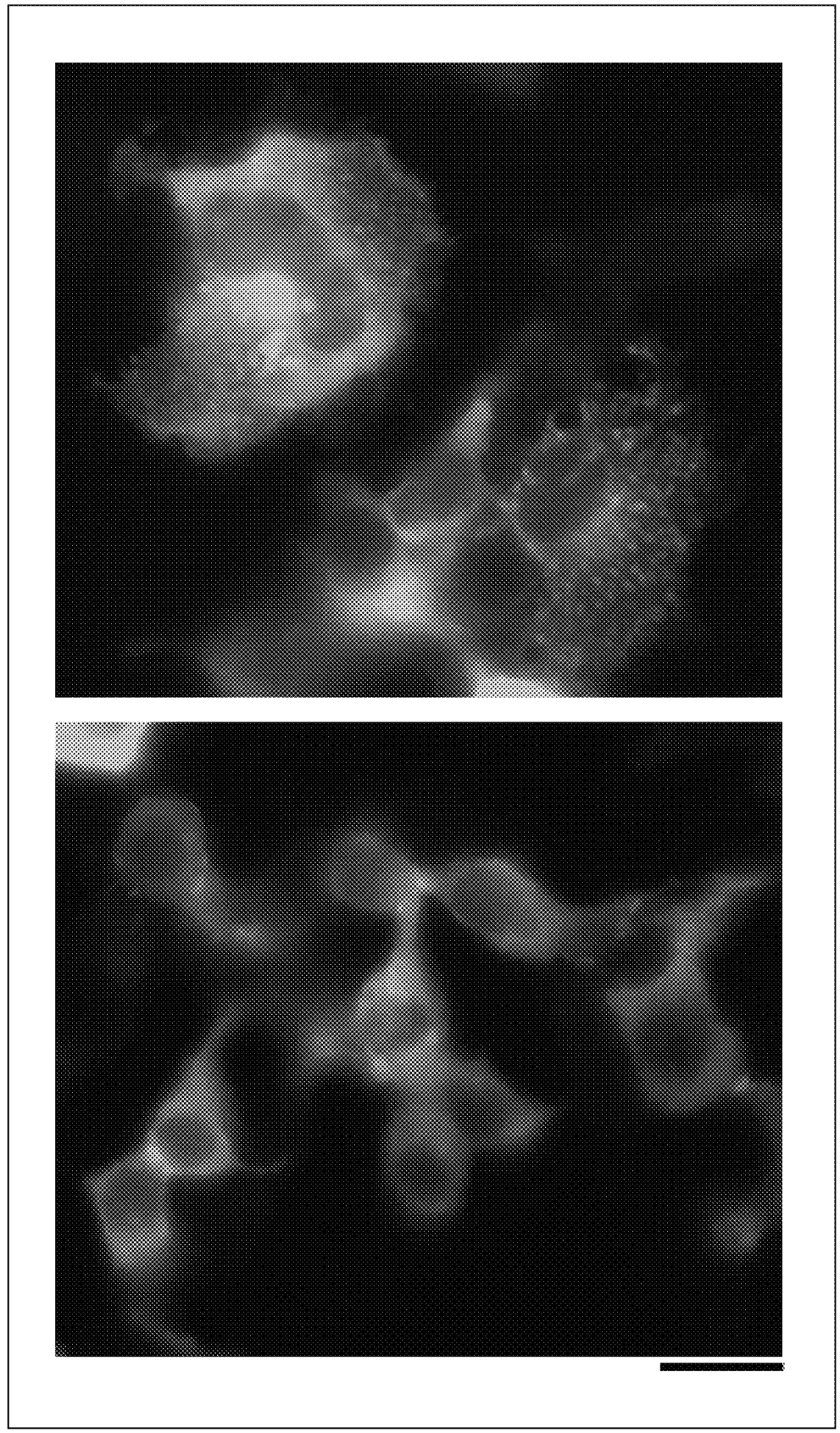

FIG. 32 shows micrographs for illustrating the result of analyzing whether or not it is possible to determine homodimer formation of CD80 on the basis of a fluorescent focus after rapamycin for inducing the binding between FKBP12 and a FRB domain of a mTOR protein was added to cells expressing: a protein (CD80-FRB) composed of a FRB domain of a mTOR protein as an affinity tag fused to the N-terminus of the analysis target CD80; and a protein (PB1-mAG1-FKBP12) composed of FKBP12 as a binding partner of the affinity tag, a PB1 domain of a p62 protein as a multimerizable protein, and mAG1 as a fluorescent protein fused to each other. In the figure, the upper panel shows the result of analyzing the above-described CD80, and the lower panel shows the result of analyzing CD2 used as a negative control thereof in place of CD80. In the figure, the scale bar represents 20 μm.

Figure 33:
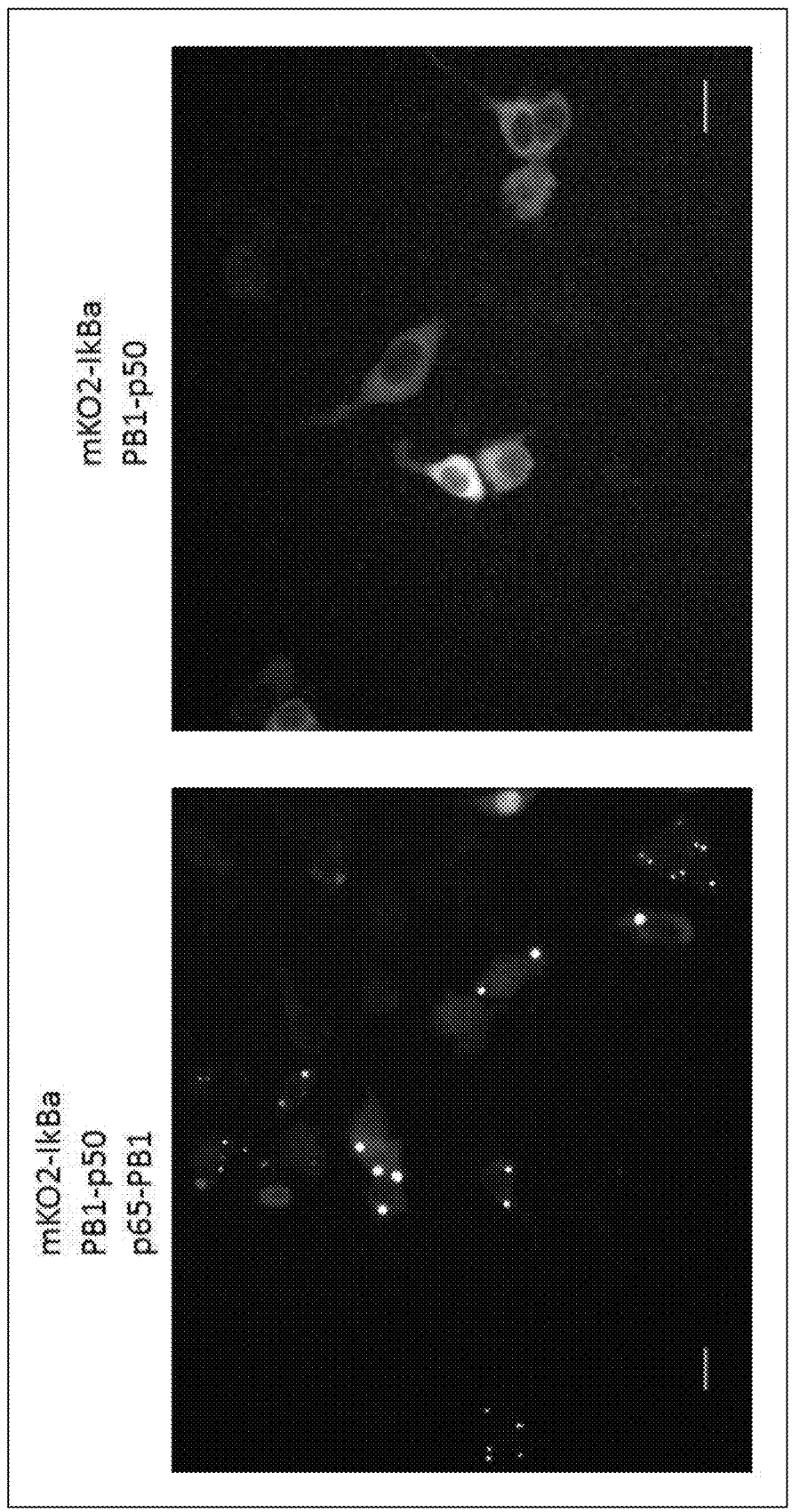

FIG. 33 shows micrographs for illustrating the result of analyzing whether or not it is possible to determine trimer formation among p50, p65, and IκBα on the basis of a fluorescent focus in cells expressing: a protein (PB1-p50) composed of a PB1 domain of a p62 protein fused to the N-terminus of the analysis target p50; a protein (p65-PB1) composed of a PB1 domain of a p62 protein fused to the C-terminus of the analysis target p65; and a protein (mKO2-IκBα) composed of mKO2 as a fluorescent protein fused to the N-terminus of IκBα. In the figure, the left panel shows the result. The right panel shows the result of analyzing a negative control in which the p65-PB1 was not expressed. In the figure, the scale bars represent 20 μm.

Figure 34:
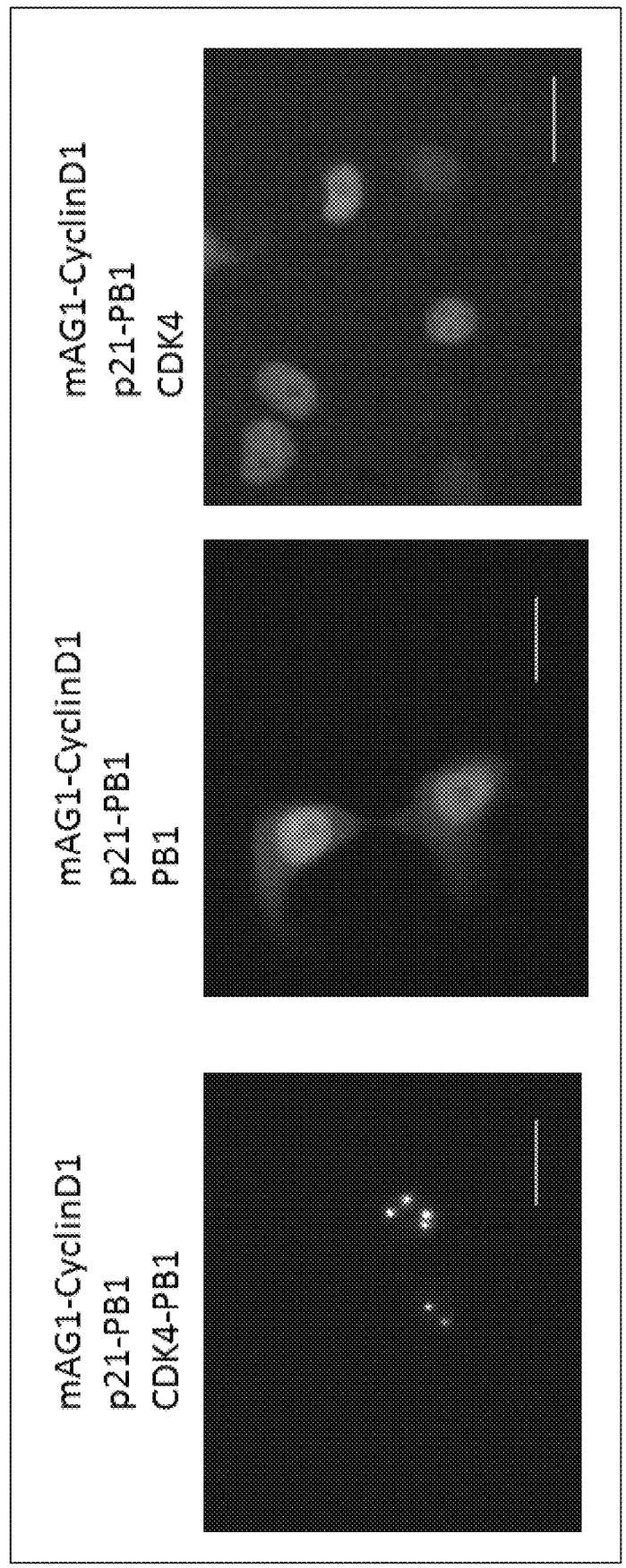

FIG. 34 shows micrographs for illustrating the result of analyzing whether or not it is possible to determine trimer formation among Cyclin D1, p21, and CDK4 on the basis of a fluorescent focus in cells expressing: a protein (mAG1-Cyclin D1) composed of mAG1 fused to the N-terminus of the analysis target Cyclin D1; a protein (p21-PB1) composed of a PB1 domain of a p62 protein fused to the C-terminus of the analysis target p21; and a protein (CDK4-PB1) composed of a PB1 domain of a p62 protein fused to the C-terminus of the analysis target CDK4. In the figure, the left panel shows the result. The panel in the middle shows the result of analyzing a negative control in which only PB1 was expressed in place of the CDK4-PB1. The right panel shows the result of analyzing a negative control in which CDK4 not fused to other proteins was expressed in place of the CDK4-PB1. In the figure, the scale bars represent 20 μm.

Figure 35:
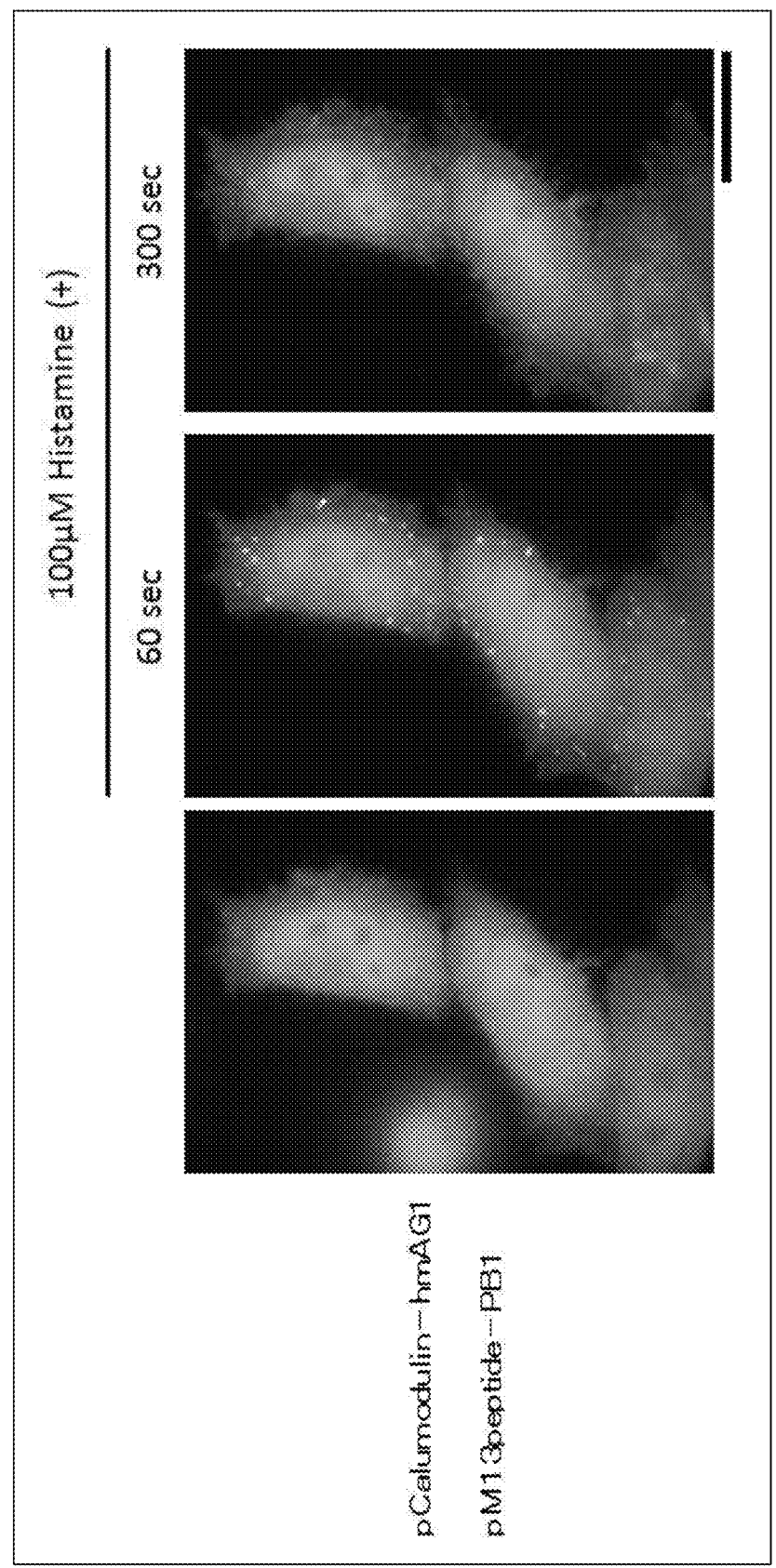

FIG. 35 shows micrographs for illustrating the result of analyzing whether or not it is possible to determine, on the basis of a fluorescent focus, heterotetramer formation from calmodulin and an M13 peptide by adding histamine, which induces the tetramer formation, to cells expressing: a protein (Calumodulin-mAG1) composed of mAG1 fused to the C-terminus of the analysis target calmodulin; and a protein (M13peptide-PB1) composed of a PB1 domain of a p62 protein fused to the C-terminus of the analysis target M13 peptide. In the figure, the left panel shows the result of analyzing the cells before the histamine addition. The panel in the middle shows the result of analyzing the cells 60 seconds after the histamine addition. The right panel shows the result of analyzing the cells 300 seconds after the histamine addition. In the figure, the scale bar represents 20 μm.

Figure 36:
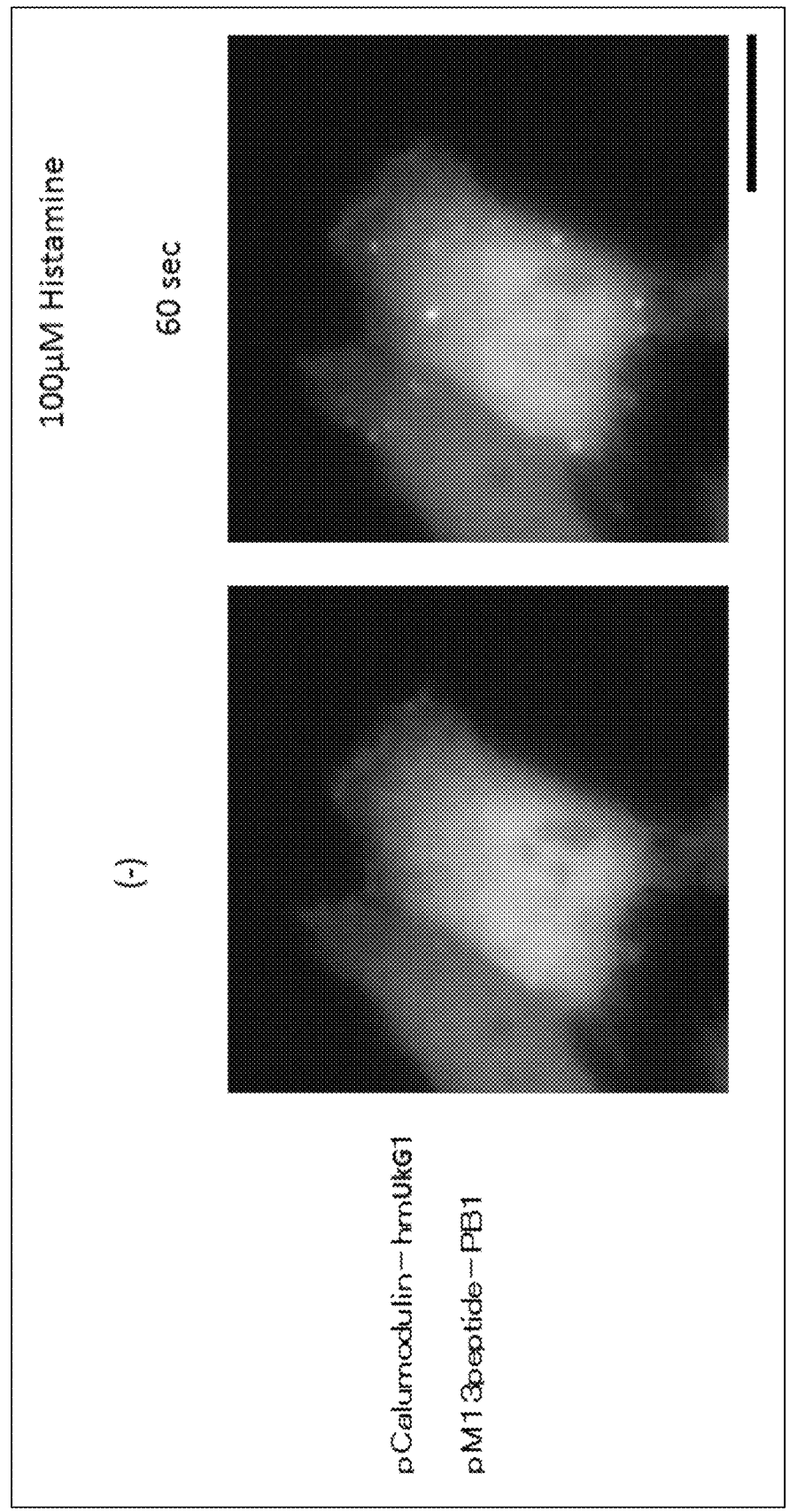

FIG. 36 shows micrographs for illustrating the result of analyzing whether or not it is possible to determine, on the basis of a fluorescent focus, heterotetramer formation from calmodulin and an M13 peptide by adding histamine, which induces the tetramer formation, to cells expressing: a protein (Calumodulin-mUkG1) composed of mUkG1 as a fluorescent protein fused to the C-terminus of the analysis target calmodulin; and the protein (M13peptide-PB1) composed of a PB1 domain of a p62 protein fused to the C-terminus of the analysis target M13 peptide. In the figure, the left panel shows the result of analyzing the cells before the histamine addition. The right panel shows the result of analyzing the cells 60 seconds after the histamine addition. In the figure, the scale bar represents 20 μm.

Figure 37:
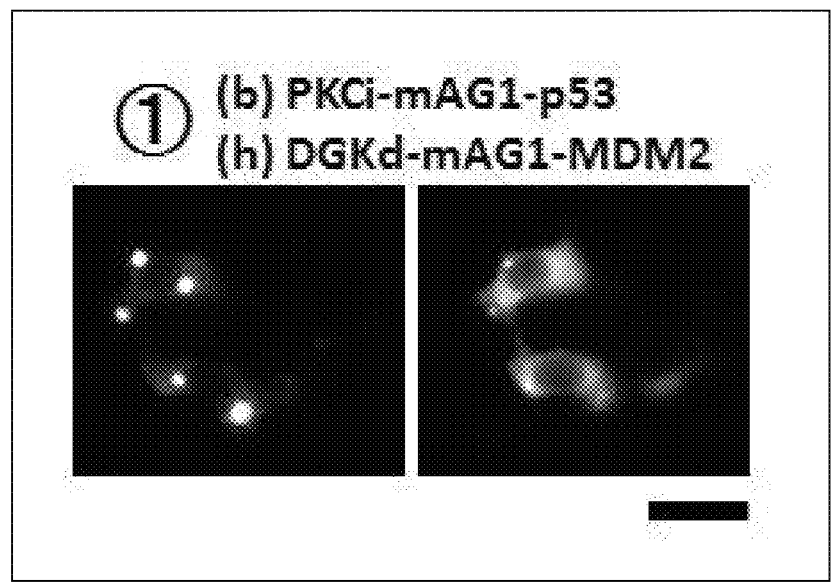

FIG. 37 shows micrographs for illustrating the result of analyzing whether or not it is possible to determine a protein-protein interaction between p53 and MDM2 on the basis of a fluorescent focus in cells expressing: a protein (PKCi-mAG1-p53) composed of a PB1 domain of a PKCiota protein as a multimerizable protein and mAG1 fused to the N-terminus of p53; and a protein (DGKd-mAG1-MDM2) composed of a SAM domain of a DGK delta protein as a multimerizable protein and mAG1 fused to the N-terminus of MDM2. In the figure, the left panel shows the result of analyzing the cells before the Nutlin-3 addition, and the right panel shows the result of analyzing the cells 60 minutes after the Nutlin-3 addition. In the figure, the scale bar represents 10 μm (hereinafter, regarding the representations in the drawings, the same shall apply to FIGS. 38 to 45).

Figure 38:
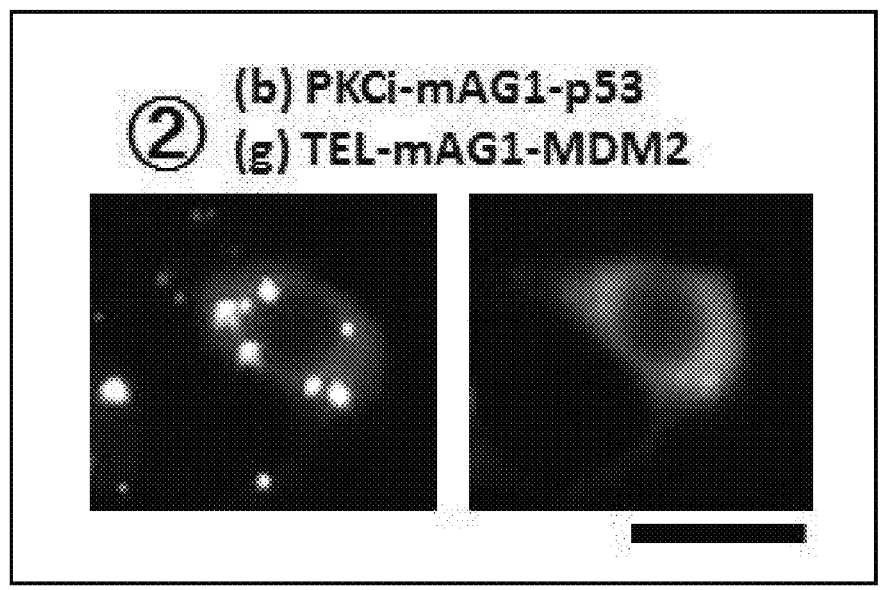

FIG. 38 shows micrographs for illustrating the result of analyzing whether or not it is possible to determine a protein-protein interaction between p53 and MDM2 on the basis of a fluorescent focus in cells expressing: the PKCi-mAG1-p53; and a protein (TEL-mAG1-MDM2) composed of a SAM domain of a TEL protein as a multimerizable protein and mAG1 fused to the N-terminus of MDM2.

Figure 39:
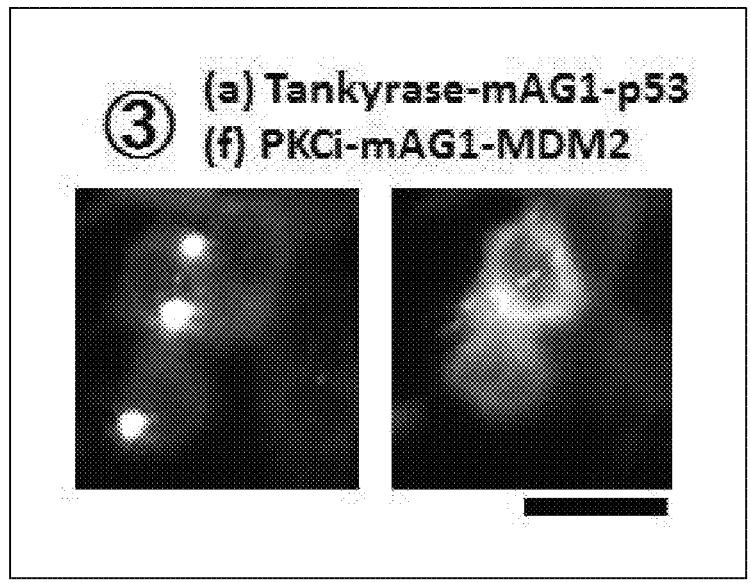

FIG. 39 is shows micrographs for illustrating the result of analyzing whether or not it is possible to determine a protein-protein interaction between p53 and MDM2 on the basis of a fluorescent focus in cells expressing: a protein (Tankyrase-mAG1-p53) composed of a SAM domain of a Tankyrase 1 protein as a multimerizable protein and mAG1 fused to the N-terminus of p53; and a protein (PKCi-mAG1-MDM2) composed of a PB1 domain of a PKCiota protein as a multimerizable protein and mAG1 fused to the N-terminus of MDM2.

Figure 40:
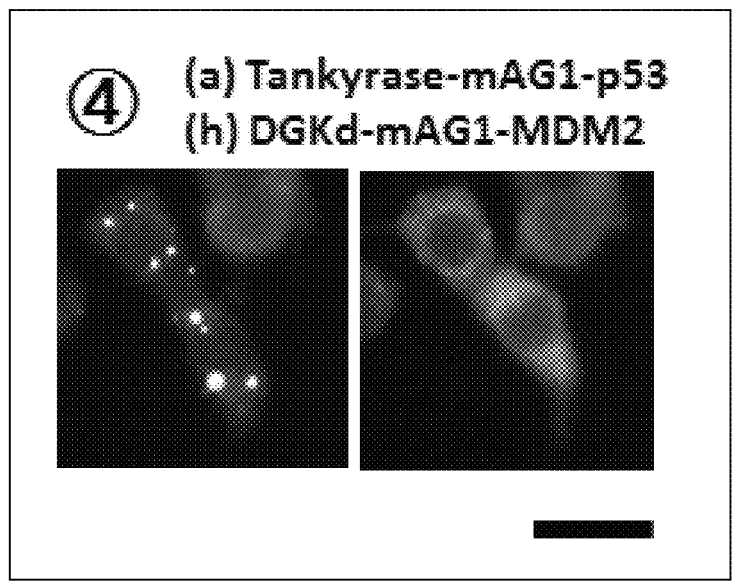

FIG. 40 shows micrographs for illustrating the result of analyzing whether or not it is possible to determine a protein-protein interaction between p53 and MDM2 on the basis of a fluorescent focus in cells expressing: the Tankyrase-mAG1-p53; and the DGKd-mAG1-MDM2.

Figure 41:
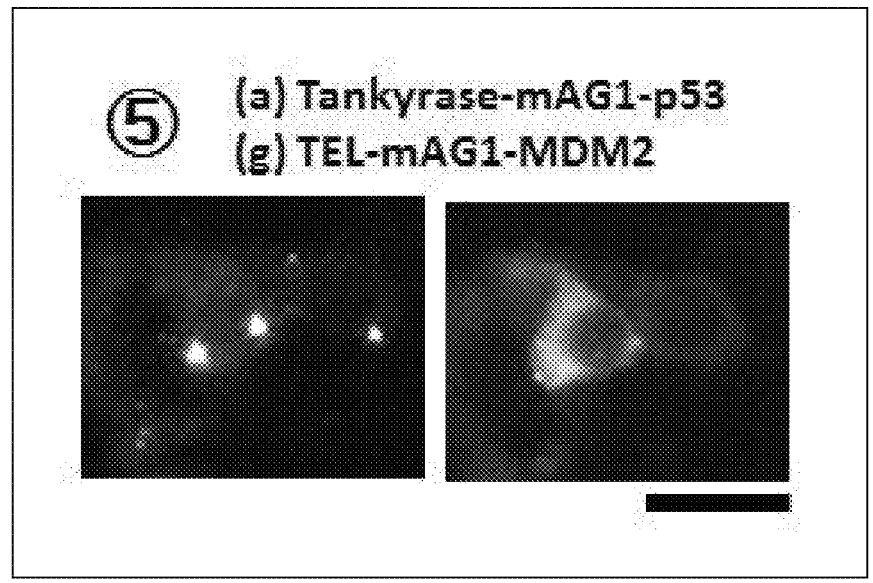

FIG. 41 shows micrographs for illustrating the result of analyzing whether or not it is possible to determine a protein-protein interaction between p53 and MDM2 on the basis of a fluorescent focus in cells expressing: the Tankyrase-mAG1-p53; and the TEL-mAG1-MDM2.

Figure 42:
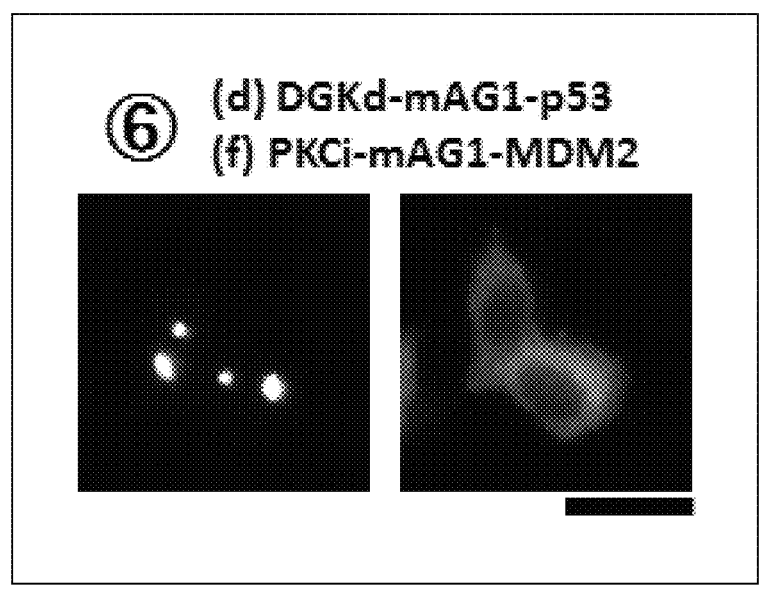

FIG. 42 shows micrographs for illustrating the result of analyzing whether or not it is possible to determine a protein-protein interaction between p53 and MDM2 on the basis of a fluorescent focus in cells expressing: a protein (DGKd-mAG1-p53) composed of a SAM domain of a DGK delta protein as a multimerizable protein and mAG1 fused to the N-terminus of p53; and the PKCi-mAG1-MDM2.

Figure 43:
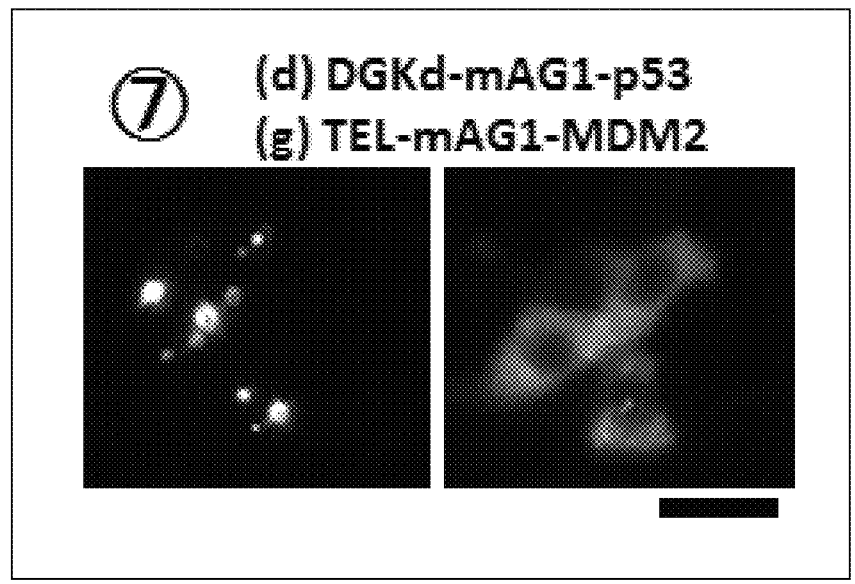

FIG. 43 shows micrographs for illustrating the result of analyzing whether or not it is possible to determine a protein-protein interaction between p53 and MDM2 on the basis of a fluorescent focus in cells expressing: the DGKd-mAG1-p53; and the TEL-mAG1-MDM2.

Figure 44:
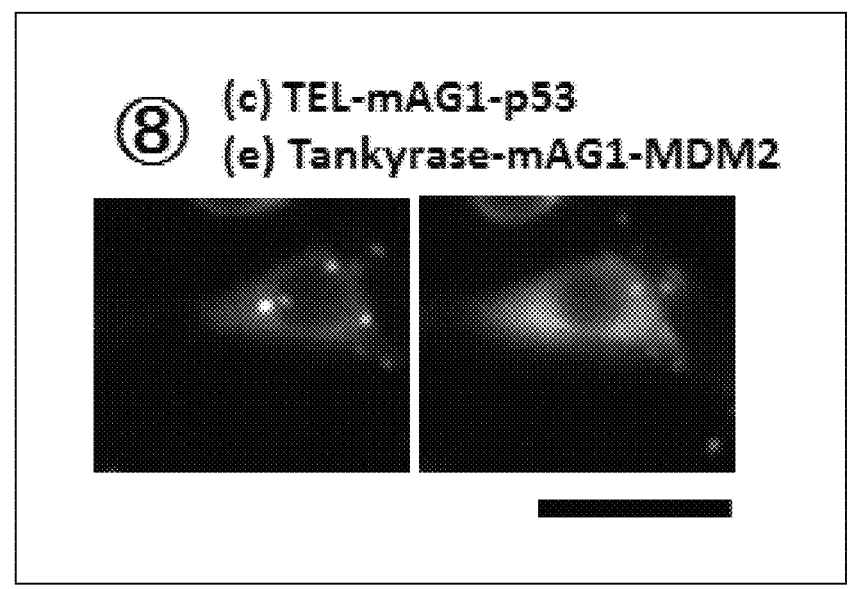

FIG. 44 shows micrographs for illustrating the result of analyzing whether or not it is possible to determine a protein-protein interaction between p53 and MDM2 on the basis of a fluorescent focus in cells expressing: a protein (TEL-mAG1-p53) composed of a SAM domain of a TEL protein as a multimerizable protein and mAG1 fused to the N-terminus of p53; and a protein (Tankyrase-mAG1-MDM2) composed of a SAM domain of a Tankyrase 1 protein as a multimerizable protein and mAG1 fused to the N-terminus of MDM2.

Figure 45:
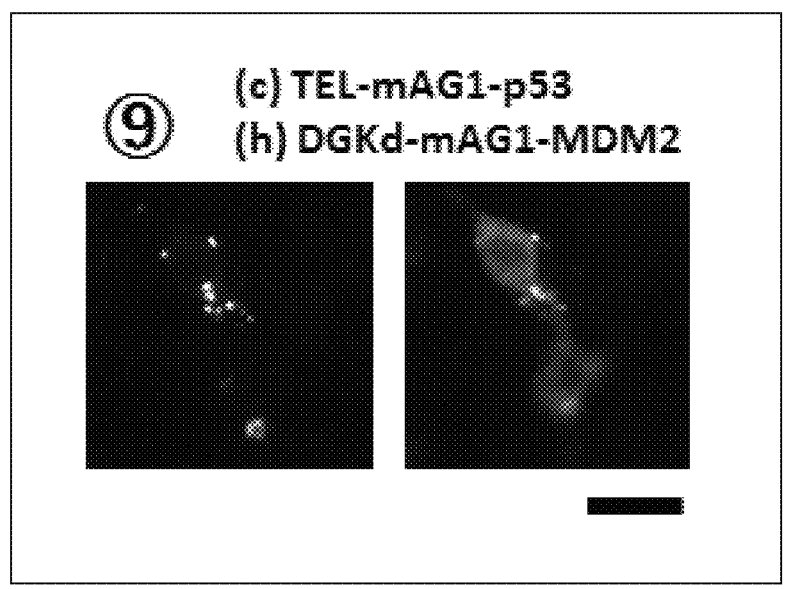

FIG. 45 shows micrographs for illustrating the result of analyzing whether or not it is possible to determine a protein-protein interaction between p53 and MDM2 on the basis of a fluorescent focus in cells expressing: the TEL-mAG1-p53; and the DGKd-mAG1-MDM2.

DESCRIPTION OF EMBODIMENTS

Hereinafter, the present invention will be described in detail based on preferred embodiments thereof. Moreover, as a matter of course, unless otherwise specified, those described in the following sections should be construed in the same manner in other sections and so forth also throughout the present invention.

<Method 1 for Detecting Protein-Protein Interaction>

A first embodiment of a method for determining a protein-protein interaction of the present invention is a method comprising the steps (1) to (3):

(1) expressing in a cell or introducing into a cell
 a first fusion protein comprising a first protein, a multimerizable protein, and a fluorescent protein, and
 a second fusion protein comprising a second protein and a multimerizable protein;

(2) detecting a fluorescent focus formed by an association between the first fusion protein and the second fusion protein in the cell; and (3) determining an interaction between the first protein and the second protein according to the detection of the fluorescent focus.

According to the method, as described in Examples 1 to 12 later, when the first fusion protein comprising the first protein, the multimerizable protein, and the fluorescent protein, and the second fusion protein comprising the second protein and the multimerizable protein are expressed in a cell or introduced into a cell, an interaction if any between the first protein and the second protein induces multimer formation between the multimerizable protein and the other multimerizable protein. Thereby, the fusion proteins autonomously form an assembly, and the fluorescent protein contained in the fusion protein is detected as a fluorescent focus (see FIGS. 1 and 2).

In the present invention, the term "protein" means a molecule in which 2 or more amino acids are linked by a peptide bond(s), and modified products thereof. Thus, the term is a concept including not only full-length proteins, but also so-called oligopeptides and polypeptides. Examples of the modification of the protein include phosphorylation, glycosylation, palmitoylation, prenylation (for example, geranylgeranylation), methylation, acetylation, ubiquitination, SUMOylation, hydroxylation, and amidation.

As the "first protein" and the "second protein" according to the present invention, it is possible to use desired proteins intended for detection of interaction. Moreover, the first protein may be different from or the same as the second protein. Nevertheless, as described in Examples 1 to 12 and Comparative Example 1 later, the method of the present invention is capable of efficiently determining homomultimer formation and dissociation (disruption); accordingly, the method of the present invention is more useful when the first protein is the same as the second protein.

The "interaction between the first protein and the second protein" according to the present invention includes not only direct interactions, but also indirect interactions such as an interaction for forming a complex in which another molecule (protein, nucleic acid, sugar, lipid, low-molecular-weight compound, or the like) is interposed between the first protein and the second protein.

The "multimerizable protein" according to the present invention is not particularly limited, as long as the protein is capable of forming a multimer. Nevertheless, from the viewpoint of facilitating detection of a fluorescent focus in the method of the present invention, the protein is preferably capable of forming a trimer or a higher multimer. Examples of such a multimerizable protein include a PB1 domain of p62, a PB1 domain of TFG, a PB1 domain of PKCiota, a SAM domain of TEL, a SAM domain of DGK delta, and a SAM domain of Tankyrase-1. Among these, from the viewpoint of facilitating detection of a fluorescent focus in the method of the present invention to form homotetramer to homooctamer, a PB1 domain of p62 is more preferable.

Note that, typically, a PB1 domain of p62, a PB1 domain of TFG, a PB1 domain of PKCiota, a SAM domain of TEL, a SAM domain of DGK delta, and a SAM domain of Tankyrase-1 are respectively a protein having the amino acid sequence specified under SEQ ID NO: 2, a protein having the amino acid sequence specified under SEQ ID NO: 4, a protein having the amino acid sequence specified under SEQ ID NO: 6, a protein having the amino acid sequence specified under SEQ ID NO: 8, a protein having the amino acid sequence specified under SEQ ID NO: 10, and a protein having the amino acid sequence specified under SEQ ID NO: 12.

The amino acid sequences of these "multimerizable proteins" may be mutated naturally (i.e., non-artificially). Moreover, a mutation can also be introduced artificially. Such a mutant can also be used in the present invention, as long as it has a multimerization ability and a nature of forming an assembly (fluorescent focus) when the fused first protein and second protein interact with each other.

The "fluorescent protein" according to the present invention should be a protein capable of emitting fluorescence. Examples thereof include monomeric Azami Green 1 (mAG1), monomeric Umikinoko-Green (mUkG), monomeric Kusabira-Orange 2 (mKO2), monomeric Keima-Red (mKeima, mKeima-Red), monomeric Midoriishi-Cyan1 (mMiCy), monomeric Kusabira-Orange 1 (mKO1), monomeric Cherry (mCherry), FusionRed, Dronpa-Green1 (DG1), Midoriishi-Cyan1 (MiCy1), Kusabira-Cyan1 (KCy1), dimeric Azami-Green (AB) (dAG (AB)), Kusabira-Orange 1 (KO1), dimeric Keima-Red (dKeima, dKeima-Red), and TGuv. In a case where the fluorescent protein is a protein capable of forming a multimer, preferable are monomeric fluorescent proteins (such as mAG1, mUkG, mKO2, mKeima, mMiCy, mKO1, mCherry, FusionRed, DG1), more preferable are mAG1 and FusionRed, and furthermore preferable is mAG1, from the viewpoint of facilitating formation of an assembly (fluorescent focus) regardless of the interaction between the first protein and the second protein when the fluorescent protein is fused to the above-described multimerizable protein.

Note that, typically, mAG1, mUkG, mKO2, mKeima, mMiCy, mKO1, MiCy1, KCy1, dAG (AB), KO1, dKeima, TGuv, mCherry, FusionRed, and DG1 are respectively a protein having the amino acid sequence of SEQ ID NO: 14, a protein having the amino acid sequence of SEQ ID NO: 16, a protein having the amino acid sequence of SEQ ID NO: 18, a protein having the amino acid sequence specified under Genbank ACCESSION No: AB209969, a protein having the amino acid sequence of SEQ ID NO: 20, a protein having the amino acid sequence specified under Genbank ACCESSION No: AB128821, a protein having the amino acid sequence specified under Genbank ACCESSION No: AB128822, a protein having the amino acid sequence of SEQ ID NO: 22, a protein having the amino acid sequence of SEQ ID NO: 24, a protein having the amino acid sequence specified under Genbank ACCESSION No: AB128820, a protein having the amino acid sequence specified under Genbank ACCESSION No: AB209968, a protein having the amino acid sequence of SEQ ID NO: 26, a protein having the amino acid sequence specified under GenBank ACCESSION No: AAV52164, a protein having the amino acid sequence of SEQ ID NO: 40, and a protein having the amino acid sequence specified under GenBank ACCESSION No: BAD72874.

The amino acid sequences of these fluorescent proteins may be mutated naturally (i.e., non-artificially). Moreover, a mutation can also be introduced artificially. Such a mutant can also be used in the present invention, as long as it can emit fluorescence.

Alternatively, a chemiluminescent protein such as luciferases can also be used in place of the above-described fluorescent protein in the present invention. A fluorescent protein emits an electromagnetic wave (light) released when electrons of the protein having been excited by electromagnetic wave radiation return to the ground state (photo luminessence). On the other hand, in the case of a chemiluminescent protein, an electromagnetic wave (light) is emitted when electrons of a light emitting substrate are excited through a chemical reaction catalyzed by the protein. As described above, a fluorescent protein and a chemiluminescent protein are similar to each other in the light emitting mechanisms in principle. Hence, a chemiluminescent protein is also usable in the present invention.

Such a chemiluminescent protein is not particularly limited. Examples thereof include luciferases, and preferable examples thereof include Promega NanoLuc(registered trademark, Nluc) luciferase (manufactured by Promega Corporation) and Gaussia luciferase (see Chem. Sci., 2013, vol. 4, pp. 4395 to 4400).

Moreover, in the present invention, it is also possible to use, in place of the above-described fluorescent protein, a fusion protein between a fluorescent protein and a luciferase in which the fluorescent protein emits an electromagnetic wave (light) by utilizing an energy of the chemical reaction (Nano-lantern, see Nat Commun., 2012, vol. 3, p. 1262).

Further, a protein capable of specifically binding to a fluorescent dye can be used in place of the fluorescent protein. This is because by expressing such a protein in a cell and then introducing the fluorescent dye into the cell, the resultant can be used as a fluorescent protein. An example of such a protein capable of specifically binding to a fluorescent dye includes HaloTag (manufactured by Promega Corporation).

The "first fusion protein" according to the present invention comprises the first protein, the multimerizable protein, and the fluorescent protein. As long as the formation of an assembly (fluorescent focus) with the second fusion protein is not inhibited, the first protein, the multimerizable protein, and the fluorescent protein may be fused in this order from the N-terminus side, or in the following orders: the first protein, the fluorescent protein, and the multimerizable protein; the multimerizable protein, the first protein, and the fluorescent protein; the multimerizable protein, the fluorescent protein, and the first protein; the fluorescent protein, the first protein, and the multimerizable protein; and the fluorescent protein, the multimerizable protein, and the first protein.

The "second fusion protein" according to the present invention comprises the second protein and the multimerizable protein. As long as the formation of an assembly (fluorescent focus) with the first fusion protein is not inhibited, the multimerizable protein may be fused to either the N-terminus or the C-terminus of the second protein. Moreover, from the viewpoint of facilitating detection of a fluorescent focus, the second fusion protein preferably further comprises a fluorescent protein (see FIG. 2). In addition, the fluorescent protein may be fused to one or both of the N-terminus and the C-terminus of the fusion protein, or may be fused between the second protein and the multimerizable protein. The fluorescent protein to be contained in the second fusion protein is as described above, and may be the same as or different from the fluorescent protein contained in the first fusion protein. Nevertheless, from the viewpoint of enabling tracing of a change in intracellular localization of each of the first protein and the second protein in accordance with when a protein-protein interaction takes place and terminates and so forth, the fluorescent protein contained in the first fusion protein and the fluorescent protein contained in the second fusion protein are preferably different from each other. Further, the use of such different fluorescent proteins, which enable separate spectrometries, makes it possible to measure amounts of the first protein and the second protein expressed, too. Furthermore, since such different fluorescent proteins exist at high concentrations inside an assembly (fluorescent focus) and very close to each other, FRET or fluorescence reabsorption may occur. Then, in such a case, without performing imaging or the like, measuring the intensity of fluorescence emitted from the fluorescent focus as a result of the FRET or fluorescence reabsorption makes it possible to determine a protein-protein interaction (as to the fluorescence reabsorption, see "Fluorescent imaging revolution (27th); To understand FRET in distinction from reabsorption" in Cell Technology, 25 (1), 67-69, 2006-01).

The proteins in the "first fusion protein" and the "second fusion protein" may be fused to each other directly, or may be fused indirectly via a linker or a spacer protein. Additionally, as long as the formation of an assembly (fluorescent focus) is not inhibited, the "first fusion protein" and the "second fusion protein" may comprise another functional protein. In this case, the other functional protein may be fused to one or both of the N-terminus and the C-terminus of each fusion protein, or may be fused directly or indirectly among the first protein or second protein, the multimerizable protein, and fluorescent protein. The other functional protein is not particularly limited, and selected as appropriate depending on a function desirably provided to the fusion proteins according to the present invention. Examples of a functional protein used to facilitate purification of the fusion protein include a Myc-tag protein, a His-tag protein, a hemagglutin (HA)-tag protein, a FLAG-tag protein (registered trademark, Sigma-Aldrich Co.), and a glutathione S-transferase (GST) protein.

The "cell" according to the present invention is not particularly limited, and may be a eukaryotic cell, or may be a prokaryotic cell. Examples of the "cell" include an animal cell (HEK293 cell, U2OS cell, Hela cell, and the like), an insect cell (Sf9 cell, and the like), a plant cell, yeast, and *Escherichia coli*. Moreover, such cells may be in a state of being cultured in vitro (for example, cells grown in a medium or on a medium), or in a state of being present in vivo (for example, cells in a transgenic animal in which a DNA encoding the first fusion protein and a DNA encoding the second fusion protein are introduced). Further, the fusion proteins and so forth according to the present invention are normally introduced into or expressed in the same cell, but may be introduced into or expressed in different cells. Then, in such a case, it is also possible to determine protein-protein interactions between different cells such as an interaction between a cytokine and a receptor and an interaction between receptors.

The expression of the fusion proteins in the cell may be a transient expression or a constitutive expression, depending on the purpose. The fusion proteins in the cell can be expressed by introducing into the cell a vector according to the present invention, which will be described later. Examples of known techniques for introducing the vector into the cell include, in the case of an animal cell, a lipofection method, an electroporation method, a phosphate calcium method, a DEAE-dextran method, and methods utilizing a virus (adenovirus, lentivirus, adeno-associated virus, or the like) and a microinjection method. Moreover, in the case of an insect cell, the examples include methods utilizing a baculovirus. Further, in the case of a plant cell, the examples include an *Agrobacterium* method, an electroporation method, a particle gun method, and the like. In addition, in the case of yeasts, the examples include a lithium acetate method, an electroporation method, and a spheroplast method. Furthermore, in the case of *Escherichia coli*, the examples include a heat shock method (for example, a calcium chloride method, a rubidium chloride method), an electroporation method, and the like.

Meanwhile, in the present invention, those skilled in the art can introduce the fusion proteins into the cell by selecting known techniques as appropriate in accordance with the type of the cell. Examples of known techniques for introducing the proteins into the cell include a method using a reagent for introducing the proteins, an electroporation method, and a microinjection method.

A "fluorescent focus" to be detected in the present invention is formed by high-density localization of the fluorescent protein contained in an assembly formed between the fusion proteins and so forth as a result of a protein-protein interaction according to the present invention. Typically, in a two-dimensional observation with a microscope, the "fluorescent focus" has a fluorescence intensity, in a region whose size diameter is 0.2 to 5 μm (0.03 to 20 μm$^2$), higher than a fluorescence intensity of the fluorescent protein present in a dispersed state.

The "detection of the fluorescent focus" can be carried out, for example, through observation using a fluorescence microscope including an excitation filter and an absorption filter corresponding to a fluorescent protein, and analysis using an imaging cytometer such as IN Cell Analyzer (manufactured by GE Healthcare). Moreover, a fluorescent focus can be detected also by processing the obtained image with an image analysis program (for example, an icy spot detection program to be described below). Note that, in the detection of the fluorescent focus, those skilled in the art can select and set as appropriate a filter, a detector, various parameters, and so forth in accordance with the characteristics of a fluorescent focus to be detected (such as the wavelength and the intensity of a fluorescence emitted by the fluorescent focus), as well as the device, the program, and so on.

For example, as described in Example 2 later, in a spot detection analysis program Icy.5.4.2 (see J.-C. Olivo-Marin "Extraction of spots in biological images using multiscale products" Pattern recognition, vol. 35-9, pp. 1989 to 1996, 2002, icy.bioimageanalysis.com), if a "fluorescence intensity value per unit calculated by the analysis program," which is detectable with set values of Spot Detector plugin (under conditions when all of Scale 1, Scale 2, and Scale 3 are checked and all sensitivities thereof are set to 100), is at least 2.0 times or more, more preferably 2.5 times or more, furthermore preferably 5.0 times or more, and particularly preferably 10 times or more, as large as the background (for example, the aforementioned fluorescence intensity value in a cell serving as a negative control), it can be determined that a fluorescent focus is detected.

In the method of the present invention, if the fluorescent focus is detected in the cell, it can be determined that the first protein and the second protein interact with each other; meanwhile, if the fluorescent focus is not detected, it can be determined that the first protein and the second protein do not interact with each other.

Hereinabove, one embodiment of the method for determining a protein-protein interaction of the present invention has been described. However, the method for determining a protein-protein interaction of the present invention is not limited to the above-described embodiment. For example, the present invention also makes it possible to determine a protein-protein interaction by expressing in a cell or introducing into a cell the first fusion protein and the second fusion protein separately, and then reconstituting the fusion proteins in the cell. To be more specific, the present invention can also encompass second to fifth embodiments described below.

<Method 2 for Detecting Protein-Protein Interaction>

A second embodiment of the method for determining a protein-protein interaction of the present invention is a method for detecting an interaction between a first protein and a second protein, the method comprising the following steps (1) to (3):

(1) expressing in a cell or introducing into a cell
    a third fusion protein comprising the first protein and a multimerizable protein,
    a fourth fusion protein comprising the second protein and a multimerizable protein, and
    a fifth fusion protein comprising a multimerizable protein and a fluorescent protein;

(2) detecting a fluorescent focus formed by an association among the third fusion protein, the fourth fusion protein, and the fifth fusion protein in the cell; and (3) determining an interaction between the first protein and the second protein according to the detection of the fluorescent focus.

According to the method, as described in Examples later 13 and 14, when the third fusion protein comprising the first protein and the multimerizable protein, the fourth fusion protein comprising the second protein and the multimerizable protein, and the fifth fusion protein comprising the multimerizable protein and the fluorescent protein are expressed in a cell or introduced into a cell, the multimerizable proteins associates with each other. Thereby, the third fusion protein binds to the fifth fusion protein while the fourth fusion protein binds to the fifth fusion protein, so that proteins respectively corresponding to the first fusion protein and the second fusion protein described above are expressed in the cell (see FIG. 3). Moreover, as in the case of the above-described method utilizing the first fusion protein and the second fusion protein, an interaction if any between the first protein and the second protein induces multimer formation between the multimerizable protein and another multimerizable protein. Thereby, the fusion proteins autonomously form an assembly, and the fluorescent protein contained in the fusion protein is detected as a fluorescent focus.

The "third fusion protein" according to the present invention should comprise the first protein and the multimerizable protein, while the "fourth fusion protein" according to the present invention should comprise the second protein and the multimerizable protein. As long as the formation of an assembly (fluorescent focus) is not inhibited, the multimerizable protein may be fused to either the N-terminus or the C-terminus of the first protein or the second protein. Moreover, the proteins in the "third fusion protein" and the "fourth fusion protein" may be fused to each other directly, or may be fused indirectly via a linker or a spacer protein.

Further, as long as the formation of an assembly (fluorescent focus) is not inhibited, each of the "third fusion protein" and the "fourth fusion protein" may comprise another functional protein. In this case, the other functional protein may be fused to one or both of the N-terminus and the C-terminus of each fusion protein, or may be fused directly or indirectly between the first protein or second protein and the multimerizable protein. The other functional protein is not particularly limited, and selected as appropriate depending on a function desirably provided to the fusion proteins according to the present invention as in the cases of the above-described first and second fusion proteins.

The "fifth fusion protein" according to the present invention should comprise the multimerizable protein and the fluorescent protein. As long as the formation of an assembly (fluorescent focus) is not inhibited, the multimerizable protein may be fused to either the N-terminus or the C-terminus of the fluorescent protein. Moreover, the proteins may be fused to each other directly, or may be fused indirectly via a linker or a spacer protein.

Further, as long as the formation of an assembly (fluorescent focus) is not inhibited, the "fifth fusion protein" may comprise another functional protein. In this case, the other functional protein may be fused to one or both of the N-terminus and the C-terminus of the fusion protein, or may be fused directly or indirectly between the multimerizable protein and the fluorescent protein. The other functional protein is not particularly limited, and selected as appropriate depending on a function desirably provided to the fusion protein according to the present invention as in the cases of the above-described first and second fusion proteins.

<Method 3 for Detecting Protein-Protein Interaction>

A third embodiment of the method for determining a protein-protein interaction of the present invention is a method comprising the following steps (1) to (3):

(1) expressing in a cell or introducing into a cell
   a first labeled protein comprising an affinity tag and the first protein,
   a second labeled protein comprising an affinity tag and the second protein, and
   a sixth fusion protein comprising a multimerizable protein, a fluorescent protein, and a binding partner having an affinity for any of the affinity tags and bound to the sixth fusion protein;

(2) detecting a fluorescent focus formed by an association among the first labeled protein, the second labeled protein, and the sixth fusion protein comprising the binding partner bound thereto in the cell; and (3) determining an interaction between the first protein and the second protein according to the detection of the fluorescent focus.

Figure 1:
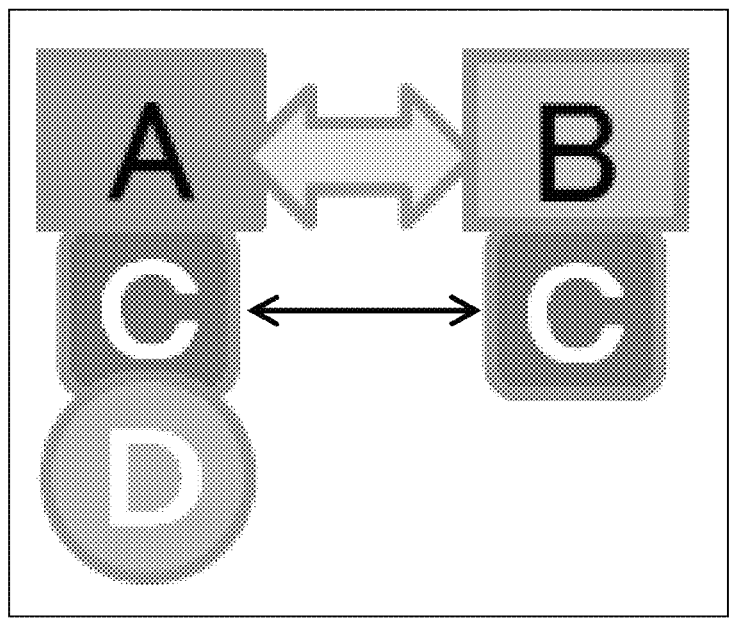
FIG. 1 is a conceptual diagram for illustrating one embodiment of a first method for determining a protein-protein interaction of the present invention. Specifically, the diagram illustrates that when a first fusion protein comprising a first protein (in the figure, A), a multimerizable protein (in the figure, C) and a fluorescent protein (in the figure, D), and a second fusion protein comprising a second protein (in the figure, B) and a multimerizable protein (in the figure, C) are expressed in a cell or introduced into a cell, an interaction between the first protein and the second protein can be determined according to the detection of a fluorescent focus formed by assembly formation between the first fusion protein and the second fusion protein in the cell.
Figure 2:
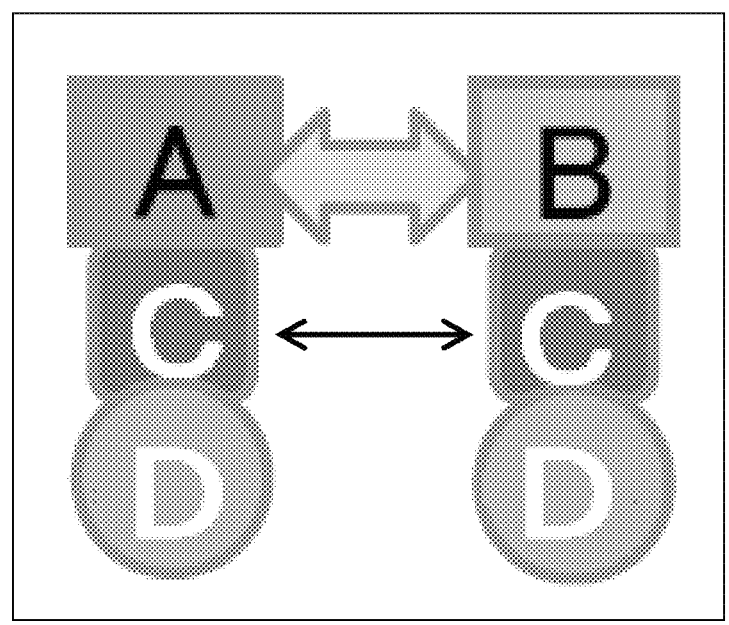
FIG. 2 is a conceptual diagram for illustrating one embodiment of the first method for determining a protein-protein interaction of the present invention. Specifically, the diagram illustrates that when the first fusion protein comprising the first protein (in the figure, A), the multimerizable protein (in the figure, C) and the fluorescent protein (in the figure, D), and the second fusion protein comprising the second protein (in the figure, B) and multimerizable protein (in the figure, C) and further comprising a fluorescent protein (in the figure, D) are expressed in a cell or introduced into a cell, an interaction between the first protein and the second protein can be determined according to the detection of a fluorescent focus formed by assembly formation between the first fusion protein and the second fusion protein in the cell.

According to the method, as described in Example 15 later, when the first labeled protein comprising the affinity tag and the first protein, the second labeled protein comprising the affinity tag and the second protein, and the sixth fusion protein comprising the multimerizable protein, the fluorescent protein, and the binding partner having an affinity for any of the affinity tags and bound to the sixth fusion protein are expressed in a cell or introduced into a cell, each affinity tag binds to the binding partner. Thereby, the first labeled protein binds to the sixth fusion protein comprising the binding partner bound thereto while the second labeled protein binds to the sixth fusion protein comprising the binding partner bound thereto, so that proteins respectively corresponding to the first fusion protein and the second fusion protein shown in FIGS. 1 and 2 are expressed in the cell (see FIG. 4). Moreover, as in the case of the above-described method utilizing the first fusion protein and the second fusion protein, an interaction if any between the first protein and the second protein induces multimer formation between the multimerizable protein and another multimerizable protein. Thereby, the fusion proteins autonomously form an assembly, and the fluorescent protein contained in the fusion protein is detected as a fluorescent focus.

The "affinity tag" and the "binding partner" according to the present invention are not particularly limited, as long as the two have such a relation that they can bind to each other in a cell, and the two compounds are capable of binding to the proteins. For example, it is possible to use combinations of proteins known to interact. As such combinations, FKBP12 and a FRB domain of a mTOR protein and other combinations are suitably used as described in Examples later. In addition, phytochrome B (PHYB) and phytochrome-interacting factor (PIF), cryptochrome 2 (CRY2) and cryptochrome-interacting bHLH1 (CIB1), LOV and ePDZ, Dronpa145K-CAAX and mNeptune, and others which interact with each other depending on light irradiation can also be suitably used (as to combinations of proteins which interact with each other depending on light irradiation, see Nat Rev Mol Cell Biol., 2014, vol. 15, no. 8, pp. 551 to 558). Further, it is also possible to suitably use subunits constituting enzymes such as dihydrofolate reductase, β-galactosidase, β-lactamase, firefly luciferase, and Gaussia luciferase. Moreover, as the "affinity tag" and the "binding partner" according to the present invention, it is also possible to utilize not only known protein-protein interactions as described above, but also to utilize, for example, biotin and avidin, a lectin and a sugar, Protein A (or G) and an immunoglobulin constant region, an antigen and an antibody, and other similar combinations.

The affinity tag may bind to the binding partner autonomously as in antigen-antibody reactions, or the binding may be induced in response to a stimulus. The stimulus for inducing the binding is not particularly limited. Examples thereof include low-molecular-weight compounds such as rapamycin which induces the binding between FKBP12 and a FRB domain of a mTOR protein, and light irradiation which can induce the binding between PHYB and PIF, and so on. In addition, in the case of using the affinity tag and the binding partner whose binding is induced by such a stimulus, it is necessary to apply the stimulus to the cell in the step (1) or between the steps (1) and (2).

In the "first labeled protein" and the "second labeled protein" according to the present invention, the first protein and the second protein should be labeled with the affinity tags, respectively. As long as the formation of an assembly (fluorescent focus) is not inhibited, the affinity tag may be bound to any of the N-terminus, the C-terminus, and a region at a middle portion of the first protein or the second protein.

The "sixth fusion protein" according to the present invention should comprise the multimerizable protein, the fluorescent protein, and the binding partner bound to the sixth fusion protein. As long as the formation of an assembly (fluorescent focus) is not inhibited, the binding partner may be bound to any of the N-terminus, the C-terminus, and a region at a middle portion of the sixth fusion protein. Moreover, the proteins in the "sixth fusion protein" may be fused to each other directly, or may be fused indirectly via a linker or a spacer protein.

The "binding" of the affinity tag or the binding partner to the corresponding protein is not particularly limited. The binding may be accomplished at a gene level, or may be chemical bonding. The binding at a gene level is so-called "fusion" as described in Examples above or later, and accomplished by adding or inserting a DNA encoding the affinity tag or the binding partner to or into a DNA encoding the first protein, the second protein, or the sixth fusion protein, in accordance with the reading frame. Meanwhile, the chemical bonding may be covalent bonding or may be non-covalent bonding. The "covalent bonding" is not particularly limited. Examples thereof include an amide bond between an amino group and a carboxyl group, an alkylamine bond between an amino group and an alkyl halide group, a disulfide bond between thiols, and a thioester bond between a thiol group and a maleimide group or an alkyl halide group.

Further, all of the first labeled protein, the second labeled protein, and the sixth fusion protein may comprise another functional protein, as long as the formation of an assembly (fluorescent focus) is not inhibited. In this case, the other functional protein may be fused to one or both of the N-terminus and the C-terminus of each protein, or may be fused directly or indirectly between the constituent proteins (for example, the multimerizable protein and the fluorescent protein). The other functional protein is not particularly limited, and selected as appropriate depending on a function desirably provided to the fusion protein according to the present invention as in the cases of the above-described first and second fusion proteins.

<Method 4 for Detecting Protein-Protein Interaction>

A fourth embodiment of the method for determining a protein-protein interaction of the present invention is a method comprising the following steps (1) to (3):

(1) expressing in a cell or introducing into a cell
  a seventh fusion protein comprising the first protein and a first partial peptide constituting a fluorescent protein,
  an eighth fusion protein comprising the second protein and a first partial peptide constituting a fluorescent protein, and
  a ninth fusion protein comprising a multimerizable protein and a second partial peptide capable of reconstituting any of the fluorescent proteins by binding to the first partial peptide;

(2) detecting a fluorescent focus formed by an association among the seventh fusion protein, the eighth fusion protein, and the ninth fusion protein in the cell; and (3) determining an interaction between the first protein and the second protein according to the detection of the fluorescent focus.

Figure 5:
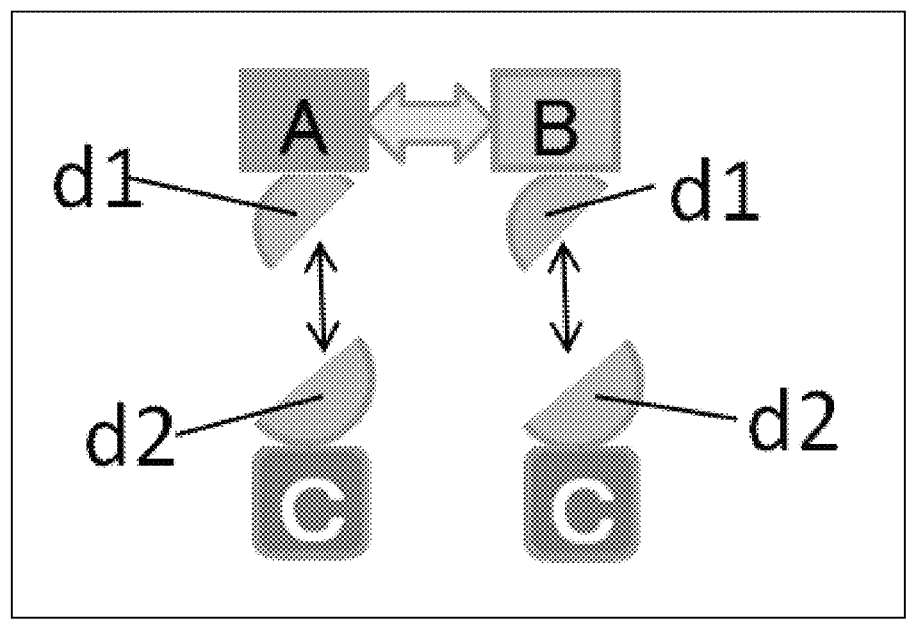
FIG. 5 is a conceptual diagram for illustrating one embodiment of a fourth method for determining a protein-protein interaction of the present invention. Specifically, the diagram illustrates that when a seventh fusion protein comprising a first protein (in the figure, A) and a first partial peptide (in the figure, d1) constituting a fluorescent protein, an eighth fusion protein comprising a second protein (in the figure, B) and a first partial peptide (in the figure, d1) constituting a fluorescent protein, and a ninth fusion protein comprising a multimerizable protein (in the figure, C) and a second partial peptide (in the figure, d2) capable of reconstituting any of the fluorescent proteins by binding to the first partial peptide are expressed in a cell or introduced into a cell, an interaction between the first protein and the second protein can be determined according to the detection of a fluorescent focus formed by assembly formation among the seventh fusion protein, the eighth fusion protein, and the ninth fusion protein in the cell.

According to the method, when the seventh fusion protein comprising the first protein and the first partial peptide constituting a fluorescent protein, the eighth fusion protein comprising the second protein and the first partial peptide constituting a fluorescent protein, and the ninth fusion protein comprising the multimerizable protein and the second partial peptide capable of reconstituting any of the fluorescent proteins by binding to the first partial peptide are expressed in a cell or introduced into a cell, the fluorescent proteins are expressed in the cell by the reconstitution. Eventually, proteins respectively corresponding to the first fusion protein and the second fusion protein shown in FIGS. 1 and 2 are expressed in the cell (see FIG. 5). Moreover, as in the case of the above-described method utilizing the first fusion protein and the second fusion protein, an interaction if any between the first protein and the second protein induces multimer formation between the multimerizable protein and another multimerizable protein. Thereby, the fusion proteins autonomously form an assembly, and the fluorescent proteins contained in the fusion proteins are detected as fluorescent foci.

The "first partial peptide" and the "second partial peptide" according to the present invention should be capable of reconstituting a fluorescent protein in a cell as these peptides are linked to each other. Note that, in the present invention, "reconstitution" and related terms mean that multiple partial peptides are returned to a state where a protein the partial peptides having originally constituted can function (for example, in the case of a fluorescent protein, a state where fluorescence can be emitted; in a case of a multimerizable protein, a state where a multimer can be formed) by linking the partial peptides as described above.

Additionally, those skilled in the art can design and prepare the partial peptides capable of such reconstitution as appropriate with reference to the descriptions of, for example, Cabantous S et al., Nature Biotechnology, 2005, vol. 23, pp. 102 to 107 and so forth.

Note that, as described in Cabantous S et al., Sci Rep., October 2013, 4; 3: 2854 and so forth, it has been revealed that even when a fluorescent protein is split into three or more parts, the fluorescent protein can be reconstituted. Thus, the first partial peptide and the second partial peptide may be selected from such three or more fragments. Further, in this case, the fragment(s) not used as the first and second partial peptides need to be expressed in the cell or introduced into the cell in the step (1) or between the steps (1) and (2).

In addition, the first partial peptide may be fused to either the N-terminus or the C-terminus of the first or second protein, while the second partial peptide may be fused to either the N-terminus or the C-terminus of the multimerizable protein. Further, the proteins in all of the seventh fusion protein, the eighth fusion protein, and the ninth fusion protein may be fused to each other directly, or may be fused indirectly via a linker or a spacer protein.

Furthermore, all of the seventh fusion protein, the eighth fusion protein, and the ninth fusion protein may comprise another functional protein, as long as the formation of an assembly (fluorescent focus) is not inhibited. In this case, the other functional protein may be fused to one or both of the N-terminus and the C-terminus of each fusion protein, or may be fused directly or indirectly between the constituent proteins (for example, between the first partial peptide and the first or second protein, between the second partial peptide and the multimerizable protein). The other functional protein is not particularly limited, and selected as appropriate depending on a function desirably provided to the fusion proteins according to the present invention as in the cases of the above-described first and second fusion proteins.

<Method 5 for Detecting Protein-Protein Interaction>

A fifth embodiment of the method for determining a protein-protein interaction of the present invention is a method comprising the following steps (1) to (3):

(1) expressing in a cell or introducing into a cell
  a tenth fusion protein comprising the first protein and a third partial peptide constituting a multimerizable protein,
  an eleventh fusion protein comprising the second protein and a third partial peptide constituting a multimerizable protein, and
  a twelfth fusion protein comprising a fluorescent protein and a fourth partial peptide capable of reconstituting any of the multimerizable proteins by binding to the third partial peptide;

(2) detecting a fluorescent focus formed by an association among the tenth fusion protein, the eleventh fusion protein, and the twelfth fusion protein in the cell; and (3) determining an interaction between the first protein and the second protein according to the detection of the fluorescent focus.

Figure 6:
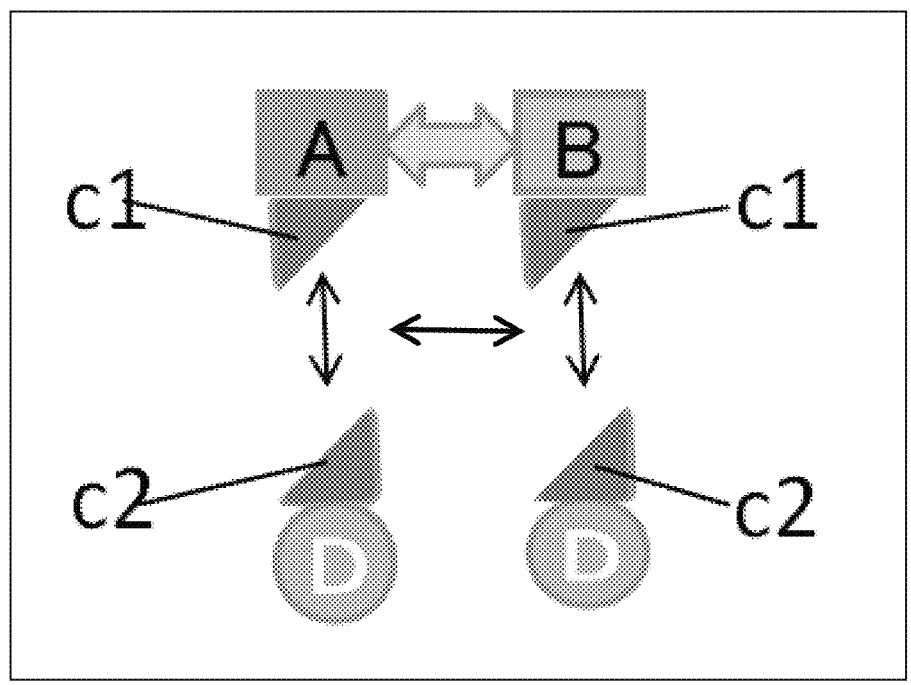
FIG. 6 is a conceptual diagram for illustrating one embodiment of a fifth method for determining a protein-protein interaction of the present invention. Specifically, the diagram illustrates that when a tenth fusion protein comprising a first protein (in the figure, A) and a third partial peptide (in the figure, c1) constituting a multimerizable protein, an eleventh fusion protein comprising a second protein (in the figure, B) and a third partial peptide (in the figure, c1) constituting a multimerizable protein, and a twelfth fusion protein comprising a fluorescent protein (in the figure, D) and a fourth partial peptide (in the figure, c2) capable of reconstituting any of the multimerizable proteins by binding to the third partial peptide are expressed in a cell or introduced into a cell, an interaction between the first protein and the second protein can be determined according to the detection of a fluorescent focus formed by assembly formation among the tenth fusion protein, the eleventh fusion protein, and the twelfth fusion protein in the cell.

According to the method, when the tenth fusion protein comprising the first protein and the third partial peptide constituting a multimerizable protein, the eleventh fusion protein comprising the second protein and the third partial peptide constituting a multimerizable protein, and the twelfth fusion protein comprising the fluorescent protein and the fourth partial peptide capable of reconstituting any of the multimerizable proteins by binding to the third partial peptide are expressed in a cell or introduced into a cell, the multimerizable proteins are expressed in the cell by the reconstitution. Eventually, proteins respectively corresponding to the first fusion protein and the second fusion protein shown in FIGS. 1 and 2 are expressed in the cell (see FIG. 6). Moreover, as in the case of the above-described method utilizing the first fusion protein and the second fusion protein, an interaction if any between the first protein and the second protein induces multimer formation between the multimerizable protein and another multimerizable protein thus reconstituted. Thereby, the fusion proteins autonomously form an assembly, and the fluorescent protein contained in the fusion protein is detected as a fluorescent focus.

The "third partial peptide" and the "fourth partial peptide" according to the present invention should be capable of reconstituting a multimerizable protein in a cell as these peptides are linked to each other. Those skilled in the art can design and prepare the partial peptides as appropriate as described above with reference to the descriptions of Ohashi K et al., Biotechniques., 2012, vol. 52, no. 1, pp. 45 to 50 and so forth.

In addition, the third partial peptide may be fused to either the N-terminus or the C-terminus of the first or second protein, while the fourth partial peptide may be fused to either the N-terminus or the C-terminus of the multimerizable protein. Moreover, the proteins in all of the tenth fusion protein, the eleventh fusion protein, and the twelfth fusion protein may be fused to each other directly, or may be fused indirectly via a linker or a spacer protein.

Further, all of the tenth fusion protein, the eleventh fusion protein, and the twelfth fusion protein may comprise another functional protein, as long as the formation of an assembly (fluorescent focus) is not inhibited. In this case, the other functional protein may be fused to one or both of the N-terminus and the C-terminus of each fusion protein, or may be fused directly or indirectly between the constituent proteins (for example, between the third partial peptide and the first or second protein, between the fourth partial peptide and the fluorescent protein). The other functional protein is not particularly limited, and selected as appropriate depending on a function desirably provided to the fusion proteins according to the present invention as in the cases of the above-described first and second fusion proteins.

Hereinabove, the description has been given of the second to fifth embodiments of the method for determining a protein-protein interaction of the present invention. In these methods, since the first fusion protein and the second fusion protein are expressed in a cell or introduced into a cell separately, this allows a reduction in the molecular weight of tags such as the proteins fused to the first or second protein to be analyzed. Therefore, in the determination and the like of a protein-protein interaction, the functions of proteins to be analyzed, change in the localization, and so forth are hardly affected.

Additionally, proteins to be analyzed can be kept in a cell while being fused to a tag having a low molecular weight in this manner. This makes it possible to set a state where a protein-protein interaction can be determined at any timing by constructing a system in which the fusion protein(s) according to the present invention are reconstituted in response to a stimulus such as the addition of a compound, light irradiation, or the like, as described above.

Moreover, preparing cells constitutively expressing a fusion protein(s) comprising a fluorescent protein in advance reduces the influence of a variation in the fluorescent signal among the cells, even if fusion proteins comprising proteins to be analyzed are transiently expressed in these cells. This makes it also possible to more stably determine a protein-protein interaction.

<Method 6 for Detecting Protein-Protein Interaction>

For a case where analysis targets are three or more proteins, the present invention can also apply the above-described first embodiment to provide a method comprising the following steps (1) to (3) as a sixth embodiment of the method for determining a protein-protein interaction:

(1) expressing in a cell or introducing into a cell
  a thirteenth fusion protein comprising the first protein and a multimerizable protein,
  a fourteenth fusion protein comprising the second protein and a multimerizable protein, and
  a fifteenth fusion protein comprising the third protein and a fluorescent protein;

(2) detecting a fluorescent focus formed by an association among the thirteenth fusion protein, the fourteenth fusion protein, and the fifteenth fusion protein in the cell; and (3) determining an interaction among the first protein, the second protein, and the third protein according to the detection of the fluorescent focus.

According to the method, as described in Examples to 18 later, when the thirteenth fusion protein comprising the first protein and the multimerizable protein, the fourteenth fusion protein comprising the second protein and the multimerizable protein, and the fifteenth fusion protein comprising the third protein and the fluorescent protein are expressed in a cell or introduced into a cell, an interaction if any among the first protein, the second protein, and the third protein induces multimer formation between the multimerizable protein and another multimerizable protein, as in the cases of the systems shown in FIG. 1 and so forth. Thereby, the fusion proteins autonomously form an assembly, and the fluorescent protein contained in the fusion protein is detected as a fluorescent focus (see FIG. 7).

As the "third protein" according to the present invention, it is possible to use desired proteins intended for detection of interaction as in the cases of the above-described first and second proteins. Moreover, the first protein, the second protein, and the third protein may be different from each other. Alternatively, two of them may be the same, or all the three may be the same.

The "interaction among the first protein, the second protein, and the third protein" according to the present invention includes not only direct interactions, but also indirect interactions such as an interaction for forming a complex in which another molecule (protein, nucleic acid, sugar, lipid, low-molecular-weight compound, or the like) is interposed among the proteins.

The "thirteenth fusion protein" according to the present invention should be a protein comprising the first protein and the multimerizable protein. Moreover, the "fourteenth fusion protein" should be a protein comprising the second protein and the multimerizable protein. In each of these fusion proteins, the multimerizable protein may be fused to either the N-terminus or the C-terminus of the first or second protein, as long as the formation of an assembly (fluorescent focus) is not inhibited. In addition, the proteins may be fused to each other directly, or may be fused indirectly via a linker or a spacer protein.

The "fifteenth fusion protein" according to the present invention should be a protein comprising the third protein and the fluorescent protein. As long as the formation of an assembly (fluorescent focus) is not inhibited, the fluorescent protein may be fused to either the N-terminus or the C-terminus of the third protein. Moreover, the proteins may be fused to each other directly, or may be fused indirectly via a linker or a spacer protein.

<Method 7 for Detecting Protein-Protein Interaction>

The present invention can also provide the following method as a seventh embodiment for determining a protein-protein interaction.

A method for determining an interaction between a first protein and a second protein, wherein
a first multimerizable protein is a different protein from a second multimerizable protein, and
the method comprises the following steps (1) to (3):
(1) expressing in a cell or introducing into a cell
a sixteenth fusion protein comprising the first protein, the first multimerizable protein, and a fluorescent protein, and
a seventeenth fusion protein comprising the second protein and the second multimerizable protein;
(2) detecting a fluorescent focus formed by an association between the sixteenth fusion protein and the seventeenth fusion protein in the cell; and
(3) determining an interaction between the first protein and the second protein according to the detection of the fluorescent focus.

The "sixteenth fusion protein" and the "seventeenth fusion protein" according to the present invention are proteins respectively similar to the above-described first fusion protein and second fusion protein, except that the multimerizable proteins (the first multimerizable protein and the second multimerizable protein) are different. Note that the fusion proteins are the same regarding the first protein and the second protein, too, so that these proteins may be different from each other, or may be the same. As described in Examples later, the seventh embodiment for determining a protein-protein interaction of the present invention is more useful when the first protein is different from the second protein.

Hereinabove, preferred embodiments for determining a protein-protein interaction have been described. Additionally, the present invention can also utilize these methods to provide methods described below.

<Method for Obtaining Temporal Information and the like on Protein-Protein Interaction>

As described in Examples such as Examples 2 and 11 to 13 later, the method of the present invention is capable of determining not only a protein-protein interaction taking place, but also a protein-protein interaction ending, on the basis of the present or absence of a fluorescent focus. Moreover, it is also possible to trace occurrence or the like of such a protein-protein interaction over time. Further, the present invention is also capable of determining a protein-protein interaction in any region in a cell without being influenced by localization of a multimerizable protein and a fluorescent protein, and so forth.

Thus, the present invention can provide a method, wherein a fluorescent focus is detected to determine a protein-protein interaction taking place or ending, a period until the interaction takes place or ends, or a duration of the interaction.

In determining the "protein-protein interaction taking place or ending" in the manner described above, the present invention is also capable of specifying an intracellular region where the protein-protein interaction takes place. Additionally, according to the present invention, determining the "protein-protein interaction taking place or ending" makes it possible to determine a signal transduction occurring and ending, in which the protein-protein interaction is involved, a period until the signal transduction occurs or ends, and a duration of the signal transduction, and also to specify an intracellular region where the signal transduction occurs. Moreover, the present invention is capable of determining the interaction between the first protein and the second protein (or the interaction among the first protein, the second protein, and the third protein) even if the interaction takes place or ends in response to a particular stimulus. Thus, the present invention can also provide a method for detecting the fluorescent focus according to the present invention, wherein the fluorescent focus is detected to determine the protein-protein interaction taking place or ending in response to a particular stimulus, a period until the interaction takes place or ends, or a duration of the interaction.

It is only necessary that the "particular stimulus" according to the present invention be a stimulus capable of directly or indirectly inducing or inhibiting a protein-protein interaction. Moreover, the "particular stimulus" may be a stimulus attributable to an endogenous factor produced in a cell (for example, increase or decrease in intracellular calcium ion concentration, activation or inactivation of an enzyme), or may be a stimulus applied to a cell from the outside (for example, administration of a ligand (agonist or antagonist) to a receptor in a cell).

Further, the method of the present invention is also capable of determining a particular stimulation starting or ending, a period until the stimulation starts or ends, or a duration of the stimulation, by detecting a fluorescent focus.

Furthermore, the method of the present invention is also capable of determining an increase or decrease of a protein-protein interaction in accordance with a degree of the particular stimulus (for example, in a case where the particular stimulus is a drug, its concentration). Thus, in the case where the particular stimulus is a drug, the 50% effective concentration (EC50) and the 50% inhibitory concentration (IC50) of the drug against a protein-protein interaction can be determined by the present invention.

In addition, the method of the present invention is capable of determining, in a single cell, multiple types of protein-protein interactions, multiple types of protein-protein interactions dependent respectively on particular stimuli, and eventually a signal transduction in which these protein-protein interactions are involved.

<Screening Method for Protein Interacting with Particular Protein>

The present invention makes it possible to determine any protein-protein interaction. Thus, the present invention can provide a method for screening for a protein interacting with a particular protein, wherein one of the first protein and the second protein is the particular protein, while the other is a test protein, and a protein interacting with the particular protein is selected according to the detection of the fluorescent focus according to the present invention. Moreover, for a case of targeting an interaction among three or more proteins, the present invention can provide a method for screening for a protein interacting with particular proteins, wherein two proteins of the first to third proteins are the particular proteins, while the remaining one is a test protein, and a protein interacting with the particular proteins is selected according to the detection of the fluorescent focus according to the present invention.

The "test protein" according to the present invention is not particularly limited. Protein groups encoded by cDNA libraries can be suitably used from the viewpoint that it is possible to comprehensively and efficiently select proteins interacting with particular proteins.

<Method for Identifying Amino Acid Residue Involved in Protein-Protein Interaction>

As described in Examples such as Example 2 later, the present invention is also capable of quantitatively analyzing a strength of a protein-protein interaction by utilizing a fluorescence intensity of a fluorescent focus. Thus, the present invention can provide a method for identifying any one of an amino acid residue in the first protein and an amino acid residue in the second protein (or amino acid residues in the first to third proteins), which are involved in the protein-protein interaction, wherein in a case where a protein in which a mutation is introduced is used as any one of the first protein and the second protein (or a mutation is introduced in any one of the first to third proteins), if an intensity of the fluorescent focus is reduced in comparison with a case of using a protein in which no mutation is introduced, the amino acid residue in which the mutation is introduced is determined to be involved in the interaction.

The "fluorescence intensity of the fluorescent focus" according to the present invention includes not only a fluorescence intensity of a single fluorescent focus, but also a total fluorescence intensity of fluorescent foci present in a certain region (for example, in one cell, in one field of view and in one fluorescence image observed with a fluorescence microscope).

Those skilled in the art can prepare the "protein obtained by introducing a mutation into the first protein and the like" by selecting known techniques as appropriate. An example of such known techniques includes site-directed mutagenesis.

<Screening Method for Substance Capable of Modulating Protein-Protein Interaction>

As described above, in the method of the present invention, a strength of a protein-protein interaction can be grasped on the basis of the fluorescence intensity of the fluorescent focus. Thus, the present invention can provide a method comprising the steps of:

expressing in a cell or introducing into a cell a first fusion protein and a second fusion protein in presence of a test compound;

detecting a fluorescent focus formed by an association between the first fusion protein and the second fusion protein in the cell; and selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

The test compound used in the screening method of the present invention is not particularly limited. Examples thereof include an expression product from a gene library, a synthetic low-molecular-weight compound library, a peptide library, an antibody, a substance released by a bacterium, a liquid extract and a culture supernatant of cells (microorganisms, plant cells, animal cells), a purified or partially purified polypeptide, an extract derived from a marine organism, plant, or animal, soil, and a random phage peptide display library.

Moreover, examples of a state of being in the presence of the test compound include a state where the cell according to the present invention is in contact with the test compound by addition or the like of the test compound to a medium, and a state where the test compound is introduced in the cell according to the present invention.

Note that, the screening method of the present invention is not limited to the above-described embodiment, as long as the method is based on the intensity of the fluorescent focus. Thus, the method can also encompass embodiments described below as other embodiments.

A method comprising the steps of:

expressing in a cell or introducing into a cell a third fusion protein, a fourth fusion protein, and a fifth fusion protein in presence of a test compound;

detecting a fluorescent focus formed by an association among the third fusion protein, the fourth fusion protein, and the fifth fusion protein in the cell; and selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

A method comprising the steps of:

expressing in a cell or introducing into a cell a first labeled protein, a second labeled protein, and a sixth fusion protein comprising a binding partner bound thereto in presence of a test compound;

detecting a fluorescent focus formed by an association among the first labeled protein, the second labeled protein, and the sixth fusion protein comprising the binding partner bound thereto in the cell; and selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

A method comprising the steps of:
expressing in a cell or introducing into a cell a seventh fusion protein, an eighth fusion protein, and a ninth fusion protein in presence of a test compound;
detecting a fluorescent focus formed by an association among the seventh fusion protein, the eighth fusion protein, and the ninth fusion protein in the cell; and
selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

A method comprising the steps of:
expressing in a cell or introducing into a cell a tenth fusion protein, an eleventh fusion protein, and a twelfth fusion protein in presence of a test compound;
detecting a fluorescent focus formed by an association among the tenth fusion protein, the eleventh fusion protein, and the twelfth fusion protein in the cell; and
selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

A method comprising the steps of:
expressing in a cell or introducing into a cell a thirteenth fusion protein, a fourteenth fusion protein, and a fifteenth fusion protein in presence of a test compound;
detecting a fluorescent focus formed by an association among the thirteenth fusion protein, the fourteenth fusion protein, and the fifteenth fusion protein in the cell; and
selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

A method comprising the steps of:
expressing in a cell or introducing into a cell a sixteenth fusion protein and a seventeenth fusion protein in presence of a test compound;
detecting a fluorescent focus formed by an association between the sixteenth fusion protein and the seventeenth fusion protein in the cell; and
selecting the test compound as a substance inducing the interaction if an intensity of the fluorescent focus is higher than an intensity of a fluorescent focus formed in absence of the test compound, or selecting the test compound as a substance suppressing the interaction if the intensity of the fluorescent focus is lower than the intensity of the fluorescent focus formed in the absence of the test compound.

<Kit for Use in Methods of the present invention>

The present invention can provide a kit for use in the above-described methods. The kit of the present invention is a kit comprising an instruction and at least one substance selected from the group consisting of the following (a) to (h):

(a) a vector comprising a DNA encoding a multimerizable protein, a DNA encoding a fluorescent protein, and a cloning site, wherein the vector is capable of expressing a fusion protein comprising the multimerizable protein, the fluorescent protein, and a certain protein when a DNA encoding the certain protein is inserted in the cloning site;

(b) a vector encoding the first fusion protein;

(c) a vector encoding the second fusion protein;

(d) a transformed cell comprising a vector encoding the first fusion protein;

(e) a transformed cell comprising a vector encoding the second fusion protein;

(f) a transformed cell comprising a vector encoding the first fusion protein and a vector encoding the second fusion protein;

(g) the first fusion protein; and (h) the second fusion protein.

It is only necessary that the vectors according to the present invention comprise a regulatory sequence necessary for an expression (transcription and translation) of the inserted DNA in the above-described cell. Examples of such a regulatory sequence include a promoter, an enhancer, a silencer, a terminator, a poly(A) tail, and a ribosomal binding site (Shine-Dalgarno (SD) sequence). Further, the vectors according to the present invention may comprise a selection marker (such as a drug resistance gene), and a reporter gene (such as a luciferase gene, a β-galactosidase gene, a chloramphenicol acetyltransferase (CAT) gene). Moreover, examples of a type of such vectors according to the present invention include a plasmid vector, an episomal vector, and a viral vector.

The proteins encoded by the vectors according to the present invention are the above-described fusion proteins and the like. From the viewpoint of further improving the efficiency of expressing such proteins, a DNA having codons optimized in accordance with the species of a cell expressing the proteins (for example, humanized-codon DNA) may be inserted in the vectors according to the present invention.

Additionally, those skilled in the art can prepare the vectors according to the present invention as appropriate by utilizing known techniques such as DNA chemical synthesis methods and genetic recombination techniques as described in Examples later.

Examples of the "cloning site allowing an insertion of a DNA encoding a certain protein" in (a) above include a multiple cloning site containing one or more restriction-enzyme recognition sites, a TA cloning site, and a GATEWAY (registered trademark) cloning site.

Those skilled in the art can synthesize and prepare the fusion proteins according to the present invention based on the nucleotide sequences of these fusion protein by genetic techniques using a cell-free protein synthesis system (for example, reticulocyte extract, wheat germ extract), *Escherichia coli*, animal cells, insect cells, plant cells, or the like. Alternatively, the fusion proteins according to the present invention can be chemically synthesized and prepared based on the amino acid sequences by using a commercially-available polypeptide synthesizer.

To preparations of the vectors or the fusion proteins according to the present invention, other components such as a buffer, a stabilizer, a preservative, and an antiseptic may be added.

The transformed cell according to the present invention can be prepared, as described above, by introducing the vectors according to the present invention into a cell. Moreover, to a preparation of the transformed cell according to the present invention, a medium necessary for storage and culturing of the cell and other components such as a stabilizer, a preservative, and an antiseptic may be added or attached.

The "instruction" according to the present invention is an instruction for utilizing the vectors or the transformed cell in the methods of the present invention. The instruction may comprise, for example, experimental techniques and experimental conditions for the methods of the present invention, and information on the preparations of the present invention (for example, information such as a vector map indicating the base sequence, cloning site, and the like of the vectors, information on the origin and nature of the transformed cell, culture conditions of the cell, and so forth).

Note that the kit of the present invention is not limited to the above-described embodiment and can also encompass embodiments as follows in accordance with the above-described embodiments for determining a protein-protein interaction.

A kit for use in the second method for determining a protein-protein interaction, the kit comprising an instruction and at least one substance selected from the group consisting of the following (a) to (h):

(a) a vector comprising a DNA encoding the multimerizable protein and a cloning site, wherein the vector is capable of expressing a fusion protein comprising the multimerizable protein and a certain protein when a DNA encoding the certain protein is inserted in the cloning site;

(b) a vector encoding the third fusion protein;

(c) a vector encoding the fourth fusion protein;

(d) a vector encoding the fifth fusion protein;

(e) a transformed cell comprising a vector encoding the fifth fusion protein;

(f) the third fusion protein;

(g) the fourth fusion protein; and (h) the fifth fusion protein.

A kit for use in the third method for determining a protein-protein interaction, the kit comprising an instruction and at least one substance selected from the group consisting of the following (a) to (h):

(a) a vector comprising a DNA encoding the affinity tag and a cloning site, wherein the vector is capable of expressing a fusion protein comprising the affinity tag when a DNA encoding a certain protein is inserted in the cloning site;

(b) a vector encoding the first labeled protein;

(c) a vector encoding the second labeled protein;

(d) a vector encoding the sixth fusion protein comprising the binding partner bound thereto;

(e) a transformed cell comprising a vector encoding the sixth fusion protein comprising the binding partner bound thereto;

(f) the first labeled protein;

(g) the second labeled protein; and (h) the sixth fusion protein comprising the binding partner bound thereto.

A kit for use in the fourth method for determining a protein-protein interaction, the kit comprising an instruction and at least one substance selected from the group consisting of the following (a) to (h):

(a) a vector comprising a DNA encoding the first partial peptide and a cloning site, wherein the vector is capable of expressing a fusion protein comprising the first partial peptide when a DNA encoding a certain protein is inserted in the cloning site;

(b) a vector encoding the seventh fusion protein;

(c) a vector encoding the eighth fusion protein;

(d) a vector encoding the ninth fusion protein;

(e) a transformed cell comprising a vector encoding the ninth fusion protein;

(f) the seventh fusion protein;

(g) the eighth fusion protein; and (h) the ninth fusion protein.

A kit for use in the fifth method for determining a protein-protein interaction, the kit comprising an instruction and at least one substance selected from the group consisting of the following (a) to (h):

(a) a vector comprising a DNA encoding the third partial peptide and a cloning site, wherein the vector is capable of expressing a fusion protein comprising the third partial peptide when a DNA encoding a certain protein is inserted in the cloning site;

(b) a vector encoding the tenth fusion protein;

(c) a vector encoding the eleventh fusion protein;

(d) a vector encoding the twelfth fusion protein;

(e) a transformed cell comprising a vector encoding the twelfth fusion protein;

(f) the tenth fusion protein;

(g) the eleventh fusion protein; and (h) the twelfth fusion protein.

A kit for use in the sixth method for determining a protein-protein interaction, the kit comprising an instruction and at least one substance selected from the group consisting of the following (a) to (h):

(a) a vector comprising a DNA encoding the multimerizable protein and a cloning site, wherein the vector is capable of expressing a fusion protein comprising the multimerizable protein when a DNA encoding a certain protein is inserted in the cloning site;

(b) a vector comprising a DNA encoding the fluorescent protein and a cloning site, wherein the vector is capable of expressing a fusion protein comprising the fluorescent protein when a DNA encoding a certain protein is inserted in the cloning site;

(c) a vector encoding the thirteenth fusion protein;

(d) a vector encoding the fourteenth fusion protein;

(e) a vector encoding the fifteenth fusion protein;

(f) the thirteenth fusion protein;

(g) the fourteenth fusion protein; and (h) the fifteenth fusion protein.

A kit for use in the seventh method for determining a protein-protein interaction, the kit comprising an instruction and at least one substance selected from the group consisting of the following (a) to (f):

(a) a vector comprising a DNA encoding the first multimerizable protein, a DNA encoding the fluorescent protein, and a cloning site, wherein the vector is capable of expressing a fusion protein comprising the first multimerizable protein, the fluorescent protein, and a certain protein when a DNA encoding the certain protein is inserted in the cloning site;

(b) a vector comprising a DNA encoding the second multimerizable protein, a DNA encoding the fluorescent protein, and a cloning site, wherein the vector is capable of expressing a fusion protein comprising the second multimerizable protein, the fluorescent protein, and a certain protein when a DNA encoding the certain protein is inserted in the cloning site;

(c) a vector encoding the sixteenth fusion protein;

(d) a vector encoding the seventeenth fusion protein;

(e) the sixteenth fusion protein; and (f) the seventeenth fusion protein.

EXAMPLES

Hereinafter, the present invention will be described more specifically based on Examples and Comparative Example. However, the present invention is not limited to the following Examples.

Example 1

The present inventors came up with an idea of utilizing, in determining an interaction between two proteins (a first protein and a second protein): a first fusion protein comprising the first protein, a multimerizable protein, and a fluorescent protein; and a second fusion protein comprising the second protein and a multimerizable protein (see FIG. 1). To be more specific, the inventors came up with a construction of a system as follows. When these two fusion proteins are expressed in a cell, an interaction if any between the first protein and the second protein induces multimer formation between the multimerizable protein and another multimerizable protein. Thereby, the fusion proteins autonomously form an assembly, and the fluorescent protein contained in the fusion protein is detected as a fluorescent focus.

Then, the effectiveness of this system was actually examined by selecting a PB1 domain of a p62 protein as the multimerizable protein and selecting monomeric Azami Green (mAG1) as the fluorescent protein. Further, this examination was conducted on an embodiment in which both of the first fusion protein and the second fusion protein comprised mAG1 in order to facilitate detection of a fluorescent focus (see FIG. 2). Additionally, a humanized-codon DNA encoding the fluorescent protein (humanized-codon monomeric Azami Green 1, hmAG1) was used for the expression of mAG1.

Moreover, in this examination, a FKBP12 protein mutant was used which had been known to form a homodimer by an addition of a drug (AP1903 or AP20187). Specifically, in the examination this time, the first protein was the same protein as the second protein, and the first fusion protein was the same protein as the second fusion protein. Note that, as to the homodimer formation of the FKBP12 protein mutant controlled by AP1903 or the like, see TIM CLACKSON et al., Proc. Natl. Acad. Sci. USA, 1998, vol. 95, pp. 10437 to 10442. Hereinafter, the materials and methods for constructing this detection system will be described.

<Preparation of pPB1-hmAG1-MCLinker and phmAG1-PB1-MCLinker>

In this detection system, prepared were expression vectors (pPB1-hmAG1-MCLinker and phmAG1-PB1-MCLinker) respectively encoding as the fusion proteins composed of the multimerizable protein and the fluorescent protein: a protein tag (PB1-mAG1) composed of mAG1 fused to the C-terminus of the PB1 domain of the p62 protein; and a protein tag (mAG1-PB1) composed of mAG1 fused to the N-terminus of the PB1 domain of the p62 protein. Specifically, a DNA having the nucleotide sequence of SEQ ID NO: 27 was artificially synthesized which contained restriction enzyme sites at either end of a DNA having a nucleotide sequence encoding the PB1-mAG1 (the DNA encoding a protein having the amino acid sequence of SEQ ID NO: 28). Moreover, a DNA having the nucleotide sequence of SEQ ID NO: 29 was artificially synthesized which contained restriction enzyme sites at either end of a DNA having a nucleotide sequence encoding the mAG1-PB1 (the DNA encoding a protein having the amino acid sequence of SEQ ID NO: 30). Then, the synthetic DNAs obtained in this manner were cleaved with NheI and AgeI, and inserted into phmAG1-MCLinker (manufactured by limited company Amalgaam Co., Ltd.) having been treated with a combination of the same restriction enzymes. Thus, pPB1-hmAG1-MCLinker and phmAG1-PB1-MCLinker were constructed.

<Preparation of pPB1-hmAG1-FKBP12 Mutant>

Next, the pPB1-hmAG1-MCLinker prepared as described above was used to prepare a vector for expressing the fusion protein according to the present invention (FKBP12 mutant fused to the PB1-mAG1). Specifically, a DNA having the nucleotide sequence of SEQ ID NO: 31 was artificially synthesized which contained restriction enzyme sites at either end of a DNA having a nucleotide sequence encoding the FKBP12 mutant (the DNA encoding a protein having the amino acid sequence of SEQ ID NO: 32). Then, the obtained synthetic DNA was cleaved with EcoRI and XhoI, and inserted into the pPB1-hmAG1-MCLinker having been treated with a combination of the same restriction enzymes. Thus, a pPB1-hmAG1-FKBP12 mutant was constructed.

<Cell Culturing and Transfection>

Next, the pPB1-hmAG1-FKBP12 mutant prepared as described above was introduced into HEK293 cells, and the fusion protein according to the present invention was expressed in the cells. Specifically, first, HEK293 cells were cultured in DMEM (high glucose, manufactured by SIGMA ALDRICH CO.) supplemented with 10% FBS (manufactured by Equitech-Bio Inc.) and 1% penicillin-streptomycin (manufactured by Life Technologies Corporation). Then, on the day before the transfection, the HEK293 cells cultured in this manner were seeded onto an 8-well chamber slide (manufactured by Nunc A/S), and cultured in 200 µL of the culture solution per well. Subsequently, 100 ng of the pPB1-hmAG1-FKBP12 mutant was diluted with 10 µL of OptiMEM (manufactured by Life Technologies Corporation), and 0.4 µL of Turbofect Transfection Reagent (manufactured by Thermo Fisher Scientific Inc.) was added thereto and then stirred. Thereafter, the resultant was further mixed with 100 µL of the culture solution, then added to the HEK293 cells, and cultured for 20 hours.

<Observation of Cells>

Figure 9:
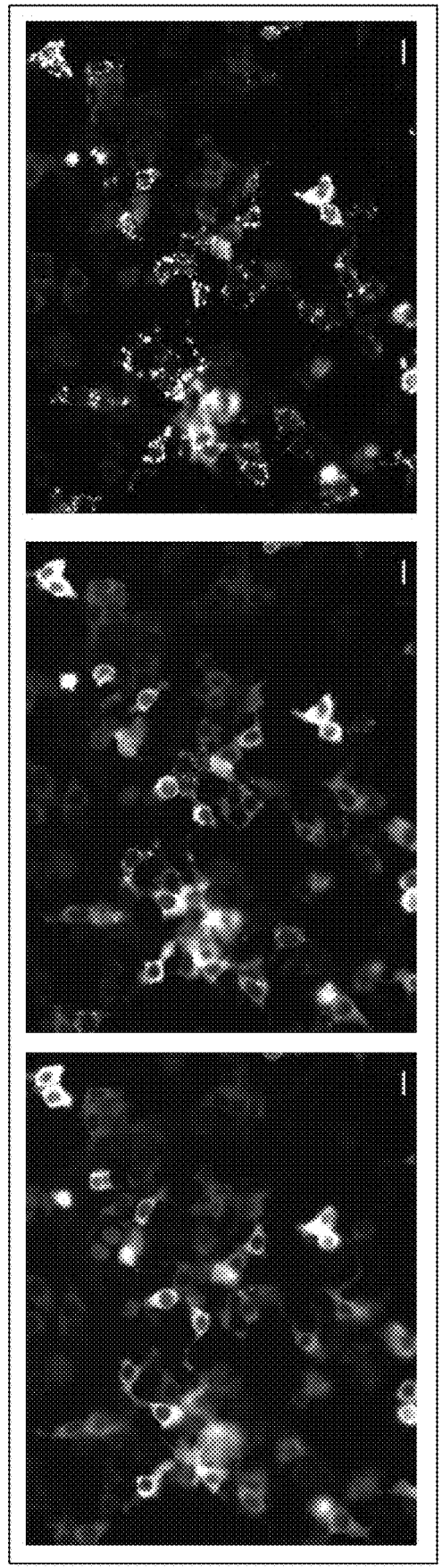
FIG. 9 shows micrographs for illustrating the result of expressing in cells a fusion protein according to the present invention (PB1-mAG1-FKBP12 mutant) composed of a PB1 domain of a p62 protein as a multimerizable protein and mAG1 as a fluorescent protein fused to an analysis target FKBP12 mutant, and then adding a drug B/B Homodimerizer to the cells to analyze whether or not it is possible to determine, on the basis of a fluorescent focus, homodimer formation of the FKBP12 mutant attributable to the drug addition. The figure shows the result of analyzing the cells before the drug addition, the cells 38 minutes after the drug addition, and the cells 76 minutes after the drug addition, in this order from the left. Moreover, in the figure, the scale bars represent 20 µm.

After the transfection treatment, the HEK293 cells were observed using an IX-71 inverted fluorescence microscope (manufactured by Olympus Corporation, the magnification of the objective lens: 20×), a U-MGFPHQ filter (manufactured by Olympus Corporation), and an ORCA-ER digital camera (manufactured by Hamamatsu Photonics K. K.). The homodimer formation of the FKBP12 mutant was induced by adding 500 nM B/B Homodimerizer (AP20187, manufactured by Takara Bio Inc.) to the medium. In addition, after the drug was added, images were obtained over time. FIG. 9 shows the obtained result.

As apparent from the result shown in FIG. 9, no fluorescent focus was detected before the drug was added, and fluorescent signals were dispersedly observed in the cytoplasms (see the image on the left in FIG. 9). Then, 38 minutes after the drug addition, fluorescent foci were observed in multiple cells (see the image in the middle of FIG. 9). As the observation was further continued, many cells which exhibited distinctive fluorescent foci were observed 76 minutes after the addition (see the image on the right in FIG. 9). Thus, the result of this examination revealed that the use of the system utilizing the protein tag composed of the multimerizable protein and the fluorescent protein shown in FIG. 1 or 2 enabled determination of homodimer formation, eventually determination of a protein-protein interaction. Further, as shown in FIG. 9, it was also revealed that the present invention made it possible to determine the homodimer formation of the FKBP12 mutant in the cytoplasm, that is, an intracellular environment unique to the homodimer formation.

Comparative Example 1

The present inventors have invented another system for determining a protein-protein interaction, that is, a system in which a first fusion protein comprising a first protein and an association-inducing protein, and a second fusion protein comprising a second protein and a fluorescent multimerizable protein are expressed in a cell, and a fluorescent focus formed by an association between the first fusion protein and the second fusion protein is detected to determine an interaction between the first protein and the second protein (see PTL 4).

Hence, using this system, the homodimer formation of the FKBP12 protein mutant described above was determined and compared with the result described in Example 1 above to evaluate the effectiveness of the present invention. Hereinafter, the materials and methods for constructing the detection system described in PTL 4 will be described.

<Preparation of pPB1-FKBP12 Mutant and phAG-FKBP12 Mutant>

In the detection system described in PTL 4, the PB1 domain of the p62 protein was selected as the association-inducing protein. Moreover, AG was selected as the fluorescent multimerizable protein, and a DNA encoding humanized-codon AG (hAG) was used.

Further, an expression vector (pPB1-FKBP12 mutant) encoding a fusion protein composed of the FKBP12 mutant fused to the C-terminus of the PB1 domain of the p62 protein was prepared as follows. Specifically, a DNA having the nucleotide sequence of SEQ ID NO: 31 was artificially synthesized which contained restriction enzyme sites at either end of a DNA having a nucleotide sequence encoding the FKBP12 mutant (the DNA encoding a protein having the amino acid sequence of SEQ ID NO: 32). Then, the obtained synthetic DNA was cleaved with EcoRI and XhoI, and inserted into pAsh-MCLinker (manufactured by MEDICAL & BIOLOGICAL LABORATORIES CO., LTD.) having been treated with a combination of the same restriction enzymes. Thus, a pPB1-FKBP12 mutant was constructed.

Moreover, an expression vector (phAG-FKBP12 mutant) encoding a fusion protein composed of the FKBP12 mutant fused to the C-terminus of the AG protein was constructed by inserting the synthetic DNA encoding the FKBP12 mutant into phAG-MCLinker (manufactured by MEDICAL & BIOLOGICAL LABORATORIES CO., LTD.) according to the same method as that described above.

Figure 10:
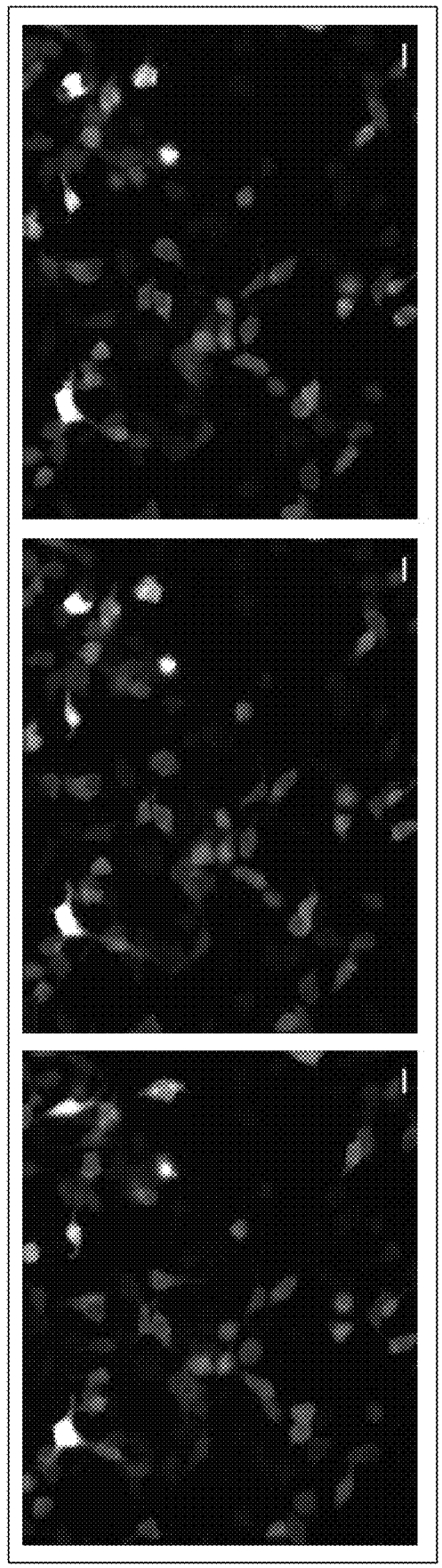
FIG. 10 shows micrographs for illustrating the result of detecting fluorescent foci indicating the homodimer formation of the FKBP12 mutant attributable to the drug addition according to the method described in International Publication No. WO2013/084950. The figure shows the result of analyzing the cells before the drug addition, the cells 58 minutes after the drug addition, and the cells 66 minutes after the drug addition, in this order from the left. Moreover, in the figure, the scale bars represent 20 µm.

Further, 100 ng of each of the expression vectors thus constructed was mixed, that is, 200 ng of these were mixed in total, and fluorescent foci in cells before and after the drug addition were detected according to the same methods as <Cell Culturing and Transfection> and <Observation of Cells> described in Example 1. FIG. 10 shows the obtained result.

As shown in FIG. 10, it was confirmed that the method described in PTL 4 was also capable of detecting a fluorescent focus indicating the homodimer formation of the FKBP12 protein mutant. However, in this method, even at the time point when 66 minutes elapsed after the drug addition, fluorescent foci were formed only in a few cells. This revealed that the method of the present invention was superior to the method described in WO2013/084950 in at least the efficiency of the homodimer formation determination.

Example 2

Next, an examination was conducted on whether or not the method of the present invention was capable of determining reversible homodimer formation, in other words, whether or not fluorescent foci having been formed were extinguished as the homodimer dissociated.

It has been known that a homodimer of the FKBP12 protein mutant induced and formed by the above-described B/B Homodimerizer (AP20187) is dissociated by B/B Washout Ligand (manufactured by Takara Bio Inc.). Hence, the examination was conducted using materials and methods described below.

<Preparation of Cells Constitutively Expressing PB1-hmAG1-FKBP12 Mutant>

The pPB1-hmAG1-FKBP12 mutant was introduced into HEK293 cells, and cells constitutively expressing the fusion protein according to the present invention (PB1-hmAG1-FKBP12 mutant) were prepared. Specifically, on the day before the introduction of the expression vector, HEK293 cells were seeded onto a 35-mm dish (manufactured by BD Falcon), and cultured in 1.5 mL of the culture solution. Then, 1 μg of the pPB1-hmAG1-FKBP12 mutant was diluted with 100 μL of OptiMEM (manufactured by Life Technologies Corporation), and 10 μL of PolyFect (registered trademark) Transfection Reagent (manufactured by QIAGEN N.V.) was added thereto and then stirred. Subsequently, the resultant was further mixed with 600 μL of the culture solution, then added to the HEK293 cells, and cultured for 20 hours. Thereafter, G418 was added thereto at a concentration of 500 μg/mL, and further cultured for one week. After that, viable cells were detached using a trypsin solution, diluted with a culture solution containing G418 (500 μg/ml), and then cultured in a 96-well plate at 0.5 cells/well. Subsequently, cells which formed single colonies were cultured to expand.

<Observation of Cells>

Figure 11:
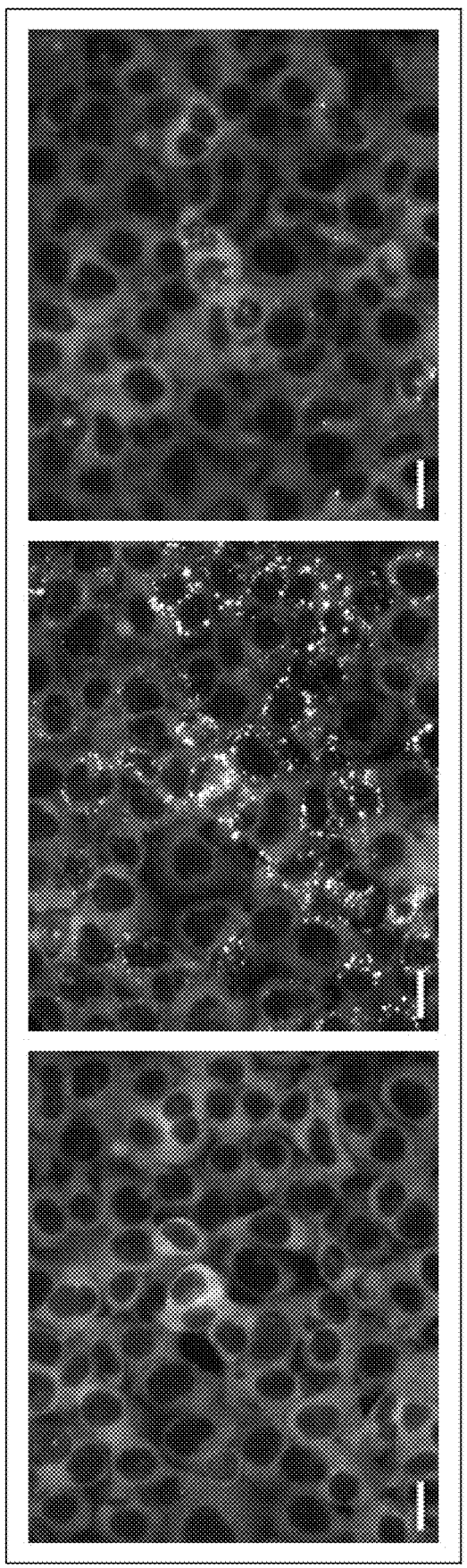
FIG. 11 shows micrographs for illustrating the result of analyzing whether or not it is possible to determine, on the basis of a fluorescent focus, that the homodimer formation of the FKBP12 mutant attributable to the addition of the B/B Homodimerizer to cells constitutively expressing the PB1-mAG1-FKBP12 mutant is dissociated (disrupted) by adding B/B Washout Ligand. The figure shows the result of analyzing the cells before the drug addition, the cells 90 minutes after the B/B Homodimerizer addition, and the cells 90 minutes after the B/B Homodimerizer was washed away and then the B/B Washout Ligand was added, in this order from the left. Moreover, in the figure, the scale bars represent 20 μm.

The cells constitutively expressing the PB1-hmAG1-FKBP12 mutant established above were observed by the same method as that described in Example 1. Moreover, after no fluorescent focus was confirmed in the steady state, 500 nM B/B Homodimerizer was added to the culture solution, and the cells were photographed over time for 150 minutes. Note that, in this observation, the formation of fluorescent foci indicating the homodimer formation of the FKBP12 mutant were observed as in Example 1 above. Next, the cells were washed by replacing the culture solution containing the B/B Homodimerizer with a culture solution normally used for culturing. Then, 500 nM B/B Washout Ligand was added, and images were obtained over time for 100 minutes. FIG. 11 shows the obtained result.

<Image Analysis>

The images captured over time by the above method were analyzed using spot detection (spot detector) of an icy image analysis program (icy.bioimageanalysis.org/). Moreover, from the images, a graph was created in which the X axis represents the operation time (minutes), and the Y axis represents a numerical value of a total fluorescence intensity in regions of the fluorescent foci within boxes drawn around the regions by lines. Note that the analysis with the spot detector was performed by setting parameters (processing paths) as follows.

Figure 12:
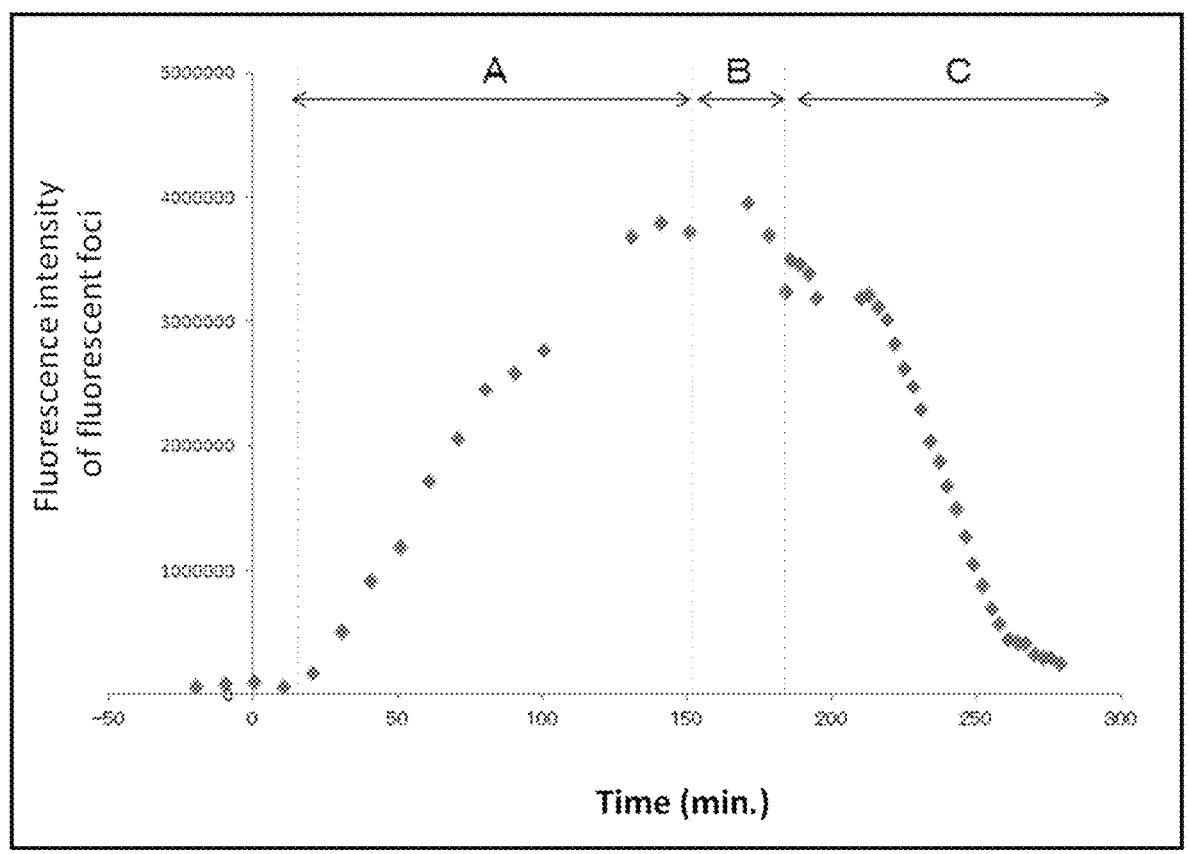
FIG. 12 is a graph for illustrating the result of analyzing whether or not it is possible to determine, on the basis of a fluorescent focus, that the homodimer formation of the FKBP12 mutant attributable to the addition of the B/B Homodimerizer to the cells constitutively expressing the PB1-mAG1-FKBP12 mutant is dissociated by adding the B/B Washout Ligand. In the figure, A shows the elapsed time after the B/B Homodimerizer was added to the cells. B shows the time of washing away the B/B Homodimerizer having been added to the cells. C shows the elapsed time after the washing followed by the B/B Washout Ligand addition to the cells.

Pre Processing: null,
Detector: UDWTWaveletDetector, Detect bright spot over dark background,
Scale enabled: scale 3, Threshold: 50.
FIG. 12 shows the obtained result.

As apparent from the result shown in FIG. 11, similarly to the result described in Example 1, no fluorescent focus was detected before the drug addition, and fluorescent signals were dispersedly observed in the cytoplasms (see the image on the left in FIG. 11). Then, 90 minutes after the B/B Homodimerizer addition, distinctive fluorescent foci were observed in multiple cells (see the image in the middle in FIG. 11).

Moreover, it was revealed that as a result of adding the B/B Washout Ligand, most of the fluorescent foci were extinguished (see the image on the right in FIG. 11). Further, it can be seen from the graph shown in FIG. 12, the fluorescent foci were formed and extinguished in a stepwise manner. These revealed that the present invention was capable of grasping, on the basis of the formation and extinction of the fluorescent foci, a change over time in the protein-protein interaction attributable to the drugs added. Furthermore, as shown in FIG. 11, it was also revealed that the present invention made it possible to determine the homodimer formation and disruption of the FKBP12 mutant in the cytoplasm, that is, an intracellular environment unique to the homodimer formation and disruption. Additionally, when the formation of the fluorescent foci started to be observed under the microscope observation immediately after the B/B Homodimerizer addition, the value of a fluorescence intensity was 1.9 times as large as that before the addition. This revealed that it was possible to determine formation of a fluorescent focus indicating the protein-protein interaction when a detected value was at least twice as large as a fluorescence intensity in a negative control (for example, cells before a protein-protein interaction took place).

As described above, it was also revealed that the present invention was capable of determining a reversible change in a protein-protein interaction on the basis of formation and extinction of fluorescent foci to be detected. Moreover, since the fluorescent foci increased or decreased in a stepwise manner as time elapsed, this revealed that the present invention was also capable of quantitatively analyzing a protein-protein interaction. Further, the cells constitutively expressing the fusion protein according to the present invention were successfully prepared by introducing the fusion protein into the cells, thereby confirming that the protein tag contained in the fusion protein exhibited no cytotoxicity and the like.

Example 3

Whether or not the present invention was also capable of determining homomultimer formation was examined using materials and methods described below. Note that this examination was conducted by targeting homomultimer formation of ap53 protein (as to the homomultimer formation, see Yoko Itahana et al., J Biol Chem., 2009, vol. 284, no. 8, pp. 5158 to 5164).

<Preparation of phmAG1-PB1-p53 and phmAG1-p53>

A nucleotide sequence was designed in which a BamHI recognition sequence was added to the 5' end of a nucleotide sequence encoding p53 (the nucleotide sequence encoding a protein having the amino acid sequence of NCBI RefSeq ACCESSION No: NP_000537) while the stop codon and a NotI recognition sequence were the 3' end. Then, a DNA having the resulting nucleotide sequence was artificially synthesized, cleaved with BamHI and NotI, and subsequently inserted into phmAG1-PB1-MCLinker and phmAG1-MCLinker (manufactured by limited company Amalgaam Co., Ltd.) having been treated with a combination of the same restriction enzymes. Thus, phmAG1-PB1-p53 and phmAG1-p53 were prepared.

<Preparation of pp53-hmAG1-PB1 and pp53-hmAG1>

In addition to the expression vectors encoding the fusion protein having the protein tag at the N-terminus of the p53 protein, expression vectors encoding a fusion protein having the protein tag at the C-terminus were also prepared by a method described below.

Specifically, the stop codon was removed from the synthetic DNA encoding p53. The resulting synthetic DNA was cleaved with BamHI and NotI, and then inserted into phmAG1-PB1-MNLinker and phmAG1-MNLinker (manufactured by limited company Amalgaam Co., Ltd.) having been treated with a combination of the same restriction enzymes. Thus, pp53-hmAG1-PB1 and pp53-hmAG1 were prepared.

<Cell Culturing and Transfection>

U2OS cells were selected as cells into which the expression vectors prepared above were introduced. The cells were first cultured in DMEM (high glucose, manufactured by SIGMA ALDRICH CO.) supplemented with 10% FBS (manufactured by Equitech-Bio Inc.) and 1% penicillin-streptomycin (manufactured by Life Technologies Corporation). Then, on the day before the introduction of the expression vectors, these cells were seeded onto a 35-mm dish (manufactured by BD Falcon), and cultured in 1.5 ml of the culture solution. Subsequently, 1 µg of the expression vector (phmAG1-PB1-p53, phmAG1-p53, pp53-hmAG1-PB1, or pp53-hmAG1) was diluted with 100 µL of OptiMEM (manufactured by Life Technologies Corporation), and 10 µL of PolyFect(registered trademark) Transfection Reagent (manufactured by QIAGEN N.V.) was added thereto and then stirred. The resultant was further mixed with 600 µL of the culture solution. Thereafter, each mixture solution of the expression vectors was added to the cultured cells, and further cultured for 20 hours.

<Observation of Cells>

Figure 13:
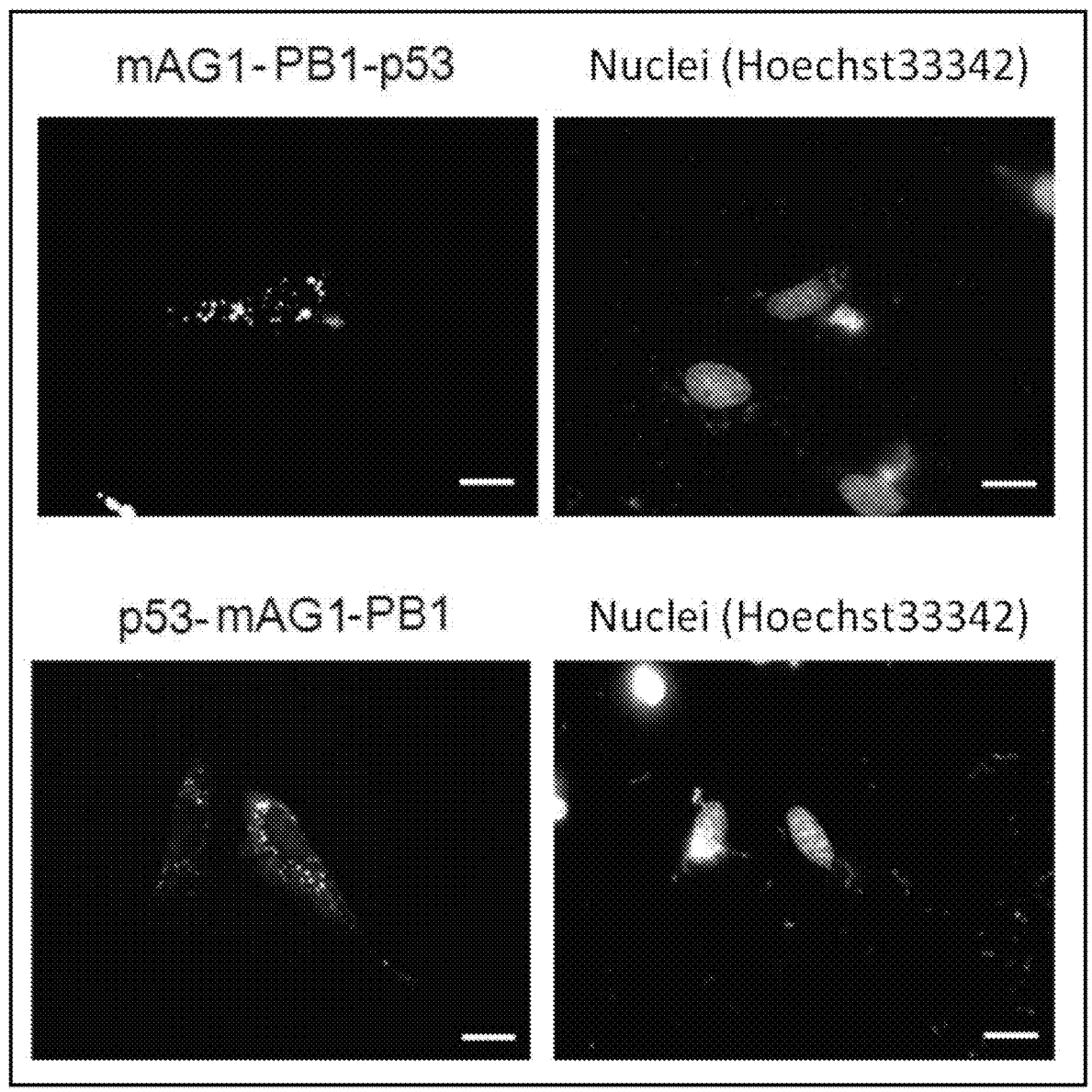
FIG. 13 shows micrographs for illustrating the result of expressing in cells a fusion protein according to the present invention (mAG1-PB1-p53 or p53-mAG1-PB1) composed of a PB1 domain of a p62 protein as a multimerizable protein and mAG1 as a fluorescent protein fused to an analysis target p53 to analyze whether or not it is possible to determine homomultimer formation of p53 on the basis of a fluorescent focus. Note that, in the figure, "mAG1-PB1-p53" shows the result of detecting fluorescent signals derived from the protein composed of a protein tag according to the present invention (the fusion protein comprising the multimerizable protein and the fluorescent protein) fused to the N-terminus of p53. The panel on the right of "mAG1-PB1-p53" shows the result of detecting nuclei by treating the cells with Hoechst 33342. Moreover, "p53-mAG1-PB1" shows the result of detecting fluorescent signals derived from the protein composed of the protein tag according to the present invention fused to the C-terminus of p53. The panel on the right of "p53-mAG1-PB1" shows the result of detecting nuclei by treating the cells with Hoechst 33342. In the figure, the scale bars represent 20 μm.
Figure 14:
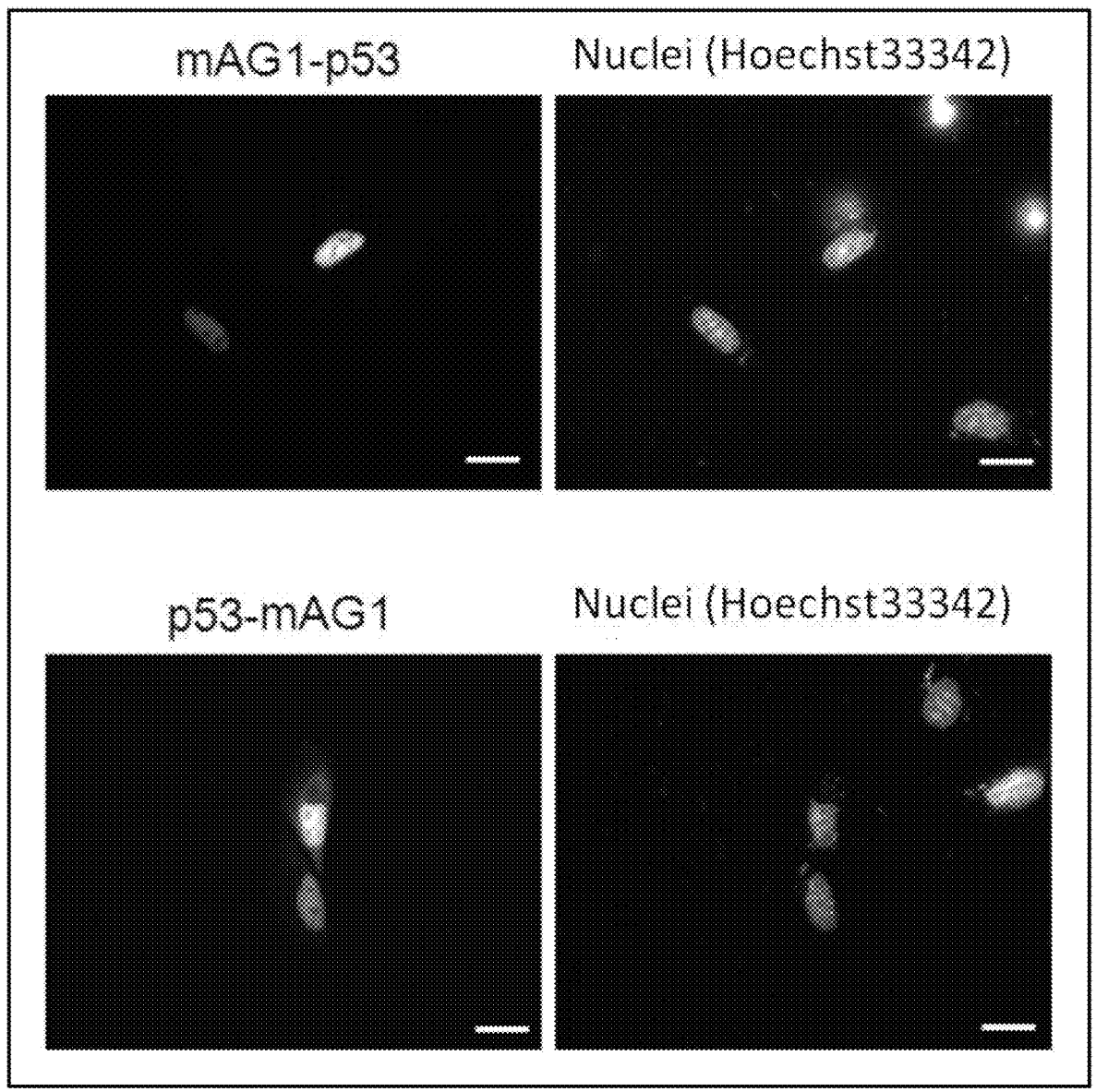
FIG. 14 shows micrographs for illustrating the result of expressing in cells a fusion protein (mAG1-p53 or p53-mAG1) composed of only mAG1 as a fluorescent protein fused to an analysis target p53 to analyze whether or not it is possible to determine homomultimer formation of p53 on the basis of a fluorescent focus. Note that, in the figure, "mAG1-p53" shows the result of detecting fluorescent signals derived from the protein composed of the fluorescent protein fused to the N-terminus of p53. The panel on the right of "mAG1-p53" shows the result of detecting nuclei by treating the cells with Hoechst 33342. Moreover, "p53-mAG1" shows the result of detecting fluorescent signals derived from the protein composed of the fluorescent protein fused to the C-terminus of p53. The panel on the right of "p53-mAG1" shows the result of detecting nuclei by treating the cells with Hoechst 33342. In the figure, the scale bars represent 20 μm.

The cells transfected above were observed in a buffer at pH of 7.4 containing 20 mM HEPES (manufactured by Dojindo Laboratories) and Hanks' Balanced Salt Solutions (manufactured by Life Technologies Corporation) having been diluted with Hoechst 33342 (manufactured by Dojindo Laboratories) to 1 µg/ml. FIGS. 13 and 14 show the obtained result. Note that micrographs shown in FIGS. 13 and 14 are results of the observation with a 40× magnification of the objective lens.

As apparent from the result shown in FIG. 13, distinctive fluorescent focus formations were observed in cells expressing the mAG1-PB1-p53 fusion protein and cells expressing the p53-mAG1-PB1 fusion protein, that is, cells expressing the fusion proteins according to the present invention.

On the other hand, as shown in FIG. 14, no fluorescent focus was observed in cells expressing the mAG1-p53 fusion protein and cells expressing the p53-mAG1 fusion protein, and fluorescent signals were observed in a dispersed state.

Thus, it was revealed that the present invention was capable of determining not only the homodimer formation but also the homomultimer formation. Further, as shown in FIG. 13, it was also revealed that the present invention was capable of uniformly determining the p53 homomultimer formation in the nuclei and the cytoplasms in the cells by utilizing uniform fluorescent focus formation. Moreover, it was also confirmed that the protein tag according to the present invention functioned even when fused to any of the N-terminus and the C-terminus of the analysis-target protein.

Example 4

It was confirmed that the system shown in FIG. 1 was effective in determining not only the above-described homomultimer formation but also heteromultimer formation. Note that the detection target in this examination was an interaction between a p53 protein and an MDM2 protein, and that Nutlin-3 known as an inhibitor against the interaction was also used in this confirmation experiment (see Vassilev L T et al., Science, Feb. 6, 2004, vol. 303, no. 5659, pp. 844 to 848). Further, in this confirmation experiment, a PB1 domain of a p62 protein was used as the multimerizable protein, and a mAG1 protein was used as the fluorescent protein.

<Preparation of pPB1-p53(70)>

To express a partial peptide of p53 whose N-terminus was fused to the PB1 domain of the p62 protein (PB1-p53 (70)) as a second fusion protein in cells, a pPB1-p53 (70) vector was prepared as follows.

In preparing pPB1-p53(70), first, a nucleotide sequence was designed in which a BamHI recognition sequence was added to the 5' end of a DNA encoding a portion of p53 (a region (p53(70)) having the 1st to 70th amino acids of the p53 protein, the region had the amino acid sequence of SEQ ID NO: 34) while the stop codon and a NotI recognition sequence were added to the 3' end of the DNA. Then, a DNA having the nucleotide sequence was artificially synthesized, cleaved with BamHI and NotI, and subsequently inserted into pAsh-MCLinker having been treated with a combination of the same restriction enzymes. Thus, pPB1-p53(70) was prepared.

<Preparation of pPB1-hmAG1-MDM2>

To express MDM2 whose N-terminus was fused to the PB1 domain of the p62 protein and mAG1 (PB1-mAG1-MDM2) as a first fusion protein in cells, a pPB1-hmAG1-MDM2 vector was prepared as follows.

pPB1-MDM2 was cleaved with BamHI and NotI, and then inserted into pPB1-hmAG1-MCLinker having been treated with a combination of the same restriction enzymes. Thus, pPB1-hmAG1-MDM2 was prepared.

Note that the pPB1-MDM2 is a plasmid vector for expressing, as a second fusion protein, an MDM2 protein whose N-terminus was fused to the PB1 domain of the p62 protein (PB1-MDM2). As to the preparation method and so forth of the pPB1-MDM2, see Example 13 described later.

<Preparation of pp53(70)-hmAG1-PB1>

To express a partial peptide of p53 whose C-terminus was fused to the PB1 domain of the p62 protein and mAG1 (p53(70)-mAG1-PB1)) as a first fusion protein in cells, a pp53(70)-hmAG1-PB1 vector was prepared as follows.

In preparing pp53(70)-hmAG1-PB1, first, a nucleotide sequence was designed in which a BamHI recognition sequence and a NotI recognition sequence were respectively added to the 5' end and the 3' end of the DNA encoding p53(70). Then, a DNA having the nucleotide sequence was artificially synthesized, cleaved with BamHI and NotI, and subsequently inserted into phmAG1-PB1-MNLinker having been treated with a combination of the same restriction enzymes. Thus, pp53(70)-hmAG1-PB1 was prepared.

<Cell Culturing and Transfection>

To express the fusion proteins in a combination according to the following (A) or (B) in cells, the vectors encoding these fusion proteins were introduced into HEK293 cells by a method described below:

(A) PB1-p53(70) and PB1-mAG1-MDM2; and
(B) p53(70)-mAG1-PB1 and PB1-MDM2.

First, HEK293 cells were cultured in a culture solution (DMEM high glucose (manufactured by SIGMA ALDRICH CO.), 10% FBS (manufactured by Equitech-Bio Inc.), 1% penicillin-streptomycin (manufactured by Life Technologies Corporation)). On the day before the transfection, the cells were seeded onto an 8-well chamber slide (manufactured by Nunc A/S), and cultured in 200 μL of the culture solution per well. Then, a DNA solution in which 100 ng of each of the vectors were mixed was diluted with 10 μL of OptiMEM (manufactured by Life Technologies Corporation), and 0.8 μl of Fugene HD (manufactured by Promega Corporation) was added thereto and then stirred. The resultant was further mixed with 100 μl of the culture solution, then added to the cultured cells, and cultured for 20 hours.

<Observation of Cells>

Figure 15:
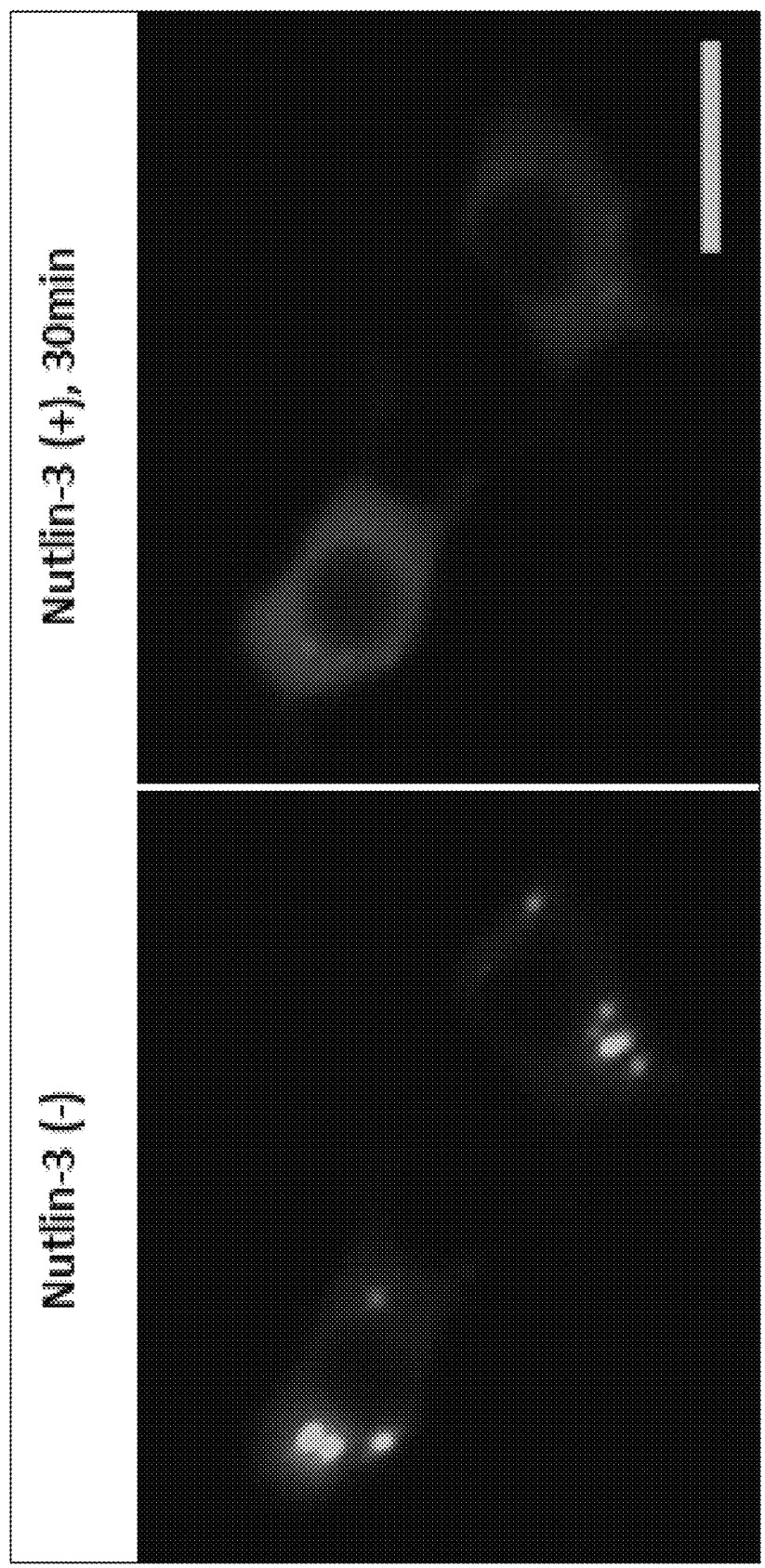
FIG. 15 shows micrographs for illustrating the result of expressing in cells a protein (PB1-p53(70)) composed of a PB1 domain of a p62 protein fused to the N-terminus of a partial peptide of an analysis target p53, and (PB1-mAG1-MDM2) composed of a PB1 domain of a p62 protein and mAG1 fused to the N-terminus of an analysis target MDM2 to analyze whether or not it is possible to determine a protein-protein interaction between p53(70) and MDM2 on the basis of a fluorescent focus. Note that, in the figure, "Nutlin-3 (−)" shows the result of observing the cells before the addition of Nutlin-3, which is an inhibitor against the protein-protein interaction. "Nutlin-3 (+), 30 min" shows the result of observing the cells when 30 minutes elapsed after the Nutlin-3 addition. In the figure, the scale bar represents 20 μm.
Figure 16:
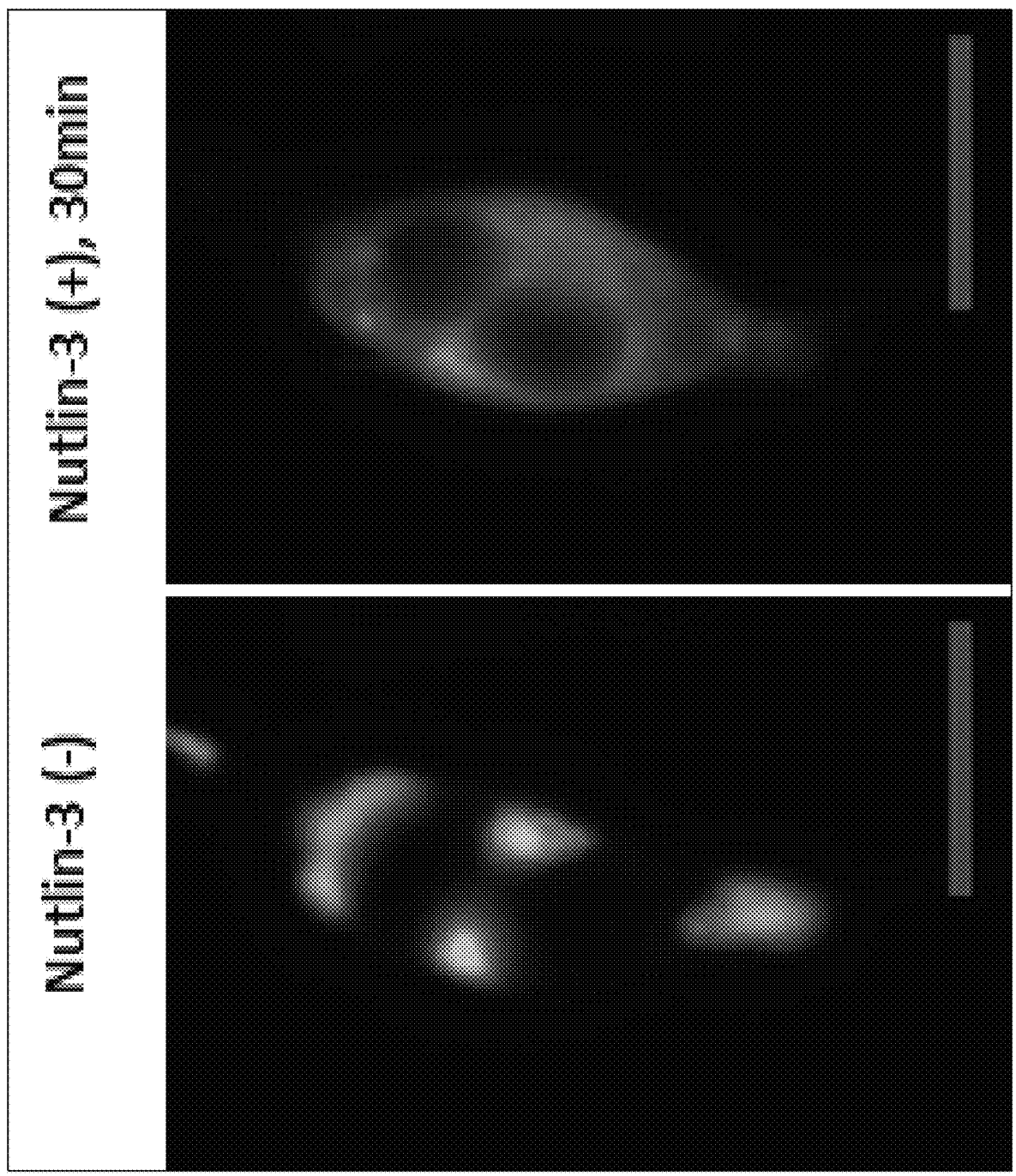
FIG. 16 shows micrographs for illustrating the result of expressing in cells a protein (p53(70)-mAG1-PB1) composed of mAG1 and a PB1 domain of a p62 protein fused to the C-terminus of a partial peptide of an analysis target p53, and (PB1-MDM2) composed of a PB1 domain of a p62 protein fused to the N-terminus of an analysis target MDM2 to analyze whether or not it is possible to determine a protein-protein interaction between p53(70) and MDM2 on the basis of a fluorescent focus. Note that, in the figure, "Nutlin-3 (−)" shows the result of observing the cells before the addition of Nutlin-3, which is an inhibitor against the protein-protein interaction. "Nutlin-3 (+), 30 min" shows the result of observing the cells when 30 minutes elapsed after the Nutlin-3 addition. In the figure, the scale bars represent 20 μm.

After the transfection treatment, the HEK293 cells were observed using an IX-81 inverted microscope, a U-MNIBA3 filter (manufactured by Olympus Corporation), and an ORCA-Flash 4.0 digital camera (manufactured by Hamamatsu Photonics K. K.). As an inhibitor against the protein-protein interaction between p53 and MDM2, Nutlin-3 was added to the culture solution to the final concentration of 40 μM. After the drug addition, the resultant was left standing at room temperature for 30 minutes, and the cells were observed. FIGS. 15 and 16 show images before the Nutlin-3 addition and 30 minutes after the addition.

As apparent from the result shown in FIGS. 15 and 16, distinctive fluorescent foci were observed in cells expressing the PB1-p53(70) and the PB1-mAG1-MDM2 and in cells expressing the p53(70)-mAG1-PB1 and the PB1-MDM2. Further, these fluorescent foci were extinguished by the Nutlin-3 addition, and the fluorescent signals were dispersed. As apparent from these, it was confirmed that the fluorescent foci were formed dependently on the protein-protein interaction between the p53 protein and the MDM2 protein.

Thus, it was confirmed that the present invention was capable of determining not only the homomultimer formation but also the heteromultimer formation. As verified in Example 3 also, Example 4 confirmed that the protein tags according to the present invention functioned even when fused to any of the N-terminus and the C-terminus of the analysis-target protein.

Example 5

The effectiveness of the system shown in FIG. 1 in determining a protein-protein interaction was confirmed by a method described below. Note that the detection targets in this examination were a FRB domain of a mTOR protein (hereinafter also referred to as "mTOR(FRB domain)") and a FKBP12 protein. These proteins have been known to interact with each other in the presence of rapamycin (see Chen J et al., Proc Natl Acad Sci USA., May 23, 1995, vol. 92, no. 11, pp. 4947 to 4951). Additionally, in this confirmation experiment also, a PB1 domain of a p62 protein was used as the multimerizable protein, and a mAG1 protein was used as the fluorescent protein, as in Example 5.

<Preparation of pPB1-hmAG1-FKBP12>

In constructing a vector (pPB1-hmAG1-FKBP12) for expressing a protein (PB1-mAG1-FKBP12) composed of the PB1 domain of the p62 protein and the mAG1 protein fused to the N-terminus of the FKBP12 protein, first, a pPB1-FKBP12 vector was prepared as follows.

A DNA was artificially synthesized which contained recognition sites of restriction enzymes (EcoRI and XhoI) and the stop codon at either end of a nucleotide sequence encoding the FKBP12 protein (the protein having the amino acid sequence of NCBI RefSeq ACCESSION No: NP_463460.1). Then, the obtained synthetic DNA was cleaved with EcoRI and XhoI, and inserted into pAsh-MCLinker having been treated with a combination of the same restriction enzymes. Thus, an expression vector (pPB1-FKBP12) encoding PB1-FKBP12 was constructed.

Next, the pPB1-FKBP12 was cleaved with BamHI and NotI, and then inserted into pPB1-hmAG1-MCLinker having been treated with a combination of the same restriction enzymes. Thus, pPB1-hmAG1-FKBP12 was prepared.

<Preparation of pmTOR(FRB domain)-PB1>

A vector (pmTOR(FRB domain)-PB1) for expressing a protein (mTOR(FRB domain)-PB1) composed of the PB1 domain of the p62 protein fused to the C-terminus of the FRB domain of the mTOR protein was prepared as follows. A DNA was artificially synthesized which contained EcoRI and XhoI recognition sites respectively at both ends of a nucleotide sequence encoding a portion of the mTOR protein (a region having the amino acids from positions 2025 to 2114 of the mTOR protein; a polypeptide having the amino acid sequence of SEQ ID NO: 41). Then, the obtained synthetic DNA was cleaved with EcoRI and XhoI, and inserted into pAsh-MNLinker having been treated with a combination of the same restriction enzymes. Thus, an expression vector (pmTOR(FRB domain)-PB1) encoding mTOR(FRB domain)-PB1 was prepared.

<Cell Culturing and Transfection>

To express the fusion proteins in a combination according to the following (C) in the cells, the vectors encoding these fusion proteins were introduced into HEK293 cells by the same method as that described in Example 4. (C) PB1-mAG1-FKBP12 and mTOR(FRB domain)-PB1

<Observation of Cells>

Figure 17:
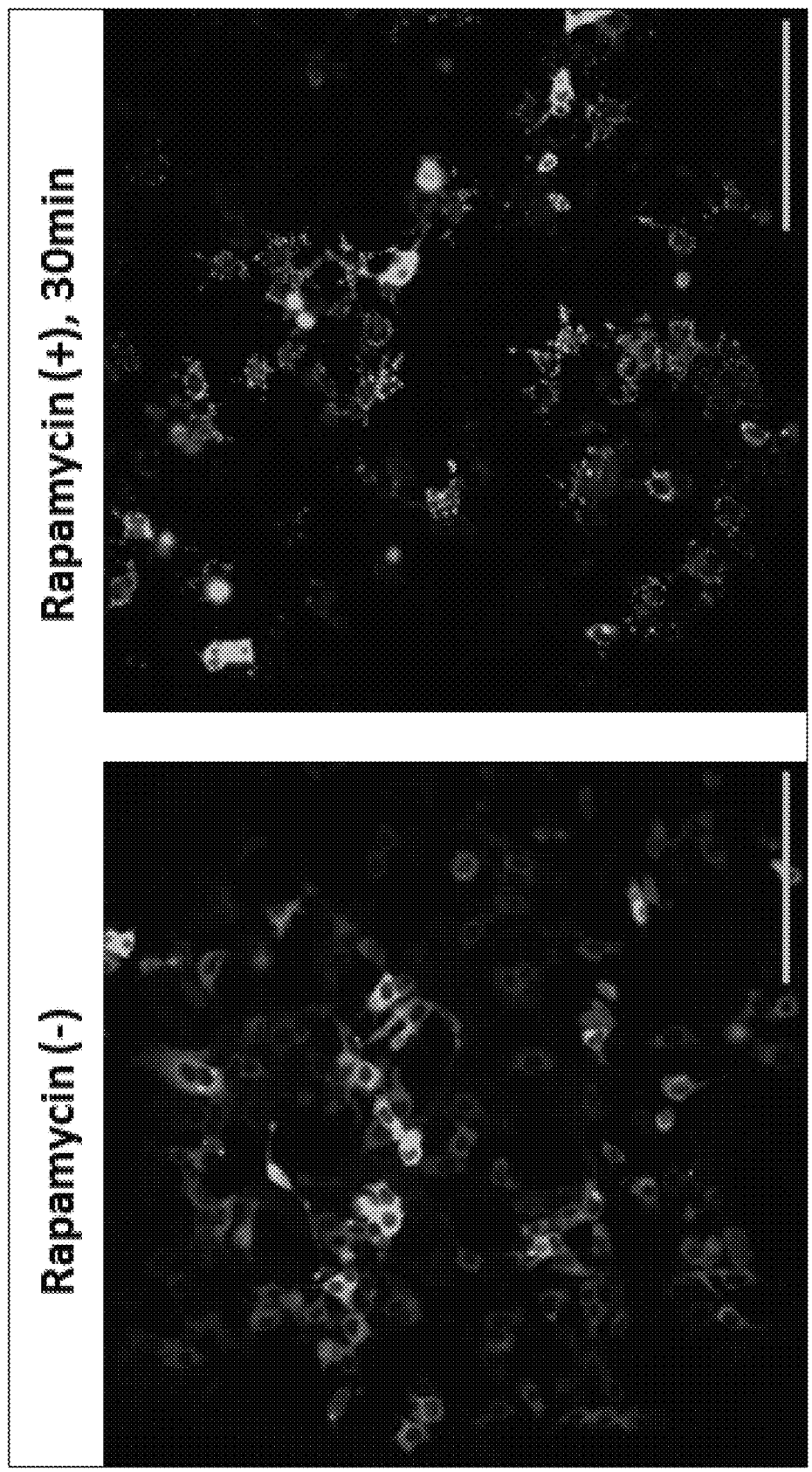
FIG. 17 shows micrographs for illustrating the result of expressing in cells a protein (PB1-mAG1-FKBP12) composed of a PB1 domain of a p62 protein and mAG1 fused to the N-terminus of an analysis target FKBP12, and a protein (mTOR(FRB domain)-PB1) composed of a PB1 domain of a p62 protein fused to the C-terminus of an analysis target FRB domain of a mTOR protein to analyze whether or not it is possible to determine a protein-protein interaction between FKBP12 and mTOR(FRB domain) on the basis of a fluorescent focus. Note that, in the figure, "Rapamycin (−)" shows the result of observing the cells before the addition of rapamycin, which is an inducer for the protein-protein interaction. "Rapamycin (+), 30 min" shows the result of observing the cells when 30 minutes elapsed after the rapamycin addition. In the figure, the scale bars represent 100 μm.

After the transfection treatment, the HEK293 cells were observed by the same method as that described in Example 4. Moreover, as an inducer for the protein-protein interaction between mTOR (FRB domain) and FKBP12, rapamycin was added to the culture solution to the final concentration of 500 nM. After the drug addition, the resultant was left standing at room temperature for 30 minutes, and the cells were observed. FIG. 17 shows images before the drug addition and 30 minutes after the addition.

As apparent from the result shown in FIG. 17, no fluorescent focus was observed in cells expressing the PB1-mAG1-FKBP12 and the mTOR(FRB domain)-PB1 before rapamycin was added. However, 30 minutes after the rapamycin addition, fluorescent foci were observed. As described above, since the fluorescent foci were formed in a manner dependent on rapamycin, it was confirmed that these fluorescent foci were formed dependently on the protein-protein interaction between FKBP12 and mTOR(FRB domain).

Thus, as verified in Example 4 also, it was confirmed that the present invention is capable of detecting not only the homomultimer formation as described in Examples 1 to 3, but also an interaction between different proteins.

Example 6

The effectiveness of the system shown in FIG. 2 in determining a protein-protein interaction was confirmed by a method described below. Note that the detection target in this examination was an interaction between a p53 protein and an MDM2 protein, and that Nutlin-3 known as an inhibitor against the interaction was also used in this confirmation experiment. Further, in this confirmation experiment, a PB1 domain of a p62 protein was used as the multimerizable protein. Moreover, a mAG1 protein was used as the fluorescent protein. In fusion proteins used, both of the p53 protein and the MDM2 protein were directly or indirectly bound to the fluorescent protein.

<Preparation of pPB1hmAG1-MNLinker>

A DNA (the DNA having the nucleotide sequence of SEQ ID NO: 27) was artificially synthesized which contained NheI and AgeI recognition sites respectively at both ends of a DNA fragment encoding a protein composed of mAG fused to the C-terminus of the PB1 domain of the PB1p62 protein. The DNA was cleaved with NheI and AgeI, and inserted into pAsh-MNLinker from which the DNA encoding the PB1 domain of the PB1p62 protein had been removed. Thus, a pPB1hmAG1-MNLinker plasmid vector was prepared.

<Preparation of pp53(70)-PB1-hmAG1>

To express a partial peptide of p53 whose C-terminus was fused to the PB1 domain of the p62 protein and mAG1 (p53(70)-PB1-mAG1) as a first fusion protein in cells, a pp53(70)-PB1-hmAG1 vector was prepared as follows.

In preparing pp53(70)-PB1-hmAG1, first, a nucleotide sequence was designed in which a BamHI recognition sequence and a NotI recognition sequence were respectively added to the 5' end and the 3' end of the DNA encoding p53(70). Then, a DNA having the nucleotide sequence was artificially synthesized, cleaved with BamHI and NotI, and subsequently inserted into pPB1-hmAG1-MNLinker having been treated with a combination of the same restriction enzymes. Thus, pp53(70)-PB1-hmAG1 was prepared.

<Cell Culturing and Transfection>

To express the fusion proteins in a combination according to the following (A) or (B) in cells, the vectors encoding these fusion proteins were introduced into HEK293 cells by the same method as that described in Example 5; (A) p53(70)-mAG1-PB1 and PB1-mAG1-MDM2; and (B) p53(70)-PB1-mAG1 and PB1-mAG1-MDM2.

<Observation of Cells>

Figure 18:
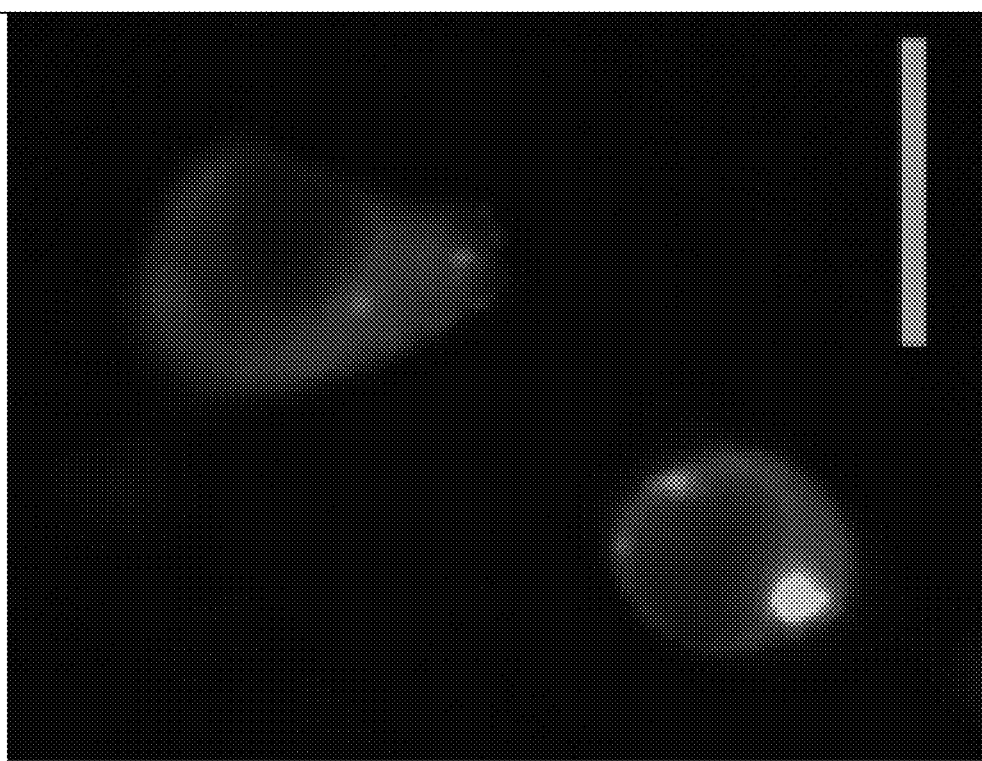
FIG. 18 shows micrographs for illustrating the result of expressing in cells a protein (p53(70)-mAG1-PB1) composed of mAG1 and a PB1 domain of a p62 protein fused to the N-terminus of a partial peptide of an analysis target p53, and (PB1-mAG1-MDM2) composed of a PB1 domain of a p62 protein and mAG1 fused to the N-terminus of an analysis target MDM2 to analyze whether or not it is possible to determine a protein-protein interaction between p53(70) and MDM2 on the basis of a fluorescent focus. Note that, in the figure, "Nutlin-3 (−)" shows the result of observing the cells before the addition of Nutlin-3, which is an inhibitor against the protein-protein interaction. "Nutlin-3 (+), 30 min" shows the result of observing the cells when 30 minutes elapsed after the Nutlin-3 addition. In the figure, the scale bars represent 20 μm.
Figure 18:
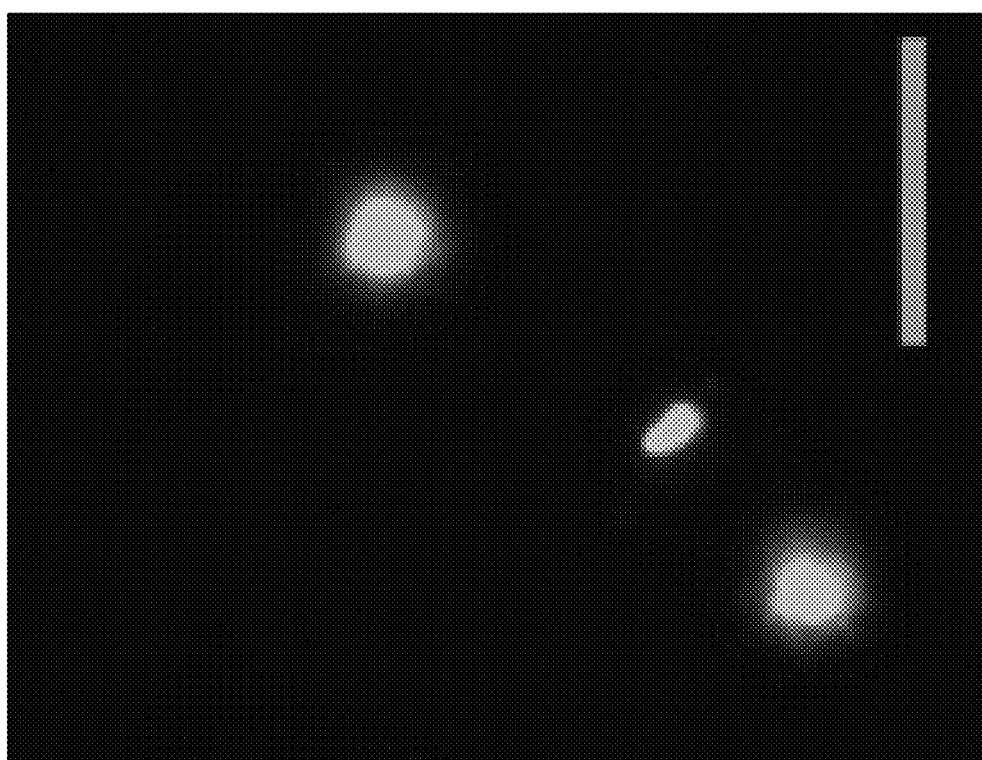
Figure 19:
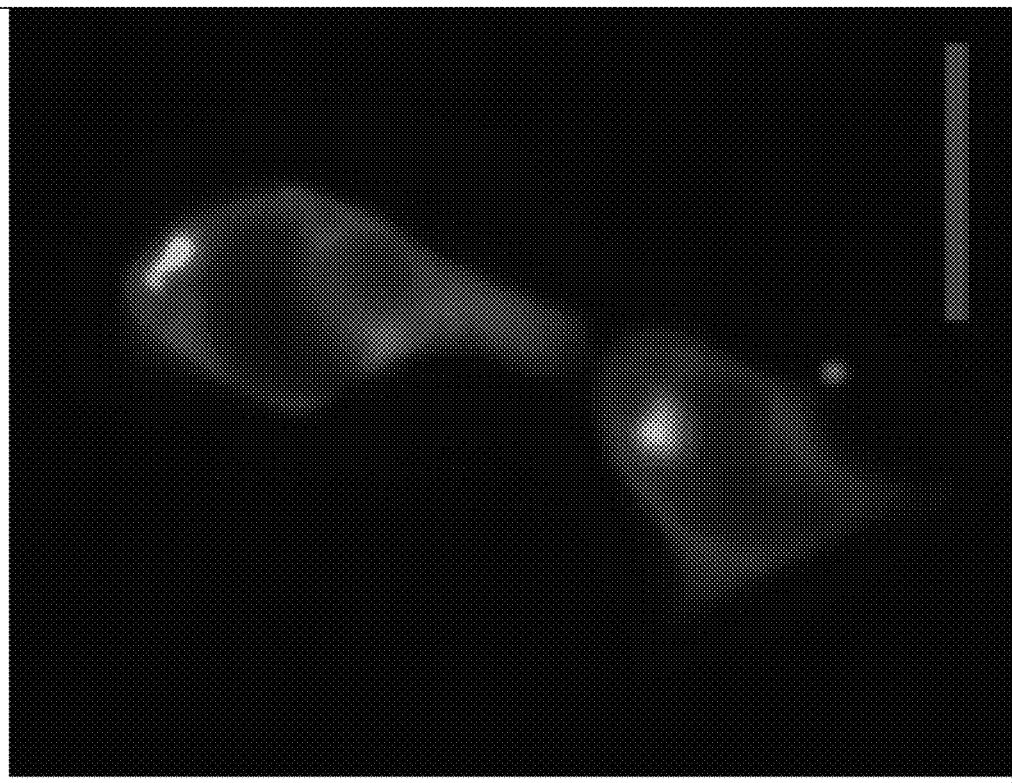
FIG. 19 shows micrographs for illustrating the result of expressing in cells a protein (p53(70)-PB1-mAG1) composed of a PB1 domain of a p62 protein and mAG1 fused to the C-terminus of a partial peptide of an analysis target p53, and (PB1-mAG1-MDM2) composed of a PB1 domain of a p62 protein and mAG1 fused to the N-terminus of an analysis target MDM2 to analyze whether or not it is possible to determine a protein-protein interaction between p53(70) and MDM2 on the basis of a fluorescent focus. Note that, in the figure, "Nutlin-3 (−)" shows the result of observing the cells before the addition of Nutlin-3, which is an inhibitor against the protein-protein interaction. "Nutlin-3 (+), 30 min" shows the result of observing the cells when 30 minutes elapsed after the Nutlin-3 addition. In the figure, the scale bars represent 20 μm.
Figure 19:
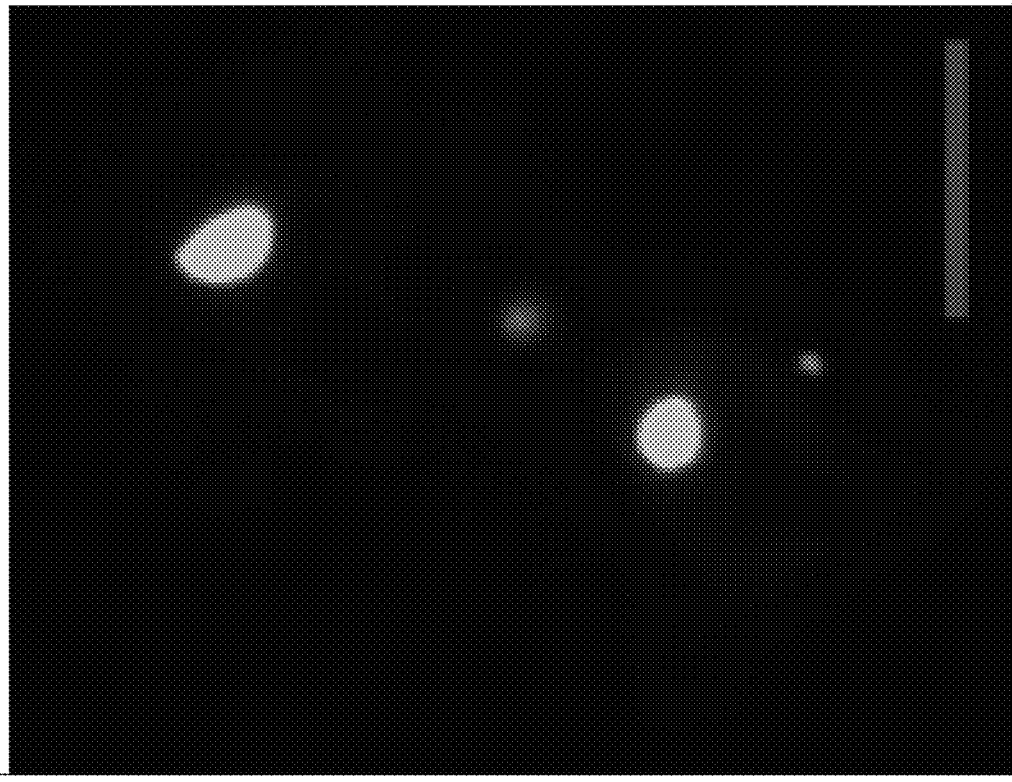

After the transfection treatment, the HEK293 cells were observed by the same method as that described in Example 4. Specifically, as an inhibitor against the protein-protein interaction between p53 and MDM2, Nutlin-3 was added to the culture solution to the final concentration of 40 µM. After the drug addition, the resultant was left standing at room temperature for 30 minutes, and the cells were observed. FIGS. 18 and 19 show images before the Nutlin-3 addition and 30 minutes after the addition.

As apparent from the result shown in FIGS. 18 and 19, distinctive fluorescent foci were observed in all cells. Further, these fluorescent foci were extinguished by the Nutlin-3 addition, and the fluorescent signals were dispersed. As apparent from these, it was confirmed that the fluorescent foci were formed dependently on the protein-protein interaction between the p53 protein and the MDM2 protein. Moreover, it was also confirmed that the method of the present invention was capable of determining the protein-protein interaction regardless of whether the protein directly fused to p53(70) was either mAG1 (in the case of (A) above) or the PB1 domain (in the case of (B) above).

Example 7

The effectiveness of the system shown in FIG. 2 in determining a protein-protein interaction was confirmed by a method described below. Note that the detection target in this examination was a protein-protein interaction between mTOR(FRB domain) and a FKBP12 protein. Moreover, to induce the interaction, rapamycin was also used in this system. Additionally, in this confirmation experiment also, a PB1 domain of a p62 protein was used as the multimerizable protein, and a mAG1 protein was used as the fluorescent protein, as in Example 7.

<Preparation of pmTOR(FRB domain)-hmAG1-PB1>

A vector (pmTOR(FRB domain)-hmAG1-PB1) for expressing a protein (mTOR(FRB domain)-mAG1-PB1) composed of mAG1 and the PB1 domain of the p62 protein fused to the C-terminus of the FRB domain of the mTOR protein was prepared as follows.

The pmTOR (FRB domain)-PB1 was cleaved with BamHI and NotI, and the mTOR(FRB domain) fragment was purified. Then, the fragment was inserted into phmAG1-PB1-MNLinker having been treated with a combination of the same restriction enzymes. Thus, pmTOR(FRB domain)-hmAG1-PB1 was prepared.

<Cell Culturing and Transfection>

To express the fusion proteins in a combination according to the following (C) in the cells, the vectors encoding these fusion proteins were introduced into HEK293 cells by the same method as that described in Example 5. (C) mTOR (FRB domain)-mAG1-PB1 and PB1-mAG1-FKBP12.

<Observation of Cells>

After the transfection treatment, the HEK293 cells were observed by the same method as that described in Example 5. Specifically, as an inducer for the protein-protein interaction between mTOR(FRB domain) and FKBP12, rapamycin was added to the culture solution to the final concentration of 500 nM. After the drug addition, the resultant was left standing at room temperature for 30 minutes, and the cells were observed. FIGS. 20 and 21 show images before the drug addition and 30 minutes after the addition.

As apparent from the result shown in FIGS. 20 and 21, no fluorescent focus was observed in cells expressing the mTOR(FRB domain)-mAG1-PB1 and the PB1-mAG1-FKBP12 before rapamycin was added. However, 30 minutes after the rapamycin addition, fluorescent foci were observed. As described above, since the fluorescent foci were formed in a manner dependent on rapamycin, it was confirmed that these fluorescent foci were formed dependently on the protein-protein interaction between FKBP12 and mTOR (FRB domain).

As verified in Examples 1 to 3 also, the effectiveness of the system for detecting a fluorescent focus formed by assembly formation between a first fusion protein and a second fusion protein shown in FIG. 2 was confirmed in Examples 6 and 7, too. Particularly, it was confirmed that the system shown in FIG. 2 according to the present invention was capable of determining not only the homomultimer formations as described in Examples 1 to 3, but also the interactions between different proteins.

Example 8

It was confirmed that the fluorescent protein used in the present invention was not limited to mAG1 by a method described below in which the fluorescent protein in Example 1 was changed from mAG1 to DG1 or mCherry.

<Preparation of pPB1-hDG1-FKBP12 Mutant>

A vector (pPB1-hDG1-FKBP12 mutant) for expressing a protein (PB1-DG1-FKBP12 mutant) composed of the PB1 domain of the p62 protein and the Dronpa-Green1 fluorescent protein fused to the N-terminus of the FKBP12 mutant was prepared as follows.

A DNA sequence was artificially synthesized which encoded DG1 (a protein having the amino acid sequence of Genbank ACCESSION No: BAD72874), and which had a SpeI recognition sequence at the 5' end and an AgeI recognition sequence at the 3' end. Then, the obtained DNA was cleaved with these restriction enzymes, and inserted into the pPB1-hmAG1-FKBP12 mutant which had been treated with a combination of the same restriction enzymes, and from which the hmAG1 portion had been removed. Thus, a pPB1-hDG1-FKBP12 mutant was prepared.

<Preparation of pPB1-mCherry-FKBP12 Mutant>

A vector (pPB1-mCherry-FKBP12 mutant) for expressing a protein (PB1-mCherry-FKBP12 mutant) composed of the PB1 domain of the p62 protein and the mCherry fluorescent protein fused to the N-terminus of the FKBP12 mutant was prepared as follows.

In preparing pPB1-mCherry-FKBP12, first, a nucleotide sequence was designed in which a SpeI recognition sequence and an AgeI recognition sequence were respectively added to the 5' end and the 3' end of a DNA encoding mCherry (a protein having the amino acid sequence of Genbank ACCESSION No: AAV52164). Then, a DNA having the nucleotide sequence was artificially synthesized, cleaved with SpeI and AgeI, and subsequently inserted into the pPB1-hmAG1-FKBP12 mutant which had been treated with a combination of the same restriction enzymes, and from which the hmAG1 portion had been removed. Thus, a pPB1-mCherry-FKBP12 mutant was prepared.

<Cell Culturing and Transfection>

To express the PB1-hDG1-FKBP12 mutant or the PB1-mCherry-FKBP12 mutant in cells, the vectors encoding these fusion proteins were introduced into HEK293 cells by the same method as that described in Example 4.

<Observation of Cells>

After the transfection treatment, the HEK293 cells were observed using an IX-81 inverted microscope and an ORCA-Flash 4.0 digital camera. A U-MNIBA3 filter (manufactured by Olympus Corporation) and a U-MWIG3 filter (manufactured by Olympus Corporation) were used respectively for the DG1 and mCherry observations. The homodimer formation of the FKBP12 mutant was induced by adding 500 nM B/B Homodimerizer. After the drug addition, the resultant was left standing at room temperature. The cells were observed after 1, 2, and 3 hours elapsed. FIGS. 22 and 23 show images before the drug addition and 1, 2, and 3 hours after the addition.

As apparent from the result shown in FIGS. 22 and 23, drug-addition dependent increases in fluorescent foci were observed in both of cells expressing the PB1-DG1-FKBP12 mutant and cells expressing the PB1-mCherry-FKBP12 mutant. Thus, it was confirmed that the fluorescent protein used in the present invention was not limited to mAG1.

Example 9

It was confirmed that a protein other than the PB1 domain of the p62 protein was also utilizable as a multimerizable protein in the present invention. Specifically, a SAM domain of a Tankyrase 1 protein was used in place of the PB1 domain in the method described in Example 1, and the homodimer formation of the FKBP12 protein mutant was detected using materials and methods described below.

<Preparation of pTankyrase-hmAG1-FKBP12 Mutant>

A vector (pTankyrase-hmAG1-FKBP12 mutant) for expressing a protein (Tankyrase-mAG1-FKBP12 mutant) composed of the SAM domain of the Tankyrase 1 protein and mAG1 fused to the N-terminus of the FKBP12 mutant was prepared as follows.

A DNA sequence was artificially synthesized which encoded a protein (Tankyrase-mAG1, the protein had the amino acid sequence of SEQ ID NO: 43) composed of mAG1 fused to the C-terminus of the SAM domain of the Tankyrase 1 protein, and which had a NheI recognition sequence at the 5' end and an AgeI recognition sequence at the 3' end. The DNA was cleaved with NheI and AgeI, and then inserted into the pPB1-hmAG1-FKBP12 mutant which had been treated with the same restriction enzymes, and from which the PB1-hmAG1 portion had been removed. Thus, a pTankyrase-hmAG1-FKBP12 mutant vector was prepared.

<Cell Culturing and Transfection>

HEK293 cells were cultured in DMEM (high glucose) supplemented with 10% FBS and 1% penicillin-streptomycin. Then, on the day before the transfection, the cells were seeded onto an 8-well chamber slide. The cells were cultured in 200 µL of the culture solution per well. Subsequently, a DNA solution was prepared by mixing 200 ng of the plasmid with 10 µL of OptiMEM, and 0.8 µl of Fugene HD (manufactured by Promega Corporation) was added thereto and then stirred. The resultant was further mixed with 100 µl of the culture solution, then added to the HEK293 cells, and cultured for 20 hours.

<Observation of Cells>

After the transfection treatment, the HEK293 cells were observed using an IX-81 inverted microscope and an ORCA-Flash 4.0 digital camera. A U-MNIBA3 filter was used for the observation. The homodimer formation of the FKBP12 mutant was induced by adding 500 nM B/B Homodimerizer to the medium. In addition, after the drug was added, the resultant was left standing at room temperature. The cells were observed after 3 hours elapsed. FIG. 24 shows images obtained before the drug addition and 3 hours after the addition.

As apparent from the result shown in FIG. 24, fluorescent focus formations attributable to the addition of the drug for inducing the homodimer formation of the Tankyrase-mAG1-FKBP12 mutant were observed in cells expressing this mutant. Thus, it was confirmed that if a protein was capable of forming a multimer, the protein was utilizable in the present invention.

Example 10

As in Example 9, it was confirmed that proteins other than the PB1 domain of the p62 protein were also utilizable as a multimerizable protein in the present invention. Specifically, a SAM domain of a Tankyrase 1 protein, a PB1 domain of a PKCiota protein, a SAM domain of a TEL protein, or a SAM domain of a DGK delta protein was used in place of the PB1 domain in the method described in Example 3, and the homomultimer formation of the p53 protein was detected using materials and methods described below.

<Preparation of pTankyrase-hmAG1-p53>

A vector (pTankyrase-hmAG1-p53) for expressing a protein (Tankyrase-mAG1-p53) composed of the SAM domain of the Tankyrase 1 protein and mAG1 fused to the N-terminus of p53 was prepared as follows.

A DNA sequence was artificially synthesized which encoded a protein (Tankyrase-mAG1, the protein had the amino acid sequence of SEQ ID NO: 43) composed of mAG1 fused to the C-terminus of the SAM domain of the Tankyrase 1 protein, and which had a NheI recognition sequence at the 5' end and an AgeI recognition sequence at the 3' end. The DNA was cleaved with NheI and AgeI, and then inserted into the phmAG1PB1-p53 which had been treated with the same restriction enzymes, and from which the hmAG1PB1 portion had been removed. Thus, a pTankyrase-hmAG1-p53 vector was prepared.

<Preparation of pPKCi-hmAG1-p53>

A vector (pTankyrase-hmAG1-p53) for expressing a protein (PKCi-mAG1-p53) composed of the PB1 domain of the PKCiota protein and mAG1 fused to the N-terminus of p53 was prepared as follows.

A DNA sequence was artificially synthesized which encoded a protein (PKCi-mAG1, the protein had the amino acid sequence of SEQ ID NO: 45) composed of mAG1 fused to the C-terminus of the PB1 domain of the PKCiota protein, and which had a NheI recognition sequence at the 5' end and an AgeI recognition sequence at the 3' end. The DNA was cleaved with NheI and AgeI, and then inserted into the phmAG1PB1-p53 which had been treated with the same restriction enzymes, and from which the hmAG1-PB1 portion had been removed. Thus, a pPKCi-hmAG1-p53 vector was prepared.

<Preparation of pTEL-hmAG1-p53>

A vector (pTEL-hmAG1-p53) for expressing a protein (TEL-mAG1-p53) composed of the SAM domain of the TEL protein and mAG1 fused to the N-terminus of p53 was prepared as follows.

A DNA sequence was artificially synthesized which encoded a protein (TEL-mAG1, the protein had the amino acid sequence of SEQ ID NO: 47) composed of mAG1 fused to the C-terminus of the SAM domain of the TEL protein, and which had a NheI recognition sequence at the 5' end and an AgeI recognition sequence at the 3' end. The DNA was cleaved with NheI and AgeI, and then inserted into the phmAG1-PB1-p53 which had been treated with the same restriction enzymes, and from which the hmAG1-PB1 portion had been removed. Thus, a pTEL-hmAG1-p53 vector was prepared.

<Preparation of pDGKd-hmAG1-p53>

A vector (pDGKd-hmAG1-p53) for expressing a protein (DGKd-mAG1-p53) composed of the SAM domain of the DGK delta protein and mAG1 fused to the N-terminus of p53 was prepared as follows.

A DNA sequence was artificially synthesized which encoded a protein (DGKd-mAG1, the protein had the amino acid sequence of SEQ ID NO: 49) composed of mAG1 fused to the C-terminus of the SAM domain of the DGK delta protein, and which had a NheI recognition sequence at the 5' end and an AgeI recognition sequence at the 3' end. The DNA was cleaved with NheI and AgeI, and then inserted into the phmAG1PB1-p53 which had been treated with the same restriction enzymes, and from which the hmAG1-PB1 portion had been removed. Thus, a pDGKd-hmAG1-p53 vector was prepared.

<Cell Culturing and Transfection>

HEK293 cells were cultured in DMEM (high glucose) supplemented with 10% FBS and 1% penicillin-streptomycin. Then, on the day before the transfection, the cells were seeded onto an 8-well chamber slide, and cultured in 200 µL of the culture solution per well. Subsequently, a DNA solution was prepared by mixing 200 ng of the plasmid with 10 μL of OptiMEM, and 0.8 μl of Fugene HD was added thereto and then stirred. The resultant was further mixed with 100 μl of the culture solution, then added to the HEK293 cells, and cultured for 48 hours.

<Observation of Cells>

After the transfection treatment, the HEK293 cells were observed using an IX-81 inverted microscope and an ORCA-Flash 4.0 digital camera. A U-MNIBA3 filter was used for the observation. FIG. 25 shows the obtained result.

As apparent from the result shown in FIG. 25, fluorescent focus formations indicating the homomultimer formation of p53 were observed in all of cells expressing the Tankyrase-mAG1-p53, cells expressing the PKCi-mAG1-p53, cells expressing the TEL-mAG1-p53, and cells expressing the DGKd-mAG1-p53. Thus, it was confirmed that any protein capable of forming a multimer was utilizable in the present invention.

Example 11

It was confirmed by a method described below that the present invention was capable of detecting a homodimer formed in a manner dependent on a signal transduction. When a signal transduction pathway involving EGF, GPCR, and so forth is activated, ERK2 located downstream thereof is phosphorylated and activated. In addition, it has been known that ERK2 forms a homodimer after the activation (see Harvey C D et al., Proc Natl Acad Sci USA, 2008, vol. 105, no. 49, pp. 19264 to 19269, Khokhlatchev A V et al., Cell, 1998, vol. 93, iss. 4, pp. 605 to 615). Hence, the detection of this homodimer formation was tested according to the present invention. Note that, in this confirmation experiment, a PB1 domain of a p62 protein was used as the multimerizable protein, and a mAG1 protein was used as the fluorescent protein. Additionally, it has also been revealed that the ERK2 activation takes place in the cytoplasm and the nucleus (see Ebisuya M et al., J Cell Sci., 2005, 118 (Pt 14), pp. 2997 to 3002).

<Preparation of pERK2-hmAG1-PB1 and pERK2-PB1-hmAG1>

Vectors (pERK2-hmAG1-PB1 and pERK2-PB1-hmAG1) for expressing proteins (ERK2-mAG1-PB1 and ERK2-PB1-mAG1) each composed of mAG1 and the PB1 domain of the p62 protein fused to the C-terminus of ERK2 were prepared as follows.

A nucleotide sequence was designed in which an XhoI recognition sequence and a NotI recognition sequence were respectively added to the 5' end and the 3' end of a nucleotide sequence encoding ERK2 (a protein having the amino acid sequence of NCBI RefSeq ACCESSION No: NP_002736.3). Then, a DNA having the resulting nucleotide sequence was artificially synthesized, and cleaved with XhoI and NotI. Meanwhile, phmAG1-PB1-MNLinker and pPB1-hmAG1-MNLinker were treated with a combination of the same restriction enzymes. Subsequently, the synthetic DNA fragment was inserted into these vectors. Thus, vectors (pERK2-hmAG1-PB1 and pERK2-PB1-hmAG1) encoding ERK2-mAG1-PB1 and ERK2-PB1-mAG1 were prepared.

<Cell Culturing and Transfection>

HEK293 cells were selected as cells into which the expression vectors prepared above were introduced. The cells were first cultured in DMEM (high glucose) supplemented with 10% FBS (manufactured by Equitech-Bio Inc.) and 1% penicillin-streptomycin. Then, on the day before the introduction of the expression vectors, these cells were seeded onto a 35-mm dish, and cultured in 1.5 ml of the culture solution. Subsequently, 1 μg of the expression vector (pERK2-hmAG1-PB1 or pERK2-PB1-hmAG1) was diluted with 100 μL of OptiMEM, and 10 μL of PolyFect(registered trademark) Transfection Reagent was added thereto and then stirred. The resultant was further mixed with 600 μL of the culture solution. Thereafter, each solution of the expression vectors was added to the cultured cells. The pERK2-hmAG1PB1 transfected cells were observed 20 hours after the vector introduction. To the pERK2-PB1-hmAG1 transfected cells, G418 was added at a concentration of 500 μg/mL, and further cultured for one week. After that, viable cells were detached using a trypsin solution, diluted with a culture solution containing G418 (500 μg/ml), and then cultured in a 96-well plate at 0.5 cells/well. Subsequently, cells which formed single colonies were cultured to expand.

<Observation of Cells>

After the transfection treatment, the HEK293 cells were cultured for 4 hours in a buffer at pH of 7.4 containing Hanks' Balanced Salt Solutions and 20 mM HEPES, so that the cells were under a serum-starved condition. Then, the cells were observed using an IX-71 inverted fluorescence microscope (the magnification of the objective lens: 20×), a U-MGFPHQ filter, and an ORCA-ER digital camera. The homodimer formation of ERK2 was induced by adding EGF (epidermal growth factor, manufactured by Sigma-Aldrich Co.) to the buffer to the final concentration of 50 ng/ml. FIGS. 26 and 27 show images before the EGF addition and 8 minutes after the addition.

As apparent from the result shown in FIG. 26, no fluorescent focus was detected before EGF was added, and fluorescent signals were dispersedly observed in the cytoplasms. Then, 8 minutes after the EGF addition, fluorescent foci were observed in multiple cells.

Moreover, as apparent from the result shown in FIG. 27, fluorescent foci indicating the homodimer formation of ERK2 were detected throughout HEK293 cells constitutively expressing the ERK2-PB1-hmAG1.

Thus, it was confirmed that the present invention was capable of detecting the homodimer formation of ERK2 attributable to the activation of the intracellular signal transduction pathway. Moreover, the present invention confirmed that detecting a fluorescent focus enabled detection of an activation attributable to the phosphorylation of ERK2, and also eventually an activation of a signal transduction pathway involving EGF and so forth located upstream of ERK2.

Example 12

It was confirmed by a method described below that the present invention was capable of detecting a homodimer formed in a manner dependent on a signal transduction. Specifically, when a signal transduction pathway involving IL-6 and so forth is activated, STAT3 located downstream thereof is phosphorylated and activated. In addition, it has been known that STAT3 forms a homodimer after the activation and transmits the extracellular signal into the nucleus (see Becker S et al., Nature, 1998, vol. 394, no 1. 6689, pp. 145 to 151, Johnston P A et al., Mol Interv., 2011, vol. 11, no. 1, pp. 18 to 26). Hence, the detection of the STAT3 homodimer formation was tested according to the present invention. Note that, in this confirmation experiment, a PB1 domain of a p62 protein was used as the multimerizable protein, and a mAG1 protein was used as the fluorescent protein.

<Preparation of pPB1-hmAG1-STAT3>

A vector (pPB1-hmAG1-STAT3) for expressing a protein (PB1-mAG1-STAT3) composed of the PB1 domain of the p62 protein and mAG1 fused to the N-terminus of STAT3 was prepared as follows.

A nucleotide sequence was designed in which an XhoI recognition sequence was added to the 5' end of a nucleotide sequence encoding STAT3 (a protein having the amino acid sequence of NCBI RefSeq ACCESSION No: NP_644805.1) while the stop codon and a NotI recognition sequence were added to the 3' end of the nucleotide sequence. Then, a DNA having the resulting nucleotide sequence was artificially synthesized, cleaved with XhoI and NotI, and then inserted into pPB1-hmAG1-MCLinker having been treated with a combination of the same restriction enzymes. Thus, pPB1-hmAG1-STAT3 was prepared.

<Cell Culturing and Transfection>

HEK293 cells were selected as cells into which the expression vector prepared above was introduced. The cells were first cultured in DMEM (high glucose) supplemented with 10% FBS and 1% penicillin-streptomycin. Then, on the day before the introduction of the expression vector, these cells were seeded onto a 35-mm dish, and cultured in 1.5 ml of the culture solution. Subsequently, 1 µg of the expression vector (pPB1-hmAG1-STAT3) was diluted with 100 µL of OptiMEM, and 10 µL of PolyFect(registered trademark) Transfection Reagent was added thereto and then stirred. The resultant was further mixed with 600 µL of the culture solution. Thereafter, the mixture solution of the expression vector was added to the cultured cells. After that, G418 was added thereto at a concentration of 500 µg/mL, and further cultured for one week. Next, viable cells were detached using a trypsin solution, diluted with a culture solution containing G418 (500 µg/ml), and then cultured in a 96-well plate at 0.5 cells/well. Subsequently, cells which formed single colonies were cultured to expand.

<Observation of Cells>

The HEK293 cells constitutively expressing the PB1-mAG1-STAT3 were cultured for 4 hours in a buffer at pH of 7.4 containing Hanks' Balanced Salt Solutions and 20 mM HEPES, so that the cells were under a serum-starved condition. Then, the cells were observed using an IX-71 inverted fluorescence microscope (the magnification of the objective lens: 20×), a U-MGFPHQ filter, and an ORCA-ER digital camera. The homodimer formation of STAT3 was induced by adding Human Recombinant IL-6 (manufactured by R&D SYSTEMS, INC.) to the buffer to the final concentration of 100 ng/ml. FIG. 28 shows images before the IL-6 addition and 50 minutes after the addition.

As apparent from the result shown in FIG. 28, no fluorescent focus was detected before IL-6 was added, and fluorescent signals were dispersedly observed in the cytoplasms. Then, 50 minutes after the IL-6 addition, fluorescent foci were observed in multiple cells.

Thus, it was confirmed that the present invention was capable of detecting the homodimer formation of STAT3 attributable to the activation of the intracellular signal transduction pathway. Moreover, the present invention confirmed that detecting a fluorescent focus enabled detection of an activation attributable to the phosphorylation of STAT3, and also eventually an activation of a signal transduction pathway involving IL-6 and so forth located upstream of STAT3.

Example 13

As described in Examples 1 to 12, it was revealed that the systems shown in FIGS. 1 and 2 were effective in determining a protein-protein interaction. Next, the present inventors came up with a system shown in FIG. 3 as another embodiment of such systems.

Specifically, when a third fusion protein comprising a first protein and a multimerizable protein, a fourth fusion protein comprising a second protein and a multimerizable protein, and a fifth fusion protein comprising a multimerizable protein and a fluorescent protein are expressed in a cell or introduced into a cell, the multimerizable proteins associates with each other. Thereby, the third fusion protein binds to the fifth fusion protein while the fourth fusion protein binds to the fifth fusion protein, so that proteins respectively corresponding to the first fusion protein and the second fusion protein shown in FIGS. 1 and 2 are presumably expressed in the cell. Moreover, if such a presumption is correct, as in the cases of the systems shown in FIGS. 1 and 2, the following is presumed also from the system shown in FIG. 3: an interaction if any between the first protein and the second protein induces multimer formation between the multimerizable protein and another multimerizable protein; thereby, the fusion proteins autonomously form an assembly, and the fluorescent protein contained in the fusion protein is detected as a fluorescent focus.

Hence, the effectiveness of the system shown in FIG. 3 in determining a protein-protein interaction was examined using materials and methods described below. Note that the detection target in this examination was an interaction between a p53 protein and an MDM2 protein, and that Nutlin-3 known as an inhibitor against the interaction was also used in this examination (see Vassilev L T et al., Science, Feb. 6, 2004, vol. 303, no. 5659, pp. 844 to 848). Further, in this examination, a PB1 domain of a p62 protein was used as the multimerizable protein, and a hmAG1 protein was used as the fluorescent protein.

<Preparation of pp53-PB1 and pPB1-MDM2>

To express in cells the third and fourth fusion proteins according to the present invention, that is, a fusion protein (p53-PB1) comprising the p53 protein and the PB1 domain of the p62 protein as well as a fusion protein (PB1-MDM2) comprising the MDM2 protein and the PB1 domain of the p62 protein, expression vectors encoding the fusion proteins were prepared by methods described below.

A DNA (the DNA having the nucleotide sequence of SEQ ID NO: 33) was artificially synthesized which contained restriction enzyme sites at either end of a nucleotide sequence encoding a portion of the p53 protein (a region having the amino acids from positions 1 to 70 of the p53 protein, the region had the amino acid sequence of SEQ ID NO: 34, hereinafter also referred to as "p53(70)"). Then, the obtained synthetic DNA was cleaved with EcoRI and XhoI, and inserted into pAsh-MNLinker (manufactured by MEDICAL & BIOLOGICAL LABORATORIES CO., LTD.) having been treated with a combination of the same restriction enzymes. Thus, an expression vector (pp53(70)-PB1) encoding p53(70)-PB1 was constructed. Note that inserting a DNA encoding a certain protein into a multiple cloning site of the pAsh-MNLinker in accordance with the reading frame allows an expression, in cells, of a protein having an Ash protein tag (the PB1 domain of the p62 protein) fused to the C-terminus of the certain protein via a linker peptide.

Moreover, a DNA (the DNA having the nucleotide sequence of SEQ ID NO: 35) was artificially synthesized which contained restriction enzyme sites at either end of a nucleotide sequence encoding a portion of MDM2 (a region having the amino acids from positions 1 to 119 of the MDM2 protein, the region had the amino acid sequence of SEQ ID NO: 36). Then, the obtained synthetic DNA was cleaved with EcoRI and XhoI, and inserted into pAsh-MCLinker (manufactured by MEDICAL & BIOLOGICAL LABORATORIES CO., LTD.) having been treated with a combination of the same restriction enzymes. Thus, an expression vector (pPB1-MDM2) encoding PB1-MDM2 was constructed. Note that inserting a DNA encoding a certain protein into a multiple cloning site of the pAsh-MCLinker in accordance with the reading frame allows an expression, in cells, of a protein having an Ash protein tag (the PB1 domain of the p62 protein) fused to the N-terminus of the certain protein via a linker peptide.

<Preparation of phmAG1PB1>

To express the fifth fusion protein in cells, an expression vector was prepared by a method described below. Specifically, first, a DNA having the nucleotide sequence of SEQ ID NO: 37 was artificially synthesized which contained restriction enzyme sites at either end of a DNA having a nucleotide sequence encoding the PB1 domain of the p62 protein (the DNA encoding a protein having the amino acid sequence of SEQ ID NO: 38). Then, the obtained synthetic DNA was cleaved with EcoRI and NotI, and inserted into phmAG1-MCLinker (manufactured by limited company Amalgaam Co., Ltd.) having been treated with a combination of the same restriction enzymes. Thus, an expression vector (phmAG1-PB1) encoding a fusion protein (mAG1-PB1) composed of mAG1 and the PB1 domain of the p62 protein was constructed.

<Preparation of Cells Constitutively Expressing mAG1-PB1>

Next, the phmAG1-PB1 prepared above was introduced into HeLaS3 cells to establish cells constitutively expressing the fifth fusion protein (mAG1-PB1) according to the present invention. Specifically, first, HeLaS3 cells were cultured in DMEM (low glucose, manufactured by SIGMA ALDRICH CO.) supplemented with 10% FBS (manufactured by Equitech-Bio Inc.). Then, on the day before the transfection, the HeLaS3 cells were seeded onto a 35-mm dish (manufactured by BD Falcon) and cultured in 1.5 mL of the culture solution. Subsequently, 1 μg of the phmAG1-PB1 was diluted with 100 μL of OptiMEM (manufactured by Life Technologies Corporation), and 10 μL of PolyFect (registered trademark) Transfection Reagent (manufactured by QIAGEN N.V.) was added thereto and then stirred. The resultant was further mixed with 600 μL of the culture solution, thereafter added to the HeLaS3 cells, and cultured for 20 hours. After that, G418 was added thereto at a concentration of 500 μg/mL, and further cultured for one week. Next, viable cells were detached using a trypsin solution, diluted with a culture solution containing G418 (500 μg/ml), and then cultured in a 96-well plate at 0.5 cells/well. Subsequently, cells which formed single colonies were cultured to expand.

<Cell Culturing and Transfection>

To additionally express the p53(70)-PB1 and the PB1-MDM2 in the cells constitutively expressing the mAG1-PB1, the pp53(70)-PB1 and the pPB1-MDM2 were introduced into the cells by a method described below.

Specifically, first, the cells constitutively expressing the mAG1-PB1 established above were cultured in DMEM (high glucose, manufactured by SIGMA ALDRICH CO.) supplemented with 10% FBS (Equitech-Bio Inc.) and 1% penicillin-streptomycin (Life Technologies Corporation). Then, on the day before the transfection, the cells were seeded onto an 8-well chamber slide (manufactured by Nunc A/S), and cultured in 200 μL of the culture solution per well. Subsequently, a DNA solution prepared by mixing 100 ng of each of the pp53(70)-PB1 and the pPB1-MDM2 was diluted with 10 μL of OptiMEM (manufactured by Life Technologies Corporation). Thereafter, 0.4 μL of Turbofect (manufactured by Thermo Fisher Scientific Inc.) was added thereto and then stirred. The resultant was further mixed with 100 μl of the culture solution. After that, the obtained mixture solution was added to the cultured cells and cultured for 20 hours.

Meanwhile, as negative controls, a DNA solution prepared by mixing 100 ng of each of the pp53(70)-PB1 and pAsh-MNLinker, and a DNA solution prepared by mixing 100 ng of each of the pPB1-MDM and pAsh-MNLinker were respectively introduced into the cells constitutively expressing the mAG1-PB1 by the same method as that described above.

<Observation of Cells>

The three types of cells prepared above and described below were observed by the method described in Example 1:

cells constitutively expressing the mAG1-PB1 and further expressing the p53(70)-PB1 and the PB1-MDM2;

cells constitutively expressing the mAG1-PB1 and further expressing the p53(70)-PB1 and the PB1 domain of the p62 protein (negative control); and cells constitutively expressing the mAG1-PB1 and further expressing the PB1-MDM and the PB1 domain of the p62 protein (negative control).

FIG. 29 shows the obtained result.

Moreover, to the cells expressing the p53(70)-PB1 and the PB1-MDM2, Nutlin-3 was added to the final concentration of 20 μM. Then, the cells were also observed under a condition of inhibiting the interaction between p53 and MDM2. FIG. 30 shows the obtained result. Note that FIG. 29 shows the result of the observation with a 20× magnification of the objective lens as in Example 1, while FIG. 30 shows the result of the observation with a 40× magnification of the objective lens.

As apparent from the result shown in FIG. 29, fluorescent foci were detected in the cells expressing the mAG1-PB1, the p53(70)-PB1, and the PB1-MDM2 (see the image on the left in FIG. 29). On the other hand, no fluorescent focus was detected in the cells expressing the mAG1-PB1, the p53(70)-PB1, and the PB1 domain of the p62 protein, and in the cells expressing the mAG1-PB1, the PB1-MDM2, and the PB1 domain of the p62 protein.

Further, Nutlin-3 was added to the cells from which the fluorescent foci were detected, and observed 15 minutes thereafter. As a result, the fluorescent foci were extinguished as shown in FIG. 30. Thus, it was confirmed that the fluorescent foci were formed dependently on the interaction between p53 and MDM2.

Example 14

As in Example 13, the effectiveness of the system shown in FIG. 3 in determining a protein-protein interaction was confirmed by a method described below. Note that the detection target in this examination was a protein-protein interaction between mTOR(FRB domain) and a FKBP12 protein. Moreover, to induce the interaction, rapamycin was also used in this system. Further, in this confirmation experiment, a PB1 domain of a p62 protein was used as the multimerizable protein, and a mAG1 protein was used as the fluorescent protein.

<Preparation of pmTOR(FRB domain)-PB1>

A vector for expressing a protein (mTOR(FRB domain)-PB1) composed of the PB1 domain of the p62 protein fused to the C-terminus of mTOR(FRB domain) as the third fusion protein according to the present invention was prepared as described in Example 5.

<Preparation of pPB1-mTOR(FRB Domain)>

A vector (pPB1-mTOR(FRB domain)) for expressing a protein (PB1-mTOR(FRB domain)) composed of the PB1 domain of the p62 protein fused to the N-terminus of mTOR(FRB domain) as the third fusion protein according to the present invention was prepared as follows.

A DNA was artificially synthesized which contained recognition sites of restriction enzymes (EcoRI and XhoI) and the stop codon at either end of a nucleotide sequence encoding mTOR(FRB domain). Then, the obtained synthetic DNA was cleaved with EcoRI and XhoI, and inserted into pAsh-MCLinker having been treated with a combination of the same restriction enzymes. Thus, an expression vector (pPB1-mTOR(FRB domain)) encoding PB1-mTOR(FRB domain) was constructed.

<Preparation of pFKBP12-PB1>

A vector (pFKBP12-PB1) for expressing a protein (FKBP12-PB1) composed of the PB1 domain of the p62 protein fused to the C-terminus of the FKBP12 protein as the fourth fusion protein according to the present invention was prepared as follows.

A DNA was artificially synthesized which contained EcoRI and XhoI recognition sites respectively at both ends of a nucleotide sequence encoding the FKBP12 protein (the protein having the amino acid sequence of NCBI RefSeq ACCESSION No: NP_463460.1). Then, the obtained synthetic DNA was cleaved with EcoRI and XhoI, and inserted into pAsh-MNLinker having been treated with a combination of the same restriction enzymes. Thus, an expression vector (pFKBP12-PB1) encoding FKBP12-PB1 was constructed.

<Preparation of pPB1-FKBP12>

A plasmid vector (pPB1-FKBP12) for expressing a protein (PB1-FKBP12) composed of the PB1 domain of the p62 protein fused to the N-terminus of FKBP12 protein as the fourth fusion protein according to the present invention was prepared as described in Example 5.

<Cell Culturing and Transfection>

(A) PB1-mTOR(FRB domain), PB1-FKBP12, and mAG1PB1
(B) PB1-mTOR(FRB domain), FKBP12-PB1, and mAG1PB1
(C) mTOR(FRB domain)-PB1, PB1-FKBP12, and mAG1PB1
(D) mTOR(FRB domain)-PB1, FKBP12-PB1, and mAG1PB1

To express the fusion proteins in combinations according to the above (A) to (D), each vector was introduced into HEK293 cells by a method described below.

Specifically, first, HEK293 cells were cultured in DMEM (high glucose) supplemented with 10% FBS and 1% penicillin-streptomycin. Then, on the day before the transfection, the cells were seeded onto a 96-well multiwell plate, and cultured in 140 μL of the culture solution per well. Subsequently, a DNA solution prepared by mixing 133 ng of each of the plasmid vectors was diluted with 10 μL of OptiMEM. Thereafter, 0.8 μL of Fugene HD was added thereto and then stirred. The resultant was further mixed with 90 μl of the culture solution. After that, the obtained mixture solution was added to the cultured cells and cultured for 20 hours.

<Observation of Cells>

The culture solution of the cells prepared above was discarded, and 100 μL of a buffer at pH 7.4 containing Hanks' Balanced Salt Solutions and 20 mM HEPES was added. Then, the cells were observed using IN Cell Analyzer 1000. Moreover, rapamycin was added to each well to the final concentration of 500 nM. After left standing at room temperature for 1 hour, the cells were observed. FIG. 31 shows the obtained result.

As apparent from the result shown in FIG. 31, no fluorescent focus was detected in any cells before rapamycin was added. However, as a result of adding rapamycin, fluorescent foci were detected. As described above, since the fluorescent foci were detected in a manner dependent on rapamycin, it was confirmed that the fluorescent foci were formed dependently on the interaction between mTOR(FRB domain) and FKBP12. Moreover, this Example also confirmed that the protein tag according to the present invention (the protein comprising the multimerizable protein or the fluorescent protein) functioned even when fused to any of the N-terminus and the C-terminus of the analysis-target protein.

Figure 3:
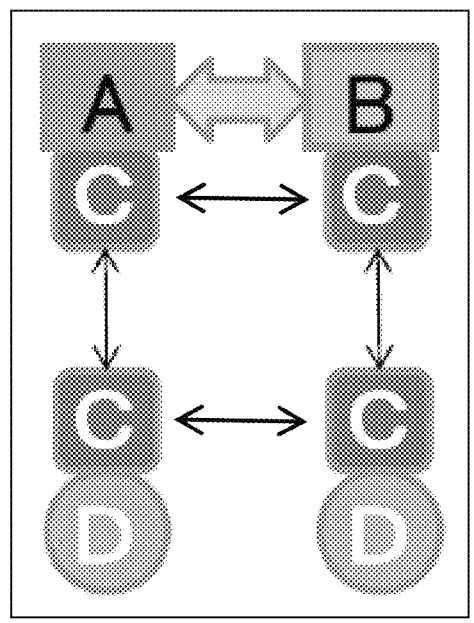
FIG. 3 is a conceptual diagram for illustrating one embodiment of a second method for determining a protein-protein interaction of the present invention. Specifically, the diagram illustrates that when a third fusion protein comprising a first protein (in the figure, A) and a multimerizable protein (in the figure, C), a fourth fusion protein comprising a second protein (in the figure, B) and a multimerizable protein (in the figure, C), and a fifth fusion protein comprising a multimerizable protein (in the figure, C) and a fluorescent protein (in the figure, D) are expressed in a cell or introduced into a cell, an interaction between the first protein and the second protein can be determined according to the detection of a fluorescent focus formed by assembly formation among the third fusion protein, the fourth fusion protein, and the fifth fusion protein in the cell.

Hereinabove, the present invention revealed as described in Examples 4 and 5 that it was possible to determine a protein-protein interaction also by utilizing an association between the multimerizable protein and the fluorescent protein in a cell as a result of an autonomous-association between the multimerizable protein and another multimerizable protein as shown in FIG. 3. Further, since the cells constitutively expressing the fifth fusion protein according to the present invention were successfully established, it was confirmed that the protein exhibited no cytotoxicity and the like.

Moreover, in the method shown in FIG. 3, the protein fused to proteins to be analyzed (first and second proteins) was a multimerizable protein. On the other hand, in the methods shown in FIGS. 1 and 2, the protein fused to proteins to be analyzed includes a fluorescent protein in addition to a multimerizable protein. Thus, the method shown in FIG. 3 allows a reduction in the molecular weight of the protein tag fused to the proteins to be analyzed, in comparison with the methods shown in FIGS. 1 and 2. Therefore, the functions of the proteins to be analyzed are hardly affected.

Furthermore, in the method shown in FIG. 3, cells constitutively expressing the fusion protein comprising the fluorescent protein are prepared in advance as described in Example 4. This reduces the influence of a variation in the fluorescent signals among the cells, even if the fusion proteins comprising the proteins to be analyzed are transiently expressed in these cells. This makes it possible to more stably determine a protein-protein interaction.

Example 15

As described above, it was revealed that the systems shown in FIGS. 1 to 3 were effective in determining a protein-protein interaction. Next, the present inventors came up with a system shown in FIG. 4 as another embodiment of these systems.

Specifically, when a first labeled protein comprising an affinity tag and a first protein, a second labeled protein comprising an affinity tag and a second protein, and a sixth fusion protein comprising a multimerizable protein, a fluorescent protein, and a binding partner having an affinity for any of the affinity tags are expressed in a cell or introduced into a cell, each affinity tag binds to the binding partner. Thereby, the first labeled protein binds to the sixth fusion protein comprising the binding partner bound thereto while the second labeled protein binds to the sixth fusion protein comprising the binding partner bound thereto, so that proteins respectively corresponding to the first fusion protein and the second fusion protein shown in FIGS. 1 and 2 are expressed in the cell. Moreover, as in the cases of the systems shown in FIGS. 1 and 2, when these proteins are expressed, an interaction if any between the first protein and the second protein induces multimer formation between the multimerizable protein and another multimerizable protein; thereby, the fusion proteins autonomously form an assembly, and the fluorescent protein contained in the fusion protein is detected as a fluorescent focus.

Then, the effectiveness of the system shown in FIG. 4 in determining a protein-protein interaction was confirmed using materials and methods described below. Note that the detection target in this confirmation experiment was homodimer formation of a cell transmembrane protein CD80. In addition, a cell transmembrane protein CD2 known to be present in the form of monomer in cells was also used as the negative control (as to the protein-protein interactions of these proteins, see James J R et al., Nat Methods., 2006, vol. 3, nol. 12, pp. 1001 to 1006).

<Preparation of pCD80-FRB>

The mTOR(FRB domain) was selected as the affinity tag. To express a CD80 protein (CD80-FRB) having this tag fused thereto as the first and second labeled proteins in cells, a pCD80-FRB vector was prepared as follows.

First, a DNA was artificially synthesized which contained BamHI and EcoRI recognition sequences respectively at both ends of a nucleotide sequence encoding CD80 (a protein having the amino acid sequence of NCBI Ref Seq ACCESSION No: NP_005182.1). Then, the obtained synthetic DNA was cleaved with BamHI and EcoRI, and inserted into phmAG1-MNLinker having been treated with a combination of the same restriction enzymes. Thus, a pCD80-hmAG1 vector was constructed.

Next, a DNA was artificially synthesized which contained AgeI and XbaI recognition sequences and the stop codon at either end of a nucleotide sequence encoding mTOR(FRB domain). Then, the obtained synthetic DNA was cleaved with AgeI and XbaI, and inserted into the pCD80-hmAG1 which had been treated with a combination of the same restriction enzymes, and from which the hmAG1 region had been removed. Thus, an expression vector (pCD80-FRB) encoding CD80-FRB was constructed.

<Preparation of pCD2-FRB>

As described above, to express a CD2 protein (CD2-FRB) having the affinity tag mTOR(FRB domain) fused thereto as the first and second labeled proteins in cells, a vector was prepared as follows.

First, a DNA was artificially synthesized which contained BamHI and EcoRI recognition sequences respectively at both ends of a nucleotide sequence encoding a CD2 protein (the protein having the amino acid sequence of Genbank ACCESSION No: AAA51946.1). Then, the obtained synthetic DNA was cleaved with BamHI and EcoRI, and inserted into phmAG1-MNLinker having been treated with a combination of the same restriction enzymes. Thus, pCD2-hmAG1 was constructed.

Next, a DNA was artificially synthesized which contained AgeI and XbaI recognition sequences and the stop codon at either end of a nucleotide sequence encoding mTOR(FRB domain). Then, the obtained synthetic DNA was cleaved with AgeI and XbaI, and inserted into the pCD2-hmAG1 which had been treated with a combination of the same restriction enzymes, and from which the hmAG1 region had been removed. Thus, an expression vector (pCD2-FRB) encoding CD2-FRB was constructed.

<Preparation of pPB1-hmAG1-FKBP12>

FKBP12 was selected as the binding partner having an affinity for the affinity tag, a PB1 domain of p62 was selected as the multimerizable protein, and mAG1 was selected as the fluorescent protein. Moreover, to express PB1-hmAG1-FKBP12 composed of these proteins fused to each other as the sixth fusion protein in cells, a pPB1-hmAG1-FKBP12 vector was prepared as described in Example 5.

<Cell Culturing and Transfection>

To express the fusion proteins in a combination according to the following (A) or (B), the plasmid vectors prepared above were introduced into HEK293 cells by a method described below;
(A) CD80-FRB and PB1-mAG1-FKBP12; and
(B) CD2-FRB and PB1-mAG1-FKBP12.

Specifically, first, HEK293 cells were cultured in a culture solution (DMEM high glucose, 10% FBS, 1% penicillin-streptomycin). Then, on the day before the transfection, the cells were seeded onto an 8-well chamber, and cultured in 100 μL of the culture solution per well. Subsequently, a DNA solution prepared by mixing 200 ng of each of the plasmids was diluted with 10 μL of OptiMEM. Thereafter, 0.8 μL of Fugene HD was added thereto and then stirred. The resultant was further mixed with 90 μl of the culture solution. After that, the obtained mixture solution was added to the cultured cells and cultured for 20 hours.

<Observation of Cells>

After the transfection treatment but before the observation, the culture solution of the HEK293 cells was replaced with an observation buffer (buffer at pH of 7.4 containing Hanks' Balanced Salt Solutions and 20 mM HEPES) containing 500 nM rapamycin. After the replacement with the drug-supplemented buffer, the resultant was left standing at room temperature for 30 minutes. Then, the cells were observed using an IX-71 inverted fluorescence microscope, a U-MGFPHQ filter, and an ORCA-ER digital camera. FIG. 32 shows the obtained result.

As shown in FIG. 32, when the CD80 was used as the detection target, fluorescent foci were observed at the cell membrane. On the other hand, when the CD2 was used as the detection target, no fluorescent focus was observed. Thus, the effectiveness of the system shown in FIG. 4 was confirmed.

Figure 4:
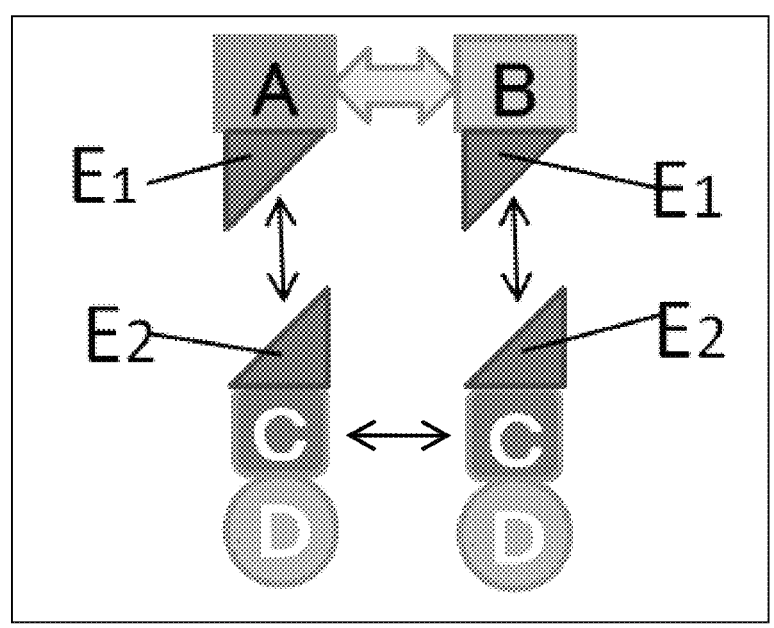
FIG. 4 is a conceptual diagram for illustrating one embodiment of a third method for determining a protein-protein interaction of the present invention. Specifically, the diagram illustrates that when a first labeled protein comprising a first protein (in the figure, A) and an affinity tag (in the figure, E1), a second labeled protein comprising a second protein (in the figure, B) and an affinity tag (in the figure, E1), and a sixth fusion protein comprising a multimerizable protein (in the figure, C), a fluorescent protein (in the figure, D), and a binding partner (in the figure, E2) having an affinity for any of the affinity tags and bound to the sixth fusion protein are expressed in a cell or introduced into a cell, an interaction between the first protein and the second protein can be determined according to the detection of a fluorescent focus formed by assembly formation among the first labeled protein, the second labeled protein, and the sixth fusion protein comprising the binding partner bound thereto in the cell.

Moreover, in the third method for determining a protein-protein interaction of the present invention shown in FIG. 4, as in the case of the method shown in FIG. 3, it is not necessary to directly or indirectly fuse a fluorescent protein to the proteins to be analyzed. This allows a reduction in the molecular weight of the protein tag fused to the proteins to be analyzed, in comparison with the methods shown in FIGS. 1 and 2. Therefore, the functions of the proteins to be analyzed are hardly affected.

Further, since the proteins to be analyzed can be kept in a cell while being fused to the tag having a low molecular weight in this manner, this makes it possible to set a state where a protein-protein interaction can be determined at any timing by constructing a system in which the fusion proteins according to the present invention are reconstituted in response to a stimulus such as rapamycin addition as described above.

Furthermore, preparing cells constitutively expressing the sixth fusion protein comprising the fluorescent protein in advance reduces the influence of a variation in the fluorescent signals among the cells, even if the fusion proteins comprising the proteins to be analyzed are transiently expressed in these cells. This makes it also possible to more stably determine a protein-protein interaction.

Meanwhile, cell transmembrane proteins such as CD80 pass through organelles such as Golgi body and are localized at the cell membrane. For this reason, when such a protein fused to a tag is expressed, this makes it difficult for the protein to pass through the organelle and reach the cell membrane. Therefore, it is generally said that it is difficult to detect an interaction of a cell membrane protein unlike those of cytoplasmic proteins and the like.

On the other hand, according to the third method for determining a protein-protein interaction of the present invention, since the tag to be fused can be relatively small, this makes it easy for cell transmembrane proteins to reach the cell membrane. Moreover, expressing the tag-fused cell transmembrane proteins such as CD80 on the membrane and then binding the multimerizable protein and the fluorescent protein expressed in the cytoplasm to the tag make it possible to easily detect protein-protein interactions of the cell transmembrane proteins, too, as apparent from the result shown in FIG. 26.

Further, the use of this third determination method also makes it possible to determine protein-protein interactions between separate cells (for example, a protein-protein interaction between PD1 and PDL1), which cannot be detected by techniques such as FRET/BRET/BiFC utilizing the proximity of tags.

Example 16

Figure 7:
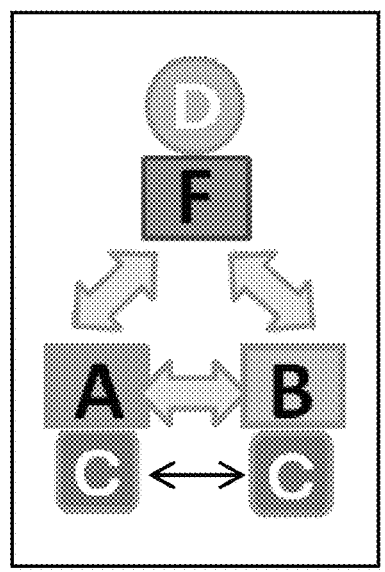
FIG. 7 is a conceptual diagram for illustrating one embodiment of a sixth method for determining a protein-protein interaction of the present invention. Specifically, the diagram illustrates that when a thirteenth fusion protein comprising a first protein (in the figure, A) and a multimerizable protein (in the figure, C), a fourteenth fusion protein comprising a second protein (in the figure, B) and a multimerizable protein (in the figure, C), and a fifteenth fusion protein comprising a third protein (in the figure, F) and a fluorescent protein (in the figure, D) are expressed in a cell or introduced into a cell, an interaction among the first protein, the second protein, and the third protein can be determined according to the detection of a fluorescent focus formed by assembly formation among the thirteenth fusion protein, the fourteenth fusion protein, and the fifteenth fusion protein in the cell.

Next, based on the systems shown in FIG. 1 and so forth, the present inventors came up with a system shown in FIG. 7 as one embodiment for detecting an interaction among three or more proteins.

Specifically, when a thirteenth fusion protein comprising a first protein and a multimerizable protein, a fourteenth fusion protein comprising a second protein and a multimerizable protein, and a fifteenth fusion protein comprising a third protein and a fluorescent protein are expressed in a cell or introduced into a cell, an interaction if any among the first protein, the second protein, and the third protein, as in the cases of the systems shown in FIG. 1 and so forth, induces multimer formation between the multimerizable protein and another multimerizable protein; thereby, the fusion proteins autonomously form an assembly, and the fluorescent protein contained in the fusion protein is detected as a fluorescent focus.

Then, the effectiveness of the system shown in FIG. 7 in determining a protein-protein interaction was confirmed using materials and methods described below. Note that the detection target in this confirmation experiment was heterotrimer formation among p50, p60, and IκBα.

Note that it has been known that p50 and p65 form a heterodimer, constituting NFκB. Further, NFκB functions in the nucleus as a transcription factor playing a role in modulating inflammatory cytokine expression. However, it has been known that a further interaction with IκBα retains NFκB in the cytoplasm, suppressing the transcription function (see Marc D. Jacobs et al., Cell, Dec. 11, 1998, vol. 95, pp. 749 to 758). Thus, in this Example, multimerizable proteins were respectively fused to p50 and p65, while a fluorescent protein was fused to IκBα. These proteins were expressed in cells. Thereby, p50 and p65 interacted with each other and formed an assembly, and further the IκBα fused to the fluorescent protein accumulated on the assembly, forming a fluorescent focus. Thus, it was confirmed that the detection of a trimer complex was possible.

<Preparation of pPB1-p50>

To express, as the thirteenth fusion protein, a p50 protein whose N-terminus was fused to a PB1 domain of p62 as the multimerizable protein (PB1-p50) in cells, a pPB1-p50 vector was constructed as described below.

A DNA was artificially synthesized which contained EcoRI and XhoI recognition sequences respectively at both ends of a nucleotide sequence encoding p50 (a protein having the amino acid sequence of NCBI RefSeq ACCESSION No: NP_003989.2). Then, the obtained synthetic DNA was treated with EcoRI and XhoI, and inserted into pAsh-MCLinker having been treated with the same restriction enzymes. Thus, a pPB1-p50 was prepared.

<Preparation of pp65-PB1>

To express, as the fourteenth fusion protein, a p65 protein whose C-terminus was fused to a PB1 domain of p62 as the multimerizable protein (p65-PB1) in cells, a pp65-PB1 vector was constructed as described below.

A DNA was artificially synthesized which contained BamHI and XhoI recognition sequences respectively at both ends of a nucleotide sequence encoding p65 (a protein having the amino acid sequence of NCBI RefSeq ACCESSION No: NP_068810.3). Then, the obtained synthetic DNA was treated with BamHI and XhoI, and inserted into pAsh-MNLinker having been treated with the same restriction enzymes. Thus, a pp65-PB1 vector was prepared.

<Preparation of phmKO2-IκBα>

To express, as the fifteenth fusion protein, an IκBα protein whose N-terminus was fused to mKO2 as the fluorescent protein (mKO2-IκBα) in cells, a phmKO2-IκBα vector was constructed as described below.

A DNA was artificially synthesized which contained BamHI and EcoRI recognition sequences respectively at both ends of a nucleotide sequence encoding IκBα (a protein having the amino acid sequence of NCBI RefSeq ACCESSION No: NP_065390.1). Then, the obtained synthetic DNA was treated with BamHI and EcoRI, and inserted into phmKO2-MCLinker (manufactured by MEDICAL & BIOLOGICAL LABORATORIES CO., LTD.) having been treated with the same restriction enzymes. Thus, a phmKO2-IκBα vector was prepared.

<Cell Culturing and Transfection>

To express the fusion proteins in a combination of the following (A) or (B), the plasmid vectors prepared above were introduced into HEK293 cells by the same method as that described in Example 12:

(A) PB1-p50, p65-PB1, and mKO2-IκBα; and
(B) PB1-p50 and mKO2-IκBα (negative control).

<Observation of Cells>

After the transfection treatment, the HEK293 cells were observed using an IX-71 inverted fluorescence microscope, a U-MGFPHQ filter, and an ORCA-Flash 4.0 digital camera. FIG. 33 shows the obtained result.

As apparent from the result shown in FIG. 33, when the PB1-p50, the p65-PB1, and the mKO2-IκBα were expressed in the cells, fluorescent foci were detected. On the other hand, when the PB1-p50 and the mKO2-IκBα were expressed in the cells, no fluorescent focus was detected. Thus, it was confirmed that, as shown in FIG. 7, the interaction between p50 and p65 formed an assembly by utilizing the multimerizable proteins, and further that the IκBα fused to the fluorescent protein accumulated on the assembly, thereby forming the fluorescent foci. To put it differently, it was confirmed that detecting the fluorescent foci enabled determination of an interaction among three types of proteins.

Example 17

As in Example 16, the effectiveness of the system shown in FIG. 7 in determining a protein-protein interaction was confirmed using materials and methods described below. Note that the detection target in this confirmation experiment was heterotrimer formation among CDK4, Cyclin D1, and p21. It has been known that, in the nucleus of a cell, p21 recognizes and interacts with a complex composed of CDK4 and Cyclin D1 (see LaBaer J et al., Genes Dev., Apr. 1, 1997, vol. 11, no. 7, pp. 847 to 862). Moreover, it has also been revealed that such heterotrimer formation inhibits cell-cycle progression (transition from a G1 phase to an S phase) otherwise promoted by a complex composed of CDK4 and Cyclin D1.

<Preparation of pp21-PB1>

To express, as the thirteenth fusion protein, a p21 protein whose C-terminus was fused to a PB1 domain of p62 as the multimerizable protein (p21-PB1) in cells, a pp21-PB1 vector was constructed as described below.

A DNA was artificially synthesized which contained BamHI and NotI recognition sequences respectively at both ends of a nucleotide sequence encoding p21 (a protein having the amino acid sequence of NCBI RefSeq ACCESSION No: NP_510867.1). Then, the obtained synthetic DNA was treated with BamHI and NotI, and inserted into pAsh-MNLinker having been treated with the same restriction enzymes. Thus, a pp21-PB1 vector was prepared.

<Preparation of pCDK4-PB1>

To express, as the fourteenth fusion protein, a CDK4 protein whose C-terminus was fused to a PB1 domain of p62 as the multimerizable protein (CDK4-PB1), in cells, a pCDK4-PB1 vector was constructed as described below.

A DNA was artificially synthesized which contained BamHI and NotI recognition sequences respectively at both ends of a nucleotide sequence encoding CDK4 (a protein having the amino acid sequence of NCBI RefSeq ACCESSION No: NP_000066.1). Then, the obtained synthetic DNA was treated with BamHI and NotI, and inserted into pAsh-MNLinker having been treated with the same restriction enzymes. Thus, a pCDK4-PB1 vector was prepared.

<Preparation of pCDK4>

To express, as a negative control, a CDK4 protein (CDK4) not fused to other proteins, a pCDK4 vector was constructed as described below.

A DNA was artificially synthesized which contained a BamHI recognition sequence at one end of the nucleotide sequence encoding CDK4 while the stop codon and a NotI recognition sequence at the other end. Then, the obtained synthetic DNA was treated with BamHI and NotI, and inserted into pAsh-MNLinker having been treated with the same restriction enzymes. Thus, a pCDK4 vector was prepared.

<phmAG1-Cyclin D1>

To express, as the fifteenth fusion protein, a Cyclin D1 protein whose N-terminus was fused to mAG1 as the fluorescent protein (mAG1-Cyclin D1) in cells, a phmAG1-Cyclin D1 vector was constructed as described below.

A DNA was artificially synthesized which contained a BamHI recognition sequence at one end of a nucleotide sequence encoding Cyclin D1 (a protein having the amino acid sequence of NCBI RefSeq ACCESSION No: NP_444284.1) while the stop codon and a NotI recognition sequence at the other end. Then, the obtained synthetic DNA was treated with BamHI and NotI, and inserted into phmAG1-MCLinker having been treated with the same restriction enzymes. Thus, a phmAG1-Cyclin D1 vector was prepared.

<Cell Culturing and Transfection>

To express the fusion proteins in a combination of the following (A), (B), or (C), the plasmid vectors prepared above were introduced into HEK293 cells by the same method as that described in Example 14:

(A) mAG1-Cyclin D1, p21-PB1, and CDK4-PB1;
(B) mAG1-Cyclin D1, p21-PB1, and PB1 (negative control); and
(C) mAG1-Cyclin D1, p21-PB1, and CDK4 (negative control).

Note that, in (B), to express PB1 (a PB1 domain of a p62 protein), pAsh-MNLinker was introduced into the cells.

<Observation of Cells>

After the transfection treatment, the HEK293 cells were observed by the same method as that described in Example 14. FIG. 34 shows the obtained result.

As apparent from the result shown in FIG. 34, fluorescent foci were detected in cells expressing the mAG1-Cyclin D1, the p21-PB1, and the CDK4-PB1. On the other hand, when no CDK4 was expressed in the cells, and when the CDK4 not fused to any multimerizable protein was expressed in the cells, no fluorescent focus was detected. Thus, it was confirmed that, as shown in FIG. 7, the interaction between CDK4 and Cyclin D1 formed a complex having the multimerizable protein and the fluorescent protein, and that the p21 fused to the multimerizable protein interacted with the complex, thereby forming the fluorescent foci. To put it differently, it was confirmed that detecting the fluorescent foci enabled determination of an interaction among three types of proteins.

Example 18

As in Examples 16 and 17, the effectiveness of the system shown in FIG. 7 in determining a protein-protein interaction was confirmed. Note that the detection target in this confirmation experiment was tetramer formation from calmodulin and a partial sequence (M13 peptide) of myosin light chain kinase 2. It has been revealed that the interaction between calmodulin and an M13 peptide takes place in response to a transient increase in intracellular calcium ion concentration (second messenger) that occurs when a G protein-coupled receptor (GPCR) receives a ligand (see Miyawaki A et al., Nature, Aug. 28, 1997, vol. 388, no. 6645, pp. 882 to 887). In addition, it has also been revealed that an interaction between calmodulin and a calmodulin-binding peptide such as M13 peptide forms a tetramer composed of two sets of these molecules (see Ye Q et al., Biochemistry, Jan. 24, 2006, vol. 45, no. 3, pp. 738 to 745). Then, it was confirmed using materials and methods described below that the system shown in FIG. 7 was capable of detecting such tetramer formation. Further, it was also confirmed that detecting a fluorescent focus enabled detection of a change in intracellular calcium ion concentration over time.

<Preparation of pM13peptide-PB1>

To express, as the thirteenth and fourteenth fusion proteins, an M13 peptide whose C-terminus was fused to a PB1 domain of p62 as the multimerizable protein (M13peptide-PB1) in cells, a pM13peptide-PB1 vector was constructed as described below.

A DNA was artificially synthesized which contained BamHI and EcoRI recognition sequences respectively at both ends of a nucleotide sequence encoding an M13 peptide (the nucleotide sequence of SEQ ID NO: 50). Then, the obtained synthetic DNA was treated with BamHI and EcoRI, and inserted into pAsh-MNLinker having been treated with the same restriction enzymes. Thus, a pM13peptide-PB1 vector was prepared.

<Preparation of pCalumodulin-hmAG1 and pCalumodulin-hmUkG1>

To express, as the fifteenth fusion protein, a calmodulin protein whose C-terminus was fused to mAG1 as the fluorescent protein (Calumodulin-mAG1), or to express, as the fifteenth fusion protein, a calmodulin protein whose C-terminus was fused to mUkG1 as the fluorescent protein (Calumodulin-mUkG1) in cells, a pCalumodulin-hmAG1 vector and a pCalumodulin-hmUkG1 vector were constructed as described below.

A DNA was artificially synthesized which contained BamHI and EcoRI recognition sequences respectively at both ends of a nucleotide sequence encoding calmodulin (the nucleotide sequence of SEQ ID NO: 52). Then, the obtained synthetic DNA was treated with BamHI and EcoRI, and inserted into phmAG1-MNLinker and phmUkG1-MNLinker (both manufactured by MEDICAL & BIOLOGICAL LABORATORIES CO., LTD.) having been treated with the same restriction enzymes. Thus, a pCalumodulin-hmAG1 vector and a pCalumodulin-hmUkG1 vector were prepared.

<Cell Culturing and Transfection>

To express the fusion proteins in a combination of the following (A) or (B), the plasmid vectors prepared above were introduced into HeLaS3 cells by a method described below:

(A) Calumodulin-mAG1 and M13peptide-PB1; and
(B) Calumodulin-mUkG1 and M13peptide-PB1.

First, HeLaS3 cells were cultured in DMEM (low glucose) containing 10% FBS (manufactured by Equitech-Bio Inc.). Then, on the day before the transfection, the HeLaS3 cells were seeded onto a 35-mm glass base dish (manufactured by Asahi Glass Co., Ltd.). Subsequently, at the time of the transfection, the plasmids (1 µg+1 µg) were diluted with OptiMEM, and 10 µl of PolyFect(registered trademark) Transfection Reagent was added thereto and stirred. The resultant was further mixed with 600 µl of the culture solution, thereafter added to the HeLaS3 cells, and cultured for 22 hours.

<Observation of Cells>

Using an IX-71 inverted fluorescence microscope, a U-MGFPHQ filter, and an ORCA-ER digital camera, the transfected HelaS3 cells cultured for 22 hours above were observed in a buffer at pH of 7.4 containing Hanks' Balanced Salt Solutions and 20 mM HEPES. Then, 100 µM histamine (manufactured by Wako Pure Chemical Industries, Ltd.) was added thereto, and fluorescence images were captured over time. Note that it has been revealed that histamine functions as a ligand of an H1 receptor, one of GPCRs, which is expressed also in HeLaS3 cells. FIGS. 35 and 36 show the obtained result.

As apparent from the result shown in FIGS. 35 and 36, before the ligand (histamine) was added, the Calumodulin-mAG1 and the Calumodulin-mUkG1 were present in a dispersed manner in the cells. Meanwhile, 60 seconds after the ligand was added, fluorescent focus formation was detected, confirming the assembly formation containing the M13peptide-PB1. Moreover, as a result of the subsequent continuous observation, 300 seconds after the ligand addition, the fluorescent foci (assemblies) were extinguished as shown in FIG. 35 because the cytoplasm calcium ion concentration transiently increased by adding the ligand was decreased.

Thus, it was confirmed that the present invention was also capable of detecting such heterotetramer formation. Further, it was also revealed that the use of the method for detecting a protein-protein interaction of the present invention enabled real-time measurement of the calcium ion concentration transiently increased by the signal transduction from the H1 receptor. Moreover, the result of this Example also demonstrated that the application was eventually possible to detection of and screening for: an endogenous factor such as a second messenger causing a protein-protein interaction; a signal transduction to which the second messenger or the like contributed; and a stimulus from the outside such as an extracellular ligand eliciting the signal transduction.

Example 19

Figure 8:
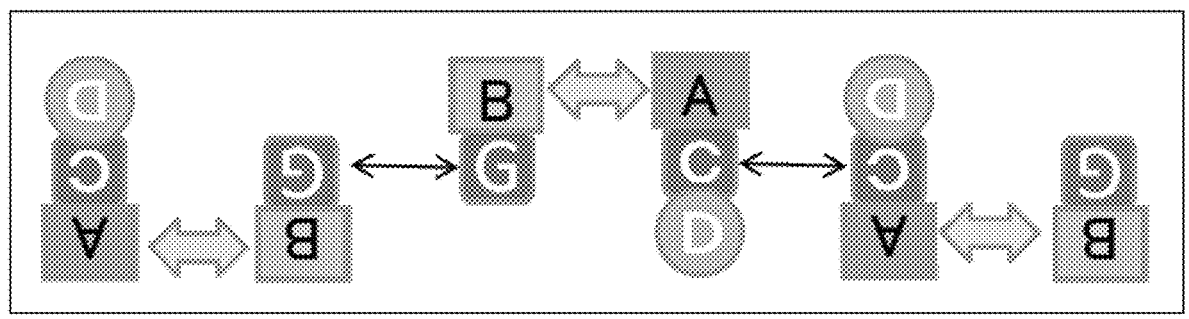
FIG. 8 is a conceptual diagram for illustrating one embodiment of a seventh method for determining a protein-protein interaction of the present invention. Specifically, the diagram illustrates that a first multimerizable protein (in the figure, C) is a different protein from a second multimerizable protein (in the figure, G), and that when a sixteenth fusion protein comprising a first protein (in the figure, A), the first multimerizable protein, and a fluorescent protein (in the figure, D), and a seventeenth fusion protein comprising a second protein (in the figure, B) and the second multimerizable protein are expressed in a cell or introduced into a cell, an interaction between the first protein and the second protein can be determined according to the detection of a fluorescent focus formed by assembly formation between the sixteenth fusion protein and the seventeenth fusion protein in the cell.

Based on the above results, the present inventors came up with a system shown in FIG. 8 as a system for determining a protein-protein interaction.

Specifically, the inventors came up with a construction of a system in which a sixteenth fusion protein comprising a first protein, a first multimerizable protein, and a fluorescent protein, and a seventeenth fusion protein comprising a second protein and a second multimerizable protein are expressed in a cell or introduced into a cell. In a case where the first protein is a different protein from the second protein and the first multimerizable protein is a different protein from the second multimerizable protein, the first protein and the second protein interact with each other, further inducing multimer formation between the multimerizable protein and another multimerizable protein; thereby, the fusion proteins autonomously form an assembly, and the fluorescent protein contained in the fusion protein is detected as a fluorescent focus.

Then, the effectiveness of the system shown in FIG. 8 in determining a protein-protein interaction was confirmed using materials and methods described below. Note that the detection target in this examination was an interaction between a p53 protein and an MDM2 protein, and an inhibitor Nutlin-3 against the interaction was also used in this examination. Further, in this examination, a SAM domain of a Tankyrase 1 protein, a PB1 domain of a PKCiota protein, a SAM domain of a TEL protein, and a SAM domain of a DGK delta protein were used as the multimerizable proteins in appropriate combinations. Moreover, a mAG1 protein was used as the fluorescent protein. Note that, in the system shown in FIG. 8, the fluorescent protein is fused to only one of the proteins to be analyzed for the protein interaction. Nevertheless, in this Example, the fluorescent protein was fused to both of the proteins for the examination.

<Preparation of Plasmid Vectors for Expressing Various Fusion Proteins> pTankyrase-hmAG1-p53, pPKCi-hmAG1-p53, pTEL-hmAG1-p53, and pDGKd-hmAG1-p53 prepared as described above were treated with restriction enzymes NheI and AgeI. Thereby, nucleotide fragments Tankyrase-hmAG1, PKCi-hmAG1, TEL-hmAG1, and DGKd-hmAG1 were prepared. Then, these were inserted into pPB1-p53 (70) which had been treated with the same restriction enzymes, and from which the PB1 region had been removed. Thus, the following plasmid vectors were prepared:

(a) pTankyrase-hmAG1-p53(70),
(b) pPKCi-hmAG1-p53(70),
(c) pTEL-hmAG1-p53(70), and
(d) pDGKd-hmAG1-p53(70).

In addition, the pPB1-MDM2 prepared in Example 4 was treated with NheI and AgeI to remove the PB1 region. Then, the above nucleotide fragments were inserted thereinto. Thus, the following plasmid vectors were also prepared:
(e) pTankyrase-hmAG1-MDM2,
(f) pPKCi-hmAG1-MDM2,
(g) pTEL-hmAG1-MDM2, and
(h) pDGKd-hmAG1-MDM2.

<Cell Culturing and Transfection>

The plasmid vectors (a) to (h) prepared as described above were introduced into HEK293 cells by a method described below in the following combinations:
combination 1: plasmid vectors (b) and (h),
combination 2: plasmid vectors (b) and (g),
combination 3: plasmid vectors (a) and (f),
combination 4: plasmid vectors (a) and (h),
combination 5: plasmid vectors (a) and (g),
combination 6: plasmid vectors (d) and (f),
combination 7: plasmid vectors (d) and (g),
combination 8: plasmid vectors (c) and (e), and
combination 9: plasmid vectors (c) and (h).

HEK293 cells were cultured in DMEM (high glucose) supplemented with 10% FBS and 1% penicillin-streptomycin. Then, on the day before the transfection, the cells were seeded onto a 96-well multiwell plate (manufactured by Greiner Bio-One International GmbH), and cultured in 100 µL of the culture solution per well. Subsequently, a DNA solution prepared by mixing 200 ng of each of the plasmids was diluted with 10 µL of OptiMEM. Thereafter, 0.8 µL of Fugene HD was added thereto and then stirred. The resultant was further mixed with 90 µl of the culture solution. After that, the obtained mixture solution was added to the cultured cells and cultured for 20 hours.

<Observation of Cells>

After the culturing, the culture solution of the cells was discarded, and 100 µL of a buffer at pH 7.4 containing Hanks' Balanced Salt Solutions and 20 mM HEPES was added. Then, the cells were observed using IN Cell Analyzer 1000. Next, Nutlin-3 was added to each well to the final concentration of 40 µM. After left standing at room temperature for 1 hour, the cells were observed. FIGS. 37 to 45 show the obtained result.

As apparent from the result shown in FIGS. 37 to 45, distinctive fluorescent foci were observed in all the combinations before Nutlin-3 was added. On the other hand, as a result of the re-observation 30 minutes after the Nutlin-3 addition, the fluorescent foci were extinguished, and the fluorescent signals were dispersed.

In this manner, the system shown in FIG. 8 was also capable of detecting fluorescent foci formed dependently on the interaction between p53 and MDM2, and the effectiveness of the system was demonstrated.

INDUSTRIAL APPLICABILITY

As has been described above, the present invention makes it possible to determine a protein-protein interaction in an intracellular environment unique thereto, and to obtain positional information and temporal information on the protein-protein interaction. Moreover, in the present invention, a strength of a protein-protein interaction correlates with the fluorescence intensity of a fluorescent focus. Accordingly, the method is utilizable in identifying an amino acid residue involved in a protein-protein interaction, and also in screening for a substance modulating a protein-protein interaction, on the basis of the fluorescence intensity.

Thus, the method for determining a protein-protein interaction and so forth of the present invention and a vector or a kit for use in these methods are useful in the development of pharmaceutical products and so on through elucidations of various signal transductions in vivo, various biological reaction controls, and the like, and eventually, through elucidations of disease mechanisms.

[Sequence Listing Free Text]
SEQ ID NOs: 1 and 2
<223> PB1 domain of p62
SEQ ID NOs: 3 and 4
<223> PB1 domain of TFG
SEQ ID NOs: 5 and 6
<223> PB1 domain of PKCiota
SEQ ID NOs: 7 and 8
<223> SAM domain of TEL
SEQ ID NOs: 9 and 10
<223> SAM domain of DGK delta
SEQ ID NOs: 11 and 12
<223> SAM domain of Tankyrase-1
SEQ ID NOs: 13 and 14
<223> humanized-codon monomeric Azami Green 1 (mAG1)
SEQ ID NOs: 15 and 16
<223> monomeric Umikinoko-Green (mUkG)
SEQ ID NOs: 17 and 18
<223> monomeric Kusabira-Orange 2 (mKO2)
SEQ ID NOs: 19 and 20
<223> monomeric Midoriishi-Cyan1 (mMiCy)
SEQ ID NOs: 21 and 22
<223> Kusabira-Cyan1 (KCy1)
SEQ ID NOs: 23 and 24
<223> dimeric Azami-Green (AB) (dAG (AB))
SEQ ID NOs: 25 and 26
<223> TGuv
SEQ ID NOs: 27 and 28
<223> PB1hmAG1
SEQ ID NOs: 29 and 30
<223> hmAG1PB1
SEQ ID NOs: 31 and 32
<223> FKBP12 mutant
SEQ ID NOs: 33 and 34
<223> p53
SEQ ID NOs: 35 and 36
<223> MDM2
SEQ ID NOs: 37 and 38
<223> PB1
SEQ ID NOs: 39 and 40
<223> FusionRed
SEQ ID NOs: 42 and 43
<223> Tankyrase-hmAG1
SEQ ID NOs: 44 and 45
<223> PKCiota-hmAG1
SEQ ID NOs: 46 and 47
<223> TEL-hmAG1
SEQ ID NOs: 48 and 49
<223> DGK delt-hmAG1
SEQ ID NOs: 50 and 51
<223> M13 peptide
SEQ ID NOs: 52 and 53
<223> calmodulin

The invention claimed is:

1. A method for determining an interaction between a first protein and a second protein, the method comprising the following steps (1) to (3):
   (1) expressing in a cell or introducing into a cell
       a first fusion protein comprising the first protein, a multimerizable protein, and a fluorescent protein, and
       a second fusion protein comprising the second protein and a multimerizable protein;
   (2) detecting a fluorescent focus formed by an association between the first fusion protein and the second fusion protein in the cell; and
   (3) determining an interaction between the first protein and the second protein according to the detection of the fluorescent focus,
   wherein the multimerizable protein in said first fusion protein, and the multimerizable protein in said second fusion protein, are the same, and
   wherein the multimerizable protein is selected from the group consisting of PB1 domain of p62, a PB1 domain of TFG, a PB1 domain of PKCiota, a SAM domain of TEL, a SAM domain of DGK delta, and a SAM domain of Tankyrase-1.

2. The method according to claim 1, wherein the second fusion protein further comprises a fluorescent protein.

3. The method according to claim 1, wherein the fluorescent protein is a monomeric fluorescent protein.

4. A kit for use in the method according to claim 1, the kit comprising an instruction and at least one substance selected from the group consisting of the following (a) to (h):
   (a) a vector comprising a DNA encoding the multimerizable protein, a DNA encoding the fluorescent protein, and a cloning site, wherein the vector is capable of expressing a fusion protein comprising the multimerizable protein, the fluorescent protein, and the first protein when a DNA encoding the first protein is inserted in the cloning site;
   (b) a vector encoding the first fusion protein;
   (c) a vector encoding the second fusion protein;
   (d) a transformed cell comprising a vector encoding the first fusion protein;
   (e) a transformed cell comprising a vector encoding the second fusion protein;
   (f) a transformed cell comprising a vector encoding the first fusion protein and a vector encoding the second fusion protein;
   (g) the first fusion protein; and
   (h) the second fusion protein.

* * * * *

SEQUENCE LISTING

<160> NUMBER OF SEQ ID NOS: 53

<210> SEQ ID NO 1
<211> LENGTH: 306
<212> TYPE: DNA
<213> ORGANISM: Homo sapiens
<220> FEATURE:
<221> NAME/KEY: CDS
<222> LOCATION: (1)..(306)
<223> OTHER INFORMATION: p62(PB1)

<400> SEQUENCE: 1

| | | | | | | | | | | | | | | | | |
|---|---|---|---|---|---|---|---|---|---|---|---|---|---|---|---|---|
| atg | gcg | tcg | ctc | acc | gtg | aag | gcc | tac | ctt | ctg | ggc | aag | gag | gac | gcg | 48 |
| Met | Ala | Ser | Leu | Thr | Val | Lys | Ala | Tyr | Leu | Leu | Gly | Lys | Glu | Asp | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| gcg | cgc | gag | att | cgc | cgc | ttc | agc | ttc | tgc | tgc | agc | ccc | gag | cct | gag | 96 |
| Ala | Arg | Glu | Ile | Arg | Arg | Phe | Ser | Phe | Cys | Cys | Ser | Pro | Glu | Pro | Glu | |
| | | | 20 | | | | | 25 | | | | | 30 | | | |

| | | | | | | | | | | | | | | | | |
|---|---|---|---|---|---|---|---|---|---|---|---|---|---|---|---|---|
| gcg | gaa | gcc | gag | gct | gcg | gcg | ggt | ccg | gga | ccc | tgc | gag | cgg | ctg | ctg | 144 |
| Ala | Glu | Ala | Glu | Ala | Ala | Ala | Gly | Pro | Gly | Pro | Cys | Glu | Arg | Leu | Leu | |
| | 35 | | | | | 40 | | | | | 45 | | | | | |

| | | | | | | | | | | | | | | | | |
|---|---|---|---|---|---|---|---|---|---|---|---|---|---|---|---|---|
| agc | cgg | gtg | gcc | gcc | ctg | ttc | ccc | gcg | ctg | cgg | cct | ggc | ggc | ttc | cag | 192 |
| Ser | Arg | Val | Ala | Ala | Leu | Phe | Pro | Ala | Leu | Arg | Pro | Gly | Gly | Phe | Gln | |
| 50 | | | | | 55 | | | | | 60 | | | | | | |

| | | | | | | | | | | | | | | | | |
|---|---|---|---|---|---|---|---|---|---|---|---|---|---|---|---|---|
| gcg | cac | tac | cgc | gat | gag | gac | ggg | gac | ttg | gtt | gcc | ttt | tcc | agt | gac | 240 |
| Ala | His | Tyr | Arg | Asp | Glu | Asp | Gly | Asp | Leu | Val | Ala | Phe | Ser | Ser | Asp | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| gag | gaa | ttg | aca | atg | gcc | atg | tcc | tac | gtg | aag | gat | gac | atc | ttc | cga | 288 |
| Glu | Glu | Leu | Thr | Met | Ala | Met | Ser | Tyr | Val | Lys | Asp | Asp | Ile | Phe | Arg | |
| | | | 85 | | | | | 90 | | | | | 95 | | | |

| | | | | | |
|---|---|---|---|---|---|
| atc | tac | att | aaa | gag | aaa | 306 |
| Ile | Tyr | Ile | Lys | Glu | Lys | |
| | | 100 | | | | |

<210> SEQ ID NO 2
<211> LENGTH: 102
<212> TYPE: PRT
<213> ORGANISM: Homo sapiens

<400> SEQUENCE: 2

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30

Ala Glu Ala Glu Ala Ala Ala Gly Pro Gly Pro Cys Glu Arg Leu Leu
        35                  40                  45

Ser Arg Val Ala Ala Leu Phe Pro Ala Leu Arg Pro Gly Gly Phe Gln
    50                  55                  60

Ala His Tyr Arg Asp Glu Asp Gly Asp Leu Val Ala Phe Ser Ser Asp
65                  70                  75                  80

Glu Glu Leu Thr Met Ala Met Ser Tyr Val Lys Asp Asp Ile Phe Arg
                85                  90                  95

Ile Tyr Ile Lys Glu Lys
            100

<210> SEQ ID NO 3
<211> LENGTH: 246
<212> TYPE: DNA
<213> ORGANISM: Homo sapiens
<220> FEATURE:
<221> NAME/KEY: CDS
<222> LOCATION: (1)..(246)

<223> OTHER INFORMATION: TFG(PB1)

<400> SEQUENCE: 3

```
aag cta atc atc aaa gct caa ctt ggg gag gat att cgg cga att cct        48
Lys Leu Ile Ile Lys Ala Gln Leu Gly Glu Asp Ile Arg Arg Ile Pro
1               5                   10                  15 att cat aat gaa gat att act tat gat gaa tta gtg cta atg atg caa        96
Ile His Asn Glu Asp Ile Thr Tyr Asp Glu Leu Val Leu Met Met Gln
            20                  25                  30 cga gtt ttc aga gga aaa ctt ctg agt aat gat gaa gta aca ata aag       144
Arg Val Phe Arg Gly Lys Leu Leu Ser Asn Asp Glu Val Thr Ile Lys
        35                  40                  45 tat aaa gat gaa gat gga gat ctt ata aca att ttt gat agt tct gac       192
Tyr Lys Asp Glu Asp Gly Asp Leu Ile Thr Ile Phe Asp Ser Ser Asp
    50                  55                  60 ctt tcc ttt gca att cag tgc agt agg ata ctg aaa ctg aca tta ttt       240
Leu Ser Phe Ala Ile Gln Cys Ser Arg Ile Leu Lys Leu Thr Leu Phe
65                  70                  75                  80 gtt aat                                                               246
Val Asn
```

<210> SEQ ID NO 4
<211> LENGTH: 82
<212> TYPE: PRT
<213> ORGANISM: Homo sapiens

<400> SEQUENCE: 4

```
Lys Leu Ile Ile Lys Ala Gln Leu Gly Glu Asp Ile Arg Arg Ile Pro
1               5                   10                  15

Ile His Asn Glu Asp Ile Thr Tyr Asp Glu Leu Val Leu Met Met Gln
            20                  25                  30

Arg Val Phe Arg Gly Lys Leu Leu Ser Asn Asp Glu Val Thr Ile Lys
        35                  40                  45

Tyr Lys Asp Glu Asp Gly Asp Leu Ile Thr Ile Phe Asp Ser Ser Asp
    50                  55                  60

Leu Ser Phe Ala Ile Gln Cys Ser Arg Ile Leu Lys Leu Thr Leu Phe
65                  70                  75                  80

Val Asn
```

<210> SEQ ID NO 5
<211> LENGTH: 252
<212> TYPE: DNA
<213> ORGANISM: Homo sapiens
<220> FEATURE:
<221> NAME/KEY: CDS
<222> LOCATION: (1)..(252)
<223> OTHER INFORMATION: PKCiota(PB1)

<400> SEQUENCE: 5

```
cag gtc cgg gtg aaa gcc tac tac cgc ggg gat atc atg ata aca cat        48
Gln Val Arg Val Lys Ala Tyr Tyr Arg Gly Asp Ile Met Ile Thr His
1               5                   10                  15 ttt gaa cct tcc atc tcc ttt gag ggc ctt tgc aat gag gtt cga gac        96
Phe Glu Pro Ser Ile Ser Phe Glu Gly Leu Cys Asn Glu Val Arg Asp
            20                  25                  30 atg tgt tct ttt gac aac gaa cag ctc ttc acc atg aaa tgg ata gat       144
Met Cys Ser Phe Asp Asn Glu Gln Leu Phe Thr Met Lys Trp Ile Asp
        35                  40                  45 gag gaa gga gac ccg tgt aca gta tca tct cag ttg gag tta gaa gaa       192
Glu Glu Gly Asp Pro Cys Thr Val Ser Ser Gln Leu Glu Leu Glu Glu
    50                  55                  60
```

```
gcc ttt aga ctt tat gag cta aac aag gat tct gaa ctc ttg att cat    240
Ala Phe Arg Leu Tyr Glu Leu Asn Lys Asp Ser Glu Leu Leu Ile His
 65                  70                  75                  80 gtg ttc cct tgt                                                    252
Val Phe Pro Cys <210> SEQ ID NO 6
<211> LENGTH: 84
<212> TYPE: PRT
<213> ORGANISM: Homo sapiens

<400> SEQUENCE: 6

Gln Val Arg Val Lys Ala Tyr Tyr Arg Gly Asp Ile Met Ile Thr His
  1               5                  10                  15

Phe Glu Pro Ser Ile Ser Phe Glu Gly Leu Cys Asn Glu Val Arg Asp
                 20                  25                  30

Met Cys Ser Phe Asp Asn Glu Gln Leu Phe Thr Met Lys Trp Ile Asp
             35                  40                  45

Glu Gly Asp Pro Cys Thr Val Ser Ser Gln Leu Glu Leu Glu Glu
         50                  55                  60

Ala Phe Arg Leu Tyr Glu Leu Asn Lys Asp Ser Glu Leu Leu Ile His
 65                  70                  75                  80

Val Phe Pro Cys

<210> SEQ ID NO 7
<211> LENGTH: 261
<212> TYPE: DNA
<213> ORGANISM: Homo sapiens
<220> FEATURE:
<221> NAME/KEY: CDS
<222> LOCATION: (1)..(261)
<223> OTHER INFORMATION: TEL(SAM)

<400> SEQUENCE: 7 cct cga gcg ctc agg atg gag gaa gac tcg atc cgc ctg cct gcg cac     48
Pro Arg Ala Leu Arg Met Glu Glu Asp Ser Ile Arg Leu Pro Ala His
  1               5                  10                  15 ctg cgc ttg cag cca att tac tgg agc agg gat gac gta gcc cag tgg     96
Leu Arg Leu Gln Pro Ile Tyr Trp Ser Arg Asp Asp Val Ala Gln Trp
                 20                  25                  30 ctc aag tgg gct gaa aat gag ttt tct tta agg cca att gac agc aac    144
Leu Lys Trp Ala Glu Asn Glu Phe Ser Leu Arg Pro Ile Asp Ser Asn
             35                  40                  45 acg ttt gaa atg aat ggc aaa gct ctc ctg ctg ctg acc aaa gag gac    192
Thr Phe Glu Met Asn Gly Lys Ala Leu Leu Leu Leu Thr Lys Glu Asp
         50                  55                  60 ttt cgc tat cga tct cct cat tca ggt gat gtg ctc tat gaa ctc ctt    240
Phe Arg Tyr Arg Ser Pro His Ser Gly Asp Val Leu Tyr Glu Leu Leu
 65                  70                  75                  80 cag cat att ctg aag cag agg                                        261
Gln His Ile Leu Lys Gln Arg
                 85

<210> SEQ ID NO 8
<211> LENGTH: 87
<212> TYPE: PRT
<213> ORGANISM: Homo sapiens

<400> SEQUENCE: 8

Pro Arg Ala Leu Arg Met Glu Glu Asp Ser Ile Arg Leu Pro Ala His
  1               5                  10                  15
```

Leu Arg Leu Gln Pro Ile Tyr Trp Ser Arg Asp Asp Val Ala Gln Trp
            20                  25                  30

Leu Lys Trp Ala Glu Asn Glu Phe Ser Leu Arg Pro Ile Asp Ser Asn
        35                  40                  45

Thr Phe Glu Met Asn Gly Lys Ala Leu Leu Leu Thr Lys Glu Asp
50                  55                  60

Phe Arg Tyr Arg Ser Pro His Ser Gly Asp Val Leu Tyr Glu Leu Leu
65                  70                  75                  80

Gln His Ile Leu Lys Gln Arg
                85

<210> SEQ ID NO 9
<211> LENGTH: 204
<212> TYPE: DNA
<213> ORGANISM: Homo sapiens
<220> FEATURE:
<221> NAME/KEY: CDS
<222> LOCATION: (1)..(204)
<223> OTHER INFORMATION: DGKdelta(SAM)

<400> SEQUENCE: 9 ccg gtt cac ctc tgg ggg aca gag gag gtt gct gcc tgg ctg gag cac    48
Pro Val His Leu Trp Gly Thr Glu Glu Val Ala Ala Trp Leu Glu His
1               5                   10                  15 ctc agt ctc tgt gag tat aag gac atc ttc aca cgg cac gac atc cgg    96
Leu Ser Leu Cys Glu Tyr Lys Asp Ile Phe Thr Arg His Asp Ile Arg
            20                  25                  30 ggc tct gag ctc ctg cac ctg gag cgg agg gac ctc aag gac ctg ggc   144
Gly Ser Glu Leu Leu His Leu Glu Arg Arg Asp Leu Lys Asp Leu Gly
        35                  40                  45 gtg acc aag gtg ggc cac atg aag agg atc ctg tgt ggc atc aag gag   192
Val Thr Lys Val Gly His Met Lys Arg Ile Leu Cys Gly Ile Lys Glu
    50                  55                  60 ctg agc cgc agc                                                    204
Leu Ser Arg Ser
65

<210> SEQ ID NO 10
<211> LENGTH: 68
<212> TYPE: PRT
<213> ORGANISM: Homo sapiens

<400> SEQUENCE: 10

Pro Val His Leu Trp Gly Thr Glu Glu Val Ala Ala Trp Leu Glu His
1               5                   10                  15

Leu Ser Leu Cys Glu Tyr Lys Asp Ile Phe Thr Arg His Asp Ile Arg
            20                  25                  30

Gly Ser Glu Leu Leu His Leu Glu Arg Arg Asp Leu Lys Asp Leu Gly
        35                  40                  45

Val Thr Lys Val Gly His Met Lys Arg Ile Leu Cys Gly Ile Lys Glu
    50                  55                  60

Leu Ser Arg Ser
65

<210> SEQ ID NO 11
<211> LENGTH: 597
<212> TYPE: DNA
<213> ORGANISM: Homo sapiens
<220> FEATURE:
<221> NAME/KEY: CDS
<222> LOCATION: (1)..(597)

<223> OTHER INFORMATION: Tankyrase(SAM)

<400> SEQUENCE: 11

```
ctg ata gat gcc atg ccc cca gag gcc tta cct acc tgt ttt aaa cct    48
Leu Ile Asp Ala Met Pro Pro Glu Ala Leu Pro Thr Cys Phe Lys Pro
1               5                   10                  15 cag gct act gta gtg agt gcc tct ctg atc tca cca gca tcc acc ccc    96
Gln Ala Thr Val Val Ser Ala Ser Leu Ile Ser Pro Ala Ser Thr Pro
            20                  25                  30 tcc tgc ctc tcg gct gcc agc agc ata gac aac ctc act ggc cct tta    144
Ser Cys Leu Ser Ala Ala Ser Ser Ile Asp Asn Leu Thr Gly Pro Leu
        35                  40                  45 gca gag ttg gcc gta gga gga gcc tcc aat gca ggg gat ggc gcc gcg    192
Ala Glu Leu Ala Val Gly Gly Ala Ser Asn Ala Gly Asp Gly Ala Ala
    50                  55                  60 gga aca gaa agg aag gaa gga gaa gtt gct ggt ctt gac atg aat atc    240
Gly Thr Glu Arg Lys Glu Gly Glu Val Ala Gly Leu Asp Met Asn Ile
65                  70                  75                  80 agc caa ttt cta aaa agc ctt ggc ctt gaa cac ctt cgg gat atc ttt    288
Ser Gln Phe Leu Lys Ser Leu Gly Leu Glu His Leu Arg Asp Ile Phe
                85                  90                  95 gaa aca gaa cag att aca cta gat gtg ttg gct gat atg ggt cat gaa    336
Glu Thr Glu Gln Ile Thr Leu Asp Val Leu Ala Asp Met Gly His Glu
            100                 105                 110 gag ttg aaa gaa ata ggc atc aat gca tat ggg cac cgc cac aaa tta    384
Glu Leu Lys Glu Ile Gly Ile Asn Ala Tyr Gly His Arg His Lys Leu
        115                 120                 125 atc aaa gga gta gaa aga ctc tta ggt gga caa caa ggc acc aat cct    432
Ile Lys Gly Val Glu Arg Leu Leu Gly Gly Gln Gln Gly Thr Asn Pro
    130                 135                 140 tat ttg act ttt cac tgt gtt aat cag gga acg att ttg ctg gat ctt    480
Tyr Leu Thr Phe His Cys Val Asn Gln Gly Thr Ile Leu Leu Asp Leu
145                 150                 155                 160 gct cca gaa gat aaa gaa tat cag tca gtg gaa gaa gag atg caa agt    528
Ala Pro Glu Asp Lys Glu Tyr Gln Ser Val Glu Glu Glu Met Gln Ser
                165                 170                 175 act att cga gaa cac aga gat ggt ggt aat gct ggc ggc atc ttc aac    576
Thr Ile Arg Glu His Arg Asp Gly Gly Asn Ala Gly Gly Ile Phe Asn
            180                 185                 190 aga tac aat gtc att cga att                                        597
Arg Tyr Asn Val Ile Arg Ile
        195
```

<210> SEQ ID NO 12
<211> LENGTH: 199
<212> TYPE: PRT
<213> ORGANISM: Homo sapiens

<400> SEQUENCE: 12

```
Leu Ile Asp Ala Met Pro Pro Glu Ala Leu Pro Thr Cys Phe Lys Pro
1               5                   10                  15

Gln Ala Thr Val Val Ser Ala Ser Leu Ile Ser Pro Ala Ser Thr Pro
            20                  25                  30

Ser Cys Leu Ser Ala Ala Ser Ser Ile Asp Asn Leu Thr Gly Pro Leu
        35                  40                  45

Ala Glu Leu Ala Val Gly Gly Ala Ser Asn Ala Gly Asp Gly Ala Ala
    50                  55                  60

Gly Thr Glu Arg Lys Glu Gly Glu Val Ala Gly Leu Asp Met Asn Ile
65                  70                  75                  80
```

```
Ser Gln Phe Leu Lys Ser Leu Gly Leu Glu His Leu Arg Asp Ile Phe
                85                  90                  95

Glu Thr Glu Gln Ile Thr Leu Asp Val Leu Ala Asp Met Gly His Glu
            100                 105                 110

Glu Leu Lys Glu Ile Gly Ile Asn Ala Tyr Gly His Arg His Lys Leu
        115                 120                 125

Ile Lys Gly Val Glu Arg Leu Leu Gly Gly Gln Gln Gly Thr Asn Pro
    130                 135                 140

Tyr Leu Thr Phe His Cys Val Asn Gln Gly Thr Ile Leu Leu Asp Leu
145                 150                 155                 160

Ala Pro Glu Asp Lys Glu Tyr Gln Ser Val Glu Glu Glu Met Gln Ser
                165                 170                 175

Thr Ile Arg Glu His Arg Asp Gly Gly Asn Ala Gly Gly Ile Phe Asn
            180                 185                 190

Arg Tyr Asn Val Ile Arg Ile
        195
```

```
<210> SEQ ID NO 13
<211> LENGTH: 678
<212> TYPE: DNA
<213> ORGANISM: Artificial Sequence
<220> FEATURE:
<223> OTHER INFORMATION: Synthetic humanized mAG1 sequence
<220> FEATURE:
<221> NAME/KEY: CDS
<222> LOCATION: (1)..(678)

<400> SEQUENCE: 13
```

```
atg gtg agc gtg atc aag ccc gag atg aag atc aag ctg tgc atg agg    48
Met Val Ser Val Ile Lys Pro Glu Met Lys Ile Lys Leu Cys Met Arg
1               5                   10                  15 ggc acc gtg aac ggc cac aac ttc gtg atc gag ggc gag ggc aag ggc    96
Gly Thr Val Asn Gly His Asn Phe Val Ile Glu Gly Glu Gly Lys Gly
                20                  25                  30 aac ccc tac gag ggc acc cag atc ctg gac ctg aac gtg acc gag ggc   144
Asn Pro Tyr Glu Gly Thr Gln Ile Leu Asp Leu Asn Val Thr Glu Gly
            35                  40                  45 gcc ccc ctg ccc ttc gcc tac gac atc ctg acc acc gtg ttc cag tac   192
Ala Pro Leu Pro Phe Ala Tyr Asp Ile Leu Thr Thr Val Phe Gln Tyr
50                  55                  60 ggc aac agg gcc ttc acc aag tac ccc gcc gac atc cag gac tac ttc   240
Gly Asn Arg Ala Phe Thr Lys Tyr Pro Ala Asp Ile Gln Asp Tyr Phe
65                  70                  75                  80 aag cag acc ttc ccc gag ggc tac cac tgg gag agg agc atg acc tac   288
Lys Gln Thr Phe Pro Glu Gly Tyr His Trp Glu Arg Ser Met Thr Tyr
                85                  90                  95 gag gac cag ggc atc tgc acc gcc acc agc aac atc agc atg agg ggc   336
Glu Asp Gln Gly Ile Cys Thr Ala Thr Ser Asn Ile Ser Met Arg Gly
            100                 105                 110 gac tgc ttc ttc tac gac atc agg ttc gac ggc acc aac ttc ccc ccc   384
Asp Cys Phe Phe Tyr Asp Ile Arg Phe Asp Gly Thr Asn Phe Pro Pro
        115                 120                 125 aac ggc ccc gtg atg cag aag aag acc ctg aag tgg gag ccc agc acc   432
Asn Gly Pro Val Met Gln Lys Lys Thr Leu Lys Trp Glu Pro Ser Thr
    130                 135                 140 gag aag atg tac gtg gag gac ggc gtg ctg aag ggc gac gtg aac atg   480
Glu Lys Met Tyr Val Glu Asp Gly Val Leu Lys Gly Asp Val Asn Met
145                 150                 155                 160 agg ctg ctg ctg gag ggc ggc ggc cac tac agg tgc gac ttc aag acc   528
Arg Leu Leu Leu Glu Gly Gly Gly His Tyr Arg Cys Asp Phe Lys Thr
```

```
                            165                 170                 175
acc  tac  aag  gcc  aag  aag  gag  gtg  agg  ctg  ccc  gac  gcc  cac  aag  atc        576
Thr  Tyr  Lys  Ala  Lys  Lys  Glu  Val  Arg  Leu  Pro  Asp  Ala  His  Lys  Ile
              180                 185                 190 gac  cac  agg  atc  gag  atc  ctg  aag  cac  gac  aag  gac  tac  aac  aag  gtg        624
Asp  His  Arg  Ile  Glu  Ile  Leu  Lys  His  Asp  Lys  Asp  Tyr  Asn  Lys  Val
              195                 200                 205 aag  ctg  tac  gag  aac  gcc  gtg  gcc  agg  tac  tcc  atg  ctg  ccc  agc  cag        672
Lys  Leu  Tyr  Glu  Asn  Ala  Val  Ala  Arg  Tyr  Ser  Met  Leu  Pro  Ser  Gln
      210                 215                 220 gcc  aag                                                                                678
Ala  Lys
225

<210> SEQ ID NO 14
<211> LENGTH: 226
<212> TYPE: PRT
<213> ORGANISM: Artificial Sequence
<220> FEATURE:
<223> OTHER INFORMATION: Synthetic Construct

<400> SEQUENCE: 14

Met  Val  Ser  Val  Ile  Lys  Pro  Glu  Met  Lys  Ile  Lys  Leu  Cys  Met  Arg
1                   5                   10                  15

Gly  Thr  Val  Asn  Gly  His  Asn  Phe  Val  Ile  Glu  Gly  Glu  Gly  Lys  Gly
              20                  25                  30

Asn  Pro  Tyr  Glu  Gly  Thr  Gln  Ile  Leu  Asp  Leu  Asn  Val  Thr  Glu  Gly
          35                  40                  45

Ala  Pro  Leu  Pro  Phe  Ala  Tyr  Asp  Ile  Leu  Thr  Thr  Val  Phe  Gln  Tyr
      50                  55                  60

Gly  Asn  Arg  Ala  Phe  Thr  Lys  Tyr  Pro  Ala  Asp  Ile  Gln  Asp  Tyr  Phe
65                  70                  75                  80

Lys  Gln  Thr  Phe  Pro  Glu  Gly  Tyr  His  Trp  Glu  Arg  Ser  Met  Thr  Tyr
              85                  90                  95

Glu  Asp  Gln  Gly  Ile  Cys  Thr  Ala  Thr  Ser  Asn  Ile  Ser  Met  Arg  Gly
          100                 105                 110

Asp  Cys  Phe  Phe  Tyr  Asp  Ile  Arg  Phe  Asp  Gly  Thr  Asn  Phe  Pro  Pro
      115                 120                 125

Asn  Gly  Pro  Val  Met  Gln  Lys  Lys  Thr  Leu  Lys  Trp  Glu  Pro  Ser  Thr
130                 135                 140

Glu  Lys  Met  Tyr  Val  Glu  Asp  Gly  Val  Leu  Lys  Gly  Asp  Val  Asn  Met
145                 150                 155                 160

Arg  Leu  Leu  Leu  Glu  Gly  Gly  Gly  His  Tyr  Arg  Cys  Asp  Phe  Lys  Thr
              165                 170                 175

Thr  Tyr  Lys  Ala  Lys  Lys  Glu  Val  Arg  Leu  Pro  Asp  Ala  His  Lys  Ile
          180                 185                 190

Asp  His  Arg  Ile  Glu  Ile  Leu  Lys  His  Asp  Lys  Asp  Tyr  Asn  Lys  Val
      195                 200                 205

Lys  Leu  Tyr  Glu  Asn  Ala  Val  Ala  Arg  Tyr  Ser  Met  Leu  Pro  Ser  Gln
          210                 215                 220

Ala  Lys
225

<210> SEQ ID NO 15
<211> LENGTH: 684
<212> TYPE: DNA
<213> ORGANISM: Artificial Sequence
<220> FEATURE:
```

<223> OTHER INFORMATION: Synthetic sequence mUkG
<220> FEATURE:
<221> NAME/KEY: CDS
<222> LOCATION: (1)..(681)

<400> SEQUENCE: 15

```
atg gtg agt gtg att aaa gag gaa atg aag atc aag ctg cat atg gaa        48
Met Val Ser Val Ile Lys Glu Glu Met Lys Ile Lys Leu His Met Glu
1               5                   10                  15 gga aat gta aac ggt cat gca ttt gtg att gaa gga gat gga aaa gga        96
Gly Asn Val Asn Gly His Ala Phe Val Ile Glu Gly Asp Gly Lys Gly
            20                  25                  30 aag cct tac gat ggg aca cag act tta aac ctg aca gtg aaa gaa ggc       144
Lys Pro Tyr Asp Gly Thr Gln Thr Leu Asn Leu Thr Val Lys Glu Gly
        35                  40                  45 gca cct ctc cct ttt tct tac gac atc ttg aca aat gcg ttc cag tac       192
Ala Pro Leu Pro Phe Ser Tyr Asp Ile Leu Thr Asn Ala Phe Gln Tyr
    50                  55                  60 gga aat aga gca ttc act aaa tat cca gcc gat ata cca gac tat ttc       240
Gly Asn Arg Ala Phe Thr Lys Tyr Pro Ala Asp Ile Pro Asp Tyr Phe
65                  70                  75                  80 aag cag acg ttt ccc gag ggg tat tca tgg gaa aga acc atg agt tat       288
Lys Gln Thr Phe Pro Glu Gly Tyr Ser Trp Glu Arg Thr Met Ser Tyr
                85                  90                  95 gaa gac aac gcc att tgc aac gtg aga agc gag atc agc atg gaa ggc       336
Glu Asp Asn Ala Ile Cys Asn Val Arg Ser Glu Ile Ser Met Glu Gly
            100                 105                 110 gac tgc ttt atc tat aaa att cgg ttt gat ggc aag aac ttt ccc ccc       384
Asp Cys Phe Ile Tyr Lys Ile Arg Phe Asp Gly Lys Asn Phe Pro Pro
        115                 120                 125 aat ggt cca gtt atg cag aag aaa act ttg aag tgg gaa cca tcc act       432
Asn Gly Pro Val Met Gln Lys Lys Thr Leu Lys Trp Glu Pro Ser Thr
    130                 135                 140 gag atg atg tac gtg cgt gat ggg ttt ctg atg ggt gat gtt aac atg       480
Glu Met Met Tyr Val Arg Asp Gly Phe Leu Met Gly Asp Val Asn Met
145                 150                 155                 160 gct ctg ttg ctt gaa gga ggt ggc cat cac cga tgt gac ttc aaa act       528
Ala Leu Leu Leu Glu Gly Gly Gly His His Arg Cys Asp Phe Lys Thr
                165                 170                 175 tcc tac aaa gcg aaa aag gtt gtg cag ttg cca gat gcc cac aag atc       576
Ser Tyr Lys Ala Lys Lys Val Val Gln Leu Pro Asp Ala His Lys Ile
            180                 185                 190 gac cat cgt atc gag atc ttg agc cat gac agg gat tac agc aaa gtc       624
Asp His Arg Ile Glu Ile Leu Ser His Asp Arg Asp Tyr Ser Lys Val
        195                 200                 205 aag ctg tat gag aat gcg gtt gct cgc aat tct ttg ctg cca agt cag       672
Lys Leu Tyr Glu Asn Ala Val Ala Arg Asn Ser Leu Leu Pro Ser Gln
    210                 215                 220 gct tcg aag taa                                                        684
Ala Ser Lys
225
```

<210> SEQ ID NO 16
<211> LENGTH: 227
<212> TYPE: PRT
<213> ORGANISM: Artificial Sequence
<220> FEATURE:
<223> OTHER INFORMATION: Synthetic Construct

<400> SEQUENCE: 16

```
Met Val Ser Val Ile Lys Glu Glu Met Lys Ile Lys Leu His Met Glu
1               5                   10                  15
```

-continued

```
Gly Asn Val Asn Gly His Ala Phe Val Ile Glu Gly Asp Gly Lys Gly
             20                  25                  30

Lys Pro Tyr Asp Gly Thr Gln Thr Leu Asn Leu Thr Val Lys Glu Gly
         35                  40                  45

Ala Pro Leu Pro Phe Ser Tyr Asp Ile Leu Thr Asn Ala Phe Gln Tyr
 50                  55                  60

Gly Asn Arg Ala Phe Thr Lys Tyr Pro Ala Asp Ile Pro Asp Tyr Phe
65                  70                  75                  80

Lys Gln Thr Phe Pro Glu Gly Tyr Ser Trp Glu Arg Thr Met Ser Tyr
                 85                  90                  95

Glu Asp Asn Ala Ile Cys Asn Val Arg Ser Ile Ser Met Glu Gly
            100                 105                 110

Asp Cys Phe Ile Tyr Lys Ile Arg Phe Asp Gly Lys Asn Phe Pro Pro
        115                 120                 125

Asn Gly Pro Val Met Gln Lys Lys Thr Leu Lys Trp Glu Pro Ser Thr
130                 135                 140

Glu Met Met Tyr Val Arg Asp Gly Phe Leu Met Gly Asp Val Asn Met
145                 150                 155                 160

Ala Leu Leu Leu Glu Gly Gly His His Arg Cys Asp Phe Lys Thr
                165                 170                 175

Ser Tyr Lys Ala Lys Lys Val Val Gln Leu Pro Asp Ala His Lys Ile
            180                 185                 190

Asp His Arg Ile Glu Ile Leu Ser His Asp Arg Asp Tyr Ser Lys Val
        195                 200                 205

Lys Leu Tyr Glu Asn Ala Val Ala Arg Asn Ser Leu Leu Pro Ser Gln
    210                 215                 220

Ala Ser Lys
225

<210> SEQ ID NO 17
<211> LENGTH: 654
<212> TYPE: DNA
<213> ORGANISM: Artificial Sequence
<220> FEATURE:
<223> OTHER INFORMATION: Synthetic sequence mKO2
<220> FEATURE:
<221> NAME/KEY: CDS
<222> LOCATION: (1)..(654)

<400> SEQUENCE: 17 atg gtg agc gtg atc aag ccc gag atg aag atg agg tac tac atg gac      48
Met Val Ser Val Ile Lys Pro Glu Met Lys Met Arg Tyr Tyr Met Asp
1               5                  10                  15 ggc tcc gtc aat ggg cat gag ttc aca atc gag ggt gag ggc aca ggc      96
Gly Ser Val Asn Gly His Glu Phe Thr Ile Glu Gly Glu Gly Thr Gly
             20                  25                  30 aga cct tac gag gga cat cag gag atg aca ctg cgc gtc aca atg gcc     144
Arg Pro Tyr Glu Gly His Gln Glu Met Thr Leu Arg Val Thr Met Ala
         35                  40                  45 gag ggc ggg cca atg cct ttc gcc ttc gac ctg gtg tcc cac gtg ttc     192
Glu Gly Gly Pro Met Pro Phe Ala Phe Asp Leu Val Ser His Val Phe
 50                  55                  60 tgt tac ggc cac aga gtt ttt acc aag tac cca gaa gag atc cca gac     240
Cys Tyr Gly His Arg Val Phe Thr Lys Tyr Pro Glu Glu Ile Pro Asp
65                  70                  75                  80 tat ttc aag cag gcc ttt cct gag ggc ctg tcc tgg gag agg tcc ctg     288
Tyr Phe Lys Gln Ala Phe Pro Glu Gly Leu Ser Trp Glu Arg Ser Leu
                 85                  90                  95
```

```
gag ttc gag gac ggc ggc tcc gcc tcc gtg agc gcc cac atc agc ctg      336
Glu Phe Glu Asp Gly Gly Ser Ala Ser Val Ser Ala His Ile Ser Leu
            100                 105                 110 agg ggc aac acc ttc tac cac aag tcc aag ttc acc ggc gtg aac ttc      384
Arg Gly Asn Thr Phe Tyr His Lys Ser Lys Phe Thr Gly Val Asn Phe
        115                 120                 125 ccc gcc gac ggc ccc atc atg cag aac cag agc gtg gac tgg gag ccc      432
Pro Ala Asp Gly Pro Ile Met Gln Asn Gln Ser Val Asp Trp Glu Pro
    130                 135                 140 tcc acc gag aag atc acc gcc agc gac ggc gtg ctg aag ggc gac gtg      480
Ser Thr Glu Lys Ile Thr Ala Ser Asp Gly Val Leu Lys Gly Asp Val
145                 150                 155                 160 acc atg tac ctg aag ctg gag ggc ggc ggc aac cac aag tgc cag atg      528
Thr Met Tyr Leu Lys Leu Glu Gly Gly Gly Asn His Lys Cys Gln Met
                165                 170                 175 aag acc acc tac aag gcc gcc aag gag atc ctg gag atg ccc ggc gac      576
Lys Thr Thr Tyr Lys Ala Ala Lys Glu Ile Leu Glu Met Pro Gly Asp
            180                 185                 190 cac tac atc ggc cac agg ctg gtg agg aag acc gag ggc aac atc acc      624
His Tyr Ile Gly His Arg Leu Val Arg Lys Thr Glu Gly Asn Ile Thr
        195                 200                 205 gag cag gtg gag gac gcc gtg gcc cac tcc                              654
Glu Gln Val Glu Asp Ala Val Ala His Ser
    210                 215

<210> SEQ ID NO 18
<211> LENGTH: 218
<212> TYPE: PRT
<213> ORGANISM: Artificial Sequence
<220> FEATURE:
<223> OTHER INFORMATION: Synthetic Construct

<400> SEQUENCE: 18

Met Val Ser Val Ile Lys Pro Glu Met Lys Met Arg Tyr Tyr Met Asp
1               5                   10                  15

Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Met
                165                 170                 175

Lys Thr Thr Tyr Lys Ala Ala Lys Glu Ile Leu Glu Met Pro Gly Asp
            180                 185                 190
```

```
                          His Tyr Ile Gly His Arg Leu Val Arg Lys Thr Glu Gly Asn Ile Thr
                                      195                 200                 205

Glu Gln Val Glu Asp Ala Val Ala His Ser
                              210                 215

<210> SEQ ID NO 19
<211> LENGTH: 696
<212> TYPE: DNA
<213> ORGANISM: Artificial Sequence
<220> FEATURE:
<223> OTHER INFORMATION: Synthetic sequence mMiCy
<220> FEATURE:
<221> NAME/KEY: CDS
<222> LOCATION: (1)..(696)

<400> SEQUENCE: 19 atg gtg tcc tac tcc aag cag ggc atc gcc cag gag atg cgc acc aag        48
Met Val Ser Tyr Ser Lys Gln Gly Ile Ala Gln Glu Met Arg Thr Lys
 1               5                  10                  15 tac cgc atg gag ggc agc gtg aac ggc cac gag ttc acc atc gag ggc        96
Tyr Arg Met Glu Gly Ser Val Asn Gly His Glu Phe Thr Ile Glu Gly
             20                  25                  30 gtg ggc acc ggc aac ccc tac gag ggc aag cag acc tcc gag ctg gtg       144
Val Gly Thr Gly Asn Pro Tyr Glu Gly Lys Gln Thr Ser Glu Leu Val
         35                  40                  45 atc atc aag ccc aag ggc aag ccc ctg ccc ttc tcc ttc gac atc ctg       192
Ile Ile Lys Pro Lys Gly Lys Pro Leu Pro Phe Ser Phe Asp Ile Leu
     50                  55                  60 tcc acc gtg ttc cag tac ggc aac agg tgc ttc acc aag tac ccc gcc       240
Ser Thr Val Phe Gln Tyr Gly Asn Arg Cys Phe Thr Lys Tyr Pro Ala
 65                  70                  75                  80 gac atg ccc gac tac ttc aag cag gcc ttc ccc gac ggc atg tcc tac       288
Asp Met Pro Asp Tyr Phe Lys Gln Ala Phe Pro Asp Gly Met Ser Tyr
                 85                  90                  95 gag agg tcc ttc ctg ttc gag gac ggc ggc gtg gcc acc gcc agc tgg       336
Glu Arg Ser Phe Leu Phe Glu Asp Gly Gly Val Ala Thr Ala Ser Trp
            100                 105                 110 agc atc cgc ctg gag ggc aac tgc ttc atc cac aac tcc atc tac cac       384
Ser Ile Arg Leu Glu Gly Asn Cys Phe Ile His Asn Ser Ile Tyr His
        115                 120                 125 ggc acc aac ttc ccc gcc gac ggc ccc gtg atg aag aag cag acc atc       432
Gly Thr Asn Phe Pro Ala Asp Gly Pro Val Met Lys Lys Gln Thr Ile
    130                 135                 140 ggc tgg gac aag tcc tcc gag aag atg agc gtg gcc aag gag gtg ctg       480
Gly Trp Asp Lys Ser Ser Glu Lys Met Ser Val Ala Lys Glu Val Leu
145                 150                 155                 160 agg ggc gac gtg acc cag ttc ctg ctg ctg gag ggc ggc ggc tac cag       528
Arg Gly Asp Val Thr Gln Phe Leu Leu Leu Glu Gly Gly Gly Tyr Gln
                165                 170                 175 agg tgc cag ctg cac tcc acc tac aag acc gag aag ccc gtg gcc atg       576
Arg Cys Gln Leu His Ser Thr Tyr Lys Thr Glu Lys Pro Val Ala Met
            180                 185                 190 ccc ccc agc cac gtg gtg gag cac cag atc gtg agg acc gac ctg ggc       624
Pro Pro Ser His Val Val Glu His Gln Ile Val Arg Thr Asp Leu Gly
        195                 200                 205 cag acc gcc aag ggc ttc aag gtg aag ctg gag gag cac gcc gag gcc       672
Gln Thr Ala Lys Gly Phe Lys Val Lys Leu Glu Glu His Ala Glu Ala
    210                 215                 220 cac gtg aac ccc ctg aag gtg aag                                       696
His Val Asn Pro Leu Lys Val Lys
225                 230
```

<210> SEQ ID NO 20
<211> LENGTH: 232
<212> TYPE: PRT
<213> ORGANISM: Artificial Sequence
<220> FEATURE:
<223> OTHER INFORMATION: Synthetic Construct

<400> SEQUENCE: 20

```
Met Val Ser Tyr Ser Lys Gln Gly Ile Ala Gln Glu Met Arg Thr Lys
1               5                   10                  15

Tyr Arg Met Glu Gly Ser Val Asn Gly His Glu Phe Thr Ile Glu Gly
                20                  25                  30

Val Gly Thr Gly Asn Pro Tyr Glu Gly Lys Gln Thr Ser Glu Leu Val
            35                  40                  45

Ile Ile Lys Pro Lys Gly Lys Pro Leu Pro Phe Ser Phe Asp Ile Leu
    50                  55                  60

Ser Thr Val Phe Gln Tyr Gly Asn Arg Cys Phe Thr Lys Tyr Pro Ala
65                  70                  75                  80

Asp Met Pro Asp Tyr Phe Lys Gln Ala Phe Pro Asp Gly Met Ser Tyr
                85                  90                  95

Glu Arg Ser Phe Leu Phe Glu Asp Gly Gly Val Ala Thr Ala Ser Trp
            100                 105                 110

Ser Ile Arg Leu Glu Gly Asn Cys Phe Ile His Asn Ser Ile Tyr His
        115                 120                 125

Gly Thr Asn Phe Pro Ala Asp Gly Pro Val Met Lys Lys Gln Thr Ile
    130                 135                 140

Gly Trp Asp Lys Ser Ser Glu Lys Met Ser Val Ala Lys Glu Val Leu
145                 150                 155                 160

Arg Gly Asp Val Thr Gln Phe Leu Leu Leu Glu Gly Gly Gly Tyr Gln
                165                 170                 175

Arg Cys Gln Leu His Ser Thr Tyr Lys Thr Glu Lys Pro Val Ala Met
            180                 185                 190

Pro Pro Ser His Val Val Glu His Gln Ile Val Arg Thr Asp Leu Gly
        195                 200                 205

Gln Thr Ala Lys Gly Phe Lys Val Lys Leu Glu Glu His Ala Glu Ala
    210                 215                 220

His Val Asn Pro Leu Lys Val Lys
225                 230
```

<210> SEQ ID NO 21
<211> LENGTH: 663
<212> TYPE: DNA
<213> ORGANISM: Artificial Sequence
<220> FEATURE:
<223> OTHER INFORMATION: Synthetic sequence KCy1
<220> FEATURE:
<221> NAME/KEY: CDS
<222> LOCATION: (1)..(663)

<400> SEQUENCE: 21

```
atg gtg agt gtg att aaa cca gag atg aag atg agg tac tac atg gac      48
Met Val Ser Val Ile Lys Pro Glu Met Lys Met Arg Tyr Tyr Met Asp
1               5                   10                  15 ggc tcc gtc aat ggg cat gag ttc aca gtt gaa ggt gaa ggc aca ggc      96
Gly Ser Val Asn Gly His Glu Phe Thr Val Glu Gly Glu Gly Thr Gly
                20                  25                  30 aga cct tac gag gga aag cac aaa ata aca ctt gac gtc acc aag ggt     144
Arg Pro Tyr Glu Gly Lys His Lys Ile Thr Leu Asp Val Thr Lys Gly
            35                  40                  45
```

```
ggg cca ctg cct ttt gcg ttt gac ttg ttg tct aca gtg ttc tct tat      192
Gly Pro Leu Pro Phe Ala Phe Asp Leu Leu Ser Thr Val Phe Ser Tyr
     50                  55                  60 ggc aac aga gcc ctt act aaa tat cct gac gat atc ccc gac tat ttc      240
Gly Asn Arg Ala Leu Thr Lys Tyr Pro Asp Asp Ile Pro Asp Tyr Phe
 65                  70                  75                  80 aaa caa tgc ttt cct gga ggc tat tca tgg gaa aga aag ttt gag ttc      288
Lys Gln Cys Phe Pro Gly Gly Tyr Ser Trp Glu Arg Lys Phe Glu Phe
                     85                  90                  95 gaa gat ggc ggg ttg gcg ata gcc aaa gcg gaa ata agc ctt aaa gga      336
Glu Asp Gly Gly Leu Ala Ile Ala Lys Ala Glu Ile Ser Leu Lys Gly
                 100                 105                 110 aac tgc ttc gaa cac aaa tcc acc att gaa ggc act ttt ccc gat agc      384
Asn Cys Phe Glu His Lys Ser Thr Ile Glu Gly Thr Phe Pro Asp Ser
             115                 120                 125 agt cct att atg caa aac aag acg cta gga tgg gaa cca tcc acc gag      432
Ser Pro Ile Met Gln Asn Lys Thr Leu Gly Trp Glu Pro Ser Thr Glu
    130                 135                 140 aag atg acc gtc cgc gac gga tca atg aag ggt gat gat gcg gcc tac      480
Lys Met Thr Val Arg Asp Gly Ser Met Lys Gly Asp Asp Ala Ala Tyr
145                 150                 155                 160 ctc aaa ttg gtg gga ggc ggc aat cac aaa tgc tac ttt aca act acc      528
Leu Lys Leu Val Gly Gly Gly Asn His Lys Cys Tyr Phe Thr Thr Thr
                165                 170                 175 tac aca gcg aag aaa aag att cct aac ctg cca gga agc cat ttc att      576
Tyr Thr Ala Lys Lys Lys Ile Pro Asn Leu Pro Gly Ser His Phe Ile
            180                 185                 190 ggc cat cgc atc tcc agt gtc gtc gag ggc act aaa att aaa gtg atg      624
Gly His Arg Ile Ser Ser Val Val Glu Gly Thr Lys Ile Lys Val Met
        195                 200                 205 gaa gat gca att gct cat ctt tac cct ttt aat ggc agc                  663
Glu Asp Ala Ile Ala His Leu Tyr Pro Phe Asn Gly Ser
    210                 215                 220
```

<210> SEQ ID NO 22
<211> LENGTH: 221
<212> TYPE: PRT
<213> ORGANISM: Artificial Sequence
<220> FEATURE:
<223> OTHER INFORMATION: Synthetic Construct

<400> SEQUENCE: 22

```
Met Val Ser Val Ile Lys Pro Glu Met Lys Met Arg Tyr Tyr Met Asp
 1               5                  10                  15

Gly Ser Val Asn Gly His Glu Phe Thr Val Glu Gly Glu Gly Thr Gly
                20                  25                  30

Arg Pro Tyr Glu Gly Lys His Lys Ile Thr Leu Asp Val Thr Lys Gly
            35                  40                  45

Gly Pro Leu Pro Phe Ala Phe Asp Leu Leu Ser Thr Val Phe Ser Tyr
        50                  55                  60

Gly Asn Arg Ala Leu Thr Lys Tyr Pro Asp Asp Ile Pro Asp Tyr Phe
 65                  70                  75                  80

Lys Gln Cys Phe Pro Gly Gly Tyr Ser Trp Glu Arg Lys Phe Glu Phe
                 85                  90                  95

Glu Asp Gly Gly Leu Ala Ile Ala Lys Ala Glu Ile Ser Leu Lys Gly
                100                 105                 110

Asn Cys Phe Glu His Lys Ser Thr Ile Glu Gly Thr Phe Pro Asp Ser
            115                 120                 125
```

```
Ser Pro Ile Met Gln Asn Lys Thr Leu Gly Trp Glu Pro Ser Thr Glu
    130                 135                 140

Lys Met Thr Val Arg Asp Gly Ser Met Lys Gly Asp Asp Ala Ala Tyr
145                 150                 155                 160

Leu Lys Leu Val Gly Gly Asn His Lys Cys Tyr Phe Thr Thr Thr
                165                 170                 175

Tyr Thr Ala Lys Lys Lys Ile Pro Asn Leu Pro Gly Ser His Phe Ile
                180                 185                 190

Gly His Arg Ile Ser Ser Val Val Glu Gly Thr Lys Ile Lys Val Met
                195                 200                 205

Glu Asp Ala Ile Ala His Leu Tyr Pro Phe Asn Gly Ser
    210                 215                 220
```

<210> SEQ ID NO 23
<211> LENGTH: 678
<212> TYPE: DNA
<213> ORGANISM: Artificial Sequence
<220> FEATURE:
<223> OTHER INFORMATION: Synthetic sequence dAG(AB)
<220> FEATURE:
<221> NAME/KEY: CDS
<222> LOCATION: (1)..(678)

<400> SEQUENCE: 23

```
atg gtg agt gtg att aaa cca gag atg aag atc aag ctg tgt atg aga      48
Met Val Ser Val Ile Lys Pro Glu Met Lys Ile Lys Leu Cys Met Arg
1               5                   10                  15 ggc act gta aac ggg cat aat ttc gtg att gaa gga gaa gga aaa gga      96
Gly Thr Val Asn Gly His Asn Phe Val Ile Glu Gly Glu Gly Lys Gly
                20                  25                  30 aat cct tac gag gga acg cag att tta gac ctg aac gtc act gaa ggc     144
Asn Pro Tyr Glu Gly Thr Gln Ile Leu Asp Leu Asn Val Thr Glu Gly
            35                  40                  45 gca cct ctg cct ttc gct tac gat atc ttg aca aca gtg ttc cag tac     192
Ala Pro Leu Pro Phe Ala Tyr Asp Ile Leu Thr Thr Val Phe Gln Tyr
        50                  55                  60 ggc aac agg gca ttc acc aag tac cca gca gat att cag gac tat ttc     240
Gly Asn Arg Ala Phe Thr Lys Tyr Pro Ala Asp Ile Gln Asp Tyr Phe
65                  70                  75                  80 aag cag act ttt cct gag ggg tat cac tgg gaa aga agc atg act tat     288
Lys Gln Thr Phe Pro Glu Gly Tyr His Trp Glu Arg Ser Met Thr Tyr
                85                  90                  95 gaa gac cag ggc att tgc acc gcc aca agc aac ata agc atg cgt ggc     336
Glu Asp Gln Gly Ile Cys Thr Ala Thr Ser Asn Ile Ser Met Arg Gly
                100                 105                 110 gac tgt ttt ttc tat gac att cgt ttt gat ggt gtg aac ttt cct ccc     384
Asp Cys Phe Phe Tyr Asp Ile Arg Phe Asp Gly Val Asn Phe Pro Pro
            115                 120                 125 aat ggt ccg gtt atg cag aag aag act ctt aaa tgg gag cca tcc act     432
Asn Gly Pro Val Met Gln Lys Lys Thr Leu Lys Trp Glu Pro Ser Thr
130                 135                 140 gag aaa atg tac gta cgt gat gga gtg ctg aag ggt gat gtt aac atg     480
Glu Lys Met Tyr Val Arg Asp Gly Val Leu Lys Gly Asp Val Asn Met
145                 150                 155                 160 gct ctg ttg ctt gaa gga ggt ggc cat tat cga tgt gat ttc aaa act     528
Ala Leu Leu Leu Glu Gly Gly Gly His Tyr Arg Cys Asp Phe Lys Thr
                165                 170                 175 act tac aaa gca aag aag gat gtc cgt ttg cca gac gcg cac aaa gtg     576
Thr Tyr Lys Ala Lys Lys Asp Val Arg Leu Pro Asp Ala His Lys Val
            180                 185                 190
```

```
gac cac cgc att gag att ttg aag cat gac aaa gat tac aac aag gtc      624
Asp His Arg Ile Glu Ile Leu Lys His Asp Lys Asp Tyr Asn Lys Val
        195                 200                 205 aag ctc tat gag aat gcc gtt gct cgc tat tct atg ctg ccg agt cag      672
Lys Leu Tyr Glu Asn Ala Val Ala Arg Tyr Ser Met Leu Pro Ser Gln
    210                 215                 220 gcc aag                                                              678
Ala Lys
225
```

<210> SEQ ID NO 24
<211> LENGTH: 226
<212> TYPE: PRT
<213> ORGANISM: Artificial Sequence
<220> FEATURE:
<223> OTHER INFORMATION: Synthetic Construct

<400> SEQUENCE: 24

```
Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
            20                  25                  30

Asn Pro Tyr Glu Gly Thr Gln Ile Leu Asp Leu Asn Val Thr Glu Gly
        35                  40                  45

Ala Pro Leu Pro Phe Ala Tyr Asp Ile Leu Thr Thr Val Phe Gln Tyr
    50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110

Asp Cys Phe Phe Tyr Asp Ile Arg Phe Asp Gly Val Asn Phe Pro Pro
        115                 120                 125

Asn Gly Pro Val Met Gln Lys Lys Thr Leu Lys Trp Glu Pro Ser Thr
130                 135                 140

Glu Lys Met Tyr Val Arg Asp Gly Val Leu Lys Gly Asp Val Asn Met
145                 150                 155                 160

Ala Leu Leu Leu Glu Gly Gly Gly His Tyr Arg Cys Asp Phe Lys Thr
                165                 170                 175

Thr Tyr Lys Ala Lys Lys Asp Val Arg Leu Pro Asp Ala His Lys Val
            180                 185                 190

Asp His Arg Ile Glu Ile Leu Lys His Asp Lys Asp Tyr Asn Lys Val
        195                 200                 205

Lys Leu Tyr Glu Asn Ala Val Ala Arg Tyr Ser Met Leu Pro Ser Gln
    210                 215                 220

Ala Lys
225
```

<210> SEQ ID NO 25
<211> LENGTH: 672
<212> TYPE: DNA
<213> ORGANISM: Artificial Sequence
<220> FEATURE:
<223> OTHER INFORMATION: Synthetic sequence TGuv
<220> FEATURE:
<221> NAME/KEY: CDS
<222> LOCATION: (1)..(672)

<400> SEQUENCE: 25

| | | |
|---|---|---|
| atg gtg agt gtt att gga aaa gac atg ata atg aaa ttg cat gtg gaa<br>Met Val Ser Val Ile Gly Lys Asp Met Ile Met Lys Leu His Val Glu<br>1               5                   10                  15 | | 48 |
| gga tgt gtc aac ggc cac tcc ttc aag att gag ggt gac ggc aaa ggc<br>Gly Cys Val Asn Gly His Ser Phe Lys Ile Glu Gly Asp Gly Lys Gly<br>            20                  25                  30 | | 96 |
| aaa ccg tac gag gga gac caa act gtg aag ctg cgt gtt act gaa gga<br>Lys Pro Tyr Glu Gly Asp Gln Thr Val Lys Leu Arg Val Thr Glu Gly<br>        35                  40                  45 | | 144 |
| ggg ccc tta cca ttc gca ttt gac atc ttg tca gcc tca atg tgt tat<br>Gly Pro Leu Pro Phe Ala Phe Asp Ile Leu Ser Ala Ser Met Cys Tyr<br>    50                  55                  60 | | 192 |
| gga aac agg tgt ttt acc aaa tat ccg gca gag att ccc gac att ttc<br>Gly Asn Arg Cys Phe Thr Lys Tyr Pro Ala Glu Ile Pro Asp Ile Phe<br>65                  70                  75                  80 | | 240 |
| aag cag aca ttt cct gaa ggc tac tca tgg gaa aga gcc ttg aca ttt<br>Lys Gln Thr Phe Pro Glu Gly Tyr Ser Trp Glu Arg Ala Leu Thr Phe<br>                85                  90                  95 | | 288 |
| gaa gat gga ggg ttt gct tca tca agc tcg cac atc agt gtc cgt ggc<br>Glu Asp Gly Gly Phe Ala Ser Ser Ser Ser His Ile Ser Val Arg Gly<br>            100                 105                 110 | | 336 |
| aac tgc ttc ttc tac gac gtc aaa tat cat ggc gta aac ttc cct tcc<br>Asn Cys Phe Phe Tyr Asp Val Lys Tyr His Gly Val Asn Phe Pro Ser<br>        115                 120                 125 | | 384 |
| aat gga cca att atg caa aga aag aca atc ggc tgg caa cca tcc aca<br>Asn Gly Pro Ile Met Gln Arg Lys Thr Ile Gly Trp Gln Pro Ser Thr<br>    130                 135                 140 | | 432 |
| gag aaa ttg tac atc gga gag gga acg ctg aag ggt gat gat acg atg<br>Glu Lys Leu Tyr Ile Gly Glu Gly Thr Leu Lys Gly Asp Asp Thr Met<br>145                 150                 155                 160 | | 480 |
| ttc ctc aag ctc gaa gga ggg gga act cat aaa tgc cac gtc cta acc<br>Phe Leu Lys Leu Glu Gly Gly Gly Thr His Lys Cys His Val Leu Thr<br>                165                 170                 175 | | 528 |
| act tac aaa acg aag aaa gat gtc cag atg cca gac agc cac ttc att<br>Thr Tyr Lys Thr Lys Lys Asp Val Gln Met Pro Asp Ser His Phe Ile<br>            180                 185                 190 | | 576 |
| gac cat cgt ctc ctg acc agc cac ctt gat aag gaa tgc aac aac gtg<br>Asp His Arg Leu Leu Thr Ser His Leu Asp Lys Glu Cys Asn Asn Val<br>        195                 200                 205 | | 624 |
| gaa ttg cgc gag cac gca gtt gcg cgt aac tca agt ctg cct tcc cgt<br>Glu Leu Arg Glu His Ala Val Ala Arg Asn Ser Ser Leu Pro Ser Arg<br>    210                 215                 220 | | 672 |

<210> SEQ ID NO 26
<211> LENGTH: 224
<212> TYPE: PRT
<213> ORGANISM: Artificial Sequence
<220> FEATURE:
<223> OTHER INFORMATION: Synthetic Construct

<400> SEQUENCE: 26

Met Val Ser Val Ile Gly Lys Asp Met Ile Met Lys Leu His Val Glu
1               5                   10                  15

Gly Cys Val Asn Gly His Ser Phe Lys Ile Glu Gly Asp Gly Lys Gly
            20                  25                  30

Lys Pro Tyr Glu Gly Asp Gln Thr Val Lys Leu Arg Val Thr Glu Gly
        35                  40                  45

Gly Pro Leu Pro Phe Ala Phe Asp Ile Leu Ser Ala Ser Met Cys Tyr
    50                  55                  60

```
Gly Asn Arg Cys Phe Thr Lys Tyr Pro Ala Glu Ile Pro Asp Ile Phe
 65                  70                  75                  80

Lys Gln Thr Phe Pro Glu Gly Tyr Ser Trp Glu Arg Ala Leu Thr Phe
                 85                  90                  95

Glu Asp Gly Gly Phe Ala Ser Ser Ser His Ile Ser Val Arg Gly
            100                 105                 110

Asn Cys Phe Phe Tyr Asp Val Lys Tyr His Gly Val Asn Phe Pro Ser
            115                 120                 125

Asn Gly Pro Ile Met Gln Arg Lys Thr Ile Gly Trp Gln Pro Ser Thr
        130                 135                 140

Glu Lys Leu Tyr Ile Gly Glu Gly Thr Leu Lys Gly Asp Asp Thr Met
145                 150                 155                 160

Phe Leu Lys Leu Glu Gly Gly Thr His Lys Cys His Val Leu Thr
                165                 170                 175

Thr Tyr Lys Thr Lys Lys Asp Val Gln Met Pro Asp Ser His Phe Ile
            180                 185                 190

Asp His Arg Leu Leu Thr Ser His Leu Asp Lys Glu Cys Asn Asn Val
        195                 200                 205

Glu Leu Arg Glu His Ala Val Ala Arg Asn Ser Ser Leu Pro Ser Arg
210                 215                 220

<210> SEQ ID NO 27
<211> LENGTH: 1084
<212> TYPE: DNA
<213> ORGANISM: Artificial Sequence
<220> FEATURE:
<223> OTHER INFORMATION: Synthetic sequence PB1hmAG1
<220> FEATURE:
<221> NAME/KEY: protein_bind
<222> LOCATION: (3)..(8)
<223> OTHER INFORMATION: NheI recognition site
<220> FEATURE:
<221> NAME/KEY: CDS
<222> LOCATION: (15)..(1076)
<220> FEATURE:
<221> NAME/KEY: protein_bind
<222> LOCATION: (1077)..(1082)
<223> OTHER INFORMATION: AgeI recognition site

<400> SEQUENCE: 27
aagctagcgc cacc atg gcg tcg ctc acc gtg aag gcc tac ctt ctg ggc        50
               Met Ala Ser Leu Thr Val Lys Ala Tyr Leu Leu Gly
                 1               5                  10 aag gag gac gct gca agg gag att aga cgt ttc agc ttc tgc tgt agc       98
Lys Glu Asp Ala Ala Arg Glu Ile Arg Arg Phe Ser Phe Cys Cys Ser
             15                  20                  25 cct gag cct gag gct gaa gca gag gct gct gct ggt cct gga cca tgt      146
Pro Glu Pro Glu Ala Glu Ala Glu Ala Ala Ala Gly Pro Gly Pro Cys
         30                  35                  40 gag cgt ctt ctg tct cgg gta gct gcc ttg ttc cca gca ctg aga cct      194
Glu Arg Leu Leu Ser Arg Val Ala Ala Leu Phe Pro Ala Leu Arg Pro
 45                  50                  55                  60 ggt ggc ttc cag gcg cac tac cgc gat gag gac ggg gac ttg gtt gcc      242
Gly Gly Phe Gln Ala His Tyr Arg Asp Glu Asp Gly Asp Leu Val Ala
                 65                  70                  75 ttt tcc agt gac gag gaa ttg aca atg gcc atg tcc tac gtg aag gat      290
Phe Ser Ser Asp Glu Glu Leu Thr Met Ala Met Ser Tyr Val Lys Asp
             80                  85                  90 gac atc ttc cga atc tac att aaa gag aaa acc ggg aac tcc gct gac      338
Asp Ile Phe Arg Ile Tyr Ile Lys Glu Lys Thr Gly Asn Ser Ala Asp
         95                 100                 105
```

```
ggt ggc gga gga tcg ggt gga agt ggt ggt tca gga gga gga tcg acc      386
Gly Gly Gly Gly Ser Gly Gly Ser Gly Gly Ser Gly Gly Gly Ser Thr
110             115             120 caa gga act agt atg gtg agc gtg atc aag ccc gag atg aag atc aag      434
Gln Gly Thr Ser Met Val Ser Val Ile Lys Pro Glu Met Lys Ile Lys
125             130             135             140 ctg tgc atg agg ggc acc gtg aac ggc cac aac ttc gtg atc gag ggc      482
Leu Cys Met Arg Gly Thr Val Asn Gly His Asn Phe Val Ile Glu Gly
                145             150             155 gag ggc aag ggc aac ccc tac gag ggc acc cag atc ctg gac ctg aac      530
Glu Gly Lys Gly Asn Pro Tyr Glu Gly Thr Gln Ile Leu Asp Leu Asn
            160             165             170 gtg acc gag ggc gcc cct ctg ccc ttc gcc tac gac atc ctg acc acc      578
Val Thr Glu Gly Ala Pro Leu Pro Phe Ala Tyr Asp Ile Leu Thr Thr
        175             180             185 gtg ttc cag tac ggc aac agg gcc ttc acc aag tac cct gcc gac atc      626
Val Phe Gln Tyr Gly Asn Arg Ala Phe Thr Lys Tyr Pro Ala Asp Ile
    190             195             200 cag gac tac ttc aag cag acc ttc ccc gag ggc tac cac tgg gag agg      674
Gln Asp Tyr Phe Lys Gln Thr Phe Pro Glu Gly Tyr His Trp Glu Arg
205             210             215             220 agc atg acc tac gag gac cag ggc atc tgc acc gcc acc agc aac atc      722
Ser Met Thr Tyr Glu Asp Gln Gly Ile Cys Thr Ala Thr Ser Asn Ile
                225             230             235 agc atg agg gga gac tgc ttc ttc tac gac atc agg ttc gac ggc acc      770
Ser Met Arg Gly Asp Cys Phe Phe Tyr Asp Ile Arg Phe Asp Gly Thr
            240             245             250 aac ttc cct ccc aac ggc cca gtg atg cag aag aag act ctg aag tgg      818
Asn Phe Pro Pro Asn Gly Pro Val Met Gln Lys Lys Thr Leu Lys Trp
        255             260             265 gag cct agc acc gag aag atg tac gtg gag gac ggc gtg ctg aag ggc      866
Glu Pro Ser Thr Glu Lys Met Tyr Val Glu Asp Gly Val Leu Lys Gly
    270             275             280 gac gtg aac atg agg ctg ctg ctg gag gga ggc ggc cac tac agg tgc      914
Asp Val Asn Met Arg Leu Leu Leu Glu Gly Gly Gly His Tyr Arg Cys
285             290             295             300 gac ttc aag acc acc tac aag gcc aag aag gag gtg agg ctg ccc gac      962
Asp Phe Lys Thr Thr Tyr Lys Ala Lys Lys Glu Val Arg Leu Pro Asp
                305             310             315 gcc cac aag atc gac cac agg atc gag atc ctg aag cac gac aag gac     1010
Ala His Lys Ile Asp His Arg Ile Glu Ile Leu Lys His Asp Lys Asp
            320             325             330 tac aac aag gtg aag ctg tac gag aac gcc gtg gcc agg tac tcc atg     1058
Tyr Asn Lys Val Lys Leu Tyr Glu Asn Ala Val Ala Arg Tyr Ser Met
        335             340             345 ctg ccc agc cag gcc aag accggtaa                                    1084
Leu Pro Ser Gln Ala Lys
    350

<210> SEQ ID NO 28
<211> LENGTH: 354
<212> TYPE: PRT
<213> ORGANISM: Artificial Sequence
<220> FEATURE:
<223> OTHER INFORMATION: Synthetic Construct

<400> SEQUENCE: 28

Met Ala Ser Leu Thr Val Lys Ala Tyr Leu Leu Gly Lys Glu Asp Ala
1               5                   10                  15

Ala Arg Glu Ile Arg Arg Phe Ser Phe Cys Cys Ser Pro Glu Pro Glu
            20                  25                  30
```

```
Ala Glu Ala Glu Ala Ala Gly Pro Gly Pro Cys Glu Arg Leu Leu
         35                  40                  45

Ser Arg Val Ala Ala Leu Phe Pro Ala Leu Arg Pro Gly Gly Phe Gln
 50                  55                  60

Ala His Tyr Arg Asp Glu Asp Gly Asp Leu Val Ala Phe Ser Ser Asp
 65                  70                  75                  80

Glu Glu Leu Thr Met Ala Met Ser Tyr Val Lys Asp Asp Ile Phe Arg
                 85                  90                  95

Ile Tyr Ile Lys Glu Lys Thr Gly Asn Ser Ala Asp Gly Gly Gly Gly
            100                 105                 110

Ser Gly Gly Ser Gly Gly Ser Gly Gly Gly Ser Thr Gln Gly Thr Ser
            115                 120                 125

Met Val Ser Val Ile Lys Pro Glu Met Lys Ile Lys Leu Cys Met Arg
            130                 135                 140

Gly Thr Val Asn Gly His Asn Phe Val Ile Glu Gly Glu Gly Lys Gly
145                 150                 155                 160

Asn Pro Tyr Glu Gly Thr Gln Ile Leu Asp Leu Asn Val Thr Glu Gly
                165                 170                 175

Ala Pro Leu Pro Phe Ala Tyr Asp Ile Leu Thr Thr Val Phe Gln Tyr
            180                 185                 190

Gly Asn Arg Ala Phe Thr Lys Tyr Pro Ala Asp Ile Gln Asp Tyr Phe
            195                 200                 205

Lys Gln Thr Phe Pro Glu Gly Tyr His Trp Glu Arg Ser Met Thr Tyr
            210                 215                 220

Glu Asp Gln Gly Ile Cys Thr Ala Thr Ser Asn Ile Ser Met Arg Gly
225                 230                 235                 240

Asp Cys Phe Phe Tyr Asp Ile Arg Phe Asp Gly Thr Asn Phe Pro Pro
                245                 250                 255

Asn Gly Pro Val Met Gln Lys Lys Thr Leu Lys Trp Glu Pro Ser Thr
            260                 265                 270

Glu Lys Met Tyr Val Glu Asp Gly Val Leu Lys Gly Asp Val Asn Met
            275                 280                 285

Arg Leu Leu Leu Glu Gly Gly Gly His Tyr Arg Cys Asp Phe Lys Thr
290                 295                 300

Thr Tyr Lys Ala Lys Lys Glu Val Arg Leu Pro Asp Ala His Lys Ile
305                 310                 315                 320

Asp His Arg Ile Glu Ile Leu Lys His Asp Lys Asp Tyr Asn Lys Val
                325                 330                 335

Lys Leu Tyr Glu Asn Ala Val Ala Arg Tyr Ser Met Leu Pro Ser Gln
            340                 345                 350

Ala Lys

<210> SEQ ID NO 29
<211> LENGTH: 1084
<212> TYPE: DNA
<213> ORGANISM: Artificial Sequence
<220> FEATURE:
<223> OTHER INFORMATION: Synthetic sequence hmAG1PB1
<220> FEATURE:
<221> NAME/KEY: protein_bind
<222> LOCATION: (3)..(8)
<223> OTHER INFORMATION: NheI recognition site
<220> FEATURE:
<221> NAME/KEY: CDS
<222> LOCATION: (15)..(1076)
<220> FEATURE:
<221> NAME/KEY: protein_bind
```

<222> LOCATION: (1077)..(1082)
<223> OTHER INFORMATION: AgeI recognition site

<400> SEQUENCE: 29

```
aagctagcgc cacc atg gtg agc gtg atc aag ccc gag atg aag atc aag      50
                Met Val Ser Val Ile Lys Pro Glu Met Lys Ile Lys
                 1               5                  10 ctg tgc atg agg ggc acc gtg aac ggc cac aac ttc gtg atc gag ggc      98
Leu Cys Met Arg Gly Thr Val Asn Gly His Asn Phe Val Ile Glu Gly
         15                  20                  25 gag ggc aag ggc aac ccc tac gag ggc acc cag atc ctg gac ctg aac     146
Glu Gly Lys Gly Asn Pro Tyr Glu Gly Thr Gln Ile Leu Asp Leu Asn
     30                  35                  40 gtg acc gag ggc gcc cct ctg ccc ttc gcc tac gac atc ctg acc acc     194
Val Thr Glu Gly Ala Pro Leu Pro Phe Ala Tyr Asp Ile Leu Thr Thr
 45                  50                  55                  60 gtg ttc cag tac ggc aac agg gcc ttc acc aag tac cct gcc gac atc     242
Val Phe Gln Tyr Gly Asn Arg Ala Phe Thr Lys Tyr Pro Ala Asp Ile
                 65                  70                  75 cag gac tac ttc aag cag acc ttc ccc gag ggc tac cac tgg gag agg     290
Gln Asp Tyr Phe Lys Gln Thr Phe Pro Glu Gly Tyr His Trp Glu Arg
             80                  85                  90 agc atg acc tac gag gac cag ggc atc tgc acc gcc acc agc aac atc     338
Ser Met Thr Tyr Glu Asp Gln Gly Ile Cys Thr Ala Thr Ser Asn Ile
         95                 100                 105 agc atg agg gga gac tgc ttc ttc tac gac atc agg ttc gac ggc acc     386
Ser Met Arg Gly Asp Cys Phe Phe Tyr Asp Ile Arg Phe Asp Gly Thr
    110                 115                 120 aac ttc cct ccc aac ggc cca gtg atg cag aag aag act ctg aag tgg     434
Asn Phe Pro Pro Asn Gly Pro Val Met Gln Lys Lys Thr Leu Lys Trp
125                 130                 135                 140 gag cct agc acc gag aag atg tac gtg gag gac ggc gtg ctg aag ggc     482
Glu Pro Ser Thr Glu Lys Met Tyr Val Glu Asp Gly Val Leu Lys Gly
                145                 150                 155 gac gtg aac atg agg ctg ctg ctg gag gga ggc ggc cac tac agg tgc     530
Asp Val Asn Met Arg Leu Leu Leu Glu Gly Gly Gly His Tyr Arg Cys
            160                 165                 170 gac ttc aag acc acc tac aag gcc aag aag gag gtg agg ctg ccc gac     578
Asp Phe Lys Thr Thr Tyr Lys Ala Lys Lys Glu Val Arg Leu Pro Asp
        175                 180                 185 gcc cac aag atc gac cac agg atc gag atc ctg aag cac gac aag gac     626
Ala His Lys Ile Asp His Arg Ile Glu Ile Leu Lys His Asp Lys Asp
    190                 195                 200 tac aac aag gtg aag ctg tac gag aac gcc gtg gcc agg tac tcc atg     674
Tyr Asn Lys Val Lys Leu Tyr Glu Asn Ala Val Ala Arg Tyr Ser Met
205                 210                 215                 220 ctg ccc agc cag gcc aag act agt aac tcc gct gac ggt ggc gga gga     722
Leu Pro Ser Gln Ala Lys Thr Ser Asn Ser Ala Asp Gly Gly Gly Gly
                225                 230                 235 tcg ggt gga agt ggt ggt tca gga gga gga tcg acc caa gga act ggt     770
Ser Gly Gly Ser Gly Gly Ser Gly Gly Gly Ser Thr Gln Gly Thr Gly
            240                 245                 250 atg gcg tcg ctc acc gtg aag gcc tac ctt ctg ggc aag gag gac gct     818
Met Ala Ser Leu Thr Val Lys Ala Tyr Leu Leu Gly Lys Glu Asp Ala
        255                 260                 265 gca agg gag att aga cgt ttc agc ttc tgc tgt agc cct gag cct gag     866
Ala Arg Glu Ile Arg Arg Phe Ser Phe Cys Cys Ser Pro Glu Pro Glu
    270                 275                 280 gct gaa gca gag gct gct gct ggt cct gga cca tgt gag cgt ctt ctg     914
Ala Glu Ala Glu Ala Ala Ala Gly Pro Gly Pro Cys Glu Arg Leu Leu
```

```
                    285                 290                 295                 300
tct cgg gta gct gcc ttg ttc cca gca ctg aga cct ggt ggc ttc cag        962
Ser Arg Val Ala Ala Leu Phe Pro Ala Leu Arg Pro Gly Gly Phe Gln
                    305                 310                 315 gcg cac tac cgc gat gag gac ggg gac ttg gtt gcc ttt tcc agt gac        1010
Ala His Tyr Arg Asp Glu Asp Gly Asp Leu Val Ala Phe Ser Ser Asp
                320                 325                 330 gag gaa ttg aca atg gcc atg tcc tac gtg aag gat gac atc ttc cga        1058
Glu Glu Leu Thr Met Ala Met Ser Tyr Val Lys Asp Asp Ile Phe Arg
            335                 340                 345 atc tac att aaa gag aaa accggtaa                                       1084
Ile Tyr Ile Lys Glu Lys
        350

<210> SEQ ID NO 30
<211> LENGTH: 354
<212> TYPE: PRT
<213> ORGANISM: Artificial Sequence
<220> FEATURE:
<223> OTHER INFORMATION: Synthetic Construct

<400> SEQUENCE: 30

Met Val Ser Val Ile Lys Pro Glu Met Lys Ile Lys Leu Cys Met Arg
1               5                   10                  15

Gly Thr Val Asn Gly His Asn Phe Val Ile Glu Gly Glu Gly Lys Gly
                20                  25                  30

Asn Pro Tyr Glu Gly Thr Gln Ile Leu Asp Leu Asn Val Thr Glu Gly
            35                  40                  45

Ala Pro Leu Pro Phe Ala Tyr Asp Ile Leu Thr Thr Val Phe Gln Tyr
        50                  55                  60

Gly Asn Arg Ala Phe Thr Lys Tyr Pro Ala Asp Ile Gln Asp Tyr Phe
65                  70                  75                  80

Lys Gln Thr Phe Pro Glu Gly Tyr His Trp Glu Arg Ser Met Thr Tyr
                85                  90                  95

Glu Asp Gln Gly Ile Cys Thr Ala Thr Ser Asn Ile Ser Met Arg Gly
            100                 105                 110

Asp Cys Phe Phe Tyr Asp Ile Arg Phe Asp Gly Thr Asn Phe Pro Pro
        115                 120                 125

Asn Gly Pro Val Met Gln Lys Lys Thr Leu Lys Trp Glu Pro Ser Thr
130                 135                 140

Glu Lys Met Tyr Val Glu Asp Gly Val Leu Lys Gly Asp Val Asn Met
145                 150                 155                 160

Arg Leu Leu Leu Glu Gly Gly Gly His Tyr Arg Cys Asp Phe Lys Thr
                165                 170                 175

Thr Tyr Lys Ala Lys Lys Glu Val Arg Leu Pro Asp Ala His Lys Ile
            180                 185                 190

Asp His Arg Ile Glu Ile Leu Lys His Asp Lys Asp Tyr Asn Lys Val
        195                 200                 205

Lys Leu Tyr Glu Asn Ala Val Ala Arg Tyr Ser Met Leu Pro Ser Gln
        210                 215                 220

Ala Lys Thr Ser Asn Ser Ala Asp Gly Gly Gly Ser Gly Gly Ser
225                 230                 235                 240

Gly Gly Ser Gly Gly Gly Ser Thr Gln Gly Thr Gly Met Ala Ser Leu
                245                 250                 255

Thr Val Lys Ala Tyr Leu Leu Gly Lys Glu Asp Ala Ala Arg Glu Ile
            260                 265                 270
```

```
Arg Arg Phe Ser Phe Cys Cys Ser Pro Glu Pro Glu Ala Glu
        275                 280                 285

Ala Ala Ala Gly Pro Gly Pro Cys Glu Arg Leu Leu Ser Arg Val Ala
290                 295                 300

Ala Leu Phe Pro Ala Leu Arg Pro Gly Gly Phe Gln Ala His Tyr Arg
305                 310                 315                 320

Asp Glu Asp Gly Asp Leu Val Ala Phe Ser Ser Asp Glu Glu Leu Thr
                325                 330                 335

Met Ala Met Ser Tyr Val Lys Asp Asp Ile Phe Arg Ile Tyr Ile Lys
                340                 345                 350

Glu Lys

<210> SEQ ID NO 31
<211> LENGTH: 350
<212> TYPE: DNA
<213> ORGANISM: Artificial Sequence
<220> FEATURE:
<223> OTHER INFORMATION: Synthetic sequence FKBP12 variant
<220> FEATURE:
<221> NAME/KEY: protein_bind
<222> LOCATION: (4)..(9)
<223> OTHER INFORMATION: EcoRI recognition site
<220> FEATURE:
<221> NAME/KEY: CDS
<222> LOCATION: (17)..(340)
<220> FEATURE:
<221> NAME/KEY: protein_bind
<222> LOCATION: (343)..(348)
<223> OTHER INFORMATION: XhoI recognition site

<400> SEQUENCE: 31
gccgaattcg gccacc atg gga gtg cag gtg gaa acc atc tcc cca gga gac      52
                Met Gly Val Gln Val Glu Thr Ile Ser Pro Gly Asp
                 1                5                  10 ggg cgc acc ttc ccc aag cgc ggc cag acc tgc gtg gtg cac tac acc     100
Gly Arg Thr Phe Pro Lys Arg Gly Gln Thr Cys Val Val His Tyr Thr
         15                  20                  25 ggg atg ctt gaa gat gga aag aaa gtt gat tcc tcc cgg gac aga aac     148
Gly Met Leu Glu Asp Gly Lys Lys Val Asp Ser Ser Arg Asp Arg Asn
 30                  35                  40 aag ccc ttt aag ttt atg cta ggc aag cag gag gtg atc cga ggc tgg     196
Lys Pro Phe Lys Phe Met Leu Gly Lys Gln Glu Val Ile Arg Gly Trp
45                  50                  55                  60 gaa gaa ggg gtt gcc cag atg agt gtg ggt cag aga gcc aaa ctg act     244
Glu Glu Gly Val Ala Gln Met Ser Val Gly Gln Arg Ala Lys Leu Thr
                 65                  70                  75 ata tct cca gat tat gcc tat ggt gcc act ggg cac cca ggc atc atc     292
Ile Ser Pro Asp Tyr Ala Tyr Gly Ala Thr Gly His Pro Gly Ile Ile
             80                  85                  90 cca cca cat gcc act ctc gtc ttc gat gtg gag ctt cta aaa ctg gaa     340
Pro Pro His Ala Thr Leu Val Phe Asp Val Glu Leu Leu Lys Leu Glu
         95                 100                 105 ggctcgagcc                                                          350

<210> SEQ ID NO 32
<211> LENGTH: 108
<212> TYPE: PRT
<213> ORGANISM: Artificial Sequence
<220> FEATURE:
<223> OTHER INFORMATION: Synthetic Construct

<400> SEQUENCE: 32

Met Gly Val Gln Val Glu Thr Ile Ser Pro Gly Asp Gly Arg Thr Phe
```

```
1               5                   10                  15
Pro Lys Arg Gly Gln Thr Cys Val Val His Tyr Thr Gly Met Leu Glu
            20                  25                  30

Asp Gly Lys Lys Val Asp Ser Ser Arg Asp Arg Asn Lys Pro Phe Lys
        35                  40                  45

Phe Met Leu Gly Lys Gln Glu Val Ile Arg Gly Trp Glu Glu Gly Val
    50                  55                  60

Ala Gln Met Ser Val Gly Gln Arg Ala Lys Leu Thr Ile Ser Pro Asp
65                  70                  75                  80

Tyr Ala Tyr Gly Ala Thr Gly His Pro Gly Ile Ile Pro Pro His Ala
                85                  90                  95

Thr Leu Val Phe Asp Val Glu Leu Leu Lys Leu Glu
            100                 105
```

```
<210> SEQ ID NO 33
<211> LENGTH: 232
<212> TYPE: DNA
<213> ORGANISM: Artificial Sequence
<220> FEATURE:
<223> OTHER INFORMATION: Synthetic sequence p53
<220> FEATURE:
<221> NAME/KEY: protein_bind
<222> LOCATION: (1)..(6)
<223> OTHER INFORMATION: EcoRI recognition site
<220> FEATURE:
<221> NAME/KEY: CDS
<222> LOCATION: (14)..(226)
<220> FEATURE:
<221> NAME/KEY: protein_bind
<222> LOCATION: (227)..(232)
<223> OTHER INFORMATION: XhoI recognition site

<400> SEQUENCE: 33
gaattcggcc acc atg gag gag ccg cag tca gat cct agc gtc gag ccc     49
            Met Glu Glu Pro Gln Ser Asp Pro Ser Val Glu Pro
              1               5                  10 cct ctg agt cag gaa aca ttt tca gac cta tgg aaa cta ctt cct gaa    97
Pro Leu Ser Gln Glu Thr Phe Ser Asp Leu Trp Lys Leu Leu Pro Glu
            15                  20                  25 aac aac gtt ctg tcc ccc ttg ccg tcc caa gca atg gat gat ttg atg   145
Asn Asn Val Leu Ser Pro Leu Pro Ser Gln Ala Met Asp Asp Leu Met
    30                  35                  40 ctg tcc ccg gac gat att gaa caa tgg ttc act gaa gac cca ggt cca   193
Leu Ser Pro Asp Asp Ile Glu Gln Trp Phe Thr Glu Asp Pro Gly Pro
45                  50                  55                  60 gat gaa gct ccc aga atg cca gag gct gct taa ctcgag                 232
Asp Glu Ala Pro Arg Met Pro Glu Ala Ala
                65                  70
```

```
<210> SEQ ID NO 34
<211> LENGTH: 70
<212> TYPE: PRT
<213> ORGANISM: Artificial Sequence
<220> FEATURE:
<223> OTHER INFORMATION: Synthetic Construct

<400> SEQUENCE: 34

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45
```

Asp Ile Glu Gln Trp Phe Thr Glu Asp Pro Gly Pro Asp Glu Ala Pro
    50                  55                  60

Arg Met Pro Glu Ala Ala
65                  70

<210> SEQ ID NO 35
<211> LENGTH: 379
<212> TYPE: DNA
<213> ORGANISM: Artificial Sequence
<220> FEATURE:
<223> OTHER INFORMATION: Synthetic sequence MDM2
<220> FEATURE:
<221> NAME/KEY: protein_bind
<222> LOCATION: (1)..(6)
<223> OTHER INFORMATION: EcoRI recognition site
<220> FEATURE:
<221> NAME/KEY: CDS
<222> LOCATION: (14)..(373)
<220> FEATURE:
<221> NAME/KEY: protein_bind
<222> LOCATION: (374)..(379)
<223> OTHER INFORMATION: XhoI recognition site

<400> SEQUENCE: 35
gaattcggcc acc atg tgc aat acc aac atg tct gta cct act gat ggt        49
            Met Cys Asn Thr Asn Met Ser Val Pro Thr Asp Gly
            1               5                   10 gct gta acc acc tca cag att cca gct tcg gaa caa gag acc ctg gtt      97
Ala Val Thr Thr Ser Gln Ile Pro Ala Ser Glu Gln Glu Thr Leu Val
                15                  20                  25 aga cca aag cca ttg ctt ttg aag tta tta aag tct gtt ggt gca caa     145
Arg Pro Lys Pro Leu Leu Leu Lys Leu Leu Lys Ser Val Gly Ala Gln
        30                  35                  40 aaa gac act tat act atg aaa gag gtt ctt ttt tat ctt ggc cag tat     193
Lys Asp Thr Tyr Thr Met Lys Glu Val Leu Phe Tyr Leu Gly Gln Tyr
45                  50                  55                  60 att atg act aaa cga tta tat gat gag aag caa caa cat att gta tat     241
Ile Met Thr Lys Arg Leu Tyr Asp Glu Lys Gln Gln His Ile Val Tyr
                65                  70                  75 tgt tca aat gat ctt cta gga gat ttg ttt ggc gtg cca agc ttc tct     289
Cys Ser Asn Asp Leu Leu Gly Asp Leu Phe Gly Val Pro Ser Phe Ser
            80                  85                  90 gtg aaa gag cac agg aaa ata tat acc atg atc tac agg aac ttg gta     337
Val Lys Glu His Arg Lys Ile Tyr Thr Met Ile Tyr Arg Asn Leu Val
        95                  100                 105 gta gtc aat cag cag gaa tca tcg gac tca ggt taa ctcgag              379
Val Val Asn Gln Gln Glu Ser Ser Asp Ser Gly
            110                 115

<210> SEQ ID NO 36
<211> LENGTH: 119
<212> TYPE: PRT
<213> ORGANISM: Artificial Sequence
<220> FEATURE:
<223> OTHER INFORMATION: Synthetic Construct

<400> SEQUENCE: 36

Met Cys Asn Thr Asn Met Ser Val Pro Thr Asp Gly Ala Val Thr Thr
1               5                   10                  15

Ser Gln Ile Pro Ala Ser Glu Gln Glu Thr Leu Val Arg Pro Lys Pro
            20                  25                  30

Leu Leu Leu Lys Leu Leu Lys Ser Val Gly Ala Gln Lys Asp Thr Tyr
        35                  40                  45

```
Thr Met Lys Glu Val Leu Phe Tyr Leu Gly Gln Tyr Ile Met Thr Lys
    50                  55                  60
Arg Leu Tyr Asp Glu Lys Gln Gln His Ile Val Tyr Cys Ser Asn Asp
 65                  70                  75                  80
Leu Leu Gly Asp Leu Phe Gly Val Pro Ser Phe Ser Val Lys Glu His
                 85                  90                  95
Arg Lys Ile Tyr Thr Met Ile Tyr Arg Asn Leu Val Val Asn Gln
                100                 105                 110
Gln Glu Ser Ser Asp Ser Gly
            115
```

<210> SEQ ID NO 37
<211> LENGTH: 331
<212> TYPE: DNA
<213> ORGANISM: Artificial Sequence
<220> FEATURE:
<223> OTHER INFORMATION: Synthetic sequence PB1
<220> FEATURE:
<221> NAME/KEY: protein_bind
<222> LOCATION: (3)..(8)
<223> OTHER INFORMATION: EcoRI recognition site
<220> FEATURE:
<221> NAME/KEY: CDS
<222> LOCATION: (10)..(315)
<220> FEATURE:
<221> NAME/KEY: protein_bind
<222> LOCATION: (319)..(326)
<223> OTHER INFORMATION: NotI recognition site

<400> SEQUENCE: 37

```
aagaattcg atg gcg tcg ctc acc gtg aag gcc tac ctt ctg ggc aag gag      51
          Met Ala Ser Leu Thr Val Lys Ala Tyr Leu Leu Gly Lys Glu
           1               5                  10 gac gcg gcg cgc gag att cgc cgc ttc agc ttc tgc tgc agc ccc gag        99
Asp Ala Ala Arg Glu Ile Arg Arg Phe Ser Phe Cys Cys Ser Pro Glu
 15                  20                  25                  30 cct gag gcg gaa gcc gag gct gcg gcg ggt ccg gga ccc tgc gag cgg       147
Pro Glu Ala Glu Ala Glu Ala Ala Ala Gly Pro Gly Pro Cys Glu Arg
                 35                  40                  45 ctg ctg agc cgg gtg gcc gcc ctg ttc ccc gcg ctg cgg cct ggc ggc       195
Leu Leu Ser Arg Val Ala Ala Leu Phe Pro Ala Leu Arg Pro Gly Gly
             50                  55                  60 ttc cag gcg cac tac cgc gat gag gac ggg gac ttg gtt gcc ttt tcc       243
Phe Gln Ala His Tyr Arg Asp Glu Asp Gly Asp Leu Val Ala Phe Ser
 65                  70                  75 agt gac gag gaa ttg aca atg gcc atg tcc tac gtg aag gat gac atc       291
Ser Asp Glu Glu Leu Thr Met Ala Met Ser Tyr Val Lys Asp Asp Ile
 80                  85                  90 ttc cga atc tac att aaa gag aaa taagcggccg ccaatt                     331
Phe Arg Ile Tyr Ile Lys Glu Lys
 95                 100
```

<210> SEQ ID NO 38
<211> LENGTH: 102
<212> TYPE: PRT
<213> ORGANISM: Artificial Sequence
<220> FEATURE:
<223> OTHER INFORMATION: Synthetic Construct

<400> SEQUENCE: 38

```
Met Ala Ser Leu Thr Val Lys Ala Tyr Leu Leu Gly Lys Glu Asp Ala
 1               5                  10                  15
Ala Arg Glu Ile Arg Arg Phe Ser Phe Cys Cys Ser Pro Glu Pro Glu
                 20                  25                  30
```

```
Ala Glu Ala Glu Ala Ala Ala Gly Pro Gly Pro Cys Glu Arg Leu Leu
         35                  40                  45

Ser Arg Val Ala Ala Leu Phe Pro Ala Leu Arg Pro Gly Gly Phe Gln
 50                  55                  60

Ala His Tyr Arg Asp Glu Asp Gly Asp Leu Val Ala Phe Ser Ser Asp
 65                  70                  75                  80

Glu Glu Leu Thr Met Ala Met Ser Tyr Val Lys Asp Asp Ile Phe Arg
                 85                  90                  95

Ile Tyr Ile Lys Glu Lys
            100

<210> SEQ ID NO 39
<211> LENGTH: 708
<212> TYPE: DNA
<213> ORGANISM: Artificial Sequence
<220> FEATURE:
<223> OTHER INFORMATION: Synthetic sequence FusionRed
<220> FEATURE:
<221> NAME/KEY: CDS
<222> LOCATION: (1)..(708)

<400> SEQUENCE: 39 atg gtg agc gag ctg att aag gag aac atg ccc atg aag ctg tac atg       48
Met Val Ser Glu Leu Ile Lys Glu Asn Met Pro Met Lys Leu Tyr Met
 1               5                  10                  15 gag ggc acc gtg aac aac cac cac ttc aag tgc aca tcc gag ggc gaa       96
Glu Gly Thr Val Asn Asn His His Phe Lys Cys Thr Ser Glu Gly Glu
                 20                  25                  30 ggc aag ccc tac gag ggc acc cag acc atg aga atc aag gtc gtc gag      144
Gly Lys Pro Tyr Glu Gly Thr Gln Thr Met Arg Ile Lys Val Val Glu
             35                  40                  45 ggc ggc cct ctc ccc ttc gcc ttc gac atc ctg gct acc agc ttc atg      192
Gly Gly Pro Leu Pro Phe Ala Phe Asp Ile Leu Ala Thr Ser Phe Met
         50                  55                  60 tac ggc agc aga acc ttc atc aag cac cct ccg ggc atc ccc gac ttc      240
Tyr Gly Ser Arg Thr Phe Ile Lys His Pro Pro Gly Ile Pro Asp Phe
 65                  70                  75                  80 ttt aag cag tcc ttc cct gag ggc ttc aca tgg gag aga gtc acc aca      288
Phe Lys Gln Ser Phe Pro Glu Gly Phe Thr Trp Glu Arg Val Thr Thr
                 85                  90                  95 tac gaa gac ggg ggc gtg ctg acc gct acc cag gac acc agc ctc cag      336
Tyr Glu Asp Gly Gly Val Leu Thr Ala Thr Gln Asp Thr Ser Leu Gln
                100                 105                 110 gac ggc tgc ctc atc tac aac gtc aag gtt aga ggg gtg aac ttc cca      384
Asp Gly Cys Leu Ile Tyr Asn Val Lys Val Arg Gly Val Asn Phe Pro
            115                 120                 125 gcc aac ggc cct gtg atg cag aag aaa aca ctc ggc tgg gag gcc tcc      432
Ala Asn Gly Pro Val Met Gln Lys Lys Thr Leu Gly Trp Glu Ala Ser
        130                 135                 140 acc gag acg atg tac ccc gct gac ggc ggc ctg gaa ggc gca tgt gac      480
Thr Glu Thr Met Tyr Pro Ala Asp Gly Gly Leu Glu Gly Ala Cys Asp
145                 150                 155                 160 atg gcc ctg aag ctc gtg ggc ggg ggc cac ctg atc tgc aac ctt gag      528
Met Ala Leu Lys Leu Val Gly Gly Gly His Leu Ile Cys Asn Leu Glu
                165                 170                 175 acc aca tac aga tcc aag aaa ccc gct acg aac ctc aag atg ccc ggc      576
Thr Thr Tyr Arg Ser Lys Lys Pro Ala Thr Asn Leu Lys Met Pro Gly
                180                 185                 190 gtc tac aac gtg gac cac aga ctg gaa aga atc aag gag gcc gac gat      624
Val Tyr Asn Val Asp His Arg Leu Glu Arg Ile Lys Glu Ala Asp Asp
```

```
                    195                 200                 205
gag acc tac gtc gag cag cac gag gtg gct gtg gcc aga tac tct act        672
Glu Thr Tyr Val Glu Gln His Glu Val Ala Val Ala Arg Tyr Ser Thr
    210                 215                 220 ggt ggc gct ggt gat gga ggt aaa ggt gga gga ggt                        708
Gly Gly Ala Gly Asp Gly Gly Lys Gly Gly Gly Gly
225                 230                 235

<210> SEQ ID NO 40
<211> LENGTH: 236
<212> TYPE: PRT
<213> ORGANISM: Artificial Sequence
<220> FEATURE:
<223> OTHER INFORMATION: Synthetic Construct

<400> SEQUENCE: 40

Met Val Ser Glu Leu Ile Lys Glu Asn Met Pro Met Lys Leu Tyr Met
1               5                   10                  15

Glu Gly Thr Val Asn Asn His His Phe Lys Cys Thr Ser Glu Gly Glu
            20                  25                  30

Gly Lys Pro Tyr Glu Gly Thr Gln Thr Met Arg Ile Lys Val Val Glu
        35                  40                  45

Gly Gly Pro Leu Pro Phe Ala Phe Asp Ile Leu Ala Thr Ser Phe Met
    50                  55                  60

Tyr Gly Ser Arg Thr Phe Ile Lys His Pro Pro Gly Ile Pro Asp Phe
65                  70                  75                  80

Phe Lys Gln Ser Phe Pro Glu Gly Phe Thr Trp Glu Arg Val Thr Thr
                85                  90                  95

Tyr Glu Asp Gly Gly Val Leu Thr Ala Thr Gln Asp Thr Ser Leu Gln
            100                 105                 110

Asp Gly Cys Leu Ile Tyr Asn Val Lys Val Arg Gly Val Asn Phe Pro
        115                 120                 125

Ala Asn Gly Pro Val Met Gln Lys Lys Thr Leu Gly Trp Glu Ala Ser
    130                 135                 140

Thr Glu Thr Met Tyr Pro Ala Asp Gly Gly Leu Glu Gly Ala Cys Asp
145                 150                 155                 160

Met Ala Leu Lys Leu Val Gly Gly Gly His Leu Ile Cys Asn Leu Glu
                165                 170                 175

Thr Thr Tyr Arg Ser Lys Lys Pro Ala Thr Asn Leu Lys Met Pro Gly
            180                 185                 190

Val Tyr Asn Val Asp His Arg Leu Glu Arg Ile Lys Glu Ala Asp Asp
        195                 200                 205

Glu Thr Tyr Val Glu Gln His Glu Val Ala Val Ala Arg Tyr Ser Thr
    210                 215                 220

Gly Gly Ala Gly Asp Gly Gly Lys Gly Gly Gly Gly
225                 230                 235

<210> SEQ ID NO 41
<211> LENGTH: 90
<212> TYPE: PRT
<213> ORGANISM: Homo sapiens

<400> SEQUENCE: 41

Glu Met Trp His Glu Gly Leu Glu Glu Ala Ser Arg Leu Tyr Phe Gly
1               5                   10                  15

Glu Arg Asn Val Lys Gly Met Phe Glu Val Leu Glu Pro Leu His Ala
            20                  25                  30
```

```
Met Met Glu Arg Gly Pro Gln Thr Leu Lys Glu Thr Ser Phe Asn Gln
            35                  40                  45

Ala Tyr Gly Arg Asp Leu Met Glu Ala Gln Glu Trp Cys Arg Lys Tyr
 50                  55                  60

Met Lys Ser Gly Asn Val Lys Asp Leu Thr Gln Ala Trp Asp Leu Tyr
 65                  70                  75                  80

Tyr His Val Phe Arg Arg Ile Ser Lys Gln
                 85                  90

<210> SEQ ID NO 42
<211> LENGTH: 1356
<212> TYPE: DNA
<213> ORGANISM: Artificial Sequence
<220> FEATURE:
<223> OTHER INFORMATION: Synthetic sequence Tankyrase-hmAG1
<220> FEATURE:
<221> NAME/KEY: CDS
<222> LOCATION: (1)..(1356)

<400> SEQUENCE: 42 atg ctg ata gat gcc atg ccc cca gag gcc tta cct acc tgt ttt aaa      48
Met Leu Ile Asp Ala Met Pro Pro Glu Ala Leu Pro Thr Cys Phe Lys
 1               5                  10                  15 cct cag gct act gta gtg agt gcc tct ctg atc tca cca gca tcc acc      96
Pro Gln Ala Thr Val Val Ser Ala Ser Leu Ile Ser Pro Ala Ser Thr
             20                  25                  30 ccc tcc tgc ctc tcg gct gcc agc agc ata gac aac ctc act ggc cct     144
Pro Ser Cys Leu Ser Ala Ala Ser Ser Ile Asp Asn Leu Thr Gly Pro
         35                  40                  45 tta gca gag ttg gcc gta gga gga gcc tcc aat gca ggg gat ggc gcc     192
Leu Ala Glu Leu Ala Val Gly Gly Ala Ser Asn Ala Gly Asp Gly Ala
     50                  55                  60 gcg gga aca gaa agg aag gaa gga gaa gtt gct ggt ctt gac atg aat     240
Ala Gly Thr Glu Arg Lys Glu Gly Glu Val Ala Gly Leu Asp Met Asn
 65                  70                  75                  80 atc agc caa ttt cta aaa agc ctt ggc ctt gaa cac ctt cgg gat atc     288
Ile Ser Gln Phe Leu Lys Ser Leu Gly Leu Glu His Leu Arg Asp Ile
                 85                  90                  95 ttt gaa aca gaa cag att aca cta gat gtg ttg gct gat atg ggt cat     336
Phe Glu Thr Glu Gln Ile Thr Leu Asp Val Leu Ala Asp Met Gly His
            100                 105                 110 gaa gag ttg aaa gaa ata ggc atc aat gca tat ggg cac cgc cac aaa     384
Glu Glu Leu Lys Glu Ile Gly Ile Asn Ala Tyr Gly His Arg His Lys
        115                 120                 125 tta atc aaa gga gta gaa aga ctc tta ggt gga caa caa ggc acc aat     432
Leu Ile Lys Gly Val Glu Arg Leu Leu Gly Gly Gln Gln Gly Thr Asn
    130                 135                 140 cct tat ttg act ttt cac tgt gtt aat cag gga acg att ttg ctg gat     480
Pro Tyr Leu Thr Phe His Cys Val Asn Gln Gly Thr Ile Leu Leu Asp
145                 150                 155                 160 ctt gct cca gaa gat aaa gaa tat cag tca gtg gaa gaa gag atg caa     528
Leu Ala Pro Glu Asp Lys Glu Tyr Gln Ser Val Glu Glu Glu Met Gln
                165                 170                 175 agt act att cga gaa cac aga gat ggt ggt aat gct ggc ggc atc ttc     576
Ser Thr Ile Arg Glu His Arg Asp Gly Gly Asn Ala Gly Gly Ile Phe
            180                 185                 190 aac aga tac aat gtc att cga att acc ggg aac tcc gct gac ggt ggc     624
Asn Arg Tyr Asn Val Ile Arg Ile Thr Gly Asn Ser Ala Asp Gly Gly
        195                 200                 205 gga gga tcg ggt gga agt ggt ggt tca gga gga gga tcg acc caa gga     672
Gly Gly Ser Gly Gly Ser Gly Gly Ser Gly Gly Gly Ser Thr Gln Gly
```

| | | | | | | | | | | | | | | |
|---|---|---|---|---|---|---|---|---|---|---|---|---|---|---|
| | | 210 | | | | | 215 | | | | | 220 | | |
| act | agt | atg | gtg | agc | gtg | atc | aag | ccc | gag | atg | aag | atc | aag | ctg | tgc | 720 |
| Thr | Ser | Met | Val | Ser | Val | Ile | Lys | Pro | Glu | Met | Lys | Ile | Lys | Leu | Cys |
| 225 | | | | | 230 | | | | | 235 | | | | | 240 |

```
act agt atg gtg agc gtg atc aag ccc gag atg aag atc aag ctg tgc    720
Thr Ser Met Val Ser Val Ile Lys Pro Glu Met Lys Ile Lys Leu Cys
225                 230                 235                 240 atg agg ggc acc gtg aac ggc cac aac ttc gtg atc gag ggc gag ggc    768
Met Arg Gly Thr Val Asn Gly His Asn Phe Val Ile Glu Gly Glu Gly
                    245                 250                 255 aag ggc aac ccc tac gag ggc acc cag atc ctg gac ctg aac gtg acc    816
Lys Gly Asn Pro Tyr Glu Gly Thr Gln Ile Leu Asp Leu Asn Val Thr
                260                 265                 270 gag ggc gcc cct ctg ccc ttc gcc tac gac atc ctg acc acc gtg ttc    864
Glu Gly Ala Pro Leu Pro Phe Ala Tyr Asp Ile Leu Thr Thr Val Phe
            275                 280                 285 cag tac ggc aac agg gcc ttc acc aag tac cct gcc gac atc cag gac    912
Gln Tyr Gly Asn Arg Ala Phe Thr Lys Tyr Pro Ala Asp Ile Gln Asp
        290                 295                 300 tac ttc aag cag acc ttc ccc gag ggc tac cac tgg gag agg agc atg    960
Tyr Phe Lys Gln Thr Phe Pro Glu Gly Tyr His Trp Glu Arg Ser Met
305                 310                 315                 320 acc tac gag gac cag ggc atc tgc acc gcc acc agc aac atc agc atg   1008
Thr Tyr Glu Asp Gln Gly Ile Cys Thr Ala Thr Ser Asn Ile Ser Met
                325                 330                 335 agg gga gac tgc ttc ttc tac gac atc agg ttc gac ggc acc aac ttc   1056
Arg Gly Asp Cys Phe Phe Tyr Asp Ile Arg Phe Asp Gly Thr Asn Phe
                340                 345                 350 cct ccc aac ggc cca gtg atg cag aag aag act ctg aag tgg gag cct   1104
Pro Pro Asn Gly Pro Val Met Gln Lys Lys Thr Leu Lys Trp Glu Pro
            355                 360                 365 agc acc gag aag atg tac gtg gag gac ggc gtg ctg aag ggc gac gtg   1152
Ser Thr Glu Lys Met Tyr Val Glu Asp Gly Val Leu Lys Gly Asp Val
        370                 375                 380 aac atg agg ctg ctg ctg gag gga ggc ggc cac tac agg tgc gac ttc   1200
Asn Met Arg Leu Leu Leu Glu Gly Gly Gly His Tyr Arg Cys Asp Phe
385                 390                 395                 400 aag acc acc tac aag gcc aag aag gag gtg agg ctg ccc gac gcc cac   1248
Lys Thr Thr Tyr Lys Ala Lys Lys Glu Val Arg Leu Pro Asp Ala His
                405                 410                 415 aag atc gac cac agg atc gag atc ctg aag cac gac aag gac tac aac   1296
Lys Ile Asp His Arg Ile Glu Ile Leu Lys His Asp Lys Asp Tyr Asn
                420                 425                 430 aag gtg aag ctg tac gag aac gcc gtg gcc agg tac tcc atg ctg ccc   1344
Lys Val Lys Leu Tyr Glu Asn Ala Val Ala Arg Tyr Ser Met Leu Pro
            435                 440                 445 agc cag gcc aag                                                    1356
Ser Gln Ala Lys
    450
```

<210> SEQ ID NO 43
<211> LENGTH: 452
<212> TYPE: PRT
<213> ORGANISM: Artificial Sequence
<220> FEATURE:
<223> OTHER INFORMATION: Synthetic Construct

<400> SEQUENCE: 43

```
Met Leu Ile Asp Ala Met Pro Pro Glu Ala Leu Pro Thr Cys Phe Lys
1               5                   10                  15

Pro Gln Ala Thr Val Val Ser Ala Ser Leu Ile Ser Pro Ala Ser Thr
                20                  25                  30

Pro Ser Cys Leu Ser Ala Ala Ser Ser Ile Asp Asn Leu Thr Gly Pro
```

-continued

```
             35                  40                  45
Leu Ala Glu Leu Ala Val Gly Gly Ala Ser Asn Ala Gly Asp Gly Ala
 50                  55                  60
Ala Gly Thr Glu Arg Lys Gly Glu Val Ala Gly Leu Asp Met Asn
 65                  70                  75                  80
Ile Ser Gln Phe Leu Lys Ser Leu Gly Leu Glu His Leu Arg Asp Ile
                 85                  90                  95
Phe Glu Thr Glu Gln Ile Thr Leu Asp Val Leu Ala Asp Met Gly His
                100                 105                 110
Glu Glu Leu Lys Glu Ile Gly Ile Asn Ala Tyr Gly His Arg His Lys
                115                 120                 125
Leu Ile Lys Gly Val Glu Arg Leu Leu Gly Gly Gln Gln Gly Thr Asn
                130                 135                 140
Pro Tyr Leu Thr Phe His Cys Val Asn Gln Gly Thr Ile Leu Leu Asp
145                 150                 155                 160
Leu Ala Pro Glu Asp Lys Glu Tyr Gln Ser Val Glu Glu Met Gln
                165                 170                 175
Ser Thr Ile Arg Glu His Arg Asp Gly Gly Asn Ala Gly Gly Ile Phe
                180                 185                 190
Asn Arg Tyr Asn Val Ile Arg Ile Thr Gly Asn Ser Ala Asp Gly Gly
                195                 200                 205
Gly Gly Ser Gly Gly Ser Gly Gly Ser Gly Gly Gly Ser Thr Gln Gly
                210                 215                 220
Thr Ser Met Val Ser Val Ile Lys Pro Glu Met Lys Ile Lys Leu Cys
225                 230                 235                 240
Met Arg Gly Thr Val Asn Gly His Asn Phe Val Ile Glu Gly Glu Gly
                245                 250                 255
Lys Gly Asn Pro Tyr Glu Gly Thr Gln Ile Leu Asp Leu Asn Val Thr
                260                 265                 270
Glu Gly Ala Pro Leu Pro Phe Ala Tyr Asp Ile Leu Thr Thr Val Phe
                275                 280                 285
Gln Tyr Gly Asn Arg Ala Phe Thr Lys Tyr Pro Ala Asp Ile Gln Asp
                290                 295                 300
Tyr Phe Lys Gln Thr Phe Pro Glu Gly Tyr His Trp Glu Arg Ser Met
305                 310                 315                 320
Thr Tyr Glu Asp Gln Gly Ile Cys Thr Ala Thr Ser Asn Ile Ser Met
                325                 330                 335
Arg Gly Asp Cys Phe Phe Tyr Asp Ile Arg Phe Asp Gly Thr Asn Phe
                340                 345                 350
Pro Pro Asn Gly Pro Val Met Gln Lys Lys Thr Leu Lys Trp Glu Pro
                355                 360                 365
Ser Thr Glu Lys Met Tyr Val Glu Asp Gly Val Leu Lys Gly Asp Val
                370                 375                 380
Asn Met Arg Leu Leu Leu Glu Gly Gly Gly His Tyr Arg Cys Asp Phe
385                 390                 395                 400
Lys Thr Thr Tyr Lys Ala Lys Lys Glu Val Arg Leu Pro Asp Ala His
                405                 410                 415
Lys Ile Asp His Arg Ile Glu Ile Leu Lys His Asp Lys Asp Tyr Asn
                420                 425                 430
Lys Val Lys Leu Tyr Glu Asn Ala Val Ala Arg Tyr Ser Met Leu Pro
                435                 440                 445
Ser Gln Ala Lys
                450
```

<210> SEQ ID NO 44
<211> LENGTH: 1011
<212> TYPE: DNA
<213> ORGANISM: Artificial Sequence
<220> FEATURE:
<223> OTHER INFORMATION: Synthetic sequence PKCiota-hmAG1
<220> FEATURE:
<221> NAME/KEY: CDS
<222> LOCATION: (1)..(1011)

<400> SEQUENCE: 44

```
atg cag gtc cgg gtg aaa gcc tac tac cgc ggg gat atc atg ata aca        48
Met Gln Val Arg Val Lys Ala Tyr Tyr Arg Gly Asp Ile Met Ile Thr
1               5                   10                  15 cat ttt gaa cct tcc atc tcc ttt gag ggc ctt tgc aat gag gtt cga        96
His Phe Glu Pro Ser Ile Ser Phe Glu Gly Leu Cys Asn Glu Val Arg
            20                  25                  30 gac atg tgt tct ttt gac aac gaa cag ctc ttc acc atg aaa tgg ata       144
Asp Met Cys Ser Phe Asp Asn Glu Gln Leu Phe Thr Met Lys Trp Ile
        35                  40                  45 gat gag gaa gga gac ccg tgt aca gta tca tct cag ttg gag tta gaa       192
Asp Glu Glu Gly Asp Pro Cys Thr Val Ser Ser Gln Leu Glu Leu Glu
    50                  55                  60 gaa gcc ttt aga ctt tat gag cta aac aag gat tct gaa ctc ttg att       240
Glu Ala Phe Arg Leu Tyr Glu Leu Asn Lys Asp Ser Glu Leu Leu Ile
65                  70                  75                  80 cat gtg ttc cct tgt acc ggg aac tcc gct gac ggt ggc gga gga tcg       288
His Val Phe Pro Cys Thr Gly Asn Ser Ala Asp Gly Gly Gly Gly Ser
                85                  90                  95 ggt gga agt ggt ggt tca gga gga gga tcg acc caa gga act agt atg       336
Gly Gly Ser Gly Gly Ser Gly Gly Gly Ser Thr Gln Gly Thr Ser Met
            100                 105                 110 gtg agc gtg atc aag ccc gag atg aag atc aag ctg tgc atg agg ggc       384
Val Ser Val Ile Lys Pro Glu Met Lys Ile Lys Leu Cys Met Arg Gly
        115                 120                 125 acc gtg aac ggc cac aac ttc gtg atc gag ggc gag ggc aag ggc aac       432
Thr Val Asn Gly His Asn Phe Val Ile Glu Gly Glu Gly Lys Gly Asn
    130                 135                 140 ccc tac gag ggc acc cag atc ctg gac ctg aac gtg acc gag ggc gcc       480
Pro Tyr Glu Gly Thr Gln Ile Leu Asp Leu Asn Val Thr Glu Gly Ala
145                 150                 155                 160 cct ctg ccc ttc gcc tac gac atc ctg acc acc gtg ttc cag tac ggc       528
Pro Leu Pro Phe Ala Tyr Asp Ile Leu Thr Thr Val Phe Gln Tyr Gly
                165                 170                 175 aac agg gcc ttc acc aag tac cct gcc gac atc cag gac tac ttc aag       576
Asn Arg Ala Phe Thr Lys Tyr Pro Ala Asp Ile Gln Asp Tyr Phe Lys
            180                 185                 190 cag acc ttc ccc gag ggc tac cac tgg gag agg agc atg acc tac gag       624
Gln Thr Phe Pro Glu Gly Tyr His Trp Glu Arg Ser Met Thr Tyr Glu
        195                 200                 205 gac cag ggc atc tgc acc gcc acc agc aac atc agc atg agg gga gac       672
Asp Gln Gly Ile Cys Thr Ala Thr Ser Asn Ile Ser Met Arg Gly Asp
    210                 215                 220 tgc ttc ttc tac gac atc agg ttc gac ggc acc aac ttc cct ccc aac       720
Cys Phe Phe Tyr Asp Ile Arg Phe Asp Gly Thr Asn Phe Pro Pro Asn
225                 230                 235                 240 ggc cca gtg atg cag aag aag act ctg aag tgg gag cct agc acc gag       768
Gly Pro Val Met Gln Lys Lys Thr Leu Lys Trp Glu Pro Ser Thr Glu
                245                 250                 255 aag atg tac gtg gag gac ggc gtg ctg aag ggc gac gtg aac atg agg       816
Lys Met Tyr Val Glu Asp Gly Val Leu Lys Gly Asp Val Asn Met Arg
```

```
Lys Met Tyr Val Glu Asp Gly Val Leu Lys Gly Asp Val Asn Met Arg
            260                 265                 270 ctg ctg ctg gag gga ggc ggc cac tac agg tgc gac ttc aag acc acc      864
Leu Leu Leu Glu Gly Gly Gly His Tyr Arg Cys Asp Phe Lys Thr Thr
            275                 280                 285 tac aag gcc aag aag gag gtg agg ctg ccc gac gcc cac aag atc gac      912
Tyr Lys Ala Lys Lys Glu Val Arg Leu Pro Asp Ala His Lys Ile Asp
    290                 295                 300 cac agg atc gag atc ctg aag cac gac aag gac tac aac aag gtg aag      960
His Arg Ile Glu Ile Leu Lys His Asp Lys Asp Tyr Asn Lys Val Lys
305                 310                 315                 320 ctg tac gag aac gcc gtg gcc agg tac tcc atg ctg ccc agc cag gcc     1008
Leu Tyr Glu Asn Ala Val Ala Arg Tyr Ser Met Leu Pro Ser Gln Ala
                325                 330                 335 aag                                                                 1011
Lys

<210> SEQ ID NO 45
<211> LENGTH: 337
<212> TYPE: PRT
<213> ORGANISM: Artificial Sequence
<220> FEATURE:
<223> OTHER INFORMATION: Synthetic Construct

<400> SEQUENCE: 45

Met Gln Val Arg Val Lys Ala Tyr Tyr Arg Gly Asp Ile Met Ile Thr
1               5                   10                  15

His Phe Glu Pro Ser Ile Ser Phe Glu Gly Leu Cys Asn Glu Val Arg
            20                  25                  30

Asp Met Cys Ser Phe Asp Asn Glu Gln Leu Phe Thr Met Lys Trp Ile
        35                  40                  45

Asp Glu Glu Gly Asp Pro Cys Thr Val Ser Ser Gln Leu Glu Leu Glu
    50                  55                  60

Glu Ala Phe Arg Leu Tyr Glu Leu Asn Lys Asp Ser Glu Leu Leu Ile
65                  70                  75                  80

His Val Phe Pro Cys Thr Gly Asn Ser Ala Asp Gly Gly Gly Gly Ser
            85                  90                  95

Gly Gly Ser Gly Gly Ser Gly Gly Ser Thr Gln Gly Thr Ser Met
            100                 105                 110

Val Ser Val Ile Lys Pro Glu Met Lys Ile Lys Leu Cys Met Arg Gly
            115                 120                 125

Thr Val Asn Gly His Asn Phe Val Ile Glu Gly Glu Gly Lys Gly Asn
    130                 135                 140

Pro Tyr Glu Gly Thr Gln Ile Leu Asp Leu Asn Val Thr Glu Gly Ala
145                 150                 155                 160

Pro Leu Pro Phe Ala Tyr Asp Ile Leu Thr Thr Val Phe Gln Tyr Gly
            165                 170                 175

Asn Arg Ala Phe Thr Lys Tyr Pro Ala Asp Ile Gln Asp Tyr Phe Lys
        180                 185                 190

Gln Thr Phe Pro Glu Gly Tyr His Trp Glu Arg Ser Met Thr Tyr Glu
    195                 200                 205

Asp Gln Gly Ile Cys Thr Ala Thr Ser Asn Ile Ser Met Arg Gly Asp
    210                 215                 220

Cys Phe Phe Tyr Asp Ile Arg Phe Asp Gly Thr Asn Phe Pro Pro Asn
225                 230                 235                 240

Gly Pro Val Met Gln Lys Lys Thr Leu Lys Trp Glu Pro Ser Thr Glu
            245                 250                 255
```

```
Lys Met Tyr Val Glu Asp Gly Val Leu Lys Gly Asp Val Asn Met Arg
            260                 265                 270

Leu Leu Leu Glu Gly Gly His Tyr Arg Cys Asp Phe Lys Thr Thr
        275                 280                 285

Tyr Lys Ala Lys Glu Val Arg Leu Pro Asp Ala His Lys Ile Asp
    290                 295                 300

His Arg Ile Glu Ile Leu Lys His Asp Lys Asp Tyr Asn Lys Val Lys
305                 310                 315                 320

Leu Tyr Glu Asn Ala Val Ala Arg Tyr Ser Met Leu Pro Ser Gln Ala
                325                 330                 335

Lys

<210> SEQ ID NO 46
<211> LENGTH: 1020
<212> TYPE: DNA
<213> ORGANISM: Artificial Sequence
<220> FEATURE:
<223> OTHER INFORMATION: Synthetic sequence TEL-hmAG1
<220> FEATURE:
<221> NAME/KEY: CDS
<222> LOCATION: (1)..(1020)

<400> SEQUENCE: 46 atg cct cga gcg ctc agg atg gag gaa gac tcg atc cgc ctg cct gcg      48
Met Pro Arg Ala Leu Arg Met Glu Glu Asp Ser Ile Arg Leu Pro Ala
1               5                   10                  15 cac ctg cgc ttg cag cca att tac tgg agc agg gat gac gta gcc cag      96
His Leu Arg Leu Gln Pro Ile Tyr Trp Ser Arg Asp Asp Val Ala Gln
                20                  25                  30 tgg ctc aag tgg gct gaa aat gag ttt tct tta agg cca att gac agc     144
Trp Leu Lys Trp Ala Glu Asn Glu Phe Ser Leu Arg Pro Ile Asp Ser
            35                  40                  45 aac acg ttt gaa atg aat ggc aaa gct ctc ctg ctg acc aaa gag          192
Asn Thr Phe Glu Met Asn Gly Lys Ala Leu Leu Leu Thr Lys Glu
        50                  55                  60 gac ttt cgc tat cga tct cct cat tca ggt gat gtg ctc tat gaa ctc     240
Asp Phe Arg Tyr Arg Ser Pro His Ser Gly Asp Val Leu Tyr Glu Leu
65                  70                  75                  80 ctt cag cat att ctg aag cag agg acc ggg aac tcc gct gac ggt ggc     288
Leu Gln His Ile Leu Lys Gln Arg Thr Gly Asn Ser Ala Asp Gly Gly
                85                  90                  95 gga gga tcg ggt gga agt ggt ggt tca gga gga gga tcg acc caa gga     336
Gly Gly Ser Gly Gly Ser Gly Gly Ser Gly Gly Gly Ser Thr Gln Gly
                100                 105                 110 act agt atg gtg agc gtg atc aag ccc gag atg aag atc aag ctg tgc     384
Thr Ser Met Val Ser Val Ile Lys Pro Glu Met Lys Ile Lys Leu Cys
            115                 120                 125 atg agg ggc acc gtg aac ggc cac aac ttc gtg atc gag ggc gag ggc     432
Met Arg Gly Thr Val Asn Gly His Asn Phe Val Ile Glu Gly Glu Gly
        130                 135                 140 aag ggc aac ccc tac gag ggc acc cag atc ctg gac ctg aac gtg acc     480
Lys Gly Asn Pro Tyr Glu Gly Thr Gln Ile Leu Asp Leu Asn Val Thr
145                 150                 155                 160 gag ggc gcc cct ctg ccc ttc gcc tac gac atc ctg acc acc gtg ttc     528
Glu Gly Ala Pro Leu Pro Phe Ala Tyr Asp Ile Leu Thr Thr Val Phe
                165                 170                 175 cag tac ggc aac agg gcc ttc acc aag tac cct gcc gac atc cag gac     576
Gln Tyr Gly Asn Arg Ala Phe Thr Lys Tyr Pro Ala Asp Ile Gln Asp
                180                 185                 190
```

```
tac ttc aag cag acc ttc ccc gag ggc tac cac tgg gag agg agc atg      624
Tyr Phe Lys Gln Thr Phe Pro Glu Gly Tyr His Trp Glu Arg Ser Met
        195                 200                 205 acc tac gag gac cag ggc atc tgc acc gcc acc agc aac atc agc atg      672
Thr Tyr Glu Asp Gln Gly Ile Cys Thr Ala Thr Ser Asn Ile Ser Met
210                 215                 220 agg gga gac tgc ttc ttc tac gac atc agg ttc gac ggc acc aac ttc      720
Arg Gly Asp Cys Phe Phe Tyr Asp Ile Arg Phe Asp Gly Thr Asn Phe
225                 230                 235                 240 cct ccc aac ggc cca gtg atg cag aag aag act ctg aag tgg gag cct      768
Pro Pro Asn Gly Pro Val Met Gln Lys Lys Thr Leu Lys Trp Glu Pro
            245                 250                 255 agc acc gag aag atg tac gtg gag gac ggc gtg ctg aag ggc gac gtg      816
Ser Thr Glu Lys Met Tyr Val Glu Asp Gly Val Leu Lys Gly Asp Val
        260                 265                 270 aac atg agg ctg ctg ctg gag gga ggc ggc cac tac agg tgc gac ttc      864
Asn Met Arg Leu Leu Leu Glu Gly Gly Gly His Tyr Arg Cys Asp Phe
    275                 280                 285 aag acc acc tac aag gcc aag aag gag gtg agg ctg ccc gac gcc cac      912
Lys Thr Thr Tyr Lys Ala Lys Lys Glu Val Arg Leu Pro Asp Ala His
290                 295                 300 aag atc gac cac agg atc gag atc ctg aag cac gac aag gac tac aac      960
Lys Ile Asp His Arg Ile Glu Ile Leu Lys His Asp Lys Asp Tyr Asn
305                 310                 315                 320 aag gtg aag ctg tac gag aac gcc gtg gcc agg tac tcc atg ctg ccc     1008
Lys Val Lys Leu Tyr Glu Asn Ala Val Ala Arg Tyr Ser Met Leu Pro
            325                 330                 335 agc cag gcc aag                                                     1020
Ser Gln Ala Lys
        340

<210> SEQ ID NO 47
<211> LENGTH: 340
<212> TYPE: PRT
<213> ORGANISM: Artificial Sequence
<220> FEATURE:
<223> OTHER INFORMATION: Synthetic Construct

<400> SEQUENCE: 47

Met Pro Arg Ala Leu Arg Met Glu Glu Asp Ser Ile Arg Leu Pro Ala
1               5                   10                  15

His Leu Arg Leu Gln Pro Ile Tyr Trp Ser Arg Asp Asp Val Ala Gln
            20                  25                  30

Trp Leu Lys Trp Ala Glu Asn Glu Phe Ser Leu Arg Pro Ile Asp Ser
        35                  40                  45

Asn Thr Phe Glu Met Asn Gly Lys Ala Leu Leu Leu Leu Thr Lys Glu
    50                  55                  60

Asp Phe Arg Tyr Arg Ser Pro His Ser Gly Asp Val Leu Tyr Glu Leu
65                  70                  75                  80

Leu Gln His Ile Leu Lys Gln Arg Thr Gly Asn Ser Ala Asp Gly Gly
            85                  90                  95

Gly Gly Ser Gly Gly Ser Gly Gly Ser Gly Gly Ser Thr Gln Gly
            100                 105                 110

Thr Ser Met Val Ser Val Ile Lys Pro Glu Met Lys Ile Lys Leu Cys
        115                 120                 125

Met Arg Gly Thr Val Asn Gly His Asn Phe Val Ile Glu Gly Glu Gly
    130                 135                 140

Lys Gly Asn Pro Tyr Glu Gly Thr Gln Ile Leu Asp Leu Asn Val Thr
145                 150                 155                 160
```

```
Glu Gly Ala Pro Leu Pro Phe Ala Tyr Asp Ile Leu Thr Thr Val Phe
            165                 170                 175

Gln Tyr Gly Asn Arg Ala Phe Thr Lys Tyr Pro Ala Asp Ile Gln Asp
        180                 185                 190

Tyr Phe Lys Gln Thr Phe Pro Glu Gly Tyr His Trp Glu Arg Ser Met
    195                 200                 205

Thr Tyr Glu Asp Gln Gly Ile Cys Thr Ala Thr Ser Asn Ile Ser Met
210                 215                 220

Arg Gly Asp Cys Phe Phe Tyr Asp Ile Arg Phe Asp Gly Thr Asn Phe
225                 230                 235                 240

Pro Pro Asn Gly Pro Val Met Gln Lys Lys Thr Leu Lys Trp Glu Pro
            245                 250                 255

Ser Thr Glu Lys Met Tyr Val Glu Asp Gly Val Leu Lys Gly Asp Val
        260                 265                 270

Asn Met Arg Leu Leu Leu Glu Gly Gly Gly His Tyr Arg Cys Asp Phe
    275                 280                 285

Lys Thr Thr Tyr Lys Ala Lys Lys Glu Val Arg Leu Pro Asp Ala His
290                 295                 300

Lys Ile Asp His Arg Ile Glu Ile Leu Lys His Asp Lys Asp Tyr Asn
305                 310                 315                 320

Lys Val Lys Leu Tyr Glu Asn Ala Val Ala Arg Tyr Ser Met Leu Pro
            325                 330                 335

Ser Gln Ala Lys
            340

<210> SEQ ID NO 48
<211> LENGTH: 963
<212> TYPE: DNA
<213> ORGANISM: Artificial Sequence
<220> FEATURE:
<223> OTHER INFORMATION: Synthetic sequence DGKdelt-hmAG1
<220> FEATURE:
<221> NAME/KEY: CDS
<222> LOCATION: (1)..(963)

<400> SEQUENCE: 48 atg ccg gtt cac ctc tgg ggg aca gag gag gtt gct gcc tgg ctg gag     48
Met Pro Val His Leu Trp Gly Thr Glu Glu Val Ala Ala Trp Leu Glu
1               5                   10                  15 cac ctc agt ctc tgt gag tat aag gac atc ttc aca cgg cac gac atc     96
His Leu Ser Leu Cys Glu Tyr Lys Asp Ile Phe Thr Arg His Asp Ile
            20                  25                  30 cgg ggc tct gag ctc ctg cac ctg gag cgg agg gac ctc aag gac ctg    144
Arg Gly Ser Glu Leu Leu His Leu Glu Arg Arg Asp Leu Lys Asp Leu
        35                  40                  45 ggc gtg acc aag gtg ggc cac atg aag agg atc ctg tgt ggc atc aag    192
Gly Val Thr Lys Val Gly His Met Lys Arg Ile Leu Cys Gly Ile Lys
    50                  55                  60 gag ctg agc cgc agc acc ggg aac tcc gct gac ggt gcc gga gga tcg    240
Glu Leu Ser Arg Ser Thr Gly Asn Ser Ala Asp Gly Ala Gly Gly Ser
65                  70                  75                  80 ggt gga agt ggt ggt tca gga gga gga tcg acc caa gga act agt atg    288
Gly Gly Ser Gly Gly Ser Gly Gly Gly Ser Thr Gln Gly Thr Ser Met
            85                  90                  95 gtg agc gtg atc aag ccc gag atg aag atc aag ctg tgc atg agg ggc    336
Val Ser Val Ile Lys Pro Glu Met Lys Ile Lys Leu Cys Met Arg Gly
        100                 105                 110 acc gtg aac ggc cac aac ttc gtg atc gag ggc gag ggc aag ggc aac    384
```

```
                                                                            -continued Thr Val Asn Gly His Asn Phe Val Ile Glu Gly Glu Gly Lys Gly Asn
            115                 120                 125 ccc tac gag ggc acc cag atc ctg gac ctg aac gtg acc gag ggc gcc      432
Pro Tyr Glu Gly Thr Gln Ile Leu Asp Leu Asn Val Thr Glu Gly Ala
130                 135                 140 cct ctg ccc ttc gcc tac gac atc ctg acc acc gtg ttc cag tac ggc      480
Pro Leu Pro Phe Ala Tyr Asp Ile Leu Thr Thr Val Phe Gln Tyr Gly
145                 150                 155                 160 aac agg gcc ttc acc aag tac cct gcc gac atc cag gac tac ttc aag      528
Asn Arg Ala Phe Thr Lys Tyr Pro Ala Asp Ile Gln Asp Tyr Phe Lys
            165                 170                 175 cag acc ttc ccc gag ggc tac cac tgg gag agg agc atg acc tac gag      576
Gln Thr Phe Pro Glu Gly Tyr His Trp Glu Arg Ser Met Thr Tyr Glu
            180                 185                 190 gac cag ggc atc tgc acc gcc acc agc aac atc agc atg agg gga gac      624
Asp Gln Gly Ile Cys Thr Ala Thr Ser Asn Ile Ser Met Arg Gly Asp
            195                 200                 205 tgc ttc ttc tac gac atc agg ttc gac ggc acc aac ttc cct ccc aac      672
Cys Phe Phe Tyr Asp Ile Arg Phe Asp Gly Thr Asn Phe Pro Pro Asn
210                 215                 220 ggc cca gtg atg cag aag aag act ctg aag tgg gag cct agc acc gag      720
Gly Pro Val Met Gln Lys Lys Thr Leu Lys Trp Glu Pro Ser Thr Glu
225                 230                 235                 240 aag atg tac gtg gag gac ggc gtg ctg aag ggc gac gtg aac atg agg      768
Lys Met Tyr Val Glu Asp Gly Val Leu Lys Gly Asp Val Asn Met Arg
                245                 250                 255 ctg ctg ctg gag gga ggc ggc cac tac agg tgc gac ttc aag acc acc      816
Leu Leu Leu Glu Gly Gly Gly His Tyr Arg Cys Asp Phe Lys Thr Thr
            260                 265                 270 tac aag gcc aag aag gag gtg agg ctg ccc gac gcc cac aag atc gac      864
Tyr Lys Ala Lys Lys Glu Val Arg Leu Pro Asp Ala His Lys Ile Asp
            275                 280                 285 cac agg atc gag atc ctg aag cac gac aag gac tac aac aag gtg aag      912
His Arg Ile Glu Ile Leu Lys His Asp Lys Asp Tyr Asn Lys Val Lys
            290                 295                 300 ctg tac gag aac gcc gtg gcc agg tac tcc atg ctg ccc agc cag gcc      960
Leu Tyr Glu Asn Ala Val Ala Arg Tyr Ser Met Leu Pro Ser Gln Ala
305                 310                 315                 320 aag                                                                  963
Lys

<210> SEQ ID NO 49
<211> LENGTH: 321
<212> TYPE: PRT
<213> ORGANISM: Artificial Sequence
<220> FEATURE:
<223> OTHER INFORMATION: Synthetic Construct

<400> SEQUENCE: 49

Met Pro Val His Leu Trp Gly Thr Glu Glu Val Ala Ala Trp Leu Glu
1               5                   10                  15

His Leu Ser Leu Cys Glu Tyr Lys Asp Ile Phe Thr Arg His Asp Ile
            20                  25                  30

Arg Gly Ser Glu Leu Leu His Leu Glu Arg Arg Asp Leu Lys Asp Leu
        35                  40                  45

Gly Val Thr Lys Val Gly His Met Lys Arg Ile Leu Cys Gly Ile Lys
    50                  55                  60

Glu Leu Ser Arg Ser Thr Gly Asn Ser Ala Asp Gly Gly Gly Ser
65                  70                  75                  80
```

```
Gly Gly Ser Gly Gly Ser Gly Gly Ser Thr Gln Gly Thr Ser Met
             85                  90                  95

Val Ser Val Ile Lys Pro Glu Met Lys Ile Lys Leu Cys Met Arg Gly
            100                 105                 110

Thr Val Asn Gly His Asn Phe Val Ile Glu Gly Glu Gly Lys Gly Asn
            115                 120                 125

Pro Tyr Glu Gly Thr Gln Ile Leu Asp Leu Asn Val Thr Glu Gly Ala
        130                 135                 140

Pro Leu Pro Phe Ala Tyr Asp Ile Leu Thr Thr Val Phe Gln Tyr Gly
145                 150                 155                 160

Asn Arg Ala Phe Thr Lys Tyr Pro Ala Asp Ile Gln Asp Tyr Phe Lys
                165                 170                 175

Gln Thr Phe Pro Glu Gly Tyr His Trp Glu Arg Ser Met Thr Tyr Glu
            180                 185                 190

Asp Gln Gly Ile Cys Thr Ala Thr Ser Asn Ile Ser Met Arg Gly Asp
        195                 200                 205

Cys Phe Phe Tyr Asp Ile Arg Phe Asp Gly Thr Asn Phe Pro Pro Asn
210                 215                 220

Gly Pro Val Met Gln Lys Lys Thr Leu Lys Trp Glu Pro Ser Thr Glu
225                 230                 235                 240

Lys Met Tyr Val Glu Asp Gly Val Leu Lys Gly Asp Val Asn Met Arg
                245                 250                 255

Leu Leu Leu Glu Gly Gly Gly His Tyr Arg Cys Asp Phe Lys Thr Thr
            260                 265                 270

Tyr Lys Ala Lys Lys Glu Val Arg Leu Pro Asp Ala His Lys Ile Asp
        275                 280                 285

His Arg Ile Glu Ile Leu Lys His Asp Lys Asp Tyr Asn Lys Val Lys
    290                 295                 300

Leu Tyr Glu Asn Ala Val Ala Arg Tyr Ser Met Leu Pro Ser Gln Ala
305                 310                 315                 320

Lys

<210> SEQ ID NO 50
<211> LENGTH: 78
<212> TYPE: DNA
<213> ORGANISM: Homo sapiens
<220> FEATURE:
<221> NAME/KEY: CDS
<222> LOCATION: (1)..(78)
<223> OTHER INFORMATION: M13

<400> SEQUENCE: 50 aag agg cgc tgg aag aaa aac ttc att gcc gtc agc gct gcc aac cgg    48
Lys Arg Arg Trp Lys Lys Asn Phe Ile Ala Val Ser Ala Ala Asn Arg
1               5                   10                  15 ttc aag aag atc tcc agc tcc ggg gca ctg                            78
Phe Lys Lys Ile Ser Ser Ser Gly Ala Leu
            20                  25

<210> SEQ ID NO 51
<211> LENGTH: 26
<212> TYPE: PRT
<213> ORGANISM: Homo sapiens

<400> SEQUENCE: 51

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
```

<210> SEQ ID NO 52
<211> LENGTH: 441
<212> TYPE: DNA
<213> ORGANISM: Homo sapiens
<220> FEATURE:
<221> NAME/KEY: CDS
<222> LOCATION: (1)..(441)
<223> OTHER INFORMATION: calmodulin

<400> SEQUENCE: 52

```
gac caa ctg aca gaa gag cag att gca gag ttc aaa gaa gcc ttc tca    48
Asp Gln Leu Thr Glu Glu Gln Ile Ala Glu Phe Lys Glu Ala Phe Ser
1               5                   10                  15 tta ttc gac aag gat ggg gac ggc acc atc acc aca aag gaa ctt ggc    96
Leu Phe Asp Lys Asp Gly Asp Gly Thr Ile Thr Thr Lys Glu Leu Gly
            20                  25                  30 acc gtt atg agg tcg ctt gga caa aac cca acg gaa gca gaa ttg cag   144
Thr Val Met Arg Ser Leu Gly Gln Asn Pro Thr Glu Ala Glu Leu Gln
        35                  40                  45 gat atg atc aat gaa gtc gat gct gat ggc aat gga acg att tac ttt   192
Asp Met Ile Asn Glu Val Asp Ala Asp Gly Asn Gly Thr Ile Tyr Phe
    50                  55                  60 cct gaa ttt ctt act atg atg gct aga aaa atg aag gac aca gac agc   240
Pro Glu Phe Leu Thr Met Met Ala Arg Lys Met Lys Asp Thr Asp Ser
65                  70                  75                  80 gaa gag gaa atc cga gaa gca ttc cgt gtt ttt gac aag gat ggg aac   288
Glu Glu Glu Ile Arg Glu Ala Phe Arg Val Phe Asp Lys Asp Gly Asn
                85                  90                  95 ggc tac atc agc gct gct gaa tta cgt cac gtc atg aca aac ctc ggg   336
Gly Tyr Ile Ser Ala Ala Glu Leu Arg His Val Met Thr Asn Leu Gly
            100                 105                 110 gag aag tta aca gat gaa gaa gtt gat gaa atg ata agg gaa gca gat   384
Glu Lys Leu Thr Asp Glu Glu Val Asp Glu Met Ile Arg Glu Ala Asp
        115                 120                 125 atc gat ggt gat ggc caa gta aac tat gaa gag ttt gta caa atg atg   432
Ile Asp Gly Asp Gly Gln Val Asn Tyr Glu Glu Phe Val Gln Met Met
    130                 135                 140 aca gca aag                                                        441
Thr Ala Lys
145
```

<210> SEQ ID NO 53
<211> LENGTH: 147
<212> TYPE: PRT
<213> ORGANISM: Homo sapiens

<400> SEQUENCE: 53

```
Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asn Gly Thr Ile Tyr Phe
    50                  55                  60

Pro Glu Phe Leu Thr Met Met Ala Arg Lys Met Lys Asp Thr Asp Ser
65                  70                  75                  80

Glu Glu Glu Ile Arg Glu Ala Phe Arg Val Phe Asp Lys Asp Gly Asn
                85                  90                  95
```

-continued

```
Gly Tyr Ile Ser Ala Ala Glu Leu Arg His Val Met Thr Asn Leu Gly
                100                 105                 110

Glu Lys Leu Thr Asp Glu Glu Val Asp Glu Met Ile Arg Glu Ala Asp
            115                 120                 125

Ile Asp Gly Asp Gly Gln Val Asn Tyr Glu Glu Phe Val Gln Met Met
130                 135                 140

Thr Ala Lys
145
```